United States Patent [19]

Hillemann

[11] Patent Number: 4,710,221

[45] Date of Patent: Dec. 1, 1987

[54] HERBICIDAL SULFONAMIDES

[75] Inventor: Craig L. Hillemann, Wilmington, Del.

[73] Assignee: E. I. Du Pont de Nemours and Company, Wilmington, Del.

[21] Appl. No.: 801,165

[22] Filed: Nov. 22, 1985

Related U.S. Application Data

[63] Continuation-in-part of Ser. No. 720,702, Apr. 10, 1985, abandoned, which is a continuation-in-part of Ser. No. 613,412, May 24, 1984, abandoned.

[51] Int. Cl.$^4$ .................. C07D 251/46; A01N 43/66
[52] U.S. Cl. ......................................... 71/93; 544/211
[58] Field of Search .................... 71/93; 544/211, 206, 544/208

[56] References Cited

U.S. PATENT DOCUMENTS

| | | | |
|---|---|---|---|
| 4,383,113 | 5/1983 | Levitt | 544/212 |
| 4,452,628 | 6/1984 | Adams | 544/211 |
| 4,476,321 | 10/1984 | Meyer et al. | 564/86 |
| 4,514,212 | 4/1985 | Meyer et al. | 71/93 |
| 4,537,619 | 8/1985 | Meyer et al. | 544/211 |
| 4,545,811 | 10/1985 | Meyer et al. | 544/211 |

FOREIGN PATENT DOCUMENTS

81/4874  7/1981  South Africa.

Primary Examiner—John M. Ford

[57] ABSTRACT

This invention relates to certain sulfonylurea herbicidal compounds, agriculturally suitable compositions thereof and a method of their use.

12 Claims, No Drawings

HERBICIDAL SULFONAMIDES

RELATED APPLICATION

This application is a continuation-in-part of copending application U.S. Ser. No. 720,702 filed Apr. 10, 1985, now abandoned, which is a continuation-in-part of U.S. Ser. No. 613,412 filed May 24, 1984, now abandoned.

BACKGROUND OF THE INVENTION

This invention relates to novel sulfonylurea herbicidal compounds, agriculturally suitable compositions thereof and a method of using them to control the growth of undesired vegetation.

New compounds effective for controlling the growth of undesired vegetation are in constant demand. In the most common situation, such compounds are sought to selectively control the growth of weeds in useful crops such as cotton, rice, corn, wheat and soybeans, to name a few. Unchecked weed growth in such crops can cause significant losses, reducing profit to the farmer and increasing costs to the consumer. In other situations, herbicides are desired which will control all plant growth. Examples of areas in which complete control of all vegetation is desired are areas around fuel storage tanks, ammunition depots and industrial storage areas. There are many products commerically available for these purposes, but the search continues for products which are more effective, less costly and environmentally safe.

The "sulfonylurea" herbicides are an extremely potent class of herbicides discovered within the last few years. A multitude of structural variations exist within this class of herbicides, but they generally consist of a sulfonylurea bridge, $-SO_2NHCONH-$, linking two aromatic or heteroaromatic rings.

U.S. Pat. No. 4,394,506 discloses herbicidal ortho-alkoxycarbonylbenzenesulfonamides such as

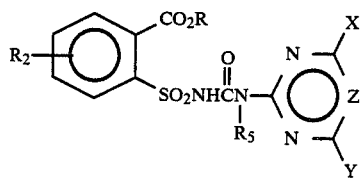

wherein
$R_2$ is H, F, Cl, Br, $C_1$-$C_3$ alkyl, $NO_2$, $SO_2CH_3$, $OCH_3$, $SCH_3$, $CF_3$, $N(CH_3)_2$, $NH_2$ or CN;
X is H, Cl, $CH_3$, $OCH_3$, $OCH_2CH_3$ or $OCH_2C$-$H_2OCH_3$; and
Y is H, halogen, $C_1$-$C_4$ alkyl, $C_1$-$C_4$ substituted alkyl, $C_1$-$C_4$ alkoxy, alkylamino, dialkylamino, etc.

South African Patent Application No. 81/4874 discloses herbicidal sulfonamides of formula

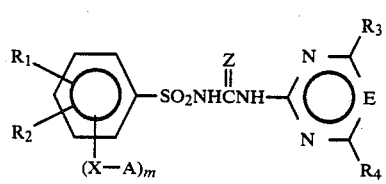

wherein

A is a $C_1$-$C_6$ alkyl radical which is substituted by halogen or various other organic substituents or a $C_2$-$C_6$ alkenyl radical which is substituted or unsubstituted.
X is O, S, SO or $SO_2$;
$R_1$ is H, halogen, $C_1$-$C_5$ alkyl, $C_2$-$C_5$ alkenyl or $YR_5$;
$R_2$ is H, halogen, $C_1$-$C_5$ alkyl, $C_2$-$C_5$ alkenyl, $C_1$-$C_4$ haloalkyl, $CO_2R_6$, $YR_5$, $NO_2$ or $CONR_7R_8$; and
$R_3$ and $R_4$, each independently of the other, are hydrogen, $C_1$-$C_4$ alkyl, $C_1$-$C_4$ alkoxy, $C_1$-$C_4$ alkylthio, $C_1$-$C_4$ haloalkyl, halogen or alkoxyalkyl of at most 4 carbon atoms.

South African Patent Application 82/5042 discloses herbicidal sulfonamides of formula

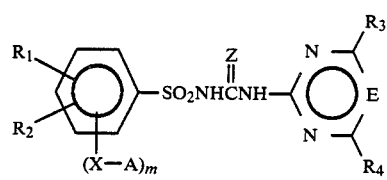

wherein
A is $C_3$-$C_6$ alkynyl;
X is O, S, SO or $SO_2$;
$R_1$ is H, halogen, $C_1$-$C_5$ alkyl, $C_2$-$C_5$ alkenyl or $YR_5$;
$R_2$ is H, halogen, $C_1$-$C_5$ alkyl, $C_2$-$C_5$ alkenyl, $C_1$-$C_4$ haloalkyl, $CO_2R_6$, $YR_5$, $NO_2$ or $CONR_7R_8$; and
$R_3$ and $R_4$, independently of one another, are hydrogen, $C_1$-$C_4$ alkyl, $C_1$-$C_4$ alkoxy, $C_1$-$C_4$ alkylthio, $C_1$-$C_4$ haloalkyl, $C_1$-$C_4$ haloalkoxy, halogen or alkoxyalkyl of at most 4 carbon atoms.

South African Patent Application No. 82/5671 discloses herbicidal sulfonamides of formula

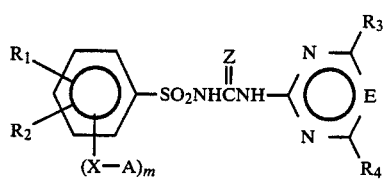

wherein
A is a $C_1$-$C_6$ alkyl radical or a $C_2$-$C_6$ alkenyl radical which is substituted by halogen or various other organic substituents;
X is O, S, SO or $SO_2$;
$R_1$ is H, halogen, $C_1$-$C_5$ alkyl, $C_2$-$C_5$ alkenyl or $YR_5$;
$R_2$ is H, halogen, $C_1$-$C_5$ alkyl, $C_2$-$C_5$ alkenyl, $C_1$-$C_4$ haloalkyl, $CO_2R_6$, $YR_5$, $NO_2$ or $CONR_7R_8$;
$R_3$ is hydrogen, $C_1$-$C_4$ alkyl, $C_1$-$C_4$ alkoxy, $C_1$-$C_4$ alkylthio, $C_1$-$C_4$ haloalkyl, $C_1$-$C_4$ haloalkoxy, halogen or alkoxyalkyl of at most 4 carbon atoms; and
$R_4$ is $C_1$-$C_4$ haloalkoxy or $C_1$-$C_4$ haloalkylthio.

South African Patent Application No. 82/7439 discloses herbicidal sulfonamides of formula

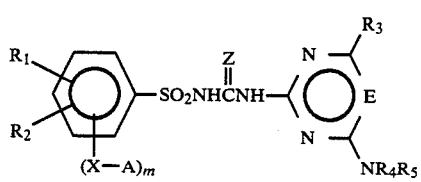

wherein

A is a $C_3$-$C_6$ alkynyl group, a $C_1$-$C_6$ alkyl group which is substituted by halogen, $C_1$-$C_4$ alkoxy, $C_1$-$C_4$ alkylthio, $C_1$-$C_4$ alkylsulfinyl, $C_1$-$C_4$ alkylsulfonyl, $C_1$-$C_4$ haloalkoxy, $C_1$-$C_4$ haloalkylthio, $C_1$-$C_4$ haloalkylsulfinyl or $C_1$-$C_4$ haloalkylsulfonyl, or it is a $C_2$-$C_6$ alkenyl group substituted by one of the above substituents;

X is O, S, SO or $SO_2$;

$R_1$ is hydrogen, halogen, $C_1$-$C_5$ alkyl, $C_2$-$C_5$ alkenyl or a $YR_6$ group;

$R_2$ is hydrogen, halogen, $C_1$-$C_5$ alkyl, $C_2$-$C_5$ alkenyl, $C_1$-$C_4$ haloalkyl, $YR_6$, $CO_2R_7$, $NO_2$ or $CONR_8R_9$;

$R_3$ is hydrogen, $C_1$-$C_4$ alkyl, $C_1$-$C_4$ alkoxy, $C_1$-$C_4$ alkylthio, $C_1$-$C_4$ haloalkyl, $C_1$-$C_4$ haloalkoxy, halogen or alkoxyalkyl having at most 4 carbon atoms;

$R_4$ is hydrogen, methyl or ethyl;

$R_5$ is hydrogen, $C_1$-$C_4$ alkyl, $C_1$-$C_3$ alkoxy, methoxymethyl, cyanomethyl or cyanoethyl;

$R_6$ and $R_7$ are each $C_1$-$C_5$ alkyl, $C_2$-$C_5$ alkenyl or $C_2$-$C_6$ alkynyl;

South African Patent Application No. 83/0441 (Swiss priority 1/25/82) discloses herbicidal benzenesulfonamides of formula

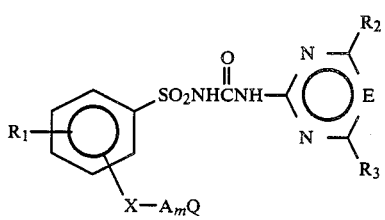

wherein $R_1$ is H, halogen, $NO_2$, $C_1$-$C_4$ haloalkyl, $C_1$-$C_4$ alkyl, $C_1$-$C_4$ alkoxy, $C_2$-$C_5$ alkenyl or $C_1$-$C_4$ alkoxycarbonyl;

$R_2$ is $C_1$-$C_3$ alkyl or $C_1$-$C_3$ alkoxy, each unsubstituted or substituted by 1 to 3 halogen atoms;

$R_3$ is halogen, H, $NR_4R_5$, $C_1$-$C_3$ alkyl, unsubstituted or substituted by 1 to 3 halogen atoms or $C_1$-$C_4$ alkoxy, or is $C_1$-$C_3$ alkoxy, unsubstituted or substituted by methoxy, ethoxy, or 1 to 3 halogen atoms;

A is $C_1$-$C_4$ alkylene or $C_2$-$C_4$ alkenylene, each unsubstituted or substituted by $C_1$-$C_4$ alkyl;

m is 0 or 1;

E is N or CH;

X is oxygen, sulfur, SO or $SO_2$; and

Q is, in part, OH, CN, $NR_6R_7$, $SO_2R_8$, cycloalkyl or $COC_1$-$C_6$ alkyl.

South African Patent Application No. 83/3779 (Swiss priority 5/26/82) discloses herbicidal benzenesulfonamides of formula

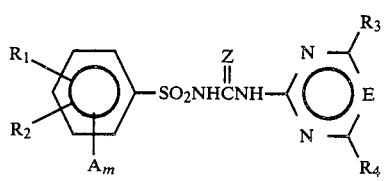

wherein

A is C≡CR;

m is 1 or 2;

E is CH or N;

Z is oxygen or sulfur,

R is, in part, H, $C_1$-$C_9$ alkyl or $C_1$-$C_9$ haloalkyl;

$R_1$ is H, halogen, $C_1$-$C_5$ alkyl, $C_2$-$C_5$ alkenyl or $YR_5$;

$R_2$ is H, halogen, $C_1$-$C_5$ alkyl, $C_2$-$C_5$ alkenyl, $C_1$-$C_4$ haloalkyl, $YR_5$, $CO_2R_6$, $NO_2$ or $CONR_7R_8$; $R_3$ and $R_4$, each independently of the other, are H, $C_1$-$C_4$ alkyl, $C_1$-$C_4$ alkoxy, $C_1$-$C_4$ alkylthio, $C_1$-$C_4$ haloalkyl, $C_1$-$C_4$ haloalkoxy, $C_1$-$C_4$ haloalkylthio, halogen, $C_2$-$C_5$ alkoxyalkyl, $NR_9R_{10}$ or $OCH_2CH_2NR_9R_{10}$.

South African Patent Application No. 83/6449 (Swiss priority 9/1/82) discloses herbicidal benzenesulfonamides of formula

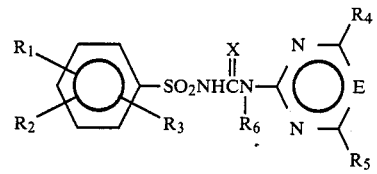

wherein $R_1$ is H, halogen, $NO_2$, amino, $C_1$-$C_5$ alkyl, $C_1$-$C_4$ haloalkyl or a $QR_7$, $CO_2R_8$ or $(CO)_nNR_9R_{10}$ radical;

$R_2$ is H, $C_1$-$C_4$ alkyl, $C_1$-$C_4$ alkoxy, $C_1$-$C_4$ alkylthio, $C_1$-$C_4$ haloalkyl, $C_1$-$C_4$ haloalkoxy, halogen or alkoxyalkyl containing not more than 4 carbon atoms;

$R_3$ is $C_2$-$C_{10}$ alkenyl which is substituted by one or more fluorine or bromine atoms or by one or more hydroxyl, cyano, nitro, $(Y)_mCO(Z)_nR_8$, $SO_2NR_{11}R_{12}$, $S(O)_pC_1$-$C_3$ haloalkyl or $S(O)_nC_1$-$C_3$ alkyl groups and which may additionally be substituted by one or more chlorine atoms;

$R_4$ is $C_1$-$C_3$ alkyl, $C_1$-$C_3$ haloalkyl, $C_1$-$C_3$ alkoxy or $C_1$-$C_3$ haloalkoxy;

$R_5$ is H, halogen, $NR_{13}R_{14}$, $C_1$-$C_3$ alkyl, $C_1$-$C_3$ haloalkyl, $C_1$-$C_3$ alkoxy or $C_1$-$C_2$ haloalkoxy; and E is CH or N.

South African Patent Application No. 84/2245 (Swiss priority 3/28/83) discloses herbicidal sulfonamides of formula

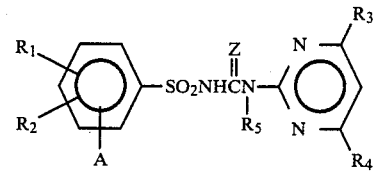

wherein

A is $C_1$-$C_6$ haloalkyl;

$R_1$ is hydrogen, halogen, nitro, cyano, $C_1$-$C_4$ alkyl, $C_1$-$C_4$ haloalkyl, $C_1$-$C_4$ alkoxy, $C_1$-$C_4$ alkylthio, $C_1$-$C_4$ alkylsulfinyl, $C_1$-$C_4$ alkylsulfonyl, $COR_6$, $NR_7R_8$, $CONR_9R_{10}$ or $SO_2NR_{11}R_{12}$;

$R_2$ is hydrogen, halogen, $C_1$-$C_4$ alkyl, $C_1$-$C_4$ alkoxy, $C_1$-$C_4$ alkylthio, $C_1$-$C_4$ alkylsulfinyl or $C_1$-$C_4$ alkylsulfonyl; and $R_3$ and $R_4$, independently of one another, are each hydrogen, halogen, $C_1$-$C_4$ alkyl, $C_1$-$C_4$ haloalkyl, $C_2$-$C_4$ haloalkoxy, $C_1$-$C_4$ alkylthio, $C_1$-$C_4$ haloalkylthio, $C_2$-$C_4$ alkoxyalkyl, $C_1$-$C_4$ alkoxy or $NR_{12}R_{13}$.

South African Patent Application No. 84/2722 (Swiss priority 4/13/83) discloses herbicidal benzenesulfonamides of formula $$\underset{A}{\underset{R_2}{R_1}}\!\!\diagdown\!\!\diagup\!\!-SO_2NHCN\!\!-\!\!\underset{R_5}{\overset{Z}{\overset{\parallel}{C}}}\!\!-\!\!\underset{N}{\overset{N=\!\!\diagdown}{\diagdown\!\!\diagup}}\!\!\underset{R_4}{\overset{R_3}{}}$$

wherein

A is a radical of the formula $CR_6R_7XR_8$, $CR_9R_{10}R_{11}$ or $CHR_7SCQR_{21}$;

$R_1$ is hydrogen, halogen, nitro, cyano, $C_1-C_4$ alkyl, $C_1-C_4$ haloalkyl, $YR_{14}$, $CONR_{12}R_{13}$, $NR_{12}R_{13}$, $SONR_{15}R_{16}$, $OSO_2R_{17}$ or $COR_{18}$;

$R_2$ is hydrogen, halogen, $C_1-C_4$ alkyl, $C_1-C_4$ alkoxy, $C_1-C_4$ alkylthio, $C_1-C_4$ alkylsulfinyl or $C_1-C_4$ alkylsulfonyl;

$R_3$ and $R_4$, independently of one another, are each hydrogen, halogen, $C_1-C_4$ alkyl, $C_1-C_4$ haloalkyl, $C_1-C_4$ alkoxy, $C_1-C_4$ haloalkoxy, $C_1-C_4$ alkylthio, $C_1-C_4$ haloalkylthio, $C_2-C_5$ alkoxyalkyl or $NR_{19}R_{20}$;

$R_9$ is hydrogen, halogen, $C_1-C_4$ alkyl, $C_1-C_4$ alkoxy, $C_1-C_4$ alkylthio, $C_1-C_4$ alkylsulfinyl or $C_1-C_4$ alkylsulfonyl;

$R_{10}$ is hydrogen, halogen or methyl;

$R_{11}$ is a radical $COR_{24}$ or a $C_1-C_4$ alkyl group that is mono- or polysubstituted by substituents selected from the group: cyano, nitro, hydroxyl, $C_1-C_4$ alkoxy, $C_1-C_4$ alkylthio, etc.

$R_{18}$ is H, $C_1-C_4$ alkoxy and various other organic radicals.

There is a continuing need for new herbicidal compounds which have safety to selective crops and which control both grassy and broadleaf weeds.

SUMMARY OF THE INVENTION

This invention relates to certain compounds of the structural formula:

$$\underset{R_2}{\diagdown}\!\!\diagup\!\!\overset{CO_2R_1}{\underset{SO_2NHCN\!-\!\!\diagdown\!\!\diagup}{\overset{\overset{O}{\parallel}}{\underset{R}{}}}}\!\!\underset{N\!\!\diagdown}{\overset{N\!\!=\!\!\diagdown}{\diagup}}\!\!\underset{Y}{\overset{X}{\underset{Z}{}}}\qquad I$$

wherein

R is H or $CH_3$;

$R_1$ is $C_1-C_3$ alkyl, $C_3-C_4$ alkoxyalkyl, $C_2-C_4$ haloalkyl, $C_3-C_4$ alkenyl or $C_3-C_4$ alkynyl;

$R_2$ is $C_2-C_6$ alkoxy, $C_3-C_6$ cycloalkoxy, $C_4-C_6$ cycloalkylalkoxy, $C_1-C_6$ haloalkoxy, $C_2-C_6$ alkenyloxy, $C_2-C_6$ haloalkenyloxy, $C_3-C_6$ alkynyloxy, $C_3-C_6$ haloalkynyloxy, $C_2-C_4$ alkoxyalkoxy, $C_2-C_4$ haloalkoxyalkoxy, $C_2-C_4$ alkylthioalkoxy, $C_2-C_4$ haloalkylthioalkoxy, $C_2-C_4$ alkylsulfinylalkoxy, $C_2-C_4$ haloalkysulfinylalkoxy, $C_2-C_4$ alkylsulfonylalkoxy, $C_2-C_4$ haloalkylsulfonylalkoxy, $C_2-C_4$ cyanoalkoxy, $OCH_2C(O)CH_3$, $OCH_2CH_2C(O)CH_3$, $C_2-C_4$ aminoalkoxy, $C_1-C_8$ alkylthio, $C_3-C_6$ cycloalkylthio, $C_4-C_6$ cycloalkylalkylthio, $C_1-C_8$ haloalkylthio, $C_2-C_6$ alkenylthio, $C_2-C_6$ haloalkenylthio, $C_3-C_6$ alkynylthio, $C_3-C_6$ haloalkynylthio, $C_2-C_4$ alkoxyalkylthio, $C_2-C_4$ haloalkoxyalkylthio, $C_2-C_4$ alkylthioalkylthio, $C_2-C_4$ haloalkylthioalkylthio, $C_2-C_4$ cyanoalkylthio, $SCH_2C(O)CH_3$, $SCH_2CH_2C(O)CH_3$, $C_2-C_4$ aminoalkylthio, $SC_6H_5$, $SCH_2C_6H_5$, $C_1-C_8$ alkylsulfinyl, $C_3-C_6$ cycloalkylsulfinyl, $C_4-C_6$ cycloalkylalkylsulfinyl, $C_1-C_8$ haloalkylsulfinyl, $C_2-C_6$ alkenylsulfinyl, $C_2-C_6$ haloalkenylsulfinyl, $C_3-C_6$ alkynylsulfinyl, $C_3-C_6$ haloalkynylsulfinyl, $C_2-C_4$ alkoxyalkylsulfinyl, $C_2-C_4$ haloalkoxyalkylsulfinyl, $C_2-C_4$ cyanoalkylsulfinyl, $S(O)CH_2C(O)CH_3$, $S(O)CH_2CH_2C(O)CH_3$, $C_2-C_4$ aminoalkylsulfinyl, $C_2-C_8$ alkylsulfonyl, $C_3-C_6$ cycloalkylsulfonyl, $C_4-C_6$ cycloalkylalkylsulfonyl, $C_1-C_8$ haloalkylsulfonyl, $C_2-C_6$ alkenylsulfonyl, $C_2-C_6$ haloalkenylsulfonyl, $C_3-C_6$ alkynylsulfonyl, $C_3-C_6$ haloalkynylsulfonyl, $C_2-C_4$ alkoxyalkylsulfonyl, $C_2-C_4$ haloalkoxyalkylsulfonyl, $C_2-C_4$ cyanoalkylsulfonyl, $SO_2CH_2C(O)CH_3$, $SO_2CH_2CH_2C(O)CH_3$, $C_2-C_4$ aminoalkylsulfonyl, $CH_2F$, $CHF_2$, $CH_2Cl$, $CHCl_2$, $CH_2Br$, $CHBr_2$, $C_2-C_6$ alkyl substituted with 1-3 atoms of F, Cl or Br, $C_2-C_6$ alkenyl, $C_2-C_6$ haloalkenyl, $C\equiv CH$, $C_2-C_6$ haloalkynyl, $OC(O)C_1-C_4$ alkyl, $CH_2C(O)NR_aR_b$, $NHCH_3$, $NR_bR_c$ or $C_1-C_4$ alkyl substituted with $C_1-C_4$ alkoxy, $C_3-C_4$ cycloalkoxy, cyclopropylmethoxy, $C_1-C_4$ haloalkoxy, $C_2-C_4$ alkenyloxy, $C_2-C_4$ haloalkenyloxy, $C_3-C_4$ alkynyloxy, $C_3-C_4$ haloalkynyloxy, $C_2-C_4$ alkoxyalkoxy, $C_2-C_4$ aminoalkoxy, $C_1-C_4$ alkylcarbonyloxy, $C_1-C_4$ haloalkylcarbonyloxy, $C_1-C_4$ carbamoyloxy, $C_1-C_4$ alkoxycarbonyloxy, OH, $OP(O)(OC_1-C_2$ alkyl$)_2$, $C_1-C_4$ alkylsulfonyloxy, $C_1-C_2$ haloalkylsulfonyloxy, $OSi(CH_3)_3$, $OSi(CH_3)_2C(CH_3)_3$, $C_1-C_4$ alkylthio, $C_3-C_4$ cycloalkylthio, cyclopropylmethylthio, $C_1-C_4$ haloalkylthio, $C_2-C_4$ alkenylthio, $C_2-C_4$ haloalkenylthio, $C_3-C_4$ alkynylthio, $C_3-C_4$ haloalkynylthio, $C_2-C_4$ alkoxyalkylthio, $C_2-C_4$ aminoalkylthio, SH, $SP(O)(OC_1-C_2$ alkyl$)_2$, $C_1-C_4$ alkylsulfinyl, $C_3-C_4$ cycloalkylsulfonyl, cyclopropylmethylsulfinyl, $C_1-C_4$ haloalkylsulfinyl, $C_2-C_4$ alkenylsulfinyl, $C_2-C_4$ haloalkenylsulfinyl, $C_3-C_4$ alkynylsulfinyl, $C_3-C_4$ haloalkynylsulfinyl, $C_2-C_4$ alkoxyalkylsulfinyl, $C_2-C_4$ aminoalkylsulfinyl, $C_1-C_4$ alkylsulfonyl, $C_3-C_4$ cycloalkylsulfonyl, cyclopropylmethylsulfonyl, $C_1-C_4$ haloalkylsulfonyl, $C_2-C_4$ alkenylsulfonyl, $C_2-C_4$ haloalkenylsulfonyl, $C_3-C_4$ alkynylsulfonyl, $C_3-C_4$ haloalkynylsulfonyl, $C_2-C_4$ alkoxyalkylsulfonyl or $C_2-C_4$ aminoalkylsulfonyl;

$R_a$ and $R_b$ are independently H or $C_1-C_3$ alkyl;

$R_c$ is $C_2-C_4$ alkyl, cyclopropylmethyl, $C_2-C_4$ cyanoalkyl, $CH_2C(O)CH_3$, $CH_2CH_2C(O)CH_3$, $C_1-C_4$ haloalkyl, $C_3-C_4$ alkenyl, $C_3-C_4$ haloalkenyl, $C_3-C_4$ alkynyl, $C_3-C_4$ haloalkynyl, $C_1-C_4$ alkyl substituted with $C_1-C_4$ alkoxy, $C_1-C_4$ alkylthio, $C_1-C_4$ alkylsulfinyl, $C_1-C_4$ alkylsulfonyl, OH, $NH_2$, $NHCH_3$ or $N(CH_3)_2$;

X is $CH_3$, $OCH_3$, $OC_2H_5$, Cl or Br;

Y is $C_1-C_2$ alkyl, $C_1-C_2$ alkoxy, $OCH_2CH_2F$, $OCH_2CHF_2$, $OCH_2CF_3$, $NHCH_3$ or $N(CH_3)_2$; and Z is CH or N; and their agriculturally suitable salts; provided that (1) when X is Cl or Br, then Z is CH and Y is $C_1-C_2$ alkoxy, $NHCH_3$ or $N(CH_3)_2$; and (2) when $R_2$ is $SCH_3$, then R is H, $R_1$ is $CH_3$, X is $OCH_3$, Y is $OCH_3$ and Z is CH.

In the above definitions, the term "alkyl", used either alone or in compound words such as "alkylthio" or "haloalkyl", denotes straight chain or branched alkyl, e.g., methyl, ethyl, n-propyl, isopropyl or the different butyl, pentyl, hexyl, heptyl and octyl isomers.

Alkoxy denotes methoxy, ethoxy, n-propoxy, isopropoxy and the different butoxy, pentoxy or hexoxy isomers.

Alkenyl denotes straight chain or branched alkenes, e.g., vinyl, 1-propenyl, 2-propenyl, 3-propenyl and the different butenyl, pentenyl and hexenyl isomers.

Alkynyl denotes straight chain or branched alkynes, e.g., ethynyl, 1-propynyl, 2-propynyl and the different butynyl, pentynyl and hexynyl isomers.

Cycloalkyl denotes cyclopropyl, cyclobutyl, cyclopentyl and cyclohexyl.

$C_4$–$C_6$ cycloalkylalkyl means cyclopropylmethyl through cyclopropylpropyl or cyclopentylmethyl.

The term "halogen", either alone or in compound words such as "haloalkyl", denotes fluorine, chlorine, bromine or iodine. Further, when used in compound words such as "haloalkyl" said alkyl may be partially or fully substituted with halogen atoms, which may be the same or different. Examples of haloalkyl include $CH_2CH_2F$, $CF_2CF_3$ and $CH_2CHFCl$.

The total number of carbon atoms in a substituent group is indicated by the $C_i$–$C_j$ prefix where i and j are numbers from 1 to 8. For example, $C_1$–$C_3$ alkylsulfonyl would designate methylsulfonyl through propylsulfonyl, $C_2$ alkoxyalkoxy would designate $OCH_2OCH_3$; $C_4$ alkoxyalkoxy would designate the various isomers of an alkoxy group substituted with a second alkoxy group containing a total of 4 carbon atoms, examples including $OCH_2OCH_2CH_2CH_3$ and $OCH_2CH_2OCH_2CH_3$; $C_2$ cyanoalkyl would designate $CH_2CN$ and $C_3$ cyanoalkyl would designate $CH_2CH_2CN$ and $CH(CN)CH_3$; $C_4$ aminoalkoxy would designate the various isomers of an alkoxy group substituted by an amino, alkylamino or dialkylamino group containing a total of 4 carbon atoms, examples including $OCH_2CH_2CH_2CH_2NH_2$ and $OCH_2CH_2N(CH_3)_2$; as further example, $CH(H, C_1$–$C_3$ alkyl)$OC_1$–$C_2$ alkyl would designate the various isomers of a methyl group substituted by a $C_1$–$C_2$ alkoxy group and optionally substituted by a $C_1$–$C_3$ alkyl group, examples including $CH_2OCH_3$ and $CH(CH_2CH_2CH_3)OCH_2CH_3$.

Compounds of the invention which are preferred for their higher herbicidal activity, greater plant growth regulant activity and/or more favorable ease of synthesis are:

(1) Compounds of Formula I wherein $R_2$ is $C_2$–$C_6$ alkoxy, $C_1$–$C_8$ alkylthio, $C_1$–$C_8$ alkylsulfinyl, $C_2$–$C_8$ alkylsulfonyl, $C_3$–$C_6$ alkenyloxy, $C_3$–$C_6$ alkynyloxy, $C_3$–$C_6$ alkenylthio, $C_3$–$C_6$ alkenylsulfinyl, $C_3$–$C_6$ alkenylsulfonyl, $C_3$–$C_6$ alkynylthio, $C_3$–$C_6$ alkynylsulfinyl, $C_3$–$C_6$ alkynylsulfonyl, $OCH_2CH_2OCH_3$, $OCH_2CH_2SCH_3$, $OCH_2CH_2S(O)CH_3$, $OCH_2CH_2SO_2CH_3$, $C_2$–$C_6$ alkyl substituted with 1–3 atoms of F, Cl or Br, $CH_2F$, $CHF_2$, $C_1$–$C_4$ alkyl substituted with $C_1$–$C_2$ alkoxy, $C_1$–$C_2$ alkylthio, $C_1$–$C_2$ alkylsulfinyl or $C_1$–$C_2$ alkylsulfonyl, $OCF_2H$, $OCH_2CH_2F$, $OCH_2CHF_2$, $OCH_2CF_3$, $OCH_2CH_2Cl$, S-cyclohexyl, $SC_6H_5$ or $SCH_2C_6H_5$;

(2) Compounds of Preferred (1) where $R_2$ is $CH_3S$, $C_3$–$C_6$ alkenyloxy, $C_3$–$C_6$ alkynyloxy, $C_3$–$C_6$ alkenylthio, $C_3$–$C_6$ alkenylsulfinyl, $C_3$–$C_6$ alkenylsulfonyl, $C_3$–$C_6$ alkynylthio, $C_3$–$C_6$ alkynylsulfinyl, $C_3$–$C_6$ alkynylsulfonyl, $C_2$–$C_6$ alkyl substituted with 1–3 atoms of F, Cl or Br, $CH_2F$, $CHF_2$, $C_1$–$C_4$ alkyl substituted in a nonbenzylic position with $C_1$–$C_2$ alkoxy, $C_1$–$C_2$ alkylthio, $C_1$–$C_2$ alkylsulfinyl or $C_1$–$C_2$ alkylsulfonyl, $OCH_2CH_2OCH_3$, $OCH_2CH_2SCH_3$, $OCH_2CH_2S(O)CH_3$, $OCH_2CH_2SO_2CH_3$, $OCF_2H$, $OCH_2CH_2F$, $OCH_2CHF_2$, $OCH_2CF_3$, $OCH_2CH_2Cl$, S-cyclohexyl, $SC_6H_5$ or $SCH_2C_6H_5$.

(3) Compounds of Preferred (2) wherein R is H;

(4) Compounds of Preferred (3) wherein $R_2$ is $CH_3S$, $C_3$–$C_4$ alkenyloxy, $C_3$–$C_4$ alkenylthio, $C_3$–$C_4$ alkenylsulfinyl, $C_3$–$C_4$ alkenylsulfonyl, $C_2$–$C_3$ alkyl substituted with 1–3 atoms of F or Cl, $CH_2F$, $CHF_2$, $OCHF_2$, $OCH_2CH_2F$, $OCH_2CF_3$ or $OCH_2CH_2Cl$.

(5) Compounds of Preferred (4) wherein
$R_1$ is $CH_3$ or $CH_2CH_3$;
X is $CH_3$, $OCH_3$ or Cl; and
Y is $CH_3$, $OCH_3$, $C_2H_5$ or $OC_2H_5$.

(6) Compounds of Preferred (5) wherein $R_2$ is allyloxy, allylthio, propargyloxy, propargylthio, $CH_2F$, $OCHF_2$, $OCH_2CH_2F$ or $CH_3S$.

(7) Compounds of Preferred (1) wherein $R_2$ is $C_2$–$C_6$ alkoxy, $C_2$–$C_8$ alkylthio, $C_2$–$C_8$ alkylsulfonyl, $C_1$–$C_8$ alkylsulfinyl, $CH(H, C_1$–$C_3$ alkyl)$OC_1$–$C_2$ alkyl, $CH(H, C_1$–$C_3$ alkyl)$SC_1$–$C_2$ alkyl, $CH(H, C_1$–$C_3$ alkyl)$S(O)C_1$–$C_2$ alkyl or $CH(H, C_1$–$C_3$ alkyl)$SO_2C_1$–$C_2$ alkyl.

(8) Compounds of Preferred (7) wherein R is H.

(9) Compounds of Preferred (8) wherein $R_2$ is $C_2$–$C_4$ alkoxy, $C_2$–$C_4$ alkylthio, $C_2$–$C_4$ alkylsulfonyl, $C_1$–$C_4$ alkylsulfinyl, $CH_2OC_1$–$C_2$ alkyl, $CH_2SC_1$–$C_2$ alkyl, $CH_2S(O)C_1$–$C_2$ alkyl or $CH_2SO_2C_1$–$C_2$ alkyl.

(10) Compounds of Preferred (9) wherein
$R_1$ is $CH_3$ or $C_2H_5$
X is $CH_3$, $OCH_3$ or Cl; and
Y is $CH_3$, $OCH_3$, $C_2H_5$ or $OC_2H_5$.

(11) Compounds of Preferred (10) wherein $R_2$ is $C_2$–$C_3$ alkoxy, $C_2$–$C_3$ alkylthio, $C_1$–$C_3$ alkylsulfinyl, $CH_2OCH_3$, $CH_2SCH_3$, $CH_2S(O)CH_3$ or $CH_2SO_2CH_3$.

(12) Compounds of Formula I wherein $R_2$ is $C_3$–$C_6$ cycloalkoxy, $C_4$–$C_6$ cycloalkylalkoxy, $OCF_2Cl$, $OCF_2Br$, $OCF_3$, $OCF_2CF_2H$, $OCF_2CHFCl$, $OCF_2CHFBr$, $OCF_2CF_3$, $OCH_2CH_2Br$, $OCH_2CCl_3$, $C_3$–$C_6$ haloalkoxy, vinyloxy, $C_2$–$C_6$ haloalkenyloxy, $C_3$–$C_6$ haloalkynyloxy, $OCH_2OCH_3$, $OCH_2OCH_2CH_3$, $OCH(CH_3)OCH_3$, $C_4$ alkoxyalkoxy, $C_2$–$C_4$ haloalkoxyalkoxy, $OCH_2SCH_3$, $OCH_2SCH_2CH_3$, $OCH(CH_3)SCH_3$, $C_4$ alkylthioalkoxy, $C_2$–$C_4$ haloalkylthioalkoxy, $OCH_2S(O)CH_3$, $OCH_2S(O)CH_2CH_3$, $OCH(CH_3)S(O)CH_3$, $C_4$ alkylsulfinylalkoxy, $C_2$–$C_4$ haloalkylsulfinylalkoxy, $OCH_2SO_2CH_3$, $OCH_2SO_2CH_2CH_3$, $OCH(CH_3)SO_2CH_3$, $C_4$ alkylsulfonylalkoxy, $C_2$–$C_4$ haloalkylsulfonylalkoxy, $C_2$–$C_4$ cyanoalkoxy, $OCH_2C(O)CH_3$, $OCH_2CH_2C(O)CH_3$, $C_2$–$C_4$ aminoalkoxy, $C_3$–$C_5$ cycloalkylthio, $C_4$–$C_6$ cycloalkylalkylthio, $SCF_2H$, $SCF_2Cl$, $SCF_2Br$, $SCF_3$, $C_2$–$C_8$ haloalkylthio, vinylthio, $C_2$–$C_6$ haloalkenylthio, $C_3$–$C_6$ haloalkynylthio, $C_2$–$C_4$ alkoxyalkylthio, $C_2$–$C_4$ haloalkoxyalkylthio, $C_2$–$C_4$ alkylthioalkylthio, $C_2$–$C_4$ haloalkylthioalkylthio, $C_2$–$C_4$ cyanoalkylthio, $SCH_2C(O)CH_3$, $SCH_2CH_2C(O)CH_3$, $C_2$–$C_4$ aminoalkylthio, $C_3$–$C_6$ cycloalkylsulfinyl, $C_4$–$C_6$ cycloalkylalkylsulfinyl, $C_1$–$C_8$ haloalkylsulfinyl, vinylsulfinyl, $C_2$–$C_6$ haloalkenylsulfinyl, $C_3$–$C_6$ haloalkynylsulfinyl, $C_2$–$C_4$ alkoxyalkylsulfinyl, $C_2$–$C_4$ haloalkoxyalkylsulfinyl, $C_2$–$C_4$ cyanoalkylsulfinyl, $S(O)CH_2C(O)CH_3$, $S(O)CH_2CH_2C(O)CH_3$, $C_2$–$C_4$ aminoalkylsulfinyl, $C_3$–$C_6$ cycloalkylsulfonyl, $C_4$–$C_6$ cycloalkylalkylsulfonyl, $C_1$–$C_8$ haloalkylsulfonyl, vinylsulfonyl, $C_2$–$C_6$ haloalkenylsulfonyl, $C_3$–$C_6$ haloalkynylsulfonyl, $C_2$–$C_4$ alkoxyalkylsulfonyl, $C_2$–$C_4$ haloalkoxysulfonyl, $C_2$–$C_4$ cyanoalkylsulfonyl, $SO_2CH_2C(O)CH_3$, $SO_2CH_2CH_2C(O)CH_3$, $C_2$-$C_4$ aminoalkylsulfonyl, $CH_2Cl$, $CHCl_2$, $CH_2Br$, $CHBr_2$, $C_2$-$C_6$ alkenyl, $C_2$-$C_6$ haloalkenyl, $C\equiv CH$, $C_2$-$C_6$ haloalkynyl, $OC(O)C_1$-$C_4$ alkyl, $CH_2C(O)NR_aR_b$, $NHCH_3$, $NR_bR_c$ or $C_1$-$C_4$ alkyl substituted with $C_3$-$C_4$ alkoxy, $C_3$-$C_4$ cycloalkoxy, cyclopropylmethoxy, $C_1$-$C_4$ haloalkoxy, $C_2$-$C_4$ alkenyloxy, $C_2$-$C_4$ haloalkenyloxy, $C_3$-$C_4$ alkynyloxy, $C_3$-$C_4$ haloalkynyloxy, $C_2$-$C_4$ alkoxyalkoxy, $C_2$-$C_4$ aminoalkoxy, $C_1$-$C_4$ alkylcarbonyloxy, $C_1$-$C_4$ haloalkylcarbonyloxy, $C_1$-$C_4$ carbamoyloxy, $C_1$-$C_4$ alkoxycarbonyloxy, OH, $OP(O)(OC_1$-$C_2$ alkyl$)_2$, $C_1$-$C_4$ alkylsulfonyloxy, $C_1$-$C_2$ haloalkylsulfonyloxy, $OSi(CH_3)_3$, $OSi(CH_3)_2C(CH_3)_3$, $C_3$-$C_4$ alkylthio, $C_3$-$C_4$ cycloalkylthio, cyclopropylmethylthio, $C_1$-$C_4$ haloalkylthio, $C_2$-$C_4$ alkenylthio, $C_2$-$C_4$ haloalkenylthio, $C_3$-$C_4$ alkynylthio, $C_3$-$C_4$ haloalkynylthio, $C_2$-$C_4$ alkoxyalkylthio, $C_2$-$C_4$ aminoalkylthio, SH, $SP(O)(OC_1$-$C_2$ alkyl$)_2$, $C_3$-$C_4$ alkylsulfinyl, $C_3$-$C_4$ cycloalkylsulfinyl, cyclopropylmethylsulfinyl, $C_1$-$C_4$ haloalkylsulfinyl, $C_2$-$C_4$ alkenylsulfinyl, $C_2$-$C_4$ haloalkenylsulfinyl, $C_3$-$C_4$ alkynylsulfinyl, $C_3$-$C_4$ haloalkynylsulfinyl, $C_2$-$C_4$ alkoxyalkylsulfinyl, $C_2$-$C_4$ aminoalkylsulfinyl, $C_3$-$C_4$ alkylsulfonyl, $C_3$-$C_4$ cycloalkylsulfonyl, cyclopropylmethylsulfonyl, $C_1$-$C_4$ haloalkylsulfonyl, $C_2$-$C_4$ alkenylsulfonyl, $C_2$-$C_4$ haloalkenylsulfonyl, $C_3$-$C_4$ alkynylsulfonyl, $C_3$-$C_4$ haloalkynylsulfonyl, $C_2$-$C_4$ alkoxyalkylsulfonyl or $C_2$-$C_4$ aminoalkylsulfonyl.

(13) Compounds of Preferred (12) wherein
$R_2$ is $C_3$-$C_6$ cycloalkoxy, $C_4$-$C_6$ cycloalkylalkoxy, $OCF_2Cl$, $OCF_2Br$, $OCF_3$, $OCF_2CF_2H$, $OCF_2CHFCl$, $OCF_2CHFBr$, $OCF_2CF_3$, $OCH_2CH_2Br$, $OCH_2CCl_3$, $C_3$-$C_6$ haloalkoxy, vinyloxy, $C_2$-$C_6$ haloalkenyloxy, $OCH_2OCH_3$, $OCH_2OCH_2CH_3$, $OCH(CH_3)OCH_3$, $C_4$ alkoxyalkoxy, $C_2$-$C_4$ haloalkoxyalkoxy, $OCH_2SCH_3$, $OCH_2SCH_2CH_3$, $OCH(CH_3)SCH_3$, $C_4$ alkylthioalkoxy, $C_2$-$C_4$ haloalkylthioalkoxy, $OCH_2S(O)CH_3$, $OCH_2S(O)CH_2CH_3$, $OCH(CH_3)S(O)CH_3$, $C_4$ alkylsulfinylalkoxy, $C_2$-$C_4$ haloalkylsulfinylalkoxy, $OCH_2SO_2CH_3$, $OCH_2SO_2CH_2CH_3$, $OCH(CH_3)SO_2CH_3$, $C_4$ alkylsulfonylalkoxy, $C_2$-$C_4$ haloalkylsulfonylalkoxy, $C_2$-$C_4$ cyanoalkoxy, $OCH_2C(O)CH_3$, $OCH_2CH_2C(O)CH_3$, $C_2$-$C_4$ aminoalkoxy, $C_3$-$C_5$ cycloalkylthio, $SCF_3$, $SCF_2Cl$, $SCF_2Br$, $C_4$-$C_6$ cycloalkylalkylthio, $SCF_2H$, $C_2$-$C_6$ haloalkylthio, vinylthio, $C_2$-$C_6$ haloalkenylthio, $C_2$-$C_4$ alkoxyalkylthio, $C_2$-$C_4$ haloalkoxyalkylthio, $C_2$-$C_4$ alkylthioalkylthio, $C_2$-$C_4$ haloalkylthioalkylthio, $C_2$-$C_4$ cyanoalkylthio, $SCH_2C(O)CH_3$, $SCH_2CH_2C(O)CH_3$, $C_2$-$C_4$ aminoalkylthio, $C_3$-$C_6$ cycloalkylsulfinyl, $C_4$-$C_6$ cycloalkylalkylsulfinyl, $C_1$-$C_6$ haloalkylsulfinyl, vinylsulfinyl, $C_2$-$C_6$ haloalkenylsulfinyl, $C_2$-$C_4$ alkoxyalkylsulfinyl, $C_2$-$C_4$ haloalkoxyalkylsulfinyl, $C_2$-$C_4$ cyanoalkylsulfinyl, $S(O)CH_2C(O)CH_3$, $S(O)CH_2CH_2C(O)CH_3$, $C_2$-$C_4$ aminoalkylsulfinyl, $C_3$-$C_6$ cycloalkylsulfonyl, $C_4$-$C_6$ cycloalkylalkylsulfonyl, $C_1$-$C_6$ haloalkylsulfonyl, vinylsulfonyl, $C_2$-$C_6$ haloalkenylsulfonyl, $C_2$-$C_4$ alkoxyalkylsulfonyl, $C_2$-$C_4$ haloalkoxyalkylsulfonyl, $C_2$-$C_4$ cyanoalkylsulfonyl, $SO_2CH_2C(O)CH_3$, $SO_2CH_2CH_2(O)CH_3$, $C_2$-$C_4$ aminoalkylsulfonyl, $CHBr_2$, $C_2$-$C_6$ alkenyl substituted by one or more fluorine or bromine atoms, $C\equiv CH$, $C_3$-$C_6$ haloalkynyl, $NR_bR_c$, CH(H, $C_1$-$C_3$ alkyl)$OC_1$-$C_4$ haloalkyl having 1 or 2 halogen atoms, CH(H, $C_1$-$C_3$ alkyl)$OC_2$-$C_4$ haloalkenyl, CH(H, $C_1$-$C_3$ alkyl)$OC_3$-$C_5$ alkynyl, CH(H, $C_1$-$C_3$ alkyl)$OC_2$-$C_4$ alkoxyalkyl, CH(H, $C_1$-$C_3$ alkyl)$SC_1$-$C_4$ haloalkyl having 1 or 2 halogen atoms, CH(H, $C_1$-$C_3$ alkyl)$SC_2$-$C_4$ haloalkenyl, CH(H,$C_1$-$C_3$ alkyl)$SC_3$-$C_4$ alkynyl, CH(H, $C_1$-$C_3$ alkyl)$SC_2$-$C_4$ alkoxyalkyl, CH(H, $C_1$-$C_3$ alkyl)$S(O)C_1$-$C_4$ haloalkyl having 1 or 2 halogen atoms, CH(H, $C_1$-$C_3$ alkyl)-$S(O)C_2$-$C_4$ haloalkenyl, CH(H, $C_1$-$C_3$ alkyl)-$S(O)C_3$-$C_4$ alkynyl, CH(H, $C_1$-$C_3$alkyl)$S(O)C_2$-$C_4$ alkoxyalkyl, CH(H, $C_1$-$C_3$ alkyl)$SO_2C_1$-$C_4$ haloalkyl having 1 or 2 halogen atoms, CH(H, $C_1$-$C_3$ alkyl)$SO_2C_2$-$C_4$ haloalkenyl, CH(H, $C_1$-$C_3$ alkyl)-$SO_2C_3$-$C_4$ *alkynyl*, CH(H, $C_1$-$C_3$ alkyl)$SO_2C_2$-$C_4$ alkoxyalkyl, or $C_1$-$C_4$ alkyl substituted in a nonbenzylic position with $C_3$-$C_4$ alkoxy, $C_1$-$C_4$ haloalkoxy, $C_1$-$C_4$ alkylcarbonyloxy, $C_1$-$C_4$ haloalkylcarbonyloxy, $C_1$-$C_4$ carbamoyloxy, alkoxycarbonyloxy, $C_1$-$C_4$ alkylsulfonyloxy, $C_1$-$C_2$ haloalkylsulfonyloxy, $C_3$-$C_4$ alkylthio, $C_1$-$C_4$ haloalkylthio, $C_3$-$C_4$ alkylsulfinyl or $C_3$-$C_4$ alkylsulfonyl; and $R_c$ is $C_2$-$C_4$ cyanoalkyl, $CH_2C(O)CH_3$, $CH_2CH_2C(O)CH_3$, $C_1$-$C_4$ haloalkyl, $C_3$-$C_4$ alkenyl, $C_3$-$C_4$ haloalkenyl, $C_3$-$C_4$ alkynyl or $C_3$-$C_4$ haloalkynyl;

(14) Compounds of Preferred (13) wherein R is H.
(15) Compounds of Preferred (14) wherein $R_2$ is $OCF_3$, $OCF_2CF_3$, $OCH_2CH_2Br$, $C_3$ haloalkoxy, $OCH_2CH_2OCH_2CH_3$, $SCF_2H$, $SCF_3$, $C_2$ haloalkylthio, $C_2$-$C_3$ alkoxyalkylthio, $C_1$-$C_2$ haloalkylsulfinyl, $C_1$-$C_2$ haloalkylsulfonyl, $C\equiv CH$, $CH_2OC_1$-$C_2$ haloalkyl having 1 or 2 halogen atoms, $CH_2SC_1$-$C_2$ haloalkyl having 1 or 2 halogen atoms, $CH_2S(O)C_1$-$C_2$ haloalkyl having 1 or 2 halogen atoms, or $CH_2SO_2C_1$-$C_2$ haloalkyl having 1 or 2 halogen atoms.
(16) Compounds of Preferred (15) wherein
$R_1$ is $CH_3$ or $CH_2CH_3$;
X is $CH_3$, $OCH_3$ or Cl; and
Y is $CH_3$, $OCH_3$, $C_2H_5$ or $OC_2H_5$.
(17) Compounds of Preferred (16) wherein $R_2$ is $OCF_2CF_3$, $SCF_2H$, $SCH_2CH_2OCH_3$, $S(O)CF_2H$, $SO_2CF_2H$, $C\equiv CH$, $CH_2OCH_2CH_2F$ or $CH_2OCH_2CHF_2$;
(18) Compounds of Preferred (12) wherein
$R_2$ is $C_3$-$C_6$ haloalkynyloxy, $C_7$-$C_8$ haloalkylthio, $C_3$-$C_6$ haloalkynylthio, $C_7$-$C_8$ haloalkylsulfinyl, $C_3$-$C_6$ haloalkynylsulfinyl, $C_7$-$C_8$ haloalkylsulfonyl, $C_3$-$C_6$ haloalkynylsulfonyl, $CH_2Cl$, $CHCl_2$, $CH_2Br$, $C_2$-$C_6$ alkenyl, $C_2$-$C_6$ alkenyl substituted with one or more chlorine atoms, $C_2$ haloalkynyl, $OC(O)C_1$-$C_4$ alkyl, $CH_2C(O)NR_aR_b$, $NHCH_3$, $NR_bR_c$, CH(H, $C_1$-$C_3$ alkyl)$OC_3$-$C_4$ alkyl, CH(H, $C_1$-$C_3$ alkyl)$OC_1$-$C_4$ haloalkyl having 3 or more halogen atoms, CH(H, $C_1$-$C_3$ alkyl)$OC(O)C_1$-$C_3$ alkyl, CH(H, $C_1$-$C_3$ alkyl)$OC(O)C_1$-$C_3$ haloalkyl, CH(H, $C_1$-$C_3$ alkyl)$OC_1$-$C_4$ carbamoyl, CH(H, $C_1$-$C_3$ alkyl-$OC(O)OC_1$-$C_3$ alkyl, CH(H, $C_1$-$C_3$ alkyl)$OSO_2C_1$-$C_4$ alkyl, CH(H, $C_1$-$C_3$ alkyl)$OSO_2C_1$-$C_2$ haloalkyl, CH(H, $C_1$-$C_3$ alkyl)$SC_3$-$C_4$ alkyl, CH(H, $C_1$-$C_3$ alkyl)$SC_1C_4$ haloalkyl having 3 or more halogen atoms, CH(H, $C_1$-$C_3$ alkyl)$S(O)C_3$-$C_4$ alkyl, CH(H, $C_1$-$C_3$ alkyl)$S(O)C_1$-$C_4$ haloalkyl having 3 or more halogen atoms, CH(H, $C_1$-$C_3$ alkyl)-$SO_2C_3$-$C_4$ alkyl, CH(H, $C_1$-$C_3$ alkyl)$SO_2C_1$-$C_4$ haloalkyl having 3 or more halogen atoms, $C_1$-$C_4$ alkyl substituted in a non-benzylic position by $C_2$-$C_4$ haloalkenyloxy, $C_3$-$C_4$ alkynyloxy, $C_2$-$C_4$ alkoxyalkoxy, $C_2$-$C_4$ haloalkenylthio, $C_3$-$C_4$ alkynylthio, $C_2$-$C_4$ alkoxyalkylthio, $C_1$-$C_4$ haloalkylsulfinyl, $C_2$-$C_4$ haloalkenylsulfinyl, $C_3$-$C_4$ alkynylsulfinyl, $C_2$-$C_4$ alkoxyalkylsulfinyl, $C_1$-$C_4$ haloalkylsulfonyl, $C_2$-$C_4$ haloalkenylsulfonyl, $C_3$-$C_4$ alkynylsulfonyl, or $C_2$-$C_4$ alkoxyalkylsulfonyl, or $C_1$-$C_4$ alkyl substituted by $C_3$-$C_4$ cycloalkoxy, cyclopropylmethoxy, $C_2$-$C_4$ alkenyloxy, $C_3$-$C_4$ haloalkynyloxy, $C_2$-$C_4$ aminoalkoxy, OH, $OP(O)(OC_1$-$C_2$ alkyl$)_2$, $OSi(CH_3)_3$, $OSi(CH_3)_2C(CH_3)_3$, cycloalkylthio, cyclopropylmethylthio, $C_2$-$C_4$ alkenylthio, $C_3$-$C_4$ haloalkynylthio, $C_2$-$C_4$ aminoalkylthio, SH, $SP(O)(OC_1$-$C_2$ alkyl$)_2$, $C_3$-$C_4$ cycloalkylsulfinyl, cyclopropylmethylsulfinyl, $C_2$-$C_4$ alkenylsulfinyl, $C_3$-$C_4$ haloalkynylsulfinyl, $C_2$-$C_4$ aminoalkylsulfinyl, $C_3$-$C_4$ cycloalkylsulfonyl, cyclopropylmethylsulfonyl, $C_2$-$C_4$ alkenylsulfonyl, $C_3$-$C_4$ haloalkynylsulfonyl, or $C_2$-$C_4$ aminoalkylsulfonyl; and $R_c$ is $C_2$-$C_4$ alkyl, cyclopropylmethyl, or $C_1$-$C_4$ alkyl substituted with $C_1$-$C_4$ alkoxy, $C_1$-$C_4$ alkylthio, $C_1$-$C_4$ alkylsulfinyl, $C_1$-$C_4$ alkylsulfonyl, OH, $NH_2$, $NHCH_3$ or $N(CH_3)_2$.

(19) Compounds of Preferred (18) wherein R is H.

(20) Compounds of Preferred (19) wherein $R_2$ is $OCF_2CF_2H$, $C_2$-$C_3$ cyanoalkoxy, $C_2$-$C_3$ aminoalkoxy, $C_2$-$C_4$ cyanoalkylthio, $C_2$-$C_3$ alkenyl, $CH_2C(O)NR_aR_b$, $NHCH_3$, $NR_bR_c$, $CH_2OC_1$-$C_2$ haloalkyl having 3 or more halogen atoms, $CH_2OC(O)C_1$-$C_2$ alkyl, $CH_2OSO_2C_1$-$C_2$ alkyl, $CH_2SC_1$-$C_2$ haloalkyl having 3 or more halogen atoms, $CH_2S(O)C_1$-$C_2$ haloalkyl having 3 or more halogen atoms or $CH_2SO_2C_1$-$C_2$ haloalkyl having 3 or more halogen atoms.

(21) Compounds of Preferred (20) wherein
$R_1$ is $CH_3$ or $C_2H_5$;
X is $CH_3$, $OCH_3$ or Cl; and
Y is $CH_3$, $OCH_3$, $C_2H_5$ or $OC_2H_5$.

(22) Compounds of Preferred (21) wherein $R_2$ is $OCF_2CF_2H$, $OCH_2CH_2CN$, $SCH_2CH_2CN$, $CH=CH_2$, $CH_2C(O)NH_2$, $NHCH_3$, $CH_2OCH_2CF_3$, $CH_2OC(O)CH_3$ or $CH_2OSO_2CH_3$.

A compound of the invention which is specifically preferred for its highest herbicidal activity, greatest plant growth regulant activity and/or most favorable ease of synthesis is:

2-[[(4,6-dimethoxypyrimidin-2-yl)aminocarbonyl]aminoaminosulfonyl]-4-(methylthio)benzoic acid, methyl ester, m.p. 201°-202° C.

DETAILED DESCRIPTION OF THE INVENTION

Synthesis

The compounds of Formula I can be prepared by one or more of the following methods described in Equations 1 to 3 and 14.

As shown in Equation 1, compounds of Formula I can be prepared by reacting an appropriately substituted sulfonyl isocyanate of Formula (1) with an appropriate amino or methylamino heterocycle of Formula (2).

A is

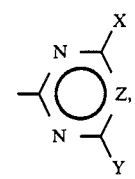

and R, $R_1$, $R_2$, X, Y and Z are as previously defined.

Equation 1

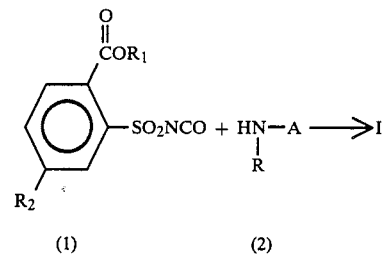

The reaction is best carried out in inert aprotic organic solvents such as dichloromethane, 1,2-dichloroethane, tetrahydrofuran, or acetonitrile, at a temperature between 20° and 85° C. The order of addition is not critical; however, it is often convenient to add the sulfonyl isocyanate or a solution of it in the reaction solvent to a stirred suspension of the amine.

In some cases, the desired product is insoluble in the reaction solvent at ambient temperature and crystallizes from it in pure form. Products soluble in the reaction solvent are isolated by evaporation of the solvent. Compounds of Formula I then may be purified by trituration of the evaporation residue with solvents such as 1-chlorobutane or ethyl ether and filtration, by recrystallization from mixtures of solvents such as 1,2-dichloroethane, 1-chlorobutane, and heptane, or by chromatography on silica gel.

Many of the compounds of Formula I can be prepared by the procedure shown in Equation 2, where A, R, $R_1$, and $R_2$ are as previously defined.

Equation 2

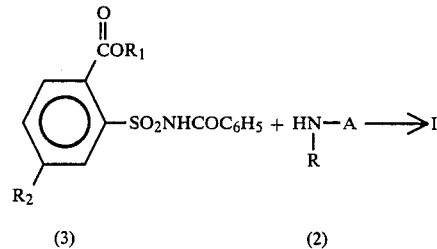

The reaction shown in Equation 2 is carried out by contacting phenyl carbamates of Formula (3) with aminoheterocycles of Formula (2) in an inert organic solvent such as dioxane or tetrahydrofuran at temperatures of about 20°-100° C. for a period of about one-half to twenty-four hours. The product can be isolated by evaporation of the reaction solvent and purified by methods previously described.

Phenyl carbamates of Formula (3) can be prepared by the methods described, or modifications thereof known to those skilled in the art, in European Patent Application No. 81810282.4 (Publication No. 44,808), published Jan. 27, 1982; or South African Patent Application No. 825042.

Alternatively, many of the compounds of Formula I can be prepared by the method described in Equation 3, where A, $R_1$, and $R_2$ are as previously defined and R is H.

Equation 3

(4) + $C_6H_5OCNRA$ $\xrightarrow{(1) DBU}{(2) H^+}$ (4)   (5, R = H)

I, R = H

The reaction of Equation 3 can be carried out by contacting equimolar amounts of a sulfonamide of Formula (4) with a heterocyclic phenyl carbamate of Formula (5) in the presence of an equimolar amount of 1,8-diazabicyclo-[5.4.0]undec-7-ene (DBU), by methods analogous to those described in South African Patent Application No. 830441. The phenyl carbamate of Formula (5) can be prepared by methods, or modifications thereof known to those skilled in the art, described in South African Patent Application No. 825671 and South African Patent Application No. 825045.

Some of the compounds of Formula I may be prepared from compounds of Formula I where $R_2$ is OH, $NR_bH$ or SH. See Equation 14 for a discussion of this method.

The unsubstituted and substituted alkoxy, alkenyloxy, and alkynyloxy benzenesulfonamide intermediates of Formula (4a) can be prepared by one or more of the following general methods.

As shown in Equation 4, one highly useful general route starts from the phenol (6).

Equation 4

(6) $\xrightarrow{R_3X_1 (7)}{Base}$ (8)   (a)

-continued
Equation 4

(8) $\xrightarrow{M_1OH (9)}$ (10)   (b)

(10) $\xrightarrow[\text{or}]{\text{1. p-TsCl/pyridine}}_{\text{HCl/R}_1\text{OH (11)} \Delta}^{\text{2. R}_1\text{OH (11)}}$ (12)   (c)

(12) $\xrightarrow[\text{or}]{\text{Fe, HOAc}}_{\text{H}_2, \text{PtS}_2-\text{C}}$ (13)   (d)

(13) $\xrightarrow{\text{1. [HONO]/H}_2\text{O}}_{\text{2. CuCl}_2, \text{SO}_2/\text{HOAc}-\text{CH}_2\text{Cl}_2}$ (14)   (e)

(14) $\xrightarrow{NH_3}$ (4a)

where $R_1$ is as previously defined, and $R_3$ is $C_2$–$C_6$ alkyl, $C_3$–$C_6$ cycloalkyl, $C_4$–$C_6$ cycloalkylalkyl, $C_1$–$C_6$ haloalkyl, $C_3$–$C_6$ alkenyl, $C_3$–$C_6$ haloalkenyl, $C_3$–$C_6$ haloalkynyl, $C_3$–$C_6$ alkynyl, $C_2$–$C_4$ alkoxyalkyl, $C_2$–$C_4$ haloalkoxyalkyl, $C_2$–$C_4$ alkylthioalkyl, $C_2$–$C_4$ haloalkylthioalkyl, $CH_2C(O)CH_3$, $CH_2CH_2C(O)CH_3$, or benzyl. $M_1$ is Na or K. $X_1$ is Cl, Br, I, $OSCH_3$, $OS$-⟨⟩-$CH_3$, $OSOR_3$, or -continued

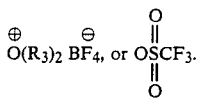

A solution or suspension of 4-hydroxy-2-nitrobenzoic acid (6) in a suitable polar aprotic solvent, such as dichloromethane or N,N-dimethylformamide (DMF), is treated with at least two equivalents of $R_3X_1$ (7) in the presence of at least two equivalents of a suitable base such as N,N-diisopropylethylamine or potassium carbonate and at a temperature between 20° and 155° C. for four to sixteen hours (Equation 4a). If the solvent is miscible with water, it is then evaporated, and the residue is taken up in dichloromethane. The product solution is washed with aqueous sodium or potassium carbonate solution and aqueous hydrochloric acid, and then is dried over a suitable desiccant such as magnesium sulfate. Filtration and evaporation of the solvent leaves (8) in semipurified form. It may be further purified through recrystallization or chromatography on a column of silica gel. The requisite alkylating, alkenylating, and alkynylating agents $R_3X_1$ (7) are either known or may be made by a wide variety of methods known in the art.

In cases where $R_3$ is not the same as $R_1$, the ester (8) is treated with at least one equivalent of sodium or potassium hydroxide in a mixture of water and a suitable organic cosolvent such as ethanol or p-dioxane at a temperature between 20° and 100° C. for four to sixteen hours (Equation 4b). The reaction mixture is then acidified with concentrated hydrochloric acid. If the product separates out in crystalline form, it is collected. Otherwise the aqueous solution is extracted with ether. The ether solution is dried over sodium sulfate and filtered, and the solvent is evaporated to afford the carboxylic acid (10).

To convert carboxylic acid (10) to ester (12), a solution of it in pyridine is treated sequentially with p-toluenesulfonyl chloride and $R_1OH$ (11) according to the general procedure of J. H. Brewster and C. J. Ciotti, Jr., *J. Am. Chem. Soc.* 1955, 77, 6214.

Alternatively, the carboxylic acid (10) may be converted to ester (12) through the use of excess $R_1OH$ (11) and a strong acid catalyst such as hydrogen chloride as reviewed by C. A. Buehler and D. E. Pearson, *Survey of Organic Syntheses*, Wiley-Interscience, New York, 1970, pp 802–807 (Equation 4c).

The nitrobenzene (12) is reduced to the aniline (13) either by use of iron in acetic acid as reviewed by C. A. Buehler and D. E. Pearson (ibid, pp. 413–414) or by hydrogenation using platinum sulfide as catalyst and the conditions of F. S. Dovel and H. Greenfield, *J. Am. Chem. Soc.*, 87, 2767 (1965) (Equation 4d). When the other substituents present are not potentially susceptible to hydrogenation or hydrogenolysis, palladium may replace platinum sulfide as catalyst.

The aniline (13) is converted to the sulfonyl chloride (14) using the general procedures of H. Meerwein, G. Dittmar, R. Gollner, K. Hafner, F. Mensch, O. Steinfort, *Chem. Ber.*, 90, 841 (1957) (Equation 4e). To limit the hydrolysis of the product during the coupling step, the use of dichloromethane as a cosolvent is advantageous.

Finally, the sulfonyl chloride (14) is animated to give (4a) using two equivalents of ammonia in dichloromethane solution at a temperature between −30° and −10° C. (Equation 4f).

Alternatively, many of the sulfonamides of Formulae (4a) or (4c') can be prepared via the route shown in Equation 5.

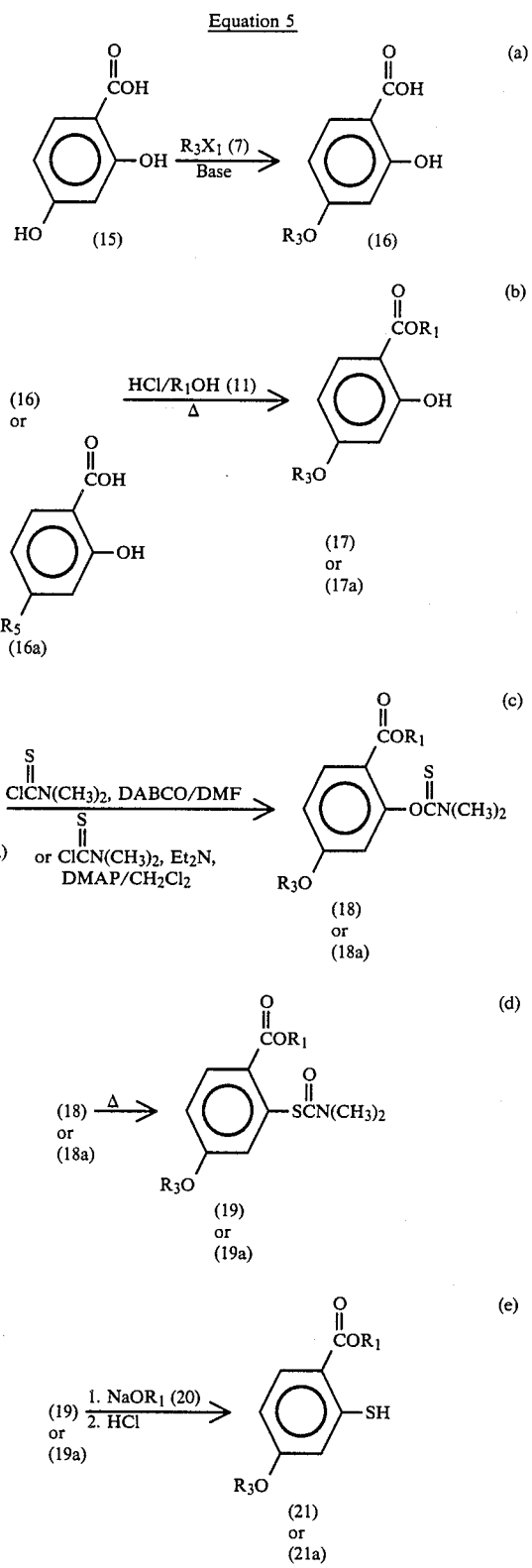

-continued

Equation 5

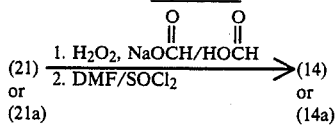  (f)

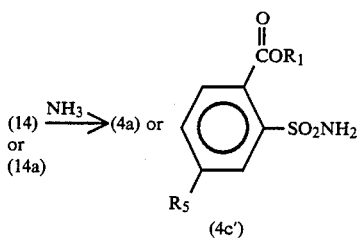  (g)

where $M_1$, $R_1$, $R_a$, $R_b$, and $X_1$ are as previously defined; $R_5$ is $C_1$-$C_6$ alkyl, $C_1$-$C_6$ haloalkyl or $CH_2C(O)NR_aR_b$; and $R_3$ is as previously defined or $C_2$-$C_4$ aminoalkyl but not $C_2$-$C_6$ alkenyl, $C_2$-$C_6$ haloalkenyl, $C_3$-$C_6$ alkynyl or $C_3$-$C_6$ haloalkynyl.

Phenol (15) is added to a solution of two equivalents of sodium in anhydrous methanol, ethanol, or amyl alcohol. A little more than one equivalent of $R_3X_1$ (7) is added and the mixture is heated at reflux for 4 to 24 hours. The solvent is removed in vacuo and the residue is partitioned between 1N hydrochloric acid and ether. The ether phase is dried over sodium sulfate, and filtered. Evaporation of the ether leaves the phenol (16) (Equation 5a).

In Equations 5b, c, d, e and f compounds 17a, 18a, 19a, 21a and 14a have the same structure as 17, 18, 19, 21, and 14 respectively except that the $OR_3$ substituent is replaced by $R_5$.

The carboxylic acid (16/16a) is converted to ester (17/17a) through the use of excess $R_1OH$ and a strong acid catalyst such as hydrogen chloride as reviewed by C. A. Buehler and D. E. Pearson (op.cit., pp 802-807) (Equation 5b).

The phenol (17/17a) is converted to the thiocarbamate (18/18a) through the use of dimethylthiocarbamoyl chloride and 1,4-diazabicyclo[2.2.2]octane (DABCO) in N,N-dimethylformamide according to the general procedure of M. S. Newman and H. A. Karnes, J. Org. Chem. 1966, 31, 3980 (Equation 5c). Alternatively a mixture of the phenol (17/17a), at least one equivalent of dimethylthiocarbamoyl chloride, at least one equivalent of triethylamine ($Et_3N$), and a catalytic amount of 4-dimethylaminopyridine (DMAP) in dichloromethane is heated at reflux for one to seven days. The reaction mixture is washed with 1N hydrochloric acid and 10% aqueous sodium hydroxide solution, then dried over magnesium sulfate and filtered. Evaporation of the solvent leaves crude (18/18a) which may be purified by chromatography on silica gel or by recrystallization if it is crystalline.

The thiocarbamate (18/18a) is converted to its isomer (19/19a) by heating according to the general procedure of M. S. Newman and H. A. Karnes (op.cit.) (Equation 5d).

To a solution of (19/19a) in anhydrous $R_1OH$ (11) is added little more than one equivalent of $NaOR_1$ (20). The mixture is heated at 60°-70° C. for 0.5-1 hour. The solvent is removed in vacuo, and the residue is partitioned between dichloromethane and water. The aqueous phase is washed with dichloromethane, acidified with 12N hydrochloric acid, and extracted with dichloromethane. The dichloromethane extracts are dried over sodium sulfate and filtered. Evaporation of the solvent leaves thiol (21/21a) (Equation 5e).

To a mixture of the thiol (21/21a) and at least one equivalent of sodium formate in formic acid is added at least three equivalents of hydrogen peroxide at such a rate as to keep the temperature between 40° and 50° C. The reaction mixture is then heated at 45°-55° C. for 1 to 5 hours. The excess peroxide is destroyed with sodium sulfite, and the solvent is evaporated. The residue is added to excess thionyl chloride, and a catalytic amount of N,N-dimethylformamide (DMF) is added. The mixture is heated at reflux for 8 to 24 hours, and then the solvent is evaporated. The residue is partitioned between water and ether. The ether solution is washed with aqueous sodium bicarbonate solution, dried over magnesium sulfate and filtered. Evaporation of the solvent leaves the sulfonyl chloride (14/14a) (Equation 5f).

Finally the sulfonyl chloride (14) is aminated giving the sulfonamide (4a) and likewise (14a) gives (4c') as already described for Equation 4f (Equation 5g).

Most of the sulfonamides (4a) can be prepared via the route shown in Equation 6 starting from 6-hydroxysaccharin (22).

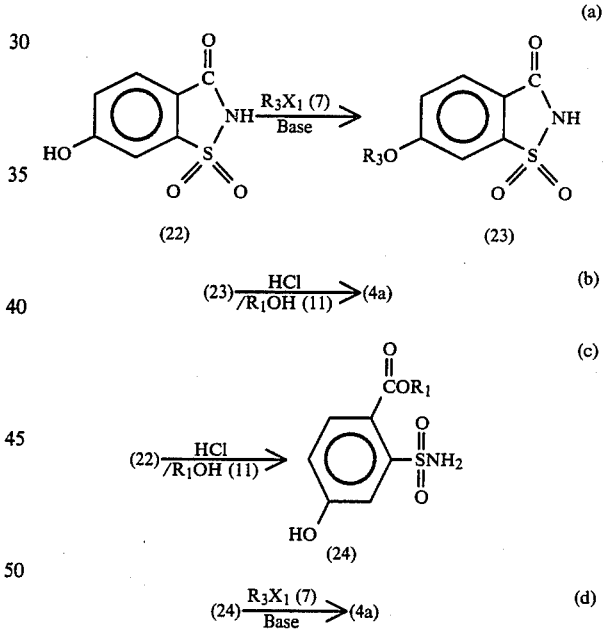

where $R_1$ and $X_1$ are as previously defined and $R_3$ is as defined for Equation 4 or $C_2$-$C_4$ cyanoalkyl.

6-Hydroxysaccharin (22) can be prepared as described by C. Finzi and M. Colonna. Atti. accad. Lincei, Classe, sci. fis., mat. mat., 1937, 26, 19 (Chem. Abst. 1938, 32, 3762). Alternatively, (4a), where $R_1=CH_3$, $R_3=C_6H_5CH_2$ may be prepared via the route described by Equation 5. A solution of this sulfonamide in dichloromethane is treated with one equivalent of 1,8-diazabicyclo[5.4.0]undec-7-ene (DBU). The solvent is evaporated, and the residue is dissolved in minimal water and acidified with concentrated hydrochloric acid to precipitate 6-benzyloxysaccharin. This is dissolved in ethanol containing palladium catalyst. The mixture is hydrogenated at 20°-40° C. and 1-10 psi until hydrogen uptake ceases. Filtration and evaporation of the solvent affords 6-hydroxysaccharin (22).

In the method described by Equation 6a, 6-hydroxysaccharin (22) is added to a solution of two equivalents sodium in anhydrous methanol, ethanol, or amyl alcohol. A little more than one equivalent of $R_3X_1$ (7) is added and the mixture is heated at reflux for 4 to 24 hours. The solvent is removed in vacuo and the residue is dissolved in minimal water. It is acidified with concentrated hydrochloric acid. If the product crystallizes, it is collected, washed with dilute hydrochloric acid, and dried. If it does not crystallize, the aqueous mixture is extracted with dichloromethane. The dichloromethane phase is dried over sodium sulfate and filtered. Evaporation of the solvent leaves the saccharin (23) (Equation 6a).

A solution or suspension of the saccharin (23) in $R_1OH$ (11) is saturated with hydrogen chloride. The mixture is heated at 65°–80° C. for 1–6 hours. The solvent and hydrogen chloride are evaporated. The residue is dissolved in dichloromethane, washed with aqueous sodium bicarbonate solution, dried over sodium sulfate, and filtered. Evaporation of the solvent affords the sulfonamide (4a) (Equation 6b).

Alternatively, saccharin (22) may be opened to the sulfonamide (24) using the conditions already described for the conversion of (23) to (4a) in Euqation 6b (Equation 6c). To a solution of the sulfonamide (24) in anhydrous methanol, ethanol, amyl alcohol, or a suitable aprotic solvent such as N,N-dimethylformamide is added one equivalent of sodium or potassium methoxide, ethoxide, or tert-butoxide followed by the alkylating agent $R_3X_1$ (7). The mixture is held at 20°–80° C. for 1–8 hours. The solvent is removed in vacuo, and the residue is dissolved in dichloromethane, washed with aqueous sodium bicarbonate solution, dried over $Na_2SO_4$, and filtered. Evaporation of the solvent affords the sulfonamide (4a) (Equation 6d).

Many sulfonamides of Formulae (4a), (4b) and (4e) can be prepared by the methods shown in Equation 7.

Equation 7

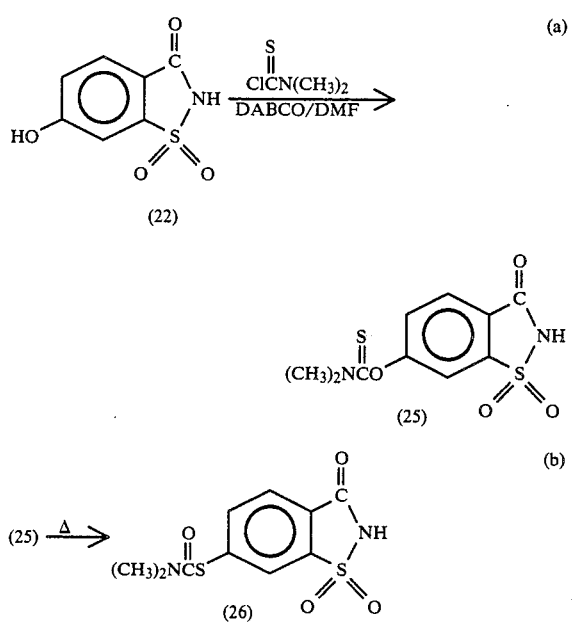

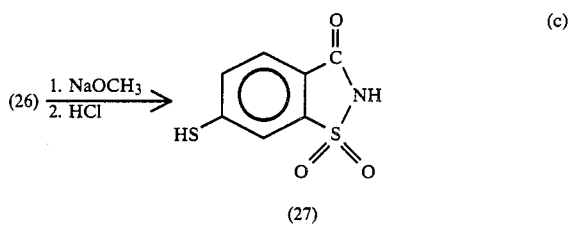

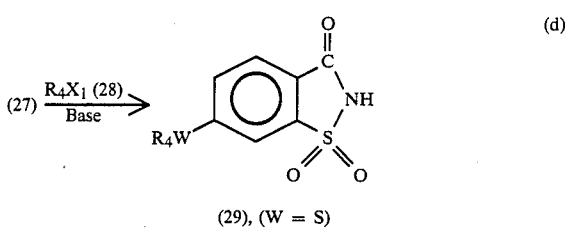

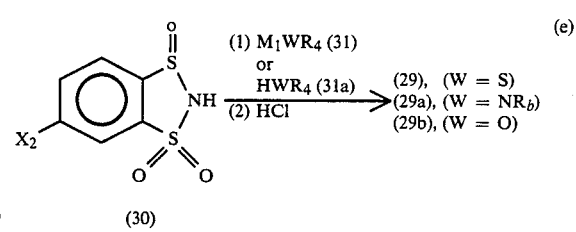

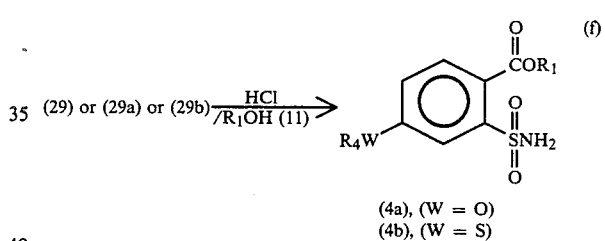

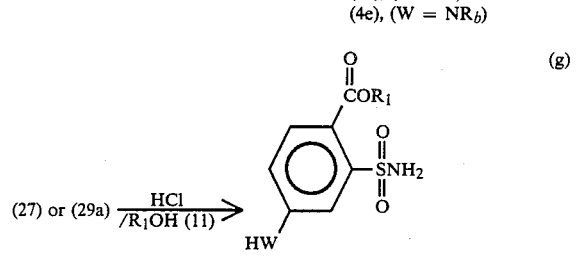

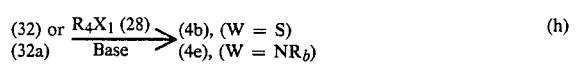

where $M_1$, $R_1$ and $X_1$ are as previously defined, $X_2$ is F, Cl, Br or I, W is O, S, or $NR_b$; $R_b$ is as previously defined; and $R_4$ is $R_3$ as defined for Equation 6 or H, $CH_3$, cyclohexyl, or phenyl.

The hydroxysaccharin (22) is converted to the thiocarbamate (25) through the use of dimethylthiocarbamoyl chloride and 1,4-diazabicyclo[2.2.2]octane (DABCO) in N,N-dimethylformamide according to the general procedure, or modifications thereof known to those skilled in the art, of M. S. Newman and H. A. Karnes (op.cit.) (Equation 7a).

The thiocarbamate (25) is converted to its isomer (26) by heating according to the general procedure, or modifications thereof known to those skilled in the art, of M. S. Newman and H. A. Karnes (ibid.) (Equation 7b).

To a solution of (26) in anhydrous methanol is added a little more than two equivalents of sodium methoxide. The mixture is heated at 60°–70° C. for 0.5–1 hour. The solvent is removed in vacuo, and the residue is partitioned between dichloromethane and water. The aqueous phase is washed with dichloromethane and acidified with concentrated hydrochloric acid. If the saccharin (27) crystallizes, it is collected, rinsed with dilute cold hydrochloric acid, and dried. If it does not crystallize, the aqueous phase is extracted with dichloromethane. The dichloromethane extracts are dried over sodium sulfate and filtered. Evaporation of the solvent leaves saccharin (27) (Equation 7c).

The mercaptan (27) is added to a solution of two equivalents sodium in anhydrous methanol, ethanol, or amyl alcohol. A little more than one equivalent of $R_4X_1$ (28) is added, and the mixture is heated at reflux for 1 to 8 hours. The requisite alkylating, alkenylating, and alkynylating agents $R_4X_1$ (28) are either known in the art or may be made by a wide variety of methods known in the art.

The solvent is removed in vacuo, and the residue is dissolved in minimal water. It is acidified with concentrated hydrochloric acid. If the saccharin (29) crystallizes, it is controlled, washed with cold dilute hydrochloric acid, and dried. If it does not crystallize, the aqueous mixture is extracted with dichloromethane. The dichloromethane phase is dried over sodium sulfate and filtered. Evaporation of the solvent leaves the saccharin (29) (Equation 7d).

Alternatively, in many cases, the saccharins of Formula (29) or (29b) may be prepared by treating a halosaccharin (30) in a polar aprotic solvent such as N-N-dimethylformamide at 20°–100° C. with at least two equivalents of the corresponding thiolate or alkoxide of Formula (31) for 4–24 hours. The reaction is worked up by evaporation of the solvent. The residue is dissolved in minimal water and acidified with concentrated hydrochloric acid. If the saccharin (29/29b) crystallizes, it is filtered. Otherwise the aqueous solution is extracted with dichloromethane, and evaporation of the solvent leaves the saccharin (29/29b) (Equation 7e).

Many 5-aminosaccharins (29a) can be prepared by heating the halosaccharin (30) in N,N-dimethylformamide under pressure at 125°–190° C. in the presence of amines for 8–16 hours. The reaction is worked up as described in the preceeding paragraph.

In addition, aminosaccharins (29a) wherein $R_4$ is H can be alkylated in the same fashion as described previously for alkoxy and mercapto saccharins in Equations (6a) and (7d). The conversion of aminosaccharins (29a) into aminosulfonamides (4e) or (32a) can be effected using conditions described previously in Equations (6b and c) (Equation 7f).

The requisite precursor halosaccharins of Formula (30) may be prepared by conversion of the corresponding 4-halo-2-nitrobenzoic acids to esters of 2-(aminosulfonyl)-4-halobenzoic acids by use of methods analogous to those described for Equation 4. These esters are closed to the corresponding saccharins of Formula (30) by treatment with DBU according to the general method already described for the preparation of 6-benzyloxysaccharin.

Saccharins (29/29b) are similarly opened to the corresponding sulfonamides (4b/4a) using the conditions already described for the conversion of (23) to (4a) in Equation 6b (Equation 7f).

Alternatively, saccharin (27/29a) may be opened to the sulfonamide (32/32a) using the conditions already described for the conversion of (23) to (4a) in Equation 6b (Equation 7g). The thiol (32) or aniline (32a) is then converted to (4b/4e) using the method already described for the conversion of (24) to (4a) in Equation 6d (Equation 7h).

Most sulfonamides of Formula (4b) ($R_1$ and $R_4$ as previously defined) can also be prepared by synthetic routes analogous to that described for $R_1=R_4=CH_3$ in Examples 9 through 16.

Sulfonamides of Formula (4c) can be prepared by the method shown in Equation 8.

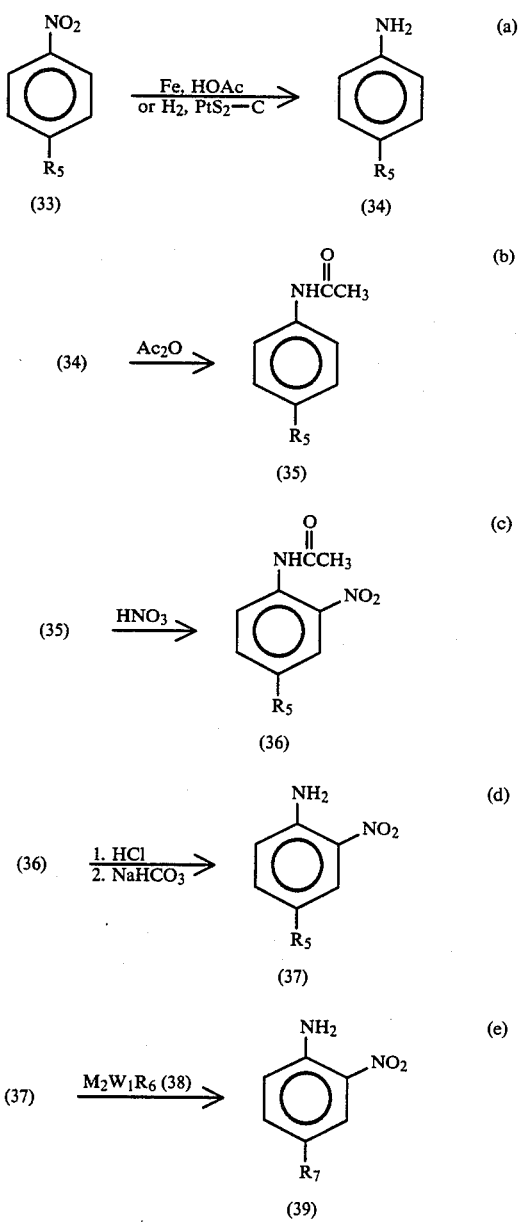

Equation 8

-continued
Equation 8

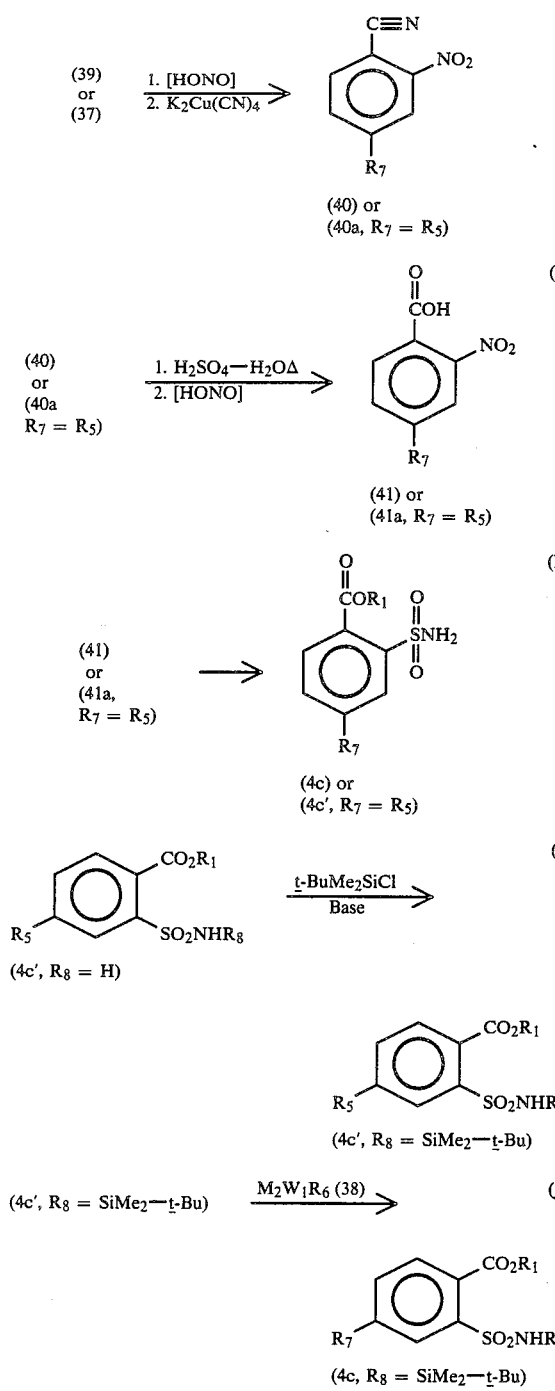

where $R_1$ is as previously defined; $R_5$ is alkyl, haloalkyl, alkenyl, haloalkenyl, alkynyl, haloalkynyl or $CH_2C(O)NR_aR_b$; $R_a$ and $R_b$ are as previously defined; $W_1$ is O or S; $M_2$ is Na or K; $R_6$ is H, $C_1$-$C_4$ alkyl, $C_1$-$C_4$ haloalkyl, $C_3$-$C_4$ cycloalkyl, cyclopropylmethyl, $C_3$-$C_4$ alkenyl, $C_3$-$C_4$ haloalkenyl, $C_3$-$C_4$ alkynyl, $C_3$-$C_4$ haloalkynyl, $C_2$-$C_4$ alkoxyalkyl, or $C_2$-$C_4$ aminoalkyl; and $R_7$ is $C_1$-$C_4$ alkyl substituted with $W_1R_6$.

The starting nitrobenzenes (33) are either known in the art or may be made by a wide variety of methods known in the art. Some of these methods include the nitration (for a review, see G. Lehmann, H. Eichmann "Formation of Carbon-Nitrogen Bonds" in *Preparative Organic Chemistry*, G. Hilgetag, A. Martini ed., Wiley-Interscience, New York, 1972) of the coupling product obtained from reaction of the appropriate halide with diphenylcuprate (for a review, see G. H. Posner "Substitution Reactions Using Organo-copper Reagents" in *Organic Reactions*, Vol. 22, W. G. Dauben ed., Wiley, New York, 1975).

Another method is the Friedel-Crafts acylation of benzene with the appropriate acid halide or anhydride (for a review, see G. A. Olah, *Friedel-Crafts and Related Reactions*, Volumes I-IV, Wiley-Interscience, New York, 1963-1965), followed by reductive removal of the carbonyl oxidation (for a review, see C. Bischoff, P.-G. Dietrich. E. Höft, D. Murowski, "Formation of Carbon-Hydrogen Bonds" in *Preparative Organic Chemistry*, G. Hilgetag, A. Martini ed., Wiley-Interscience, New York, 1972) and then nitration.

Still another method involves conversion of the appropriate 4-nitrobenzyl alcohols, aldehydes, or ketones to their mono or difluoro alkyl homologues using the conditions reviewed by G. A. Boswell, Jr., W. C. Ripka, R. M. Scribner, C. W. Tullock, "Fluorination by Sulfur Tetrafluoride" and C. M. Sharts, W. A. Sheppard "Modern Methods to Prepare Monofluoroaliphatic Compounds" in *Organic Reactions*, Vol. 21, W. G. Dauben ed., Wiley, New York, 1974).

The nitrobenzene (33) is reduced to the aniline (34) using the conditions already described for the conversion of (12) to (13) in Equation 4d (Equation 8a).

The aniline (34) in a suitable solvent such as benzene is treated with at least one equivalent of acetic anhydride and heated at reflux for 8-24 hours. The reaction mixture is cooled, and if the acetanilide (35) crystallizes, it is collected and dried. If it does not crystallize, the benzene solution is washed with 1N hydrochloric acid and aqueous sodium bicarbonate solution, dried over magnesium sulfate, and filtered. Evaporation of the solvent leaves the acetanilide (35) (Equation 8b).

The acetanilide (35) is then nitrated using the general conditions reviewed by G. Lehmann and H. Teichmann (op.cit.) to give nitroacetanilide (36) (Equation 8c).

A slurry of acetanilide (36) in 1N hydrochloric acid is heated at reflux until all of the solid dissolves. The solution is then made slightly basic with sodium bicarbonate and is extracted with dichloromethane. The dichloromethane extracts are dried over sodium sulfate and filtered. Evaporation of the solvent leaves the aniline (37) (Equation 8d).

Many of the substituents described within $R_7$ are prepared from aniline (37) having an $R_5$ substituent containing a displaceable halogen atom at the position where the substituent $W_1R_6$ is to be placed. Thus the halide (37) in a suitable solvent such as N,N-dimethylformamide is treated with a little more than one equivalent of the appropriate sodium or potassium salt (38).

The mixture is held at 20°-100° C. for 1-8 hours. The solvent is then evaporated, and the residue is partitioned between water and dichloromethane. The dichloromethane solution is dried over sodium sulfate and filtered. Evaporation leaves the desired compound (39) (Equation 8e).

The aniline (39/37) is then diazotized and subjected to the Sandmeyer reaction according to the general experimental procedure of G. T. Morgan and E. A.

Coulson, J. Chem. Soc. 1929, 2551 to give nitrile (40/40a) (Equation 8f).

A suspension of the nitrile (40/40a) in 75–80% aqueous sulfuric acid is heated at 95°–100° C. for 2–5 hours. Then over 1–2 hours and at a temperature of 80°–100° C. 1.5–2.5 equivalents of sodium nitrite is added in small portions. The heating is continued 0.5–1 hour longer, then the mixture is cooled and poured onto excess ice. If the carboxylic acid (41/41a) crystallizes, it is collected, rinsed with ice water and dried. If it does not crystallize, the aqueous mixture is extracted with dichloromethane. The dichloromethane solution is extracted with aqueous 10% sodium carbonate solution. The aqueous extract is made acidic with concentrated hydrochloric acid. If the carboxylic acid (41/41a) then crystallizes, it is collected, rinsed with ice water and dried. If it does not crystallize, the aqueous solution is extracted with ether. The ether extracts are dried over magnesium sulfate and filtered. Evaporation of the solvent leaves carboxylic acid (41/41a) (Equation 8g).

By use of the methods previously described, carboxylic acid (41) can be converted to sulfonamide (4c) and likewise (41a) give (4c′) (Equation 8h).

In the case where $R_7$ substituents of sulfonamide (4c) are incompatible with the strongly acidic conditions described in Equation 8g, an alternative scheme is used.

Sulfonamide of Formula (4c′) wherein $R_5$ is $C_1$–$C_4$ alkyl substituted with Cl, Br or I in a suitable solvent such as acetonitrile is treated with one equivalent of tert-butyldimethylsilyl chloride in the presence of a mild base such as pyridine at 15°–25° C. for 1–8 hours. When the reaction is judged complete by thin layer chromatography the mixture is poured onto ice water. If the silylsulfonamide crystallizes, it is collected, rinsed with water and dried. If not, the aqueous solution is extracted with ether. The ether extracts are dried and concentrated to furnish the silylsulfonamide of (4c′) (Equation 8i).

A stirred solution of the silylsulfonamide of (4c′) in a solvent such as DMF is treated at 0°–80° C. with at least one equivalent of (38) for 1–8 hours. When the reaction is judged complete by thin layer chromatography the mixture is poured onto ice water and the reaction is worked up as described in the previous paragraph (Equation 8j).

The silylsulfonamide of (4c) can then be converted directly into sulfonylurea (I) using the same conditions described in Equation 3, with the exception that tetra-n-butyl ammonium fluoride is used as base in lieu of 1,8-diazabicyclo[5.4.0]undec-7-ene (DBU).

Sulfonamides of Formula (4) where $R_2$ contains sulfinyl or sulfonyl groups can be prepared by peracid oxidation of the corresponding mercapto sulfonamides using methods analogous to those described for the preparation of sulfinyl sulfonamides of Formula (4d, n=1) and sulfonyl sulfonamides of Formula (4d, n=2) in Equation 9 (vide infra).

For example, the sulfinyl sulfonamides of Formula (4d, n=1) and sulfonyl sulfonamides of Formula (4d, n=2) can be be prepared from the corresponding thio sulfonamides of Formula (4b) as shown in Equation 9.

Equation 9

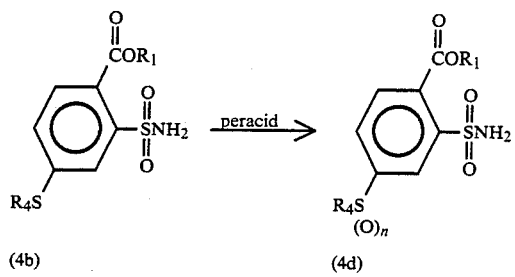

(4b)     (4d)

where $R_1$ and $R_4$ are as previously defined, except that $R_4$ cannot be alkylthioalkyl or haloalkylthioalkyl, and n is 1 or 2.

To prepare the sulfinyl sulfonamides of Formula (4d, n=1) a solution of one equivalent of a peracid, such as 3-chloroperoxybenzoic acid, in an inert solvent, such as dichloromethane, is added to a stirred solution of the appropriate thio sulfonamide (4b) in an inert solvent, such as a mixture of dichloromethane and tetrahydrofuran, at 0°–5° C. The mixture is then warmed to 20°–40° C. When thin layer chromatography has revealed the sulfonamide (4b) to have been oxidized, the mxiture is washed in turn with 5% aqueous sodium sulfite solution, saturated aqueous sodium bicarbonate solution, water, and brine, and then dried (MgSO$_4$). Evaporation of the solvent then leaves the sulfinyl sulfonamide of Formula (4d, n=1).

To prepare sulfonyl sulfonamides of Formula (4d, n=2) a solution of more than two equivalents (only two equivalents when $R_4$ is alkenyl or alkynyl) of a peracid, such as 3-chloroperoxybenzoic acid, in an inert solvent, such as 1,2-dichloroethane, is added to a stirred mixture of the appropriate thio sulfonamide (4b) in an inert solvent, such as 1,2-dichloroethane, containing 1–5 mol % of a free radical inhibitor, such as 4,4-thiobis(6-tert-butyl-m-cresol). The mixture is heated to 50°–80° C. When thin layer chromatography shows the thio sulfonamide (4b) and intermediate sulfinyl sulfonamide (4d, n=1) to have been consumed, the mixture is cooled and diluted with tetrahydrofuran to maintain sulfonamide solubility. Using the same work up method as already described for the preparation of sulfinyl sulfonamides (4d, n=1), one obtains the sulfonyl sulfonamides of Formula (4d, n=2).

Sulfonamides of Formula (4d) where $R_4$ is alkylthioalkyl or haloalkylthioalkyl and n is 1 or 2 can be prepared from the homologous sulfonamides of Formula (4d) having a $R_4$ monohaloalkyl substituent with a displaceable halogen atom at the position where the alkylthioalkyl or haloalkylthioalkyl group is to be placed. These monohaloalkyl sulfonamides are first closed to the corresponding saccharins by use of DBU as previously described for the preparation of 6-benzyloxysaccharin. The halogen atom is then replaced with the appropriate alkylthio or haloalkylthio group using the displacement conditions previously described for the conversion of halide (37) to thioether (39) in Equation 8. When the appropriate haloalkylthiolate reagent is unstable to self-condensation, the corresponding hydroxy-, carbonyl-, and/or carboxy-containing alkylthiolate can be used. After formation of the thioether bridge, these oxygen-containing groups can be converted to the desired halogen substitution pattern by use of a wide variety of methods known in the art. Finally, the saccharins are opened to the desired sulfonamides of Formula (4d) where $R_4$ is alkylthioalkyl or haloalkylthioalkyl and n is 1 or 2 by the method already described for the conversion of (23) to (4a) in Equation 6b.

Sulfonyl isocyanates (1) are prepared from the corresponding sulfonamides (4) with compatible $R_2$ substituents by one of the following two general methods.

<u>Equation 10</u>

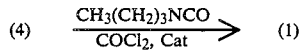

where $R_1$ and $R_2$ are as previously defined.

The sulfonamide (4) and an alkyl isocyanate (e.g., n-butyl isocyanate) in xylene or other solvent boiling above 135° C. are mixed in the presence or absence of a catalytic amount of 1,4-diaza[2.2.2]bicyclooctane (DABCO) and heated to 135°-140° C. After 5-60 minutes phosgene is slowly added to the heated mixture at such a rate that the temperature remains between 133°-135° C. When the consumption of phosgene has ceased, the mixture is cooled and filtered to remove insoluble material. Finally, the solvent, alkyl isocyanate, and excess phosgene are evaporated, leaving the sulfonyl isocyanate (1).

If desired, the alkyl isocyanate-sulfonamide adduct can be made and isolated before reaction with the phosgene. In this case, the sulfonamide (4), alkyl isocyanate, and anhydrous base (e.g., $K_2CO_3$) in a polar, aprotic solvent (e.g. acetone, butanone, or acetonitrile) are mixed and heated under reflux for 1 to 6 hours. The reaction mixture is then diluted with water, and the pH is adjusted to about 3 with acid (e.g. HCl, $H_2SO_4$). The adduct is filtered out and dried, and then reacted with phosgene as described above. This procedure modification is especially useful when sulfonamide (4) is high melting and has low solubility in the phosgenation solvent.

Sulfonyl isocyanates (1) can also be prepared by the following method.

<u>Equation 11</u>

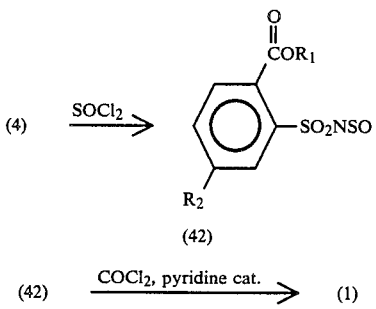

where $R_1$ and $R_2$ are as previously defined.

The sulfonamide (4) is heated at reflux in an excess of thionyl chloride. The reaction is continued until the sulfonamide protons are no longer detectable in the proton magnetic resonance spectrum. From 16 hours to 5 days is typically sufficient for complete conversion to the thionylamide (42) (Equation 11a).

The thionyl chloride is evaporated and the residue is treated with an inert solvent (e.g. toluene) containing at least one equivalent (typically 2-3 equivalents) of phosgene. A catalytic amount of pyridine (typically 0.1 equivalent) is added, and the mixture is heated to about 60°-140 ° C. with 80°-100° C. preferred. Conversion to the isocyanate (1) is usually substantially complete within 15 minutes to 3 hours (Equation 11b). The mixture is then cooled and filtered, and the solvent is evaporated, leaving the sulfonyl isocyanate (1).

The heterocyclic amines of Formula (2) below are either known, disclosed in this application, or can be prepared by obvious methods by one skilled in the art.

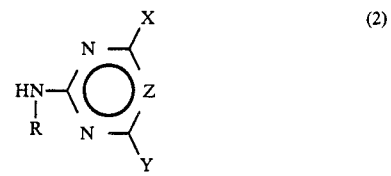

For a review of the synthesis and reactions of 2-amino and 2-methylaminopyrimidines (2, Z=CH) see *The Chemistry of Heterocyclic Compounds,* Vol. 16, Wiley-Interscience, New York (1962). For a review of the synthesis and reactions 2-amino- and 2-methylamino-s-triazines (2, Z=N) see *The Chemistry of Heterocyclic Compounds,* Vol. 13, Wiley-Interscience, New York (1959), F. C: Schaefer, U.S. Pat. No. 3,154,537 and F. C. Schaefer and K. R. Huffman *J. Org. Chem.,* 28, 1812 (1963).

In some cases, heterocycles of Formula (2) may be more easily prepared with R being H than with R being $CH_3$. Many heterocycles (2, $R=CH_3$) can be prepared from the corresponding heterocycles (2, R=H) by one or more of the following two methods.

<u>Equation 12</u>

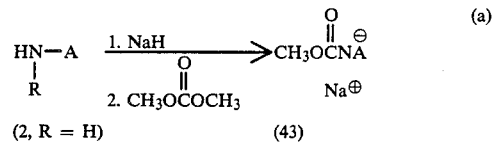

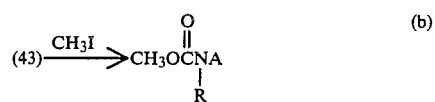

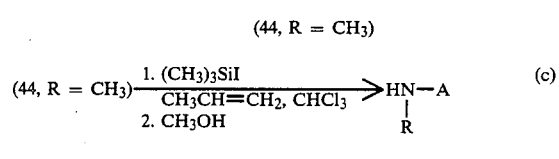

where A is as previously defined.

In this method, a solution or slurry of the appropriate heterocycle (2, R=H) in a suitable aprotic solvent (e.g., tetrahydrofuran, dioxane, glyme) at 0°-30° C. is treated with two equivalents of sodium hydride. After gas evolution ceases, the reaction mixture is treated with one equivalent of dimethyl carbonate and stirred at 20°-30° C. for 8 to 24 hours to provide a suspension of the sodium salt (43) (Equation 12a).

The reaction mixture containing (43) is treated with at least two equivalents of iodomethane and then heated at 60°-80° C. for 8 to 24 hours. The mixture is cooled and filtered, and the solvent is evaporated. The residue is taken up in dichloromethane, washed with water, and the solvent is evaporated, leaving the N-methyl carbamate (44, R=CH₃) (Equation 12b).

The carbamate (44, R=CH₃) is dissolved in anhydrous, alcohol-free chloroform saturated with propylene gas. Slightly more than one equivalent (typically 1.1-1.2 equivalents) of iodotrimethylsilane is added and the stirred solution is heated at 50°-60° C. for 2 to 4 hours. The mixture is cooled and two equivalents of methanol is added. The solvent is evaporated and the residue is taken up in methanol. The mixture is carefully neutralized with 10% sodium methoxide in methanol, and then the solvent is evaporated. The residue is triturated with ice water. If a precipitate forms, it is filtered out, rinsed with ice water and dried to provide (2, R=CH₃). If no precipitate forms, the solution is saturated with sodium chloride and extracted with ethyl acetate. Evaporation of the solvent leaves heterocycle (2, R=CH₃) (Equation 12c).

Alternatively, the following two-step procedure is useful in many cases.

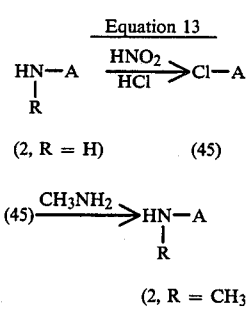

where A is as previously defined.

A solution of the amine (2, R=H) in concentrated hydrochloric acid is treated with sodium nitrite solution and the chloro compound (45) is isolated in the usual manner by filtration of the acidic solution (Equation 13a). A representative procedure is described by Bee and Rose in *J. Chem. Soc. C.* 1966, 2031, for the case in which Z=CH, and X=Y=OCH₃.

The heterocycle (45) is then treated with at least two equivalents of methylamine in a suitable inert solvent (e.g. tetrahydrofuran, glyme, or diglyme) at a temperature between 20° and 80° C. for 1-18 hours (Equation 13b). The reaction mixture is then cooled and filtered. Evaporation of the solvent leaves (2, R=CH₃) contaminated with a little CH₃NH₃⁺Cl⁻ salt. The product may be purified by trituration with ice water or by dissolution in dichloromethane, followed by washing with a small amount of water, drying, and evaporation of solvent. Further purification may be accomplished by recrystallization or column chromatography on silica gel.

As an alternative to the methods already described in which the sulfonamides of Formulae (4a), (4b), and (4e) are fully elaborated prior to construction of the urea bridge of compounds of Formula I, many compounds of Formula Ia may be prepared by the method described in Equation 14.

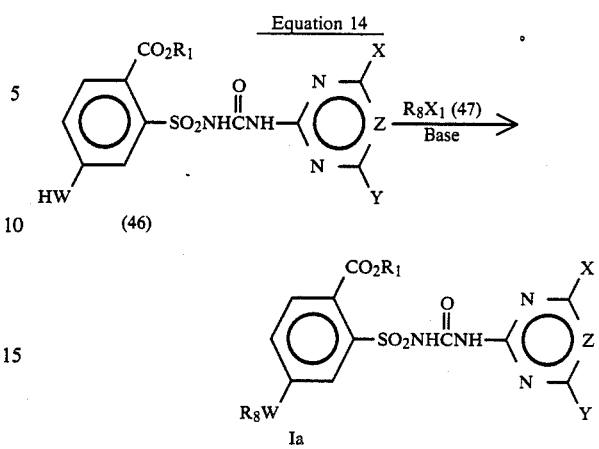

where R₁, X, X₁, Y and Z are as previously defined; W is S, O or NR$_b$; R$_b$ is as previously defined; R₈ is C₄–C₆ cycloalkylalkyl, C₂–C₆ alkenyl, C₂–C₆ haloalkenyl, C₃–C₆ alkynyl, C₃–C₆ haloalkynyl, C₂–C₈ alkoxyalkyl, C₂–C₄ haloalkoxyalkyl, C₂–C₈ alkylthioalkyl, C₂–C₄ haloalkylthioalkyl, C₂–C₄ cyanoalkyl, CH₂C(O)CH₃, CH₂CH₂C(O)CH₃ or C₁–C₆ alkyl.

In this method a solution of the appropriate compound of Formula (46) in a polar solvent such as a mixture of acetonitrile and N,N-dimethylformamide is treated with two equivalents of a strong base such as sodium methoxide or sodium hydride with catalytic methanol followed by a little more than one equivalent of the appropriate alkylating, alkenylating, or alkynylating agent (47). The mixture is held at 20°-60° C. for 2-24 hours. Then the mixture is poured into excess hydrochloric acid. If the compound of Formula Ia crystallizes, it is filtered. Otherwise the aqueous mixture is extracted with dichloromethane, and evaporation of the solvent leaves the compound of Formula Ia. The compounds of Formula (46) are in turn prepared by coupling the appropriate sulfonamides of Formulae (4a, 4b or 4e) with the appropriate heterocyclic phenyl carbamates of Formula (5, R=H) according to the general method described for Equation 3.

Many of the compounds of Formula Ia where R₈ is alkyl, cycloalkyl, cycloalkylalkyl, haloalkyl, alkenyl, haloalkenyl, alkynyl, haloalkynyl, alkoxyalkyl, haloalkoxyalkyl, cyanoalkyl, —CH₂C(O)CH₃, or —CH₂CH₂C(O)CH₃ and W is S(O) or S(O)₂ can be made by oxidation of the corresponding compounds of Formula Ia where W is S using methods similar to those already described for the conversion of (4b) to (4d) in Equation 9.

Compounds of Formula I where R₂ contains a carbonyloxy, carbamoyloxy, phosphoryloxy, sulfonyloxy, silyloxy, or phosphorylthio group are prepared from the corresponding compounds of Formula I where R₂ contains a hydroxyl or thiol group by use of a wide variety of methods known in the art.

The following examples further illustrate the synthesis of this invention.

EXAMPLE 1

Methyl 4-ethoxy-2-hydroxybenzoate

Hydrogen chloride was bubbled into a stirred solution of 4-ethoxy-2-hydroxybenzoic acid (10.10 g, 0.554 mol) in methanol (2000 mL) until the solution was saturated. The solution was heated under reflux for 3 days and then cooled to 15° C. This caused the product to crystallize out. The crystals were collected, rinsed with methanol and hexanes, and dried. Methyl 4-ethoxy-2-hydroxybenzoate was obtained as a pale amber solid (49.3 g) melting at 77°–78° C.

PMR (CDCl$_3$, 90 MHZ): δ11.90 (slightly broadened s, 1H, OH); 7.76 (d, 1H, H ortho to CO$_2$CH$_3$); 6.35–6.55 (m, 2H, other aryl H's); 4.06 (q, 2H, OCH$_2$CH$_3$); 3.89 (s, 3H, OCH$_3$); 1.41 (t, 3H, OCH$_2$CH$_3$). IR (Nujol); 3130 (broad, w, OH): 1668 (s, C=O) cm$^{-1}$. More product was obtained by reworking the mother liquor.

EXAMPLE 2

Methyl 2-[(dimethylamino)thioxomethoxy]-4-ethoxybenzoate

Triethylamine (76.6 mL, 0.550 mol) was added via syringe to a stirred solution of methyl 4-ethoxy-2-hydroxybenzoate (49.3 g, 0.251 mol), 4-dimethylaminopyridine (3.06 g, 0.025 mol), and dimethylthiocarbamoyl chloride (54.4 g, 0.440 mol) in dry dichloromethane (411 mL). The reaction solution was heated at reflux three days and then allowed to stand at room temperature overnight. It was washed with hydrochloric acid (1N, 3×300 mL) and then dried (MgSO$_4$) and filtered. Rotary evaporation of the solvent left crude product (95.2 g) as a brown oil. This was applied to a column of silica gel and eluted with 2:1 followed by 1:1 hexanes-ether. Fractions containing product (R$_f$=0.43, 1:1 hexanes-ether, UV) were rotary evaporated to give partially purified product (60.2 g) as a yellowish solid. Further purification was achieved by additional column chromatography employing a greater silica gel to sample ratio. Finally, the doubly chromatographed product (48.7 g, including 7.4 g from another similar run) was recrystallized from boiling methanol (3 mL/g). After cooling in an ice bath, the crystals were collected, rinsed with icecold methanol and dried. Methyl 2-[(dimethylamino)thioxomethoxy]-4-ethoxybenzoate was obtained as large white prisms (46.1 g) melting at 77°–79° C.

PMR (CDCl$_3$, 200 MHz): δ7.96 (d, 1H, H ortho to CO$_2$CH$_3$); 7.81 (dd, 1H, H para to OCSN); 6.62 (d, 1H, H ortho to OCSN); 4.08 (q, 2H, OCH$_2$CH$_3$); 3.81 (s, 3H, CO$_2$CH$_3$); 3.47 (s, 3H, NCH$_3$); 3.40 (s, 3H, NCH$_3$); 1.42 (t, 3H, OCH$_2$CH$_3$). IR (Nujol): 1715 cm$^{-1}$ (vs, C=O).

EXAMPLE 3

Methyl 2-[(dimethylamino)carbonylthio]-4-ethoxybenzoate

Methyl 2-[(dimethylamino)thioxomethoxy]-4-ethoxybenzoate (28.3 g, 0.100 mol) was heated under nitrogen at 220° C. for 1.5 hours. Thin layer chromatography (6:3:1 CH$_3$Cl$_2$-hexanes-ether, UV) showed a very faint spot at a R$_f$ of 0.63 (starting material) and a very intense spot at a R$_f$ of 0.35 (product). In this case the crude product was used in the next reaction step without further characterization or purification.

Crude product from a similar but smaller scale run was chromatographed on a column of silica gel using 4:1 ether-hexanes as eluant. Fractions containing product (R$_f$=0.40, same solvent, UV) were rotary evaporated to give an oil that slowly crystallized. This was dissolved in a little dichloromethane, diluted with 1-chlorobutane, seeded, and rotary evaporated. The residue was collected, rinsed with hexanes, and dried. Methyl 2-[(dimethylamino)carbonylthio]-4-ethoxybenzoate was obtained as white prisms melting at 65°–67° C. PMR (CDCl$_3$, 200 MHz): δ7.93 (d, 1H, H ortho to CO$_2$CH$_3$); 7.16 (d, 1H, H ortho to SCON); 6.89 (dd, 1H, H para to SCON); 4.08 (q, 2H, OCH$_2$CH$_3$); 3.84 (s, 3H, CO$_2$CH$_3$); 3.09 (broad s, 6H, N(CH$_3$)$_2$); 1.42 (t, 3H, OCH$_2$CH$_3$). IR (Nujol): 1730 (s, ester C=O); 1680 (s, carbonyl C=O) cm$^{-1}$.

EXAMPLE 4

Methyl 4-ethoxy-2-mercaptobenzoate

Methanolic sodium methoxide (4.9M, 22.4 mL, 0.11 mol) was added via syringe to a solution of methyl 2-[(dimethylamino)carbonylthio]-4-ethoxybenzoate (crude, ca. 28.3 g, 0.10 mol) in methanol (100 mL) under nitrogen. The reaction mixture was heated at reflux for 30 minutes, then cooled with the aid of a water bath. Rotary evaporation yielded a solid. This was partitioned between dichloromethane (100 mL) and water (100 mL). The aqueous layer was washed with dichloromethane (3×40 mL), acidified to pH <1 with concentrated hydrochloric acid, and then extracted with dichloromethane (3×40 mL). These dichloromethane extracts were combined, dried (Na$_2$SO$_4$), and filtered. Rotary evaporation yielded methyl 4-ethoxy-2-mercaptobenzoate as an oil (18.4 g) that on standing formed a crystalline solid melting at 42°–44° C. PMR (CDCl$_3$, 200 MHz): δ7.97 (d, 1H, H ortho to CO$_2$CH$_3$); 6.78 (d, 1H, H ortho to SH); 6.64 (dd, 1H, H para to SH); 5.06 (s, 1H, SH); 4.05 (q, 2H, OCH$_2$CH$_3$); 3.88 (s, 3H, CO$_2$CH$_3$); 1.42 (t, 3H, OCH$_2$CH$_3$). IR (Nujol): 1686 (vs. C=O) cm$^{-1}$.

EXAMPLE 5

Methyl 2-(chlorosulfonyl)-4-ethoxybenzoate

Hydrogen peroxide (30%, 9.79M, 30.7 mL, 300 mmol) was added dropwise to a stirred solution of methyl 4-ethoxy-2-mercaptobenzoate (18.2 g, 85.7 mmol) and sodium formate (11.7 g, 172 mmol) in formic acid (171.4 mL). Through the use of an ice bath, the internal temperature was held to 40°–50° C. during the first half of the hydrogen peroxide addition and 45°–50° C. during the second half of the addition. After completion of the addition and cessation of the exothermic reaction, the mixture was heated at 45°–55° C. for two hours. The excess hydrogen peroxide was destroyed with sodium sulfite, the solution was filtered, and the solvent was rotary evaporated. The residue was slurried in toluene and rotary evaporated. The process was repeated to give the sodium sulfonate salt as a moist white crystalline solid (21.7 g).

Without further purification or characterization, the sodium sulfonate salt was added portionwise to stirred thionyl chloride (150 mL, 2.1 mmol). Anhydrous N,N-dimethylformamide (1.0 mL, 13 mmol) was added slowly, and the reaction mixture was heated at reflux overnight. The reaction mixture was then rotary evaporated. Dichloromethane (150 mL) was added, and the solvent was again evaporated. The residue was partitioned between ether (100 mL) and ice water (100 mL). The aqueous layer was extracted with ether (2×50 mL). The combined ether solutions were washed with water (50 mL), saturated aqueous sodium bicarbonate solution (2×50 mL), dried (MgSO$_4$), and filtered. Rotary evaporation of the solvent left methyl 2-(chlorosulfonyl)-4-ethoxy-benzoate as pale orange oil (22.5 g) that crystallized on scratching. The crystalline solid melted at 45°–48° C. PMR (CDCl$_3$, 200 MHz): δ7.76 (d, 1H, H ortho to CO$_2$CH$_3$); 7.65 (d, 1H, H ortho to SO$_2$Cl); 7.21 (dd, 1H, H para to SO$_2$Cl); 4.16 (q, 2H, OC$\underline{H_2}$CH$_3$); 3.96 (s, 3H, CO$_2$CH$_3$); 1.48 (t, 3H, OCH$_2$C$\underline{H_3}$). IR (Nujol): 1722 (vs, C=O) cm$^{-1}$.

EXAMPLE 6

Methyl 2-(aminosulfonyl)-4-ethoxybenzoate

Liquified ammonia (4.4 mL, 180 mmol) was added to a stirred solution of methyl 2-(chlorosulfonyl)-4-ethoxybenzoate (22.1 g, 79.3 mmol) in dichloromethane (221 mL) at −70° C. The reaction mixture was allowed to warm to −10° C. and was held at this temperature for 30 minutes. The mixture was then poured into water (221 mL). More water and dichloromethane were used for rinsing, and tetrahydrofuran (ca. 40 mL) was also added. The layers were shaken and separated, and the aqueous layer was extracted with dichloromethane (2×221 mL). The combined dichloromethane solutions were washed with water (221 mL), and the aqueous wash was back-extracted with dichloromethane (ca. 120 mL). The combined dichloromethane solutions were dried (Na$_2$SO$_4$), and filtered. Rotary evaporation of the solvent left crude product as an off-white crystalline solid (18.1 g). This was dissolved in hot methanol (ca. 200 mL) and hot filtered. The solution was boiled down to a volume corresponding to 3 mL/g methanol. After seeding and cooling with the aid of an ice bath, the crystals were collected, rinsed with ice-cold methanol and hexanes, and dried. Methyl 2-(aminosulfonyl)-4-ethoxybenzoate (15.3 g) was obtained as white crystalline needles melting at 146°-148° C. PMR (CDCl$_3$, 200 mHz): δ7.91 (d, 1H, H ortho to CO$_2$CH$_3$); 7.68 (d, 1H, H ortho to SO$_2$NH$_2$); 7.04 (dd, 1H, H para to SO$_2$NH$_2$); 5.91 (broad s, 2H, NH$_2$); 4.14 (q, 2H, OC$\underline{H_2}$CH$_3$); 3.95 (s, 3H, CO$_2$CH$_3$); 1.45 (t, 3H, OCH$_2$C$\underline{H_3}$). IR (Nujol): 3348 (m, NH); 3241 (m, NH); 1692 (s, C=O) cm$^{-1}$.

EXAMPLE 7

Methyl 4-ethoxy-2-(isocyanatosulfonyl)benzoate

A solution of methyl 2-(aminosulfonyl)-4-ethoxybenzoate (7.56 g, 29.2 mmol), n-butyl isocyanate (3.29 mL, 29.2 mmol), and 1,4-diaza[2.2.2]bicyclooctane (0.13 g, 1.2 mmol) in mixed xylenes was heated at reflux for 10 minutes. Phosgene was then added at such a rate that the internal temperature stayed at 133° C. or above. When consumption of phosgene ceased, the solution was cooled to room temperature and then filtered under nitrogen. Rotary evaporation gave methyl 4-ethoxy-2-(isocyanatosulfonyl)benzoate as a cloudy yellow oil (8.2 g). This was used immediately without further purification or characterization.

EXAMPLE 8

Methyl 2-[[(4,6-dimethoxy-1,3,5-triazin-2-yl)-aminocarbonyl]aminosulfonyl]-4-ethoxybenzoate To a slurry of 4,6-dimethoxy-1,3,5-triazin-2-amine (0.46 g, 2.9 mmol) in dry dichloromethane (5 mL) was added a solution of methyl 4-ethoxy-2-(isocyanatosulfonyl)benzoate (crude, ca. 1.2 g, 4.2 mmol) in dichloromethane (5 mL). The reaction mixture was heated at reflux for 1.5 hours, during which time the solid dissolved. On stirring at room temperature overnight a new solid formed. The solvent was rotary evaporated, leaving the crude product as a white solid (1.5 g). This was dissolved in warm 1,2-dichloroethane and chromatographed on a column of silica gel using as eluant 15:1, 10:1, and finally 7:1 dichloromethane-ether, all containing 2 mL/L acetic acid. The appropriate fractions were diluted with toluene and rotary evaporated to give a solid. This was dissolved in minimal warm dichloromethane, diluted with 1-chlorobutane, and rotary evaporated to give a crystalline solid. This was slurried in hexanes, collected, rinsed with 1:1 1-chlorobutane-hexanes and hexanes. and dried. The product was obtained as a white crystalline powder (0.98 g) melting at 181°-183° C. PMR (CDCl$_3$, 200 MHz); δ12.15 (slightly broadened s, 1H, SO$_2$NHCO); 7.89 (d, 1H, H ortho to SO$_2$NH); 7.77 (d, 1H, H ortho to CO$_2$CH$_3$); 7.45 (slightly broadened s, 1H, CONH—Het); 7.11 (dd, 1H, H para to SO$_2$NH); 4.17 (q, 2H, OC$\underline{H_2}$CH$_3$); 4.12 (s, 6H, Het—OCH$_3$); 3.90 (s, 3H, CO$_2$CH$_3$); 1.46 (t, 3H, OCH$_2$C$\underline{H_3}$). IR (Nujol): 1730 (vs, ester C=O); 1715 (s, urea C=O) cm$^{-1}$.

EXAMPLE 9

4-(Methylthio)-2-nitrobenzoic acid

4-Amino-2-nitrobenzoic acid (20.0 g, 110 mmol) was added to aqueous sulfuric acid (32.8 mL H$_2$O+24.0 mL conc. H$_2$SO$_4$). The stirred mixture was heated until all of the aniline dissolved, and then was plunged into an ice bath to precipitate the anilinium salt as suspension of very small crystals. Portions of aqueous sodium nitrite (8.8 g, 128 mmol in 18.4 mL H$_2$O) were then added over one hour to the stirred reaction mixture maintained at −5° to 0° C.

The diazotization mixture was then poured portionwise into a mixture of sodium hydroxide (24.4 g, 610 mmol), methanethiol (33.6 mL, 605 mmol); cupric sulfate (17.6 g, 110 mmol), and sodium acetate (55.2 g, 673 mmol) in 140 mL of water cooled with the aid of an ice bath. The addition was exothermic and accompanied by copious gas evolution. A suspension of tan-yellow solid formed. The mixture was heated to 60° C., and then was allowed to cool to room temperature.

Dichloromethane (200 mL) and tetrahydrofuran (20 mL) were stirred in. Concentrated hydrochloric acid was added to bring the pH below 1. The mixture was suction filtered through Celite®, with additional dichloromethane used for rinsing. The layers were separated, and the aqueous layer was extracted with dichloromethane (2×50 mL). The combined dichloromethane solutions were dried (Na$_2$SO$_4$) and suction filtered through Celite®. The solvent was rotary evaporated. The residue was dissolved in minimal acetone, diluted with toluene, and evaporated. The residue was dissolved in minimal acetone, diluted with toluene, and evaporated. The process was repeated to leave crude 4-(methylthio)-2-nitrobenzoic acid as an orange solid (20.4 g) melting at 165°-168° C. This was used in the next step without further purification.

PMR (DMSO-d$_6$, 200 MHz); δ13.6 (very broad s, 1H, CO$_2$H); 7.83 (d, 1H, H ortho to CO$_2$H); 7.76 (d, 1H, H ortho to NO$_2$); 7.58 (dd, 1H, H para to NO$_2$); 2.58 (s, 3H, SCH$_3$). IR (Nujol): 2800 (very broad, m. OH); 1675 (s, C=O) cm$^{-1}$.

EXAMPLE 10

Methyl-4-(methylthio)-2-nitrobenzoate

To a stirred solution of 4-(methylthio)-2-nitrobenzoic acid (24.4 g, 114 mmol) in dry pyridine (265 mL) maintained at 5° C. under nitrogen was added p-toluenesulfonyl chloride (43.6 g, 229 mmol). After one hour and with continued cooling with the aid of an ice bath, dry methanol (6.2 mL, 153 mmol) was added. After the exothermicity subsided, another portion of methanol (4.1 mL. 101 mmol) was added, and the ice bath was removed.

The reaction solution was stirred at room temperature for one hour and then poured into ice water (1060 mL). Ether (530 mL) was stirred in, and the layers were separated. The aqueous layer was extracted with ether (2×520 mL). The combined ether solutions were washed with 10% aqueous sodium hydroxide solution (2×530 mL), dried (MgSO4), and filtered. The solvent was rotary evaporated. The residue was taken up in toluene, which was subsequently rotary evaporated. This process was repeated once more to give a thick brown oil.

This oil was chromatographed on a column of silica gel using mixtures of hexanes and ether (first 2:1 then 3:2) as eluting solvents. Fractions containing product ($R_f$=0.38, UV, 2:1 hexanes-ether) were evaporated to leave a yellow solid. This was dissolved in minimal warm 1-chlorobutane, diluted with hexanes to saturation, and seeded. After crystallization was complete, the mixture was evaporated. The residue was slurried in hexanes, collected, rinsed with hexanes, and dried. Methyl 4-(methylthio)-2-nitrobenzoate was obtained as pale yellow needles (11.6 g) melting at 57°-59° C.

PMR(CDCl$_3$, 200 MHz): δ7.71 (d, 1H, H ortho to CO$_2$CH$_3$); 7.55 (d, 1H, H ortho to NO$_2$); 7.41 (dd, 1H, H para to NO$_2$); 3.90 (s, 3H, CO$_2$CH$_3$); 2.56 (s, 3H, SCH$_3$). IR (Nujol): 1709 (vs, C=O) cm$^{-1}$.

EXAMPLE 11

Methyl 2-amino-4-(methylthio)benzoate

A mixture of methyl 4-(methylthio)-2-nitrobenzoate (11.3 g, 49.7 mmol) and 5% platinum sulfide on carbon catalyst (0.7 g) in methyl acetate (40 mL) was hydrogenated at 750 psi and 75° C. until hydrogen uptake ceased. The mixture was filtered through Celite ®, and the filtrate solvent was rotary evaporated, leaving methyl 2-amino-4-(methylthio)benzoate as a slightly tan crystalline solid (8.7 g) melting at 57°-59° C.

PMR (CDCl$_3$, 200 MHz): δ7.74 (d, 1H, H ortho to CO$_2$CH$_3$); 6.50 (dd, 1H, H para to NH$_2$); 6.44 (dd, 1H, H ortho to NH$_2$); 5.75 (broad s, 2H, NH$_2$); 3.85 (s, 3H, CO$_2$CH$_3$); 2.46 (s, 3H, SCH$_3$), IR (Nujol): 3422 (m, NH); 3312 (m, NH); 1650 (s, C=O) cm$^{-1}$.

EXAMPLE 12

Methyl 2-(chlorosulfonyl)-4-(methylthio)benzoate

To a stirred aqueous sulfuric acid solution (7.2 mL concentrated H$_2$SO$_4$+51.6 mL H$_2$O) maintained at −5° to 0° C. was added alternately portions of a solution of methyl 2-amino-4-(methylthio)benzoate (12.8 g, 64.9 mL) in glacial acetic acid (6.4 mL) and portions of aqueous sodium nitrite (4.9 g, 71 mmol in 7.8 mL H$_2$O).

The diazotization mixture was then poured portionwise into a mixture of cupric chloride dihydrate (5.5 g, 32 mmol), concentrated hydrochloric acid (13.0 mL) and liquified sulfur dioxide (5.5 mL, 129 mmol) in glacial acetic acid (51.6 mL) and dichloromethane (64.6 mL) at 0° C. Using dry ice-filled Dewar condensers, the coupling mixture was heated at reflux for 45 minutes.

The reaction mixture was then poured into water (ca. 400 mL) with additional dichloromethane (ca. 60 mL) used for rinsing. The layers were shaken and separated, and the aqueous layer was extracted with dichloromethane (3×50 mL). The combined dichloromethane solutions were washed with water (ca. 100 mL). Water (25 mL) was added to the dichloromethane solution, and with vigorous stirring sodium bicarbonate was added until foaming ceased. The mixture was diluted with water (ca. 40 mL), and the layers were separated. The dichloromethane layer was washed with water (ca. 2×60 mL) and dried (MgSO$_4$). Rotary evaporation of the solvent afforded crude methyl 2-chlorosulfonyl)-4-(methylthio)benzoate as a yellow semisolid (10.0 g). This was immediately used in the next reaction step without further purification or characterization.

EXAMPLE 13

Methyl 2-(aminosulfonyl)-4-(methylthio)benzoate

Liquified ammonia (1.7 mL, 68 mmol) was added to a stirred solution of methyl 2-(chlorosulfonyl)-4-(methylthio)benzoate (10 g, 36 mmol) in dichloromethane (100 mL) at −70° C. The reaction mixture was allowed to warm to −10° C. and was held at this temperature for 10 minutes. The mixture was then poured into water (100 mL). More water and dichloromethane were used for rinsing. The layers were shaken and separated, an the aqueous layer was extracted with dichloromethane (2×50 mL). The combined dichloromethane solutions were washed with water (100 mL), dried (Na$_2$SO$_4$), and filtered through Celite ®. Rotary evaporation of the solvent left crude product as a solid (9.0 g).

This was dissolved in dichloromethane and suspended on silica gel (27 g). The material was chromatographed on a column of silica gel using dichloromethane-hexanes-ether (6:3:1 then 6:2:2) as eluant. Rotary evaporation of the appropriate fractions left a solid. This was dissolved in dichloromethane, diluted with hexanes, and rotary evaporated to give a crystalline solid. This was slurried in hexanes, collected, rinsed with 1:1 1-chlorobutane-hexanes and hexanes, and dried. Methyl 2-(aminosulfonyl)-4-(methylthio)benzoate was obtained as a white crystalline powder (6.7 g) melting at 123°-125° C.

PMR (CDCl$_3$, 200 MHz): δ7.97 (d, 1H, H ortho to SO$_2$NH$_2$); 7.82 (d, 1H, H ortho to CO$_2$CH$_3$); 7.39 (dd, 1H, H para to SO$_2$NH$_2$); 5.86 (s, 2H, NH$_2$); 3.97 (s, 3H, CO$_2$CH$_3$); 2.56 (s, 3H, SCH$_3$). IR (Nujol): 3322 (m, NH$_2$); 3245 (m, NH$_2$); 1700 (s, C=O) cm$^{-1}$.

EXAMPLE 14

Methyl 2-(isocyanatosulfonyl)-4-(methylthio)benzoate

A solution of methyl 2-(aminosulfonyl)-4-(methylthio)benzoate (5.23 g, 20.0 mmol), n-butyl isocyanate (2.25 mL, 20.0 mmol), and 1,4-diaza[2.2.2]bicyclooctane (0.09 g, 0.8 mmol) in mixed xylenes (50 mL) was heated at reflux for 10 minutes. Phosgene was then added at such a rate that the internal temperature stayed at 133° C. or above. When consumption of phosgene ceased, the solution was cooled to room temperature and then filtered under nitrogen. Rotary evaporation gave methyl 2-(isocyanatosulfonyl)-4-(methylthio)benzoate as a yellow oil (6.4 g). This was used immediately without further purification or characterization.

EXAMPLE 15

Methyl 2-[[(4,6-dimethoxypyrimidin-2-yl)aminocarbonyl]aminosulfonyl]-4-(metylthio)benzoate To a slurry of 4,6-dimethoxy-1,3-pyridimin-2-amine (0.36 g, 2.32 mmol) in dry dichloromethane (4 mL) was added a solution of methyl 2-(isocyanatosulfonyl)-4-

(methylthio)benzoate (crude, ca. 0.95 g, 3.3 mL) in dichloromethane (5 mL). The reaction mixture was heated at reflux for 2.5 hours, during which time a new solid formed.

On stirring at room temperature overnight a new solid formed. The mixture was diluted with a solution of 1:1 1-chlorobutane-hexanes (9 mL), and the solid was collected, rinsed with 1-chlorobutane and hexanes, and dried. The product was obtained as white crystalline powder (0.92 g) melting at 201°–202° C.

PMR (CDCl$_3$, 200 MHz): δ12.57 (slightly broadened s, 1H, SO$_2$NHCO); 8.20 (d, 1H. H ortho to SO$_2$NH); 7.66 (d, 1H, H ortho to CO$_2$CH$_3$); 7.43 (dd, 1H, H para to SO$_2$NH); 7.18 (slightly broadened s, 1H, CONH—Het); 5.79 (s, 1H, Het 5-H); 4.01 (s, 6H, Het—OCH$_3$); 3.87 (s, 3H, CO$_2$CH$_3$); 2.58 (s, 3H, SCH$_3$). IR (Nujol): 1721 (vs, ester C=O); 1698 (s, urea, C=O) cm$^{-1}$.

EXAMPLE 16

1,2-Benzisothiazol-3(2H)-one-6-(methylthio)-1,1-dioxide

A solution of 1,2-benzoisothiazol-3(2H)-one-6-chloro-1,1-dioxide (10 g, 46 mmol) and potassium-tert-butoxide (13 g, 115 mmol) in N,N-dimethylformamide (100 mL) maintained at 0° C. was treated with excess of methyl mercaptan for 15 minutes. The mixture was then allowed to warm to 25° C. and after 2 hours at this temperature the reaction was heated to 110° C. for 1 hour. After this time the mixture was allowed to cool and then was poured onto ice water. The pH was adjusted to 2 and the solid was collected by filtration. The product was obtained as a white solid (10.2 g) melting at 232°–234° C.

PMR (D$_6$-Acetone, 90 MHz): δ8.2-8.0 (m, 3H, aryl-H) and 3.2 (s, 3H, SCH$_3$).

Using the procedures and examples shown above, the compounds in Tables I and Ia can be prepared.

TABLE I

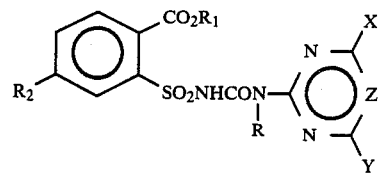

| R$_1$ | R$_2$ | R | X | Y | Z | m.p. (°C.) |
|---|---|---|---|---|---|---|
| CH$_3$ | OC$_2$H$_5$ | H | CH$_3$ | CH$_3$ | CH | 192–194 (d) |
| CH$_3$ | OC$_2$H$_5$ | H | OCH$_3$ | CH$_3$ | CH | 185–187 |
| CH$_3$ | OC$_2$H$_5$ | H | OCH$_3$ | OCH$_3$ | CH | 192–195 |
| CH$_3$ | OC$_2$H$_5$ | H | Cl | OCH$_3$ | CH | 181–183 |
| CH$_3$ | OC$_2$H$_5$ | H | OCH$_3$ | N(CH$_3$)$_2$ | CH | 176–177 |
| CH$_3$ | OC$_2$H$_5$ | H | CH$_3$ | CH$_3$ | N | 118–120 |
| CH$_3$ | OC$_2$H$_5$ | H | OCH$_3$ | CH$_3$ | N | 162–164 |
| CH$_3$ | OC$_2$H$_5$ | H | OCH$_3$ | OCH$_3$ | N | 181–183 |
| CH$_3$ | OC$_2$H$_5$ | H | OCH$_3$ | N(CH$_3$)$_2$ | N | 164–165 |
| CH$_3$ | OC$_2$H$_5$ | H | OCH$_3$ | OCH$_2$CF$_3$ | N | 172–174 |
| CH$_3$ | OC$_2$H$_5$ | CH$_3$ | OCH$_3$ | CH$_3$ | N | 117–120 |
| CH$_3$ | OC$_2$H$_5$ | CH$_3$ | OCH$_3$ | OCH$_3$ | N | 130–131 |
| CH$_3$ | OC$_2$H$_5$ | CH$_3$ | CH$_3$ | OCH$_3$ | CH | |
| CH$_3$ | OC$_2$H$_5$ | CH$_3$ | OCH$_3$ | OCH$_3$ | CH | 147–148 |
| CH$_3$ | OC$_2$H$_5$ | H | Br | OCH$_3$ | CH | |
| CH$_3$ | OC$_2$H$_5$ | CH$_3$ | OCH$_3$ | N(CH$_3$)$_2$ | N | |
| CH$_3$ | OC$_2$H$_5$ | H | CH$_3$ | OCH$_2$CF$_3$ | N | 179–180 |
| CH$_3$ | OC$_2$H$_5$ | H | CH$_3$ | OCH$_2$CF$_3$ | CH | |
| CH$_3$ | OC$_2$H$_5$ | H | OCH$_3$ | OCH$_2$CF$_3$ | CH | |
| CH$_3$ | OC$_2$H$_5$ | H | OCH$_3$ | C$_2$H$_5$ | CH | |
| CH$_3$ | OC$_2$H$_5$ | H | OCH$_3$ | C$_2$H$_5$ | N | |
| CH$_3$ | OC$_2$H$_5$ | H | OCH$_3$ | NHCH$_3$ | CH | |
| CH$_3$ | OC$_2$H$_5$ | H | OCH$_3$ | NHCH$_3$ | N | |
| CH$_3$ | OC$_2$H$_5$ | H | CH$_3$ | OC$_2$H$_5$ | CH | |
| CH$_3$ | OC$_2$H$_5$ | H | OCH$_3$ | OC$_2$H$_5$ | CH | |
| CH$_3$ | OC$_2$H$_5$ | H | CH$_3$ | OC$_2$H$_5$ | N | |
| CH$_3$ | OC$_2$H$_5$ | H | OCH$_3$ | OC$_2$H$_5$ | N | |
| CH$_3$ | OC$_2$H$_5$ | H | CH$_3$ | OCH$_2$CHF$_2$ | CH | |
| CH$_3$ | OC$_2$H$_5$ | H | OCH$_3$ | OCH$_2$CHF$_2$ | CH | |
| CH$_3$ | OC$_2$H$_5$ | H | CH$_3$ | OCH$_2$CHF$_2$ | N | |
| CH$_3$ | OC$_2$H$_5$ | H | OCH$_3$ | OCH$_2$CHF$_2$ | N | |
| CH$_3$ | OC$_2$H$_5$ | H | CH$_3$ | OCH$_2$CH$_2$F | CH | |
| CH$_3$ | OC$_2$H$_5$ | H | OCH$_3$ | OCH$_2$CH$_2$F | CH | |
| CH$_3$ | OC$_2$H$_5$ | H | CH$_3$ | OCH$_2$CH$_2$F | N | |
| CH$_3$ | OC$_2$H$_5$ | CH$_3$ | OCH$_3$ | OCH$_2$CH$_2$F | N | |
| CH$_3$ | OC$_2$H$_5$ | CH$_3$ | Cl | OCH$_3$ | CH | |
| CH$_3$ | OC$_2$H$_5$ | H | Cl | N(CH$_3$)$_2$ | CH | |
| CH$_3$ | OC$_2$H$_5$ | H | Cl | OC$_2$H$_5$ | CH | |
| C$_2$H$_5$ | OC$_2$H$_5$ | H | CH$_3$ | CH$_3$ | CH | |
| C$_2$H$_5$ | OC$_2$H$_5$ | H | OCH$_3$ | CH$_3$ | CH | |
| C$_2$H$_5$ | OC$_2$H$_5$ | H | OCH$_3$ | OCH$_3$ | CH | |
| C$_2$H$_5$ | OC$_2$H$_5$ | H | Cl | OCH$_3$ | CH | |
| C$_2$H$_5$ | OC$_2$H$_5$ | H | CH$_3$ | CH$_3$ | N | |
| C$_2$H$_5$ | OC$_2$H$_5$ | H | OCH$_3$ | CH$_3$ | N | |
| C$_2$H$_5$ | OC$_2$H$_5$ | H | OCH$_3$ | OCH$_3$ | N | |
| C$_2$H$_5$ | OC$_2$H$_5$ | H | Br | OCH$_3$ | CH | |

TABLE I-continued

| $R_1$ | $R_2$ | R | X | Y | Z | m.p. (°C.) |
|---|---|---|---|---|---|---|
| $C_2H_5$ | $OC_2H_5$ | H | $OCH_3$ | $N(CH_3)_2$ | CH | |
| $C_2H_5$ | $OC_2H_5$ | H | $OCH_3$ | $N(CH_3)_2$ | N | |
| $C_2H_5$ | $OC_2H_5$ | H | $OCH_3$ | $NHCH_3$ | N | |
| $C_2H_5$ | $OC_2H_5$ | H | $OCH_3$ | $C_2H_5$ | CH | |
| $C_2H_5$ | $OC_2H_5$ | H | $OCH_3$ | $C_2H_5$ | N | |
| $C_2H_5$ | $OC_2H_5$ | H | $CH_3$ | $OC_2H_5$ | CH | |
| $C_2H_5$ | $OC_2H_5$ | H | $CH_3$ | $OC_2H_5$ | N | |
| $C_2H_5$ | $OC_2H_5$ | H | $OCH_3$ | $OC_2H_5$ | CH | |
| $C_2H_5$ | $OC_2H_5$ | H | $OCH_3$ | $OC_2H_5$ | N | |
| $C_2H_5$ | $OC_2H_5$ | H | $CH_3$ | $OCH_2CF_3$ | CH | |
| $C_2H_5$ | $OC_2H_5$ | H | $CH_3$ | $OCH_2CF_3$ | N | |
| $C_2H_5$ | $OC_2H_5$ | H | $OCH_3$ | $OCH_2CF_3$ | CH | |
| $C_2H_5$ | $OC_2H_5$ | H | $OCH_3$ | $OCH_2CF_3$ | N | |
| $C_2H_5$ | $OC_2H_5$ | H | $OCH_3$ | $OCH_2CHF_2$ | CH | |
| $C_2H_5$ | $OC_2H_5$ | H | $OCH_3$ | $OCH_2CHF_2$ | N | |
| $C_2H_5$ | $OC_2H_5$ | H | $CH_3$ | $OCH_2CHF_2$ | N | |
| $C_2H_5$ | $OC_2H_5$ | H | $OCH_3$ | $OCH_2CH_2F$ | CH | |
| $C_2H_5$ | $OC_2H_5$ | H | $OCH_3$ | $OCH_2CH_2F$ | N | |
| $C_2H_5$ | $OC_2H_5$ | $CH_3$ | $OCH_3$ | $OCH_3$ | CH | |
| $C_2H_5$ | $OC_2H_5$ | $CH_3$ | $CH_3$ | $OCH_3$ | N | |
| $C_2H_5$ | $OC_2H_5$ | $CH_3$ | $OCH_3$ | $OCH_3$ | N | |
| $n$-$C_3H_7$ | $OC_2H_5$ | H | $OCH_3$ | $OCH_3$ | CH | |
| $n$-$C_3H_7$ | $OC_2H_5$ | H | $CH_3$ | $OCH_3$ | N | |
| $CH(CH_3)_2$ | $OC_2H_5$ | H | $OCH_3$ | $CH_3$ | CH | |
| $CH(CH_3)_2$ | $OC_2H_5$ | H | $OCH_3$ | $OCH_3$ | CH | |
| $CH(CH_3)_2$ | $OC_2H_5$ | H | Cl | $OCH_3$ | CH | |
| $CH(CH_3)_2$ | $OC_2H_5$ | H | $OCH_3$ | $CH_3$ | N | |
| $CH(CH_3)_2$ | $OC_2H_5$ | H | $OCH_3$ | $OCH_3$ | N | |
| $CH(CH_3)_2$ | $OC_2H_5$ | H | $OCH_3$ | $N(CH_3)_2$ | N | |
| $CH_3$ | $O(CH_2)_2CH_3$ | H | $CH_3$ | $CH_3$ | CH | |
| $CH_3$ | $O(CH_2)_2CH_3$ | H | $OCH_3$ | $CH_3$ | CH | 151–153 (d) |
| $CH_3$ | $O(CH_2)_2CH_3$ | H | $OCH_3$ | $OCH_3$ | CH | 169–172 (d) |
| $CH_3$ | $O(CH_2)_2CH_3$ | H | Cl | $OCH_3$ | CH | |
| $CH_3$ | $O(CH_2)_2CH_3$ | H | $OCH_3$ | $N(CH_3)_2$ | CH | |
| $CH_3$ | $O(CH_2)_2CH_3$ | H | $CH_3$ | $CH_3$ | N | |
| $CH_3$ | $O(CH_2)_2CH_3$ | H | $OCH_3$ | $CH_3$ | N | 144–147 (d) |
| $CH_3$ | $O(CH_2)_2CH_3$ | H | $OCH_3$ | $OCH_3$ | N | 176–179 (d) |
| $CH_3$ | $O(CH_2)_2CH_3$ | H | $OCH_3$ | $N(CH_3)_2$ | N | |
| $CH_3$ | $O(CH_2)_2CH_3$ | H | $OCH_3$ | $OCH_2CF_3$ | N | |
| $CH_3$ | $O(CH_2)_2CH_3$ | $CH_3$ | $OCH_3$ | $CH_3$ | N | |
| $CH_3$ | $O(CH_2)_2CH_3$ | $CH_3$ | $OCH_3$ | $OCH_3$ | N | |
| $CH_3$ | $O(CH_2)_2CH_3$ | $CH_3$ | $CH_3$ | $OCH_3$ | CH | |
| $CH_3$ | $O(CH_2)_2CH_3$ | $CH_3$ | $OCH_3$ | $OCH_3$ | CH | |
| $CH_3$ | $O(CH_2)_2CH_3$ | H | Br | $OCH_3$ | CH | |
| $CH_3$ | $O(CH_2)_2CH_3$ | $CH_3$ | $OCH_3$ | $N(CH_3)_2$ | N | |
| $CH_3$ | $O(CH_2)_2CH_3$ | H | $CH_3$ | $OCH_2CF_3$ | N | |
| $CH_3$ | $O(CH_2)_2CH_3$ | H | $CH_3$ | $OCH_2CF_3$ | CH | |
| $CH_3$ | $O(CH_2)_2CH_3$ | H | $OCH_3$ | $OCH_2CF_3$ | CH | |
| $CH_3$ | $O(CH_2)_2CH_3$ | H | $OCH_3$ | $C_2H_5$ | CH | |
| $CH_3$ | $O(CH_2)_2CH_3$ | H | $OCH_3$ | $C_2H_5$ | N | |
| $CH_3$ | $O(CH_2)_2CH_3$ | H | $OCH_3$ | $NHCH_3$ | CH | |
| $CH_3$ | $O(CH_2)_2CH_3$ | H | $OCH_3$ | $NHCH_3$ | N | |
| $CH_3$ | $O(CH_2)_2CH_3$ | H | $CH_3$ | $OC_2H_5$ | CH | |
| $CH_3$ | $O(CH_2)_2CH_3$ | H | $OCH_3$ | $OC_2H_5$ | CH | |
| $CH_3$ | $O(CH_2)_2CH_3$ | H | $CH_3$ | $OC_2H_5$ | N | |
| $CH_3$ | $O(CH_2)_2CH_3$ | H | $OCH_3$ | $OC_2H_5$ | N | |
| $CH_3$ | $O(CH_2)_2CH_3$ | H | $CH_3$ | $OCH_2CHF_2$ | CH | |
| $CH_3$ | $O(CH_2)_2CH_3$ | H | $OCH_3$ | $OCH_2CHF_2$ | CH | |
| $CH_3$ | $O(CH_2)_2CH_3$ | H | $CH_3$ | $OCH_2CHF_2$ | N | |
| $CH_3$ | $O(CH_2)_2CH_3$ | H | $OCH_3$ | $OCH_2CHF_2$ | N | |
| $CH_3$ | $O(CH_2)_2CH_3$ | H | $CH_3$ | $OCH_2CH_2F$ | CH | |
| $CH_3$ | $O(CH_2)_2CH_3$ | H | $OCH_3$ | $OCH_2CH_2F$ | CH | |
| $CH_3$ | $O(CH_2)_2CH_3$ | H | $CH_3$ | $OCH_2CH_2F$ | N | |
| $CH_3$ | $O(CH_2)_2CH_3$ | $CH_3$ | $OCH_3$ | $OCH_2CH_2F$ | N | |
| $CH_3$ | $O(CH_2)_2CH_3$ | $CH_3$ | Cl | $OCH_3$ | CH | |
| $CH_3$ | $O(CH_2)_2CH_3$ | H | Cl | $N(CH_3)_2$ | CH | |
| $CH_3$ | $O(CH_2)_2CH_3$ | H | Cl | $OC_2H_5$ | CH | |
| $C_2H_5$ | $O(CH_2)_2CH_3$ | H | $CH_3$ | $CH_3$ | CH | |
| $C_2H_5$ | $O(CH_2)_2CH_3$ | H | $OCH_3$ | $CH_3$ | CH | 154–159 (d) |
| $C_2H_5$ | $O(CH_2)_2CH_3$ | H | $OCH_3$ | $OCH_3$ | CH | 173–176 (d) |
| $C_2H_5$ | $O(CH_2)_2CH_3$ | H | Cl | $OCH_3$ | CH | 140–142 (d) |

TABLE I-continued

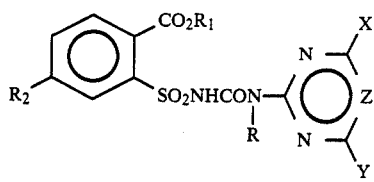

| R₁ | R₂ | R | X | Y | Z | m.p. (°C.) |
|---|---|---|---|---|---|---|
| C₂H₅ | O(CH₂)₂CH₃ | H | CH₃ | CH₃ | N | |
| C₂H₅ | O(CH₂)₂CH₃ | H | OCH₃ | CH₃ | N | 131–135 (d) |
| C₂H₅ | O(CH₂)₂CH₃ | H | OCH₃ | OCH₃ | N | 145–150 (d) |
| C₂H₅ | O(CH₂)₂CH₃ | H | Br | OCH₃ | CH | |
| C₂H₅ | O(CH₂)₂CH₃ | H | OCH₃ | N(CH₃)₂ | CH | |
| C₂H₅ | O(CH₂)₂CH₃ | H | OCH₃ | N(CH₃)₂ | N | |
| C₂H₅ | O(CH₂)₂CH₃ | H | OCH₃ | NHCH₃ | N | |
| C₂H₅ | O(CH₂)₂CH₃ | H | OCH₃ | C₂H₅ | CH | |
| C₂H₅ | O(CH₂)₂CH₃ | H | OCH₃ | C₂H₅ | N | |
| C₂H₅ | O(CH₂)₂CH₃ | H | CH₃ | OC₂H₅ | CH | |
| C₂H₅ | O(CH₂)₂CH₃ | H | CH₃ | OC₂H₅ | N | |
| C₂H₅ | O(CH₂)₂CH₃ | H | OCH₃ | OC₂H₅ | CH | |
| C₂H₅ | O(CH₂)₂CH₃ | H | OCH₃ | OC₂H₅ | N | |
| C₂H₅ | O(CH₂)₂CH₃ | H | CH₃ | OCH₂CF₃ | CH | |
| C₂H₅ | O(CH₂)₂CH₃ | H | CH₃ | OCH₂CF₃ | N | |
| C₂H₅ | O(CH₂)₂CH₃ | H | OCH₃ | OCH₂CF₃ | CH | |
| C₂H₅ | O(CH₂)₂CH₃ | H | OCH₃ | OCH₂CF₃ | N | |
| C₂H₅ | O(CH₂)₂CH₃ | H | OCH₃ | OCH₂CHF₂ | CH | |
| C₂H₅ | O(CH₂)₂CH₃ | H | OCH₃ | OCH₂CHF₂ | N | |
| C₂H₅ | O(CH₂)₂CH₃ | H | CH₃ | OCH₂CHF₂ | N | |
| C₂H₅ | O(CH₂)₂CH₃ | H | OCH₃ | OCH₂CH₂F | CH | |
| C₂H₅ | O(CH₂)₂CH₃ | H | OCH₃ | OCH₂CH₂F | N | |
| C₂H₅ | O(CH₂)₂CH₃ | CH₃ | OCH₃ | OCH₃ | CH | |
| C₂H₅ | O(CH₂)₂CH₃ | CH₃ | CH₃ | OCH₃ | N | |
| C₂H₅ | O(CH₂)₂CH₃ | CH₃ | OCH₃ | OCH₃ | N | |
| n-C₃H₇ | O(CH₂)₂CH₃ | H | OCH₃ | OCH₃ | CH | |
| n-C₃H₇ | O(CH₂)₂CH₃ | H | CH₃ | OCH₃ | N | |
| CH(CH₃)₂ | O(CH₂)₂CH₃ | H | OCH₃ | CH₃ | CH | |
| CH(CH₃)₂ | O(CH₂)₂CH₃ | H | OCH₃ | OCH₃ | CH | |
| CH(CH₃)₂ | O(CH₂)₂CH₃ | H | Cl | OCH₃ | CH | |
| CH(CH₃)₂ | O(CH₂)₂CH₃ | H | OCH₃ | CH₃ | N | |
| CH(CH₃)₂ | O(CH₂)₂CH₃ | H | OCH₃ | OCH₃ | N | |
| CH(CH₃)₂ | O(CH₂)₂CH₃ | H | OCH₃ | N(CH₃)₂ | N | |
| CH₃ | OCH(CH₃)₂ | H | CH₃ | CH₃ | CH | 165–168 (d) |
| CH₃ | OCH(CH₃)₂ | H | OCH₃ | CH₃ | CH | 143–146 (d) |
| CH₃ | OCH(CH₃)₂ | H | OCH₃ | OCH₃ | CH | 170–172 (d) |
| CH₃ | OCH(CH₃)₂ | H | Cl | OCH₃ | CH | 148–152 (d) |
| CH₃ | OCH(CH₃)₂ | H | OCH₃ | CH₃ | N | 132–134 (d) |
| CH₃ | OCH(CH₃)₂ | H | OCH₃ | OCH₃ | N | 156–159 (d) |
| CH₃ | OCH(CH₃)₂ | H | OCH₃ | N(CH₃)₂ | N | |
| C₂H₅ | OCH(CH₃)₂ | H | Cl | OCH₃ | CH | |
| C₂H₅ | OCH(CH₃)₂ | H | OCH₃ | CH₃ | N | 129–135 |
| C₂H₅ | OCH(CH₃)₂ | H | OCH₃ | OCH₃ | CH | 150–155 |
| C₂H₅ | OCH(CH₃)₂ | H | OCH₃ | CH₃ | CH | 127–133 |
| C₂H₅ | OCH(CH₃)₂ | H | CH₃ | CH₃ | CH | 165–168 |
| C₂H₅ | OCH(CH₃)₂ | H | OCH₃ | OCH₃ | N | 168–194 |
| CH₃ | O(CH₂)₃CH₃ | H | CH₃ | CH₃ | CH | |
| CH₃ | O(CH₂)₃CH₃ | H | OCH₃ | CH₃ | CH | |
| CH₃ | O(CH₂)₃CH₃ | H | OCH₃ | OCH₃ | CH | |
| CH₃ | O(CH₂)₃CH₃ | H | Cl | OCH₃ | CH | |
| CH₃ | O(CH₂)₃CH₃ | H | CH₃ | CH₃ | N | |
| CH₃ | O(CH₂)₃CH₃ | H | OCH₃ | CH₃ | N | |
| CH₃ | O(CH₂)₃CH₃ | H | OCH₃ | OCH₃ | N | |
| CH₃ | O(CH₂)₃CH₃ | H | OCH₃ | N(CH₃)₂ | CH | |
| CH₃ | O(CH₂)₃CH₃ | H | OCH₃ | N(CH₃)₂ | N | |
| CH₃ | O(CH₂)₃CH₃ | H | OCH₃ | OCH₂CF₃ | N | |
| CH₃ | O(CH₂)₃CH₃ | CH₃ | OCH₃ | CH₃ | N | |
| CH₃ | O(CH₂)₃CH₃ | CH₃ | OCH₃ | OCH₃ | N | |
| CH₃ | O(CH₂)₃CH₃ | CH₃ | CH₃ | OCH₃ | CH | |
| CH₃ | O(CH₂)₃CH₃ | CH₃ | OCH₃ | OCH₃ | CH | |
| CH₃ | O(CH₂)₃CH₃ | H | Br | OCH₃ | CH | |
| CH₃ | O(CH₂)₃CH₃ | H | CH₃ | OCH₂CF₃ | N | |
| CH₃ | O(CH₂)₃CH₃ | H | CH₃ | OCH₂CF₃ | CH | |
| CH₃ | O(CH₂)₃CH₃ | H | OCH₃ | OCH₂CF₃ | CH | |
| CH₃ | O(CH₂)₃CH₃ | H | OCH₃ | NHCH₃ | N | |
| C₂H₅ | O(CH₂)₃CH₃ | H | CH₃ | CH₃ | CH | |
| C₂H₅ | O(CH₂)₃CH₃ | H | OCH₃ | CH₃ | CH | |
| C₂H₅ | O(CH₂)₃CH₃ | H | OCH₃ | OCH₃ | CH | |
| C₂H₅ | O(CH₂)₃CH₃ | H | Cl | OCH₃ | CH | |
| C₂H₅ | O(CH₂)₃CH₃ | H | OCH₃ | CH₃ | N | |
| C₂H₅ | O(CH₂)₃CH₃ | H | OCH₃ | N(CH₃)₂ | CH | |

TABLE I-continued

[Structure: benzene ring with CO₂R₁ and SO₂NHCON(R)- linked to pyrimidine/triazine ring with X, Y, Z substituents; R₂ on benzene]

| R₁ | R₂ | R | X | Y | Z | m.p. (°C.) |
|---|---|---|---|---|---|---|
| CH(CH₃)₂ | O(CH₂)₃CH₃ | H | OCH₃ | CH₃ | CH | |
| CH(CH₃)₂ | O(CH₂)₃CH₃ | H | OCH₃ | OCH₃ | CH | |
| CH(CH₃)₂ | O(CH₂)₃CH₃ | H | Cl | OCH₃ | CH | |
| CH(CH₃)₂ | O(CH₂)₃CH₃ | H | OCH₃ | CH₃ | N | |
| CH(CH₃)₂ | O(CH₂)₃CH₃ | H | OCH₃ | OCH₃ | N | |
| CH₃ | O(CH₂)₄CH₃ | H | CH₃ | CH₃ | CH | |
| CH₃ | O(CH₂)₄CH₃ | H | OCH₃ | CH₃ | CH | |
| CH₃ | O(CH₂)₄CH₃ | H | OCH₃ | OCH₃ | CH | |
| CH₃ | O(CH₂)₄CH₃ | H | Cl | OCH₃ | CH | |
| CH₃ | O(CH₂)₄CH₃ | H | CH₃ | CH₃ | N | |
| CH₃ | O(CH₂)₄CH₃ | H | OCH₃ | CH₃ | N | |
| CH₃ | O(CH₂)₄CH₃ | H | OCH₃ | OCH₃ | N | |
| CH₃ | O(CH₂)₄CH₃ | H | OCH₃ | N(CH₃)₂ | CH | |
| CH₃ | O(CH₂)₄CH₃ | H | OCH₃ | N(CH₃)₂ | N | |
| CH₃ | O(CH₂)₄CH₃ | H | OCH₃ | OCH₂CF₃ | N | |
| CH₃ | O(CH₂)₄CH₃ | CH₃ | OCH₃ | CH₃ | N | |
| CH₃ | O(CH₂)₄CH₃ | CH₃ | OCH₃ | OCH₃ | N | |
| CH₃ | O(CH₂)₄CH₃ | CH₃ | CH₃ | OCH₃ | CH | |
| CH₃ | O(CH₂)₄CH₃ | CH₃ | OCH₃ | OCH₃ | CH | |
| CH₃ | O(CH₂)₄CH₃ | H | Br | OCH₃ | CH | |
| CH₃ | O(CH₂)₄CH₃ | H | CH₃ | OCH₂CF₃ | N | |
| CH₃ | O(CH₂)₄CH₃ | H | CH₃ | OCH₂CF₃ | CH | |
| CH₃ | O(CH₂)₄CH₃ | H | OCH₃ | OCH₂CF₃ | CH | |
| CH₃ | O(CH₂)₄CH₃ | H | OCH₃ | NHCH₃ | N | |
| C₂H₅ | O(CH₂)₄CH₃ | H | CH₃ | CH₃ | CH | |
| C₂H₅ | O(CH₂)₄CH₃ | H | OCH₃ | CH₃ | CH | |
| C₂H₅ | O(CH₂)₄CH₃ | H | OCH₃ | OCH₃ | CH | |
| C₂H₅ | O(CH₂)₄CH₃ | H | Cl | OCH₃ | CH | |
| C₂H₅ | O(CH₂)₄CH₃ | H | OCH₃ | CH₃ | N | |
| C₂H₅ | O(CH₂)₄CH₃ | H | OCH₃ | N(CH₃)₂ | CH | |
| CH(CH₃)₂ | O(CH₂)₄CH₃ | H | OCH₃ | CH₃ | CH | |
| CH(CH₃)₂ | O(CH₂)₄CH₃ | H | OCH₃ | OCH₃ | CH | |
| CH(CH₃)₂ | O(CH₂)₄CH₃ | H | Cl | OCH₃ | CH | |
| CH(CH₃)₂ | O(CH₂)₄CH₃ | H | OCH₃ | CH₃ | N | |
| CH(CH₃)₂ | O(CH₂)₄CH₃ | H | OCH₃ | OCH₃ | N | |
| CH₃ | O(CH₂)₅CH₃ | H | CH₃ | CH₃ | CH | |
| CH₃ | O(CH₂)₅CH₃ | H | OCH₃ | CH₃ | CH | |
| CH₃ | O(CH₂)₅CH₃ | H | OCH₃ | OCH₃ | CH | |
| CH₃ | O(CH₂)₅CH₃ | H | Cl | OCH₃ | CH | |
| CH₃ | O(CH₂)₅CH₃ | H | CH₃ | CH₃ | N | |
| CH₃ | O(CH₂)₅CH₃ | H | OCH₃ | CH₃ | N | |
| CH₃ | O(CH₂)₅CH₃ | H | OCH₃ | OCH₃ | N | |
| CH₃ | O(CH₂)₅CH₃ | H | OCH₃ | N(CH₃)₂ | CH | |
| CH₃ | O(CH₂)₅CH₃ | H | OCH₃ | N(CH₃)₂ | N | |
| CH₃ | O(CH₂)₅CH₃ | H | OCH₃ | OCH₂CF₃ | N | |
| CH₃ | O(CH₂)₅CH₃ | CH₃ | OCH₃ | CH₃ | N | |
| CH₃ | O(CH₂)₅CH₃ | CH₃ | OCH₃ | OCH₃ | N | |
| CH₃ | O(CH₂)₅CH₃ | CH₃ | CH₃ | OCH₃ | CH | |
| CH₃ | O(CH₂)₅CH₃ | CH₃ | OCH₃ | OCH₃ | CH | |
| CH₃ | O(CH₂)₅CH₃ | H | Br | OCH₃ | CH | |
| CH₃ | O(CH₂)₅CH₃ | H | CH₃ | OCH₂CF₃ | N | |
| CH₃ | O(CH₂)₅CH₃ | H | CH₃ | OCH₂CF₃ | CH | |
| CH₃ | O(CH₂)₅CH₃ | H | OCH₃ | OCH₂CF₃ | CH | |
| CH₃ | O(CH₂)₅CH₃ | H | OCH₃ | NHCH₃ | N | |
| C₂H₅ | O(CH₂)₅CH₃ | H | CH₃ | CH₃ | CH | |
| C₂H₅ | O(CH₂)₅CH₃ | H | OCH₃ | CH₃ | CH | |
| C₂H₅ | O(CH₂)₅CH₃ | H | OCH₃ | OCH₃ | CH | |
| C₂H₅ | O(CH₂)₅CH₃ | H | Cl | OCH₃ | CH | |
| C₂H₅ | O(CH₂)₅CH₃ | H | OCH₃ | CH₃ | N | |
| C₂H₅ | O(CH₂)₅CH₃ | H | OCH₃ | N(CH₃)₂ | CH | |
| CH(CH₃)₂ | O(CH₂)₅CH₃ | H | OCH₃ | CH₃ | CH | |
| CH(CH₃)₂ | O(CH₂)₅CH₃ | H | OCH₃ | OCH₃ | CH | |
| CH(CH₃)₂ | O(CH₂)₅CH₃ | H | Cl | OCH₃ | CH | |
| CH(CH₃)₂ | O(CH₂)₅CH₃ | H | OCH₃ | CH₃ | N | |
| CH(CH₃)₂ | O(CH₂)₅CH₃ | H | OCH₃ | OCH₃ | N | |
| CH₃ | OCH₂CH(CH₃)₂ | H | CH₃ | OCH₃ | CH | |
| CH₃ | O(CH₂)CH(CH₃)₂ | H | OCH₃ | OCH₃ | N | |
| CH₃ | O(CH₂)₃CH(CH₃)₂ | H | CH₃ | OCH₃ | N | |
| CH₃ | OCH(CH₃)(C₂H₅) | H | OCH₃ | OCH₃ | CH | |
| CH₃ | OCH₂CH(CH₃)(C₂H₅) | H | CH₃ | OCH₃ | CH | |
| CH₃ | O(CH₂)₂CH(CH₃)(C₂H₅) | H | OCH₃ | OCH₃ | N | |

TABLE I-continued

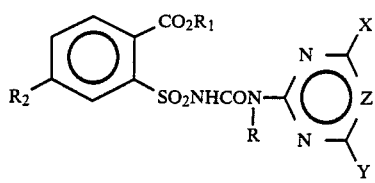

| $R_1$ | $R_2$ | R | X | Y | Z | m.p. (°C.) |
|---|---|---|---|---|---|---|
| $CH_3$ | $SCH_3$ | H | $OCH_3$ | $OCH_3$ | CH | 201–202 |
| $CH_3$ | $SC_2H_5$ | H | $CH_3$ | $CH_3$ | CH | 193–196 (d) |
| $CH_3$ | $SC_2H_5$ | H | $OCH_3$ | $CH_3$ | CH | 198–200 (d) |
| $CH_3$ | $SC_2H_5$ | H | $OCH_3$ | $OCH_3$ | CH | 193–195 (d) |
| $CH_3$ | $SC_2H_5$ | H | Cl | $OCH_3$ | CH | 205–208 (d) |
| $CH_3$ | $SC_2H_5$ | H | $OCH_3$ | $N(CH_3)_2$ | CH | |
| $CH_3$ | $SC_2H_5$ | H | $CH_3$ | $CH_3$ | N | |
| $CH_3$ | $SC_2H_5$ | H | $OCH_3$ | $CH_3$ | N | 185–187 (d) |
| $CH_3$ | $SC_2H_5$ | H | $OCH_3$ | $OCH_3$ | N | 201–204 (d) |
| $CH_3$ | $SC_2H_5$ | H | $OCH_3$ | $N(CH_3)_2$ | N | |
| $CH_3$ | $SC_2H_5$ | H | $OCH_3$ | $OCH_2CF_3$ | N | |
| $CH_3$ | $SC_2H_5$ | $CH_3$ | $OCH_3$ | $CH_3$ | N | |
| $CH_3$ | $SC_2H_5$ | $CH_3$ | $OCH_3$ | $OCH_3$ | N | |
| $CH_3$ | $SC_2H_5$ | $CH_3$ | $CH_3$ | $OCH_3$ | CH | |
| $CH_3$ | $SC_2H_5$ | $CH_3$ | $OCH_3$ | $OCH_3$ | CH | |
| $CH_3$ | $SC_2H_5$ | H | Br | $OCH_3$ | CH | |
| $CH_3$ | $SC_2H_5$ | $CH_3$ | $OCH_3$ | $N(CH_3)_2$ | N | |
| $CH_3$ | $SC_2H_5$ | H | $CH_3$ | $OCH_2CF_3$ | N | |
| $CH_3$ | $SC_2H_5$ | H | $CH_3$ | $OCH_2CF_3$ | CH | |
| $CH_3$ | $SC_2H_5$ | H | $OCH_3$ | $OCH_2CF_3$ | CH | |
| $CH_3$ | $SC_2H_5$ | H | $OCH_3$ | $C_2H_5$ | CH | |
| $CH_3$ | $SC_2H_5$ | H | $OCH_3$ | $C_2H_5$ | N | |
| $CH_3$ | $SC_2H_5$ | H | $OCH_3$ | $NHCH_3$ | CH | |
| $CH_3$ | $SC_2H_5$ | H | $OCH_3$ | $NHCH_3$ | N | |
| $CH_3$ | $SC_2H_5$ | H | $CH_3$ | $OC_2H_5$ | CH | |
| $CH_3$ | $SC_2H_5$ | H | $OCH_3$ | $OC_2H_5$ | CH | |
| $CH_3$ | $SC_2H_5$ | H | $CH_3$ | $OC_2H_5$ | N | |
| $CH_3$ | $SC_2H_5$ | H | $OCH_3$ | $OC_2H_5$ | N | |
| $CH_3$ | $SC_2H_5$ | H | $CH_3$ | $OCH_2CHF_2$ | CH | |
| $CH_3$ | $SC_2H_5$ | H | $OCH_3$ | $OCH_2CHF_2$ | CH | |
| $CH_3$ | $SC_2H_5$ | H | $CH_3$ | $OCH_2CHF_2$ | N | |
| $CH_3$ | $SC_2H_5$ | H | $OCH_3$ | $OCH_2CHF_2$ | N | |
| $CH_3$ | $SC_2H_5$ | H | $CH_3$ | $OCH_2CH_2F$ | CH | |
| $CH_3$ | $SC_2H_5$ | H | $OCH_3$ | $OCH_2CH_2F$ | CH | |
| $CH_3$ | $SC_2H_5$ | H | $CH_3$ | $OCH_2CH_2F$ | N | |
| $CH_3$ | $SC_2H_5$ | $CH_3$ | $OCH_3$ | $OCH_2CH_2F$ | N | |
| $CH_3$ | $SC_2H_5$ | $CH_3$ | Cl | $OCH_3$ | CH | |
| $CH_3$ | $SC_2H_5$ | H | Cl | $N(CH_3)_2$ | CH | |
| $CH_3$ | $SC_2H_5$ | H | Cl | $OC_2H_5$ | CH | |
| $C_2H_5$ | $SC_2H_5$ | H | $CH_3$ | $CH_3$ | CH | 158–160 (d) |
| $C_2H_5$ | $SC_2H_5$ | H | $OCH_3$ | $CH_3$ | CH | 105–107 (d) |
| $C_2H_5$ | $SC_2H_5$ | H | $OCH_3$ | $OCH_3$ | CH | 198–200 (d) |
| $C_2H_5$ | $SC_2H_5$ | H | Cl | $OCH_3$ | CH | 97–103 (d) |
| $C_2H_5$ | $SC_2H_5$ | H | $CH_3$ | $CH_3$ | N | |
| $C_2H_5$ | $SC_2H_5$ | H | $OCH_3$ | $CH_3$ | N | 170–172 (d) |
| $C_2H_5$ | $SC_2H_5$ | H | $OCH_3$ | $OCH_3$ | N | 155–157 (d) |
| $C_2H_5$ | $SC_2H_5$ | H | Br | $OCH_3$ | CH | |
| $C_2H_5$ | $SC_2H_5$ | H | $OCH_3$ | $N(CH_3)_2$ | CH | |
| $C_2H_5$ | $SC_2H_5$ | H | $OCH_3$ | $N(CH_3)_2$ | N | |
| $C_2H_5$ | $SC_2H_5$ | H | $OCH_3$ | $NHCH_3$ | N | |
| $C_2H_5$ | $SC_2H_5$ | H | $OCH_3$ | $C_2H_5$ | CH | |
| $C_2H_5$ | $SC_2H_5$ | H | $OCH_3$ | $C_2H_5$ | N | |
| $C_2H_5$ | $SC_2H_5$ | H | $CH_3$ | $OC_2H_5$ | CH | |
| $C_2H_5$ | $SC_2H_5$ | H | $CH_3$ | $OC_2H_5$ | N | |
| $C_2H_5$ | $SC_2H_5$ | H | $OCH_3$ | $OC_2H_5$ | CH | |
| $C_2H_5$ | $SC_2H_5$ | H | $OCH_3$ | $OC_2H_5$ | N | |
| $C_2H_5$ | $SC_2H_5$ | H | $CH_3$ | $OCH_2CF_3$ | CH | |
| $C_2H_5$ | $SC_2H_5$ | H | $CH_3$ | $OCH_2CF_3$ | N | |
| $C_2H_5$ | $SC_2H_5$ | H | $OCH_3$ | $OCH_2CF_3$ | CH | |
| $C_2H_5$ | $SC_2H_5$ | H | $OCH_3$ | $OCH_2CF_3$ | N | |
| $C_2H_5$ | $SC_2H_5$ | H | $OCH_3$ | $OCH_2CHF_2$ | CH | |
| $C_2H_5$ | $SC_2H_5$ | H | $OCH_3$ | $OCH_2CHF_2$ | N | |
| $C_2H_5$ | $SC_2H_5$ | H | $CH_3$ | $OCH_2CHF_2$ | N | |
| $C_2H_5$ | $SC_2H_5$ | H | $OCH_3$ | $OCH_2CH_2F$ | CH | |
| $C_2H_5$ | $SC_2H_5$ | H | $OCH_3$ | $OCH_2CH_2F$ | N | |
| $C_2H_5$ | $SC_2H_5$ | $CH_3$ | $OCH_3$ | $OCH_3$ | CH | |
| $C_2H_5$ | $SC_2H_5$ | $CH_3$ | $CH_3$ | $OCH_3$ | N | |
| $C_2H_5$ | $SC_2H_5$ | $CH_3$ | $OCH_3$ | $OCH_3$ | N | |
| $n$-$C_3H_7$ | $SC_2H_5$ | H | $OCH_3$ | $OCH_3$ | CH | |
| $n$-$C_3H_7$ | $SC_2H_5$ | H | $CH_3$ | $OCH_3$ | N | |
| $CH(CH_3)_2$ | $SC_2H_5$ | H | $OCH_3$ | $CH_3$ | CH | |

TABLE I-continued

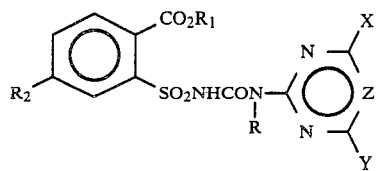

| R$_1$ | R$_2$ | R | X | Y | Z | m.p. (°C.) |
|---|---|---|---|---|---|---|
| CH(CH$_3$)$_2$ | SC$_2$H$_5$ | H | OCH$_3$ | OCH$_3$ | CH | |
| CH(CH$_3$)$_2$ | SC$_2$H$_5$ | H | Cl | OCH$_3$ | CH | |
| CH(CH$_3$)$_2$ | SC$_2$H$_5$ | H | OCH$_3$ | CH$_3$ | N | |
| CH(CH$_3$)$_2$ | SC$_2$H$_5$ | H | OCH$_3$ | OCH$_3$ | N | |
| CH(CH$_3$)$_2$ | SC$_2$H$_5$ | H | OCH$_3$ | N(CH$_3$)$_2$ | N | |
| CH$_3$ | S(CH$_2$)$_2$CH$_3$ | H | CH$_3$ | CH$_3$ | CH | 122–125 (d) |
| CH$_3$ | S(CH$_2$)$_2$CH$_3$ | H | OCH$_3$ | CH$_3$ | CH | 128–130 (d) |
| CH$_3$ | S(CH$_2$)$_2$CH$_3$ | H | OCH$_3$ | OCH$_3$ | CH | 101–104 (d) |
| CH$_3$ | S(CH$_2$)$_2$CH$_3$ | H | Cl | OCH$_3$ | CH | 137–139 (d) |
| CH$_3$ | S(CH$_2$)$_2$CH$_3$ | H | OCH$_3$ | N(CH$_3$)$_2$ | CH | |
| CH$_3$ | S(CH$_2$)$_2$CH$_3$ | H | CH$_3$ | CH$_3$ | N | |
| CH$_3$ | S(CH$_2$)$_2$CH$_3$ | H | OCH$_3$ | CH$_3$ | N | 138–140 (d) |
| CH$_3$ | S(CH$_2$)$_2$CH$_3$ | H | OCH$_3$ | OCH$_3$ | N | 111–114 (d) |
| CH$_3$ | S(CH$_2$)$_2$CH$_3$ | H | OCH$_3$ | N(CH$_3$)$_2$ | N | |
| CH$_3$ | S(CH$_2$)$_2$CH$_3$ | H | OCH$_3$ | OCH$_2$CF$_3$ | N | |
| CH$_3$ | S(CH$_2$)$_2$CH$_3$ | CH$_3$ | OCH$_3$ | CH$_3$ | N | |
| CH$_3$ | S(CH$_2$)$_2$CH$_3$ | CH$_3$ | OCH$_3$ | OCH$_3$ | N | |
| CH$_3$ | S(CH$_2$)$_2$CH$_3$ | CH$_3$ | CH$_3$ | OCH$_3$ | CH | |
| CH$_3$ | S(CH$_2$)$_2$CH$_3$ | CH$_3$ | OCH$_3$ | OCH$_3$ | CH | |
| CH$_3$ | S(CH$_2$)$_2$CH$_3$ | H | Br | OCH$_3$ | CH | |
| CH$_3$ | S(CH$_2$)$_2$CH$_3$ | CH$_3$ | OCH$_3$ | N(CH$_3$)$_2$ | N | |
| CH$_3$ | S(CH$_2$)$_2$CH$_3$ | H | CH$_3$ | OCH$_2$CF$_3$ | N | |
| CH$_3$ | S(CH$_2$)$_2$CH$_3$ | H | CH$_3$ | OCH$_2$CF$_3$ | CH | |
| CH$_3$ | S(CH$_2$)$_2$CH$_3$ | H | OCH$_3$ | OCH$_2$CF$_3$ | CH | |
| CH$_3$ | S(CH$_2$)$_2$CH$_3$ | H | OCH$_3$ | C$_2$H$_5$ | CH | |
| CH$_3$ | S(CH$_2$)$_2$CH$_3$ | H | OCH$_3$ | C$_2$H$_5$ | N | |
| CH$_3$ | S(CH$_2$)$_2$CH$_3$ | H | OCH$_3$ | NHCH$_3$ | CH | |
| CH$_3$ | S(CH$_2$)$_2$CH$_3$ | H | OCH$_3$ | NHCH$_3$ | N | |
| CH$_3$ | S(CH$_2$)$_2$CH$_3$ | H | CH$_3$ | OC$_2$H$_5$ | CH | |
| CH$_3$ | S(CH$_2$)$_2$CH$_3$ | H | OCH$_3$ | OC$_2$H$_5$ | CH | |
| CH$_3$ | S(CH$_2$)$_2$CH$_3$ | H | CH$_3$ | OC$_2$H$_5$ | N | |
| CH$_3$ | S(CH$_2$)$_2$CH$_3$ | H | OCH$_3$ | OC$_2$H$_5$ | N | |
| CH$_3$ | S(CH$_2$)$_2$CH$_3$ | H | CH$_3$ | OCH$_2$CHF$_2$ | CH | |
| CH$_3$ | S(CH$_2$)$_2$CH$_3$ | H | OCH$_3$ | OCH$_2$CHF$_2$ | CH | |
| CH$_3$ | S(CH$_2$)$_2$CH$_3$ | H | CH$_3$ | OCH$_2$CHF$_2$ | N | |
| CH$_3$ | S(CH$_2$)$_2$CH$_3$ | H | OCH$_3$ | OCH$_2$CHF$_2$ | N | |
| CH$_3$ | S(CH$_2$)$_2$CH$_3$ | H | CH$_3$ | OCH$_2$CH$_2$F | CH | |
| CH$_3$ | S(CH$_2$)$_2$CH$_3$ | H | OCH$_3$ | OCH$_2$CH$_2$F | CH | |
| CH$_3$ | S(CH$_2$)$_2$CH$_3$ | H | CH$_3$ | OCH$_2$CH$_2$F | N | |
| CH$_3$ | S(CH$_2$)$_2$CH$_3$ | CH$_3$ | OCH$_3$ | OCH$_2$CH$_2$F | N | |
| CH$_3$ | S(CH$_2$)$_2$CH$_3$ | CH$_3$ | Cl | OCH$_3$ | CH | |
| CH$_3$ | S(CH$_2$)$_2$CH$_3$ | H | Cl | N(CH$_3$)$_2$ | CH | |
| CH$_3$ | S(CH$_2$)$_2$CH$_3$ | H | Cl | OC$_2$H$_5$ | CH | |
| C$_2$H$_5$ | S(CH$_2$)$_2$CH$_3$ | H | CH$_3$ | CH$_3$ | CH | 142–143 (d) |
| C$_2$H$_5$ | S(CH$_2$)$_2$CH$_3$ | H | OCH$_3$ | CH$_3$ | CH | 109–114 (d) |
| C$_2$H$_5$ | S(CH$_2$)$_2$CH$_3$ | H | OCH$_3$ | OCH$_3$ | CH | 130–133 (d) |
| C$_2$H$_5$ | S(CH$_2$)$_2$CH$_3$ | H | Cl | OCH$_3$ | CH | 98–100 (d) |
| C$_2$H$_5$ | S(CH$_2$)$_2$CH$_3$ | H | CH$_3$ | CH$_3$ | N | |
| C$_2$H$_5$ | S(CH$_2$)$_2$CH$_3$ | H | OCH$_3$ | CH$_3$ | N | 100–103 (d) |
| C$_2$H$_5$ | S(CH$_2$)$_2$CH$_3$ | H | OCH$_3$ | OCH$_3$ | N | 108–110 (d) |
| C$_2$H$_5$ | S(CH$_2$)$_2$CH$_3$ | H | Br | OCH$_3$ | CH | |
| C$_2$H$_5$ | S(CH$_2$)$_2$CH$_3$ | H | OCH$_3$ | N(CH$_3$)$_2$ | CH | |
| C$_2$H$_5$ | S(CH$_2$)$_2$CH$_3$ | H | OCH$_3$ | N(CH$_3$)$_2$ | N | |
| C$_2$H$_5$ | S(CH$_2$)$_2$CH$_3$ | H | OCH$_3$ | NHCH$_3$ | N | |
| C$_2$H$_5$ | S(CH$_2$)$_2$CH$_3$ | H | OCH$_3$ | C$_2$H$_5$ | CH | |
| C$_2$H$_5$ | S(CH$_2$)$_2$CH$_3$ | H | OCH$_3$ | C$_2$H$_5$ | N | |
| C$_2$H$_5$ | S(CH$_2$)$_2$CH$_3$ | H | CH3 | OC$_2$H$_5$ | CH | |
| C$_2$H$_5$ | S(CH$_2$)$_2$CH$_3$ | H | CH$_3$ | OC$_2$H$_5$ | N | |
| C$_2$H$_5$ | S(CH$_2$)$_2$CH$_3$ | H | OCH$_3$ | OC$_2$H$_5$ | CH | |
| C$_2$H$_5$ | S(CH$_2$)$_2$CH$_3$ | H | OCH$_3$ | OC$_2$H$_5$ | N | |
| C$_2$H$_5$ | S(CH$_2$)$_2$CH$_3$ | H | CH$_3$ | OCH$_2$CF$_3$ | CH | |
| C$_2$H$_5$ | S(CH$_2$)$_2$CH$_3$ | H | CH$_3$ | OCH$_2$CF$_3$ | N | |
| C$_2$H$_5$ | S(CH$_2$)$_2$CH$_3$ | H | OCH$_3$ | OCH$_2$CF$_3$ | CH | |
| C$_2$H$_5$ | S(CH$_2$)$_2$CH$_3$ | H | OCH$_3$ | OCH$_2$CF$_3$ | N | |
| C$_2$H$_5$ | S(CH$_2$)$_2$CH$_3$ | H | CH$_3$ | OCH$_2$CHF$_2$ | CH | |
| C$_2$H$_5$ | S(CH$_2$)$_2$CH$_3$ | H | OCH$_3$ | OCH$_2$CHF$_2$ | CH | |
| C$_2$H$_5$ | S(CH$_2$)$_2$CH$_3$ | H | CH$_3$ | OCH$_2$CHF$_2$ | N | |
| C$_2$H$_5$ | S(CH$_2$)$_2$CH$_3$ | H | OCH$_3$ | OCH$_2$CH$_2$F | CH | |
| C$_2$H$_5$ | S(CH$_2$)$_2$CH$_3$ | H | OCH$_3$ | OCH$_2$CH$_2$F | N | |
| C$_2$H$_5$ | S(CH$_2$)$_2$CH$_3$ | CH$_3$ | OCH$_3$ | OCH$_3$ | CH | |
| C$_2$H$_5$ | S(CH$_2$)$_2$CH$_3$ | CH$_3$ | CH$_3$ | OCH$_3$ | N | |

TABLE I-continued

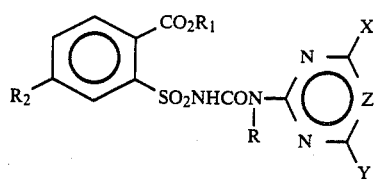

| R₁ | R₂ | R | X | Y | Z | m.p. (°C.) |
|---|---|---|---|---|---|---|
| C₂H₅ | S(CH₂)₂CH₃ | CH₃ | OCH₃ | OCH₃ | N | |
| n-C₃H₇ | S(CH₂)₂CH₃ | H | OCH₃ | OCH₃ | CH | |
| n-C₃H₇ | S(CH₂)₂CH₃ | H | CH₃ | OCH₃ | N | |
| CH(CH₃)₂ | S(CH₂)₂CH₃ | H | OCH₃ | CH₃ | CH | |
| CH(CH₃)₂ | S(CH₂)₂CH₃ | H | OCH₃ | OCH₃ | CH | |
| CH(CH₃)₂ | S(CH₂)₂CH₃ | H | Cl | OCH₃ | CH | |
| CH(CH₃)₂ | S(CH₂)₂CH₃ | H | OCH₃ | CH₃ | N | |
| CH(CH₃)₂ | S(CH₂)₂CH₃ | H | OCH₃ | OCH₃ | N | |
| CH(CH₃)₂ | S(CH₂)₂CH₃ | H | OCH₃ | N(CH₃)₂ | N | |
| CH₃ | SCH(CH₃)₂ | H | CH₃ | CH₃ | CH | 147–149 (d) |
| CH₃ | SCH(CH₃)₂ | H | OCH₃ | CH₃ | CH | 107–109 (d) |
| CH₃ | SCH(CH₃)₂ | H | OCH₃ | OCH₃ | CH | 114–117 (d) |
| CH₃ | SCH(CH₃)₂ | H | Cl | OCH₃ | CH | 144–145 (d) |
| CH₃ | SCH(CH₃)₂ | H | OCH₃ | CH₃ | N | 124–126 (d) |
| CH₃ | SCH(CH₃)₂ | H | OCH₃ | OCH₃ | N | 134–136 (d) |
| C₂H₅ | SCH(CH₃)₂ | H | OCH₃ | CH₃ | CH | 162–163 (d) |
| C₂H₅ | SCH(CH₃)₂ | H | OCH₃ | OCH₃ | CH | 87–90 (d) |
| C₂H₅ | SCH(CH₃)₂ | H | OCH₃ | Cl | CH | 152–154 (d) |
| C₂H₅ | SCH(CH₃)₂ | H | OCH₃ | CH₃ | N | |
| C₂H₅ | SCH(CH₃)₂ | H | OCH₃ | OCH₃ | N | 110–113 (d) |
| CH₃ | S(CH₂)₃CH₃ | H | CH₃ | CH₃ | CH | |
| CH₃ | S(CH₂)₃CH₃ | H | OCH₃ | CH₃ | CH | |
| CH₃ | S(CH₂)₃CH₃ | H | OCH₃ | OCH₃ | CH | |
| CH₃ | S(CH₂)₃CH₃ | H | Cl | OCH₃ | CH | |
| CH₃ | S(CH₂)₃CH₃ | H | CH₃ | CH₃ | N | |
| CH₃ | S(CH₂)₃CH₃ | H | OCH₃ | CH₃ | N | |
| CH₃ | S(CH₂)₃CH₃ | H | OCH₃ | OCH₃ | N | |
| CH₃ | S(CH₂)₃CH₃ | H | OCH₃ | N(CH₃)₂ | CH | |
| CH₃ | S(CH₂)₃CH₃ | H | OCH₃ | N(CH₃)₂ | N | |
| CH₃ | S(CH₂)₃CH₃ | H | OCH₃ | OCH₂CF₃ | N | |
| CH₃ | S(CH₂)₃CH₃ | CH₃ | OCH₃ | CH₃ | N | |
| CH₃ | S(CH₂)₃CH₃ | CH₃ | OCH₃ | OCH₃ | N | |
| CH₃ | S(CH₂)₃CH₃ | CH₃ | CH₃ | OCH₃ | CH | |
| CH₃ | S(CH₂)₃CH₃ | CH₃ | OCH₃ | OCH₃ | CH | |
| CH₃ | S(CH₂)₃CH₃ | H | Br | OCH₃ | CH | |
| CH₃ | S(CH₂)₃CH₃ | H | CH₃ | OCH₂CF₃ | N | |
| CH₃ | S(CH₂)₃CH₃ | H | CH₃ | OCH₂CF₃ | CH | |
| CH₃ | S(CH₂)₃CH₃ | H | OCH₃ | OCH₂CF₃ | CH | |
| CH₃ | S(CH₂)₃CH₃ | H | OCH₃ | NHCH₃ | N | |
| C₂H₅ | S(CH₂)₃CH₃ | H | CH₃ | CH₃ | CH | |
| C₂H₅ | S(CH₂)₃CH₃ | H | OCH₃ | CH₃ | CH | |
| C₂H₅ | S(CH₂)₃CH₃ | H | OCH₃ | OCH₃ | CH | |
| C₂H₅ | S(CH₂)₃CH₃ | H | Cl | OCH₃ | CH | |
| C₂H₅ | S(CH₂)₃CH₃ | H | OCH₃ | CH₃ | N | |
| C₂H₅ | S(CH₂)₃CH₃ | H | OCH₃ | N(CH₃)₂ | CH | |
| CH(CH₃)₂ | S(CH₂)₃CH₃ | H | OCH₃ | CH₃ | CH | |
| CH(CH₃)₂ | S(CH₂)₃CH₃ | H | OCH₃ | OCH₃ | CH | |
| CH(CH₃)₂ | S(CH₂)₃CH₃ | H | Cl | OCH₃ | CH | |
| CH(CH₃)₂ | S(CH₂)₃CH₃ | H | OCH₃ | CH₃ | N | |
| CH(CH₃)₂ | S(CH₂)₃CH₃ | H | OCH₃ | OCH₃ | N | |
| CH₃ | SC(CH₃)₃ | H | OCH₃ | OCH₃ | N | 160–162 (d) |
| CH₃ | SC(CH₃)₃ | H | OCH₃ | CH₃ | N | 158–159 (d) |
| CH₃ | SC(CH₃)₃ | H | OCH₃ | OCH₃ | CH | 157–158 (d) |
| CH₃ | SC(CH₃)₃ | H | OCH₃ | CH₃ | CH | 113–115 |
| CH₃ | SC(CH₃)₃ | H | Cl | OCH₃ | CH | 105–107 (d) |
| CH₃ | SC(CH₃)₃ | H | CH₃ | CH₃ | CH | 170–173 (d) |
| C₂H₅ | SC(CH₃)₃ | H | OCH₃ | OCH₃ | N | |
| C₂H₅ | SC(CH₃)₃ | H | OCH₃ | CH₃ | N | |
| C₂H₅ | SC(CH₃)₃ | H | OCH₃ | OCH₃ | CH | |
| C₂H₅ | SC(CH₃)₃ | H | OCH₃ | CH₃ | CH | |
| C₂H₅ | SC(CH₃)₃ | H | Cl | OCH₃ | CH | |
| C₂H₅ | SC(CH₃)₃ | H | CH₃ | CH₃ | CH | |
| CH₃ | S(CH₂)₄CH₃ | H | CH₃ | CH₃ | CH | |
| CH₃ | S(CH₂)₄CH₃ | H | OCH₃ | CH₃ | CH | |
| CH₃ | S(CH₂)₄CH₃ | H | OCH₃ | OCH₃ | CH | |
| CH₃ | S(CH₂)₄CH₃ | H | Cl | OCH₃ | CH | |
| CH₃ | S(CH₂)₄CH₃ | H | CH₃ | CH₃ | N | |
| CH₃ | S(CH₂)₄CH₃ | H | OCH₃ | CH₃ | N | |
| CH₃ | S(CH₂)₄CH₃ | H | OCH₃ | OCH₃ | N | |
| CH₃ | S(CH₂)₄CH₃ | H | OCH₃ | N(CH₃)₂ | CH | |
| CH₃ | S(CH₂)₄CH₃ | H | OCH₃ | N(CH₃)₂ | N | |

TABLE I-continued

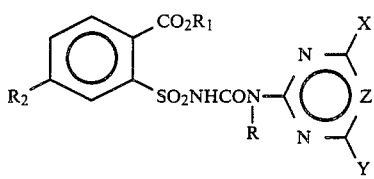

| R₁ | R₂ | R | X | Y | Z | m.p. (°C.) |
|---|---|---|---|---|---|---|
| CH₃ | S(CH₂)₄CH₃ | H | OCH₃ | OCH₂CF₃ | N | |
| CH₃ | S(CH₂)₄CH₃ | CH₃ | OCH₃ | CH₃ | N | |
| CH₃ | S(CH₂)₄CH₃ | CH₃ | OCH₃ | OCH₃ | N | |
| CH₃ | S(CH₂)₄CH₃ | CH₃ | CH₃ | OCH₃ | CH | |
| CH₃ | S(CH₂)₄CH₃ | CH₃ | OCH₃ | OCH₃ | CH | |
| CH₃ | S(CH₂)₄CH₃ | H | Br | OCH₃ | CH | |
| CH₃ | S(CH₂)₄CH₃ | H | CH₃ | OCH₂CF₃ | N | |
| CH₃ | S(CH₂)₄CH₃ | H | CH₃ | OCH₂CF₃ | CH | |
| CH₃ | S(CH₂)₄CH₃ | H | OCH₃ | OCH₂CF₃ | CH | |
| CH₃ | S(CH₂)₄CH₃ | H | OCH₃ | NHCH₃ | N | |
| C₂H₅ | S(CH₂)₄CH₃ | H | CH₃ | CH₃ | CH | |
| C₂H₅ | S(CH₂)₄CH₃ | H | OCH₃ | CH₃ | CH | |
| C₂H₅ | S(CH₂)₄CH₃ | H | OCH₃ | OCH₃ | CH | |
| C₂H₅ | S(CH₂)₄CH₃ | H | Cl | OCH₃ | CH | |
| C₂H₅ | S(CH₂)₄CH₃ | H | OCH₃ | CH₃ | N | |
| C₂H₅ | S(CH₂)₄CH₃ | H | OCH₃ | N(CH₃)₂ | CH | |
| CH(CH₃)₂ | S(CH₂)₄CH₃ | H | OCH₃ | CH₃ | CH | |
| CH(CH₃)₂ | S(CH₂)₄CH₃ | H | OCH₃ | OCH₃ | CH | |
| CH(CH₃)₂ | S(CH₂)₄CH₃ | H | Cl | OCH₃ | CH | |
| CH(CH₃)₂ | S(CH₂)₄CH₃ | H | OCH₃ | CH₃ | N | |
| CH(CH₃)₂ | S(CH₂)₄CH₃ | H | OCH₃ | OCH₃ | N | |
| CH₃ | S(CH₂)₅CH₃ | H | CH₃ | CH₃ | CH | 160–167 |
| CH₃ | S(CH₂)₅CH₃ | H | OCH₃ | CH₃ | CH | 190–195 (d) |
| CH₃ | S(CH₂)₅CH₃ | H | OCH₃ | OCH₃ | CH | 185–191 (d) |
| CH₃ | S(CH₂)₅CH₃ | H | Cl | OCH₃ | CH | 108–113 (d) |
| CH₃ | S(CH₂)₅CH₃ | H | CH₃ | CH₃ | N | |
| CH₃ | S(CH₂)₅CH₃ | H | OCH₃ | CH₃ | N | 89–95 (d) |
| CH₃ | S(CH₂)₅CH₃ | H | OCH₃ | OCH₃ | N | 90–95 (d) |
| CH₃ | S(CH₂)₅CH₃ | H | OCH₃ | N(CH₃)₂ | CH | |
| CH₃ | S(CH₂)₅CH₃ | H | OCH₃ | N(CH₃)₂ | N | |
| CH₃ | S(CH₂)₅CH₃ | H | OCH₃ | OCH₂CF₃ | N | |
| CH₃ | S(CH₂)₅CH₃ | CH₃ | OCH₃ | CH₃ | N | |
| CH₃ | S(CH₂)₅CH₃ | CH₃ | OCH₃ | OCH₃ | N | |
| CH₃ | S(CH₂)₅CH₃ | CH₃ | CH₃ | OCH₃ | CH | |
| CH₃ | S(CH₂)₅CH₃ | CH₃ | OCH₃ | OCH₃ | CH | |
| CH₃ | S(CH₂)₅CH₃ | H | Br | OCH₃ | CH | |
| CH₃ | S(CH₂)₅CH₃ | H | CH₃ | OCH₂CF₃ | N | |
| CH₃ | S(CH₂)₅CH₃ | H | CH₃ | OCH₂CF₃ | CH | |
| CH₃ | S(CH₂)₅CH₃ | H | OCH₃ | OCH₂CF₃ | CH | |
| CH₃ | S(CH₂)₅CH₃ | H | OCH₃ | NHCH₃ | N | |
| C₂H₅ | S(CH₂)₅CH₃ | H | CH₃ | CH₃ | CH | |
| C₂H₅ | S(CH₂)₅CH₃ | H | OCH₃ | CH₃ | CH | |
| C₂H₅ | S(CH₂)₅CH₃ | H | OCH₃ | OCH₃ | CH | |
| C₂H₅ | S(CH₂)₅CH₃ | H | Cl | OCH₃ | CH | |
| C₂H₅ | S(CH₂)₅CH₃ | H | OCH₃ | OCH₃ | N | |
| C₂H₅ | S(CH₂)₅CH₃ | H | OCH₃ | CH₃ | N | |
| C₂H₅ | S(CH₂)₅CH₃ | H | OCH₃ | N(CH₃)₂ | CH | |
| CH(CH₃)₂ | S(CH₂)₅CH₃ | H | OCH₃ | CH₃ | CH | |
| CH(CH₃)₂ | S(CH₂)₅CH₃ | H | OCH₃ | OCH₃ | CH | |
| CH(CH₃)₂ | S(CH₂)₅CH₃ | H | Cl | OCH₃ | CH | |
| CH(CH₃)₂ | S(CH₂)₅CH₃ | H | OCH₃ | CH₃ | N | |
| CH(CH₃)₂ | S(CH₂)₅CH₃ | H | OCH₃ | OCH₃ | N | |
| CH₃ | SCH₂CH(CH₃)₂ | H | CH₃ | OCH₃ | CH | |
| CH₃ | S(CH₂)₂CH(CH₃)₂ | H | OCH₃ | OCH₃ | N | |
| CH₃ | S(CH₂)₃CH(CH₃)₂ | H | CH₃ | OCH₃ | N | |
| CH₃ | SCH(CH₃)(C₂H₅) | H | OCH₃ | OCH₃ | CH | |
| CH₃ | SCH₂CH(CH₃)(C₂H₅) | H | OCH₃ | OCH₃ | CH | |
| CH₃ | S(CH₂)₂CH(CH₃)(C₂H₅) | H | OCH₃ | OCH₃ | N | |
| CH₃ | S(CH₂)₇CH₃ | H | OCH₃ | OCH₃ | CH | |
| CH₃ | S(CH₂)₇CH₃ | H | OCH₃ | CH₃ | N | |
| CH₃ | SCH(CH₃)(n-C₆H₁₃) | H | OCH₃ | CH₃ | CH | |
| CH₃ | S-cyclohexyl | H | CH₃ | CH₃ | CH | |
| CH₃ | S-cyclohexyl | H | OCH₃ | CH₃ | CH | |
| CH₃ | S-cyclohexyl | H | OCH₃ | OCH₃ | CH | |
| CH₃ | S-cyclohexyl | H | Cl | OCH₃ | CH | |
| CH₃ | S-cyclohexyl | H | CH₃ | CH₃ | N | |
| CH₃ | S-cyclohexyl | H | OCH₃ | OCH₃ | N | |
| CH₃ | SC₆H₅ | H | CH₃ | OCH₃ | CH | |
| CH₃ | SC₆H₅ | H | OCH₃ | OCH₃ | CH | |
| CH₃ | SC₆H₅ | H | Cl | OCH₃ | CH | |
| CH₃ | SC₆H₅ | H | CH₃ | OCH₃ | N | |

TABLE I-continued

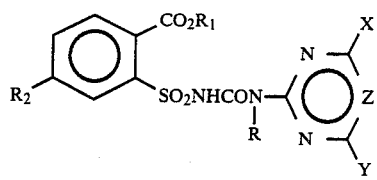

| R₁ | R₂ | R | X | Y | Z | m.p. (°C.) |
|---|---|---|---|---|---|---|
| CH₃ | SC₆H₅ | H | OCH₃ | OCH₃ | N | |
| CH₃ | SCH₂C₆H₅ | H | CH₃ | OCH₃ | CH | 187–189 |
| CH₃ | SCH₂C₆H₅ | H | OCH₃ | OCH₃ | CH | 186–188 |
| CH₃ | SCH₂C₆H₅ | H | Cl | OCH₃ | CH | 183–185 |
| CH₃ | SCH₂C₆H₅ | H | CH₃ | OCH₃ | N | 157–159 |
| CH₃ | SCH₂C₆H₅ | H | OCH₃ | OCH₃ | N | 145–147 |
| CH₃ | SCH₂C₆H₅ | H | CH₃ | CH₃ | CH | 196–198 |
| CH₃ | S(O)(CH₃) | H | CH₃ | CH₃ | CH | 119–120 (d) |
| CH₃ | S(O)(CH₃) | H | OCH₃ | CH₃ | CH | 160–161 (d) |
| CH₃ | S(O)(CH₃) | H | OCH₃ | OCH₃ | CH | 190–191 (d) |
| CH₃ | S(O)(CH₃) | H | Cl | OCH₃ | CH | 206–209 (d) |
| CH₃ | S(O)(CH₃) | H | OCH₃ | N(CH₃)₂ | CH | |
| CH₃ | S(O)(CH₃) | H | CH₃ | CH₃ | N | |
| CH₃ | S(O)(CH₃) | H | OCH₃ | CH₃ | N | 198–200 (d) |
| CH₃ | S(O)(CH₃) | H | OCH₃ | OCH₃ | N | 194–196 (d) |
| CH₃ | S(O)(CH₃) | H | OCH₃ | N(CH₃)₂ | N | |
| CH₃ | S(O)(CH₃) | H | OCH₃ | OCH₂CF₃ | N | |
| CH₃ | S(O)(CH₃) | CH₃ | OCH₃ | CH₃ | N | |
| CH₃ | S(O)(CH₃) | CH₃ | OCH₃ | OCH₃ | N | |
| CH₃ | S(O)(CH₃) | CH₃ | CH₃ | OCH₃ | CH | |
| CH₃ | S(O)(CH₃) | CH₃ | OCH₃ | OCH₃ | CH | |
| CH₃ | S(O)(CH₃) | H | Br | OCH₃ | CH | |
| CH₃ | S(O)(CH₃) | H | OCH₃ | N(CH₃)₂ | CH | |
| CH₃ | S(O)(CH₃) | CH₃ | OCH₃ | N(CH₃)₂ | N | |
| CH₃ | S(O)(CH₃) | H | CH₃ | OCH₂CF₃ | N | |
| CH₃ | S(O)(CH₃) | H | CH₃ | OCH₂CF₃ | CH | |
| CH₃ | S(O)(CH₃) | H | OCH₃ | OCH₂CF₃ | CH | |
| CH₃ | S(O)(CH₃) | H | OCH₃ | C₂H₅ | CH | |
| CH₃ | S(O)(CH₃) | H | OCH₃ | C₂H₅ | N | |
| CH₃ | S(O)(CH₃) | H | OCH₃ | NHCH₃ | CH | |
| CH₃ | S(O)(CH₃) | H | OCH₃ | NHCH₃ | N | |
| CH₃ | S(O)(CH₃) | H | CH₃ | OC₂H₅ | CH | |
| CH₃ | S(O)(CH₃) | H | OCH₃ | OC₂H₅ | CH | |
| CH₃ | S(O)(CH₃) | H | CH₃ | OC₂H₅ | N | |
| CH₃ | S(O)(CH₃) | H | OCH₃ | OC₂H₅ | N | |
| CH₃ | S(O)(CH₃) | H | CH₃ | OCH₂CHF₂ | CH | |
| CH₃ | S(O)(CH₃) | H | OCH₃ | OCH₂CHF₂ | CH | |
| CH₃ | S(O)(CH₃) | H | CH₃ | OCH₂CHF₂ | N | |
| CH₃ | S(O)(CH₃) | H | OCH₃ | OCH₂CHF₂ | N | |
| CH₃ | S(O)(CH₃) | H | CH₃ | OCH₂CHF₂ | CH | |
| CH₃ | S(O)(CH₃) | H | OCH₃ | OCH₂CHF₂ | CH | |
| CH₃ | S(O)(CH₃) | H | CH₃ | OCH₂CHF₂ | N | |
| CH₃ | S(O)(CH₃) | H | OCH₃ | OCH₂CHF₂ | N | |
| CH₃ | S(O)(CH₃) | CH₃ | Cl | OCH₃ | CH | |
| CH₃ | S(O)(CH₃) | H | Cl | N(CH₃)₂ | CH | |
| CH₃ | S(O)(CH₃) | H | Cl | OC₂H₅ | CH | |
| C₂H₅ | S(O)(CH₃) | H | CH₃ | CH₃ | CH | |
| C₂H₅ | S(O)(CH₃) | H | OCH₃ | CH₃ | CH | |
| C₂H₅ | S(O)(CH₃) | H | OCH₃ | OCH₃ | CH | |
| C₂H₅ | S(O)(CH₃) | H | Cl | OCH₃ | CH | |
| C₂H₅ | S(O)(CH₃) | H | CH₃ | CH₃ | N | |
| C₂H₅ | S(O)(CH₃) | H | OCH₃ | CH₃ | N | |
| C₂H₅ | S(O)(CH₃) | H | OCH₃ | OCH₃ | N | |
| C₂H₅ | S(O)(CH₃) | H | Br | OCH₃ | CH | |
| C₂H₅ | S(O)(CH₃) | H | OCH₃ | N(CH₃)₂ | CH | |
| C₂H₅ | S(O)(CH₃) | H | OCH₃ | N(CH₃)₂ | N | |
| C₂H₅ | S(O)(CH₃) | H | OCH₃ | NHCH₃ | N | |
| C₂H₅ | S(O)(CH₃) | H | OCH₃ | C₂H₅ | CH | |
| C₂H₅ | S(O)(CH₃) | H | OCH₃ | C₂H₅ | N | |
| C₂H₅ | S(O)(CH₃) | H | CH₃ | OC₂H₅ | CH | |
| C₂H₅ | S(O)(CH₃) | H | CH₃ | OC₂H₅ | N | |
| C₂H₅ | S(O)(CH₃) | H | OCH₃ | OC₂H₅ | CH | |
| C₂H₅ | S(O)(CH₃) | H | OCH₃ | OC₂H₅ | N | |
| C₂H₅ | S(O)(CH₃) | H | CH₃ | OCH₂CF₃ | CH | |
| C₂H₅ | S(O)(CH₃) | H | CH₃ | OCH₂CF₃ | N | |
| C₂H₅ | S(O)(CH₃) | H | OCH₃ | OCH₂CF₃ | CH | |
| C₂H₅ | S(O)(CH₃) | H | OCH₃ | OCH₂CF₃ | N | |
| C₂H₅ | S(O)(CH₃) | H | OCH₃ | OCH₂CHF₂ | CH | |
| C₂H₅ | S(O)(CH₃) | H | OCH₃ | OCH₂CHF₂ | N | |
| C₂H₅ | S(O)(CH₃) | H | CH₃ | OCH₂CHF₂ | N | |
| C₂H₅ | S(O)(CH₃) | H | OCH₃ | OCH₂CHF₂ | CH | |

TABLE I-continued

| $R_1$ | $R_2$ | R | X | Y | Z | m.p. (°C.) |
|---|---|---|---|---|---|---|
| $C_2H_5$ | $S(O)(CH_3)$ | H | $OCH_3$ | $OCH_2CH_2F$ | N | |
| $C_2H_5$ | $S(O)(CH_3)$ | $CH_3$ | $OCH_3$ | $OCH_3$ | CH | |
| $C_2H_5$ | $S(O)(CH_3)$ | $CH_3$ | $CH_3$ | $OCH_3$ | N | |
| $C_2H_5$ | $S(O)(CH_3)$ | $CH_3$ | $OCH_3$ | $OCH_3$ | N | |
| $n\text{-}C_3H_7$ | $S(O)(CH_3)$ | H | $OCH_3$ | $OCH_3$ | CH | |
| $n\text{-}C_3H_7$ | $S(O)(CH_3)$ | H | $CH_3$ | $OCH_3$ | N | |
| $CH(CH_3)_2$ | $S(O)(CH_3)$ | H | $OCH_3$ | $CH_3$ | CH | |
| $CH(CH_3)_2$ | $S(O)(CH_3)$ | H | $OCH_3$ | $OCH_3$ | CH | |
| $CH(CH_3)_2$ | $S(O)(CH_3)$ | H | Cl | $OCH_3$ | CH | |
| $CH(CH_3)_2$ | $S(O)(CH_3)$ | H | $OCH_3$ | $CH_3$ | N | |
| $CH(CH_3)_2$ | $S(O)(CH_3)$ | H | $OCH_3$ | $OCH_3$ | N | |
| $CH(CH_3)_2$ | $S(O)(CH_3)$ | H | $OCH_3$ | $N(CH_3)_2$ | N | |
| $CH_3$ | $S(O)(CH_2CH_3)$ | H | $CH_3$ | $CH_3$ | CH | |
| $CH_3$ | $S(O)(CH_2CH_3)$ | H | $OCH_3$ | $CH_3$ | CH | 115–119 (d) |
| $CH_3$ | $S(O)(CH_2CH_3)$ | H | $OCH_3$ | $OCH_3$ | CH | 105–106 (d) |
| $CH_3$ | $S(O)(CH_2CH_3)$ | H | Cl | $OCH_3$ | CH | 150–155 (d) |
| $CH_3$ | $S(O)(CH_2CH_3)$ | H | $CH_3$ | $CH_3$ | N | |
| $CH_3$ | $S(O)(CH_2CH_3)$ | H | $OCH_3$ | $CH_3$ | N | |
| $CH_3$ | $S(O)(CH_2CH_3)$ | H | $OCH_3$ | $OCH_3$ | N | |
| $CH_3$ | $S(O)(CH_2CH_3)$ | H | $OCH_3$ | $N(CH_3)_2$ | CH | |
| $CH_3$ | $S(O)(CH_2CH_3)$ | H | $OCH_3$ | $N(CH_3)_2$ | N | |
| $CH_3$ | $S(O)(CH_2CH_3)$ | H | $OCH_3$ | $OCH_2CF_3$ | N | |
| $CH_3$ | $S(O)(CH_2CH_3)$ | $CH_3$ | $OCH_3$ | $CH_3$ | N | |
| $CH_3$ | $S(O)(CH_2CH_3)$ | $CH_3$ | $OCH_3$ | $OCH_3$ | N | |
| $CH_3$ | $S(O)(CH_2CH_3)$ | $CH_3$ | $CH_3$ | $OCH_3$ | CH | |
| $CH_3$ | $S(O)(CH_2CH_3)$ | $CH_3$ | $OCH_3$ | $OCH_3$ | CH | |
| $CH_3$ | $S(O)(CH_2CH_3)$ | H | Br | $OCH_3$ | CH | |
| $CH_3$ | $S(O)(CH_2CH_3)$ | H | $CH_3$ | $OCH_2CF_3$ | N | |
| $CH_3$ | $S(O)(CH_2CH_3)$ | H | $CH_3$ | $OCH_2CF_3$ | CH | |
| $CH_3$ | $S(O)(CH_2CH_3)$ | H | $OCH_3$ | $OCH_2CF_3$ | CH | |
| $CH_3$ | $S(O)(CH_2CH_3)$ | H | $OCH_3$ | $NHCH_3$ | N | |
| $C_2H_5$ | $S(O)(CH_2CH_3)$ | H | $CH_3$ | $CH_3$ | CH | |
| $C_2H_5$ | $S(O)(CH_2CH_3)$ | H | $OCH_3$ | $CH_3$ | CH | |
| $C_2H_5$ | $S(O)(CH_2CH_3)$ | H | $OCH_3$ | $OCH_3$ | CH | |
| $C_2H_5$ | $S(O)(CH_2CH_3)$ | H | Cl | $OCH_3$ | CH | |
| $C_2H_5$ | $S(O)(CH_2CH_3)$ | H | $OCH_3$ | $CH_3$ | N | |
| $C_2H_5$ | $S(O)(CH_2CH_3)$ | H | $OCH_3$ | $N(CH_3)_2$ | N | |
| $CH(CH_3)_2$ | $S(O)(CH_2CH_3)$ | H | $OCH_3$ | $CH_3$ | CH | |
| $CH(CH_3)_2$ | $S(O)(CH_2CH_3)$ | H | $OCH_3$ | $OCH_3$ | CH | |
| $CH(CH_3)_2$ | $S(O)(CH_2CH_3)$ | H | Cl | $OCH_3$ | CH | |
| $CH(CH_3)_2$ | $S(O)(CH_2CH_3)$ | H | $OCH_3$ | $CH_3$ | N | |
| $CH(CH_3)_2$ | $S(O)(CH_2CH_3)$ | H | $OCH_3$ | $OCH_3$ | N | |
| $CH_3$ | $S(O)((CH_2)_2CH_3)$ | H | $CH_3$ | $CH_3$ | CH | |
| $CH_3$ | $S(O)((CH_2)_2CH_3)$ | H | $OCH_3$ | $CH_3$ | CH | |
| $CH_3$ | $S(O)((CH_2)_2CH_3)$ | H | $OCH_3$ | $OCH_3$ | CH | |
| $CH_3$ | $S(O)((CH_2)_2CH_3)$ | H | Cl | $OCH_3$ | CH | |
| $CH_3$ | $S(O)((CH_2)_2CH_3)$ | H | $CH_3$ | $CH_3$ | N | |
| $CH_3$ | $S(O)((CH_2)_2CH_3)$ | H | $OCH_3$ | $CH_3$ | N | |
| $CH_3$ | $S(O)((CH_2)_2CH_3)$ | H | $OCH_3$ | $OCH_3$ | N | |
| $CH_3$ | $S(O)(CH(CH_3)_2)$ | H | $CH_3$ | $CH_3$ | CH | |
| $CH_3$ | $S(O)(CH(CH_3)_2)$ | H | $OCH_3$ | $CH_3$ | CH | |
| $CH_3$ | $S(O)(CH(CH_3)_2)$ | H | $OCH_3$ | $OCH_3$ | CH | |
| $CH_3$ | $S(O)(CH(CH_3)_2)$ | H | Cl | $OCH_3$ | CH | |
| $CH_3$ | $S(O)(CH(CH_3)_2)$ | H | $CH_3$ | $CH_3$ | N | |
| $CH_3$ | $S(O)(CH(CH_3)_2)$ | H | $OCH_3$ | $CH_3$ | N | |
| $CH_3$ | $S(O)(CH(CH_3)_2)$ | H | $OCH_3$ | $OCH_3$ | N | |
| $CH_3$ | $S(O)((CH_2)_3CH_3)$ | H | $OCH_3$ | $CH_3$ | CH | |
| $CH_3$ | $S(O)((CH_2)_3CH_3)$ | H | $OCH_3$ | $OCH_3$ | CH | |
| $CH_3$ | $S(O)((CH_2)_3CH_3)$ | H | Cl | $OCH_3$ | CH | |
| $CH_3$ | $S(O)((CH_2)_3CH_3)$ | H | $OCH_3$ | $CH_3$ | N | |
| $CH_3$ | $S(O)((CH_2)_3CH_3)$ | H | $OCH_3$ | $OCH_3$ | N | |
| $CH_3$ | $S(O)((CH_2)_4CH_3)$ | H | $OCH_3$ | $CH_3$ | CH | |
| $CH_3$ | $S(O)((CH_2)_4CH_3)$ | H | $OCH_3$ | $OCH_3$ | CH | |
| $CH_3$ | $S(O)((CH_2)_4CH_3)$ | H | Cl | $OCH_3$ | CH | |
| $CH_3$ | $S(O)((CH_2)_4CH_3)$ | H | $OCH_3$ | $CH_3$ | N | |
| $CH_3$ | $S(O)((CH_2)_4CH_3)$ | H | $OCH_3$ | $OCH_3$ | N | |
| $CH_3$ | $S(O)((CH_2)_5CH_3)$ | H | $CH_3$ | $OCH_3$ | CH | |
| $CH_3$ | $S(O)((CH_2)_6CH_3)$ | H | $OCH_3$ | $OCH_3$ | N | |
| $CH_3$ | $S(O)((CH_2)_7CH_3)$ | H | $CH_3$ | $CH_3$ | CH | |
| $CH_3$ | $S(O)((CH_2)_2CH(CH_3)_2)$ | H | $OCH_3$ | $CH_3$ | N | |
| $CH_3$ | $S(O)((CH_2)_5CH(CH_3)_2)$ | H | $OCH_3$ | $OCH_3$ | CH | |

TABLE I-continued

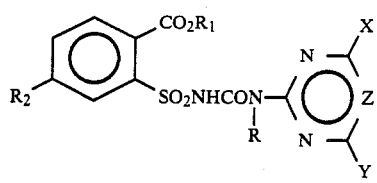

| $R_1$ | $R_2$ | R | X | Y | Z | m.p. (°C.) |
|---|---|---|---|---|---|---|
| $CH_3$ | $S(O)((CH_2CH(CH_3)(CH_2CH_3))$ | H | $OCH_3$ | $CH_3$ | CH | |
| $CH_3$ | $S(O)_2(CH_3)$ | H | $CH_3$ | $CH_3$ | CH | |
| $CH_3$ | $S(O)_2(CH_3)$ | H | $OCH_3$ | $CH_3$ | CH | |
| $CH_3$ | $S(O)_2(CH_3)$ | H | $OCH_3$ | $OCH_3$ | CH | |
| $CH_3$ | $S(O)_2(CH_3)$ | H | Cl | $OCH_3$ | CH | |
| $CH_3$ | $S(O)_2(CH_3)$ | H | $CH_3$ | $CH_3$ | N | |
| $CH_3$ | $S(O)_2(CH_3)$ | H | $OCH_3$ | $CH_3$ | N | |
| $CH_3$ | $S(O)_2(CH_3)$ | H | $OCH_3$ | $OCH_3$ | N | |
| $CH_3$ | $S(O)_2(CH_3)$ | H | $OCH_3$ | $N(CH_3)_2$ | CH | |
| $CH_3$ | $S(O)_2(CH_3)$ | H | $OCH_3$ | $N(CH_3)_2$ | N | |
| $CH_3$ | $S(O)_2(CH_3)$ | H | $OCH_3$ | $OCH_2CF_3$ | N | |
| $CH_3$ | $S(O)_2(CH_3)$ | $CH_3$ | $OCH_3$ | $CH_3$ | N | |
| $CH_3$ | $S(O)_2(CH_3)$ | $CH_3$ | $OCH_3$ | $OCH_3$ | N | |
| $CH_3$ | $S(O)_2(CH_3)$ | $CH_3$ | $CH_3$ | $OCH_3$ | CH | |
| $CH_3$ | $S(O)_2(CH_3)$ | $CH_3$ | $OCH_3$ | $OCH_3$ | CH | |
| $CH_3$ | $S(O)_2(CH_3)$ | H | Br | $OCH_3$ | CH | |
| $CH_3$ | $S(O)_2(CH_3)$ | H | $CH_3$ | $OCH_2CF_3$ | N | |
| $CH_3$ | $S(O)_2(CH_3)$ | H | $CH_3$ | $OCH_2CF_3$ | CH | |
| $CH_3$ | $S(O)_2(CH_3)$ | H | $OCH_3$ | $OCH_2CF_3$ | CH | |
| $CH_3$ | $S(O)_2(CH_3)$ | H | $OCH_3$ | $NHCH_3$ | N | |
| $C_2H_5$ | $S(O)_2(CH_3)$ | H | $CH_3$ | $CH_3$ | CH | |
| $C_2H_5$ | $S(O)_2(CH_3)$ | H | $OCH_3$ | $CH_3$ | CH | |
| $C_2H_5$ | $S(O)_2(CH_3)$ | H | $OCH_3$ | $OCH_3$ | CH | |
| $C_2H_5$ | $S(O)_2(CH_3)$ | H | Cl | $OCH_3$ | CH | |
| $C_2H_5$ | $S(O)_2(CH_3)$ | H | $OCH_3$ | $CH_3$ | N | |
| $C_2H_5$ | $S(O)_2(CH_3)$ | H | $OCH_3$ | $N(CH_3)_2$ | N | |
| $CH(CH_3)_2$ | $S(O)_2(CH_3)$ | H | $OCH_3$ | $CH_3$ | CH | |
| $CH(CH_3)_2$ | $S(O)_2(CH_3)$ | H | $OCH_3$ | $OCH_3$ | CH | |
| $CH(CH_3)_2$ | $S(O)_2(CH_3)$ | H | Cl | $OCH_3$ | CH | |
| $CH(CH_3)_2$ | $S(O)_2(CH_3)$ | H | $OCH_3$ | $CH_3$ | N | |
| $CH(CH_3)_2$ | $S(O)_2(CH_3)$ | H | $OCH_3$ | $OCH_3$ | N | |
| $CH_3$ | $S(O)_2(CH_2CH_3)$ | H | $CH_3$ | $CH_3$ | CH | |
| $CH_3$ | $S(O)_2(CH_2CH_3)$ | H | $OCH_3$ | $CH_3$ | CH | |
| $CH_3$ | $S(O)_2(CH_2CH_3)$ | H | $OCH_3$ | $OCH_3$ | CH | |
| $CH_3$ | $S(O)_2(CH_2CH_3)$ | H | Cl | $OCH_3$ | CH | |
| $CH_3$ | $S(O)_2(CH_2CH_3)$ | H | $CH_3$ | $CH_3$ | N | |
| $CH_3$ | $S(O)_2(CH_2CH_3)$ | H | $OCH_3$ | $CH_3$ | N | |
| $CH_3$ | $S(O)_2(CH_2CH_3)$ | H | $OCH_3$ | $OCH_3$ | N | |
| $CH_3$ | $S(O)_2((CH_2)_2CH_3)$ | H | $OCH_3$ | $CH_3$ | CH | |
| $CH_3$ | $S(O)_2((CH_2)_2CH_3)$ | H | $OCH_3$ | $OCH_3$ | CH | |
| $CH_3$ | $S(O)_2((CH_2)_2CH_3)$ | H | Cl | $OCH_3$ | CH | |
| $CH_3$ | $S(O)_2((CH_2)_2CH_3)$ | H | $OCH_3$ | $CH_3$ | N | |
| $CH_3$ | $S(O)_2((CH_2)_2CH_3)$ | H | $OCH_3$ | $OCH_3$ | N | |
| $CH_3$ | $S(O)_2(CH(CH_3)_2)$ | H | $OCH_3$ | $CH_3$ | CH | |
| $CH_3$ | $S(O)_2(CH(CH_3)_2)$ | H | $OCH_3$ | $OCH_3$ | CH | |
| $CH_3$ | $S(O)_2(CH(CH_3)_2)$ | H | Cl | $OCH_3$ | CH | |
| $CH_3$ | $S(O)_2(CH(CH_3)_2)$ | H | $OCH_3$ | $CH_3$ | N | |
| $CH_3$ | $S(O)_2(CH(CH_3)_2)$ | H | $OCH_3$ | $OCH_3$ | N | |
| $CH_3$ | $S(O)_2((CH_2)_3CH_3)$ | H | $OCH_3$ | $CH_3$ | CH | |
| $CH_3$ | $S(O)_2((CH_2)_3CH_3)$ | H | $OCH_3$ | $OCH_3$ | CH | |
| $CH_3$ | $S(O)_2((CH_2)_3CH_3)$ | H | Cl | $OCH_3$ | CH | |
| $CH_3$ | $S(O)_2((CH_2)_3CH_3)$ | H | $OCH_3$ | $CH_3$ | N | |
| $CH_3$ | $S(O)_2((CH_2)_3CH_3)$ | H | $OCH_3$ | $OCH_3$ | N | |
| $CH_3$ | $S(O)_2((CH_2)_4CH_3)$ | H | $OCH_3$ | $CH_3$ | CH | |
| $CH_3$ | $S(O)_2((CH_2)_5CH_3)$ | H | $OCH_3$ | $OCH_3$ | CH | |
| $CH_3$ | $S(O)_2((CH_2)_6CH_3)$ | H | $OCH_3$ | $CH_3$ | N | |
| $CH_3$ | $S(O)_2((CH_2)_7CH_3)$ | H | $OCH_3$ | $OCH_3$ | N | |
| $CH_3$ | $S(O)_2((CH_2)_2CH(CH_3)_2)$ | H | $CH_3$ | $OCH_3$ | CH | |
| $CH_3$ | $OCH_2CH=CH_2$ | H | $CH_3$ | $CH_3$ | CH | |
| $CH_3$ | $OCH_2CH=CH_2$ | H | $OCH_3$ | $CH_3$ | CH | 167–169 (d) |
| $CH_3$ | $OCH_2CH=CH_2$ | H | $OCH_3$ | $OCH_3$ | CH | 190–192 (d) |
| $CH_3$ | $OCH_2CH=CH_2$ | H | Cl | $OCH_3$ | CH | |
| $CH_3$ | $OCH_2CH=CH_2$ | H | $OCH_3$ | $N(CH_3)_2$ | CH | |
| $CH_3$ | $OCH_2CH=CH_2$ | H | $CH_3$ | $CH_3$ | N | |
| $CH_3$ | $OCH_2CH=CH_2$ | H | $OCH_3$ | $CH_3$ | N | 133–135 (d) |
| $CH_3$ | $OCH_2CH=CH_2$ | H | $OCH_3$ | $OCH_3$ | N | 174–177 |
| $CH_3$ | $OCH_2CH=CH_2$ | H | $OCH_3$ | $N(CH_3)_2$ | N | |
| $CH_3$ | $OCH_2CH=CH_2$ | H | $OCH_3$ | $OCH_2CF_3$ | N | |
| $CH_3$ | $OCH_2CH=CH_2$ | $CH_3$ | $OCH_3$ | $CH_3$ | N | |
| $CH_3$ | $OCH_2CH=CH_2$ | $CH_3$ | $OCH_3$ | $OCH_3$ | N | |
| $CH_3$ | $OCH_2CH=CH_2$ | $CH_3$ | $CH_3$ | $OCH_3$ | CH | |

TABLE I-continued

| R₁ | R₂ | R | X | Y | Z | m.p. (°C.) |
|---|---|---|---|---|---|---|
| CH₃ | OCH₂CH=CH₂ | CH₃ | OCH₃ | OCH₃ | CH | |
| CH₃ | OCH₂CH=CH₂ | H | Br | OCH₃ | CH | |
| CH₃ | OCH₂CH=CH₂ | CH₃ | OCH₃ | N(CH₃)₂ | N | |
| CH₃ | OCH₂CH=CH₂ | H | CH₃ | OCH₂CF₃ | N | |
| CH₃ | OCH₂CH=CH₂ | H | CH₃ | OCH₂CF₃ | CH | |
| CH₃ | OCH₂CH=CH₂ | H | OCH₃ | OCH₂CF₃ | CH | |
| CH₃ | OCH₂CH=CH₂ | H | OCH₃ | C₂H₅ | CH | |
| CH₃ | OCH₂CH=CH₂ | H | OCH₃ | C₂H₅ | N | |
| CH₃ | OCH₂CH=CH₂ | H | OCH₃ | NHCH₃ | CH | |
| CH₃ | OCH₂CH=CH₂ | H | OCH₃ | NHCH₃ | N | |
| CH₃ | OCH₂CH=CH₂ | H | CH₃ | OC₂H₅ | CH | |
| CH₃ | OCH₂CH=CH₂ | H | OCH₃ | OC₂H₅ | CH | |
| CH₃ | OCH₂CH=CH₂ | H | CH₃ | OC₂H₅ | N | |
| CH₃ | OCH₂CH=CH₂ | H | OCH₃ | OC₂H₅ | N | |
| CH₃ | OCH₂CH=CH₂ | H | CH₃ | OCH₂CHF₂ | CH | |
| CH₃ | OCH₂CH=CH₂ | H | OCH₃ | OCH₂CHF₂ | CH | |
| CH₃ | OCH₂CH=CH₂ | H | CH₃ | OCH₂CHF₂ | N | |
| CH₃ | OCH₂CH=CH₂ | H | OCH₃ | OCH₂CHF₂ | N | |
| CH₃ | OCH₂CH=CH₂ | H | CH₃ | OCH₂CH₂F | CH | |
| CH₃ | OCH₂CH=CH₂ | H | OCH₃ | OCH₂CH₂F | CH | |
| CH₃ | OCH₂CH=CH₂ | H | CH₃ | OCH₂CH₂F | N | |
| CH₃ | OCH₂CH=CH₂ | CH₃ | OCH₃ | OCH₂CH₂F | N | |
| CH₃ | OCH₂CH=CH₂ | CH₃ | Cl | OCH₃ | CH | |
| CH₃ | OCH₂CH=CH₂ | H | Cl | N(CH₃)₂ | CH | |
| CH₃ | OCH₂CH=CH₂ | H | Cl | OC₂H₅ | CH | |
| C₂H₅ | OCH₂CH=CH₂ | H | CH₃ | CH₃ | CH | |
| C₂H₅ | OCH₂CH=CH₂ | H | OCH₃ | CH₃ | CH | |
| C₂H₅ | OCH₂CH=CH₂ | H | OCH₃ | OCH₃ | CH | |
| C₂H₅ | OCH₂CH=CH₂ | H | Cl | OCH₃ | CH | |
| C₂H₅ | OCH₂CH=CH₂ | H | CH₃ | CH₃ | N | |
| C₂H₅ | OCH₂CH=CH₂ | H | OCH₃ | CH₃ | N | |
| C₂H₅ | OCH₂CH=CH₂ | H | OCH₃ | OCH₃ | N | |
| C₂H₅ | OCH₂CH=CH₂ | H | Br | OCH₃ | CH | |
| C₂H₅ | OCH₂CH=CH₂ | H | OCH₃ | N(CH₃)₂ | CH | |
| C₂H₅ | OCH₂CH=CH₂ | H | OCH₃ | N(CH₃)₂ | N | |
| C₂H₅ | OCH₂CH=CH₂ | H | OCH₃ | NHCH₃ | N | |
| C₂H₅ | OCH₂CH=CH₂ | H | OCH₃ | C₂H₅ | CH | |
| C₂H₅ | OCH₂CH=CH₂ | H | OCH₃ | C₂H₅ | N | |
| C₂H₅ | OCH₂CH=CH₂ | H | CH₃ | OC₂H₅ | CH | |
| C₂H₅ | OCH₂CH=CH₂ | H | CH₃ | OC₂H₅ | N | |
| C₂H₅ | OCH₂CH=CH₂ | H | OCH₃ | OC₂H₅ | CH | |
| C₂H₅ | OCH₂CH=CH₂ | H | OCH₃ | OC₂H₅ | N | |
| C₂H₅ | OCH₂CH=CH₂ | H | CH₃ | OCH₂CF₃ | CH | |
| C₂H₅ | OCH₂CH=CH₂ | H | CH₃ | OCH₂CF₃ | N | |
| C₂H₅ | OCH₂CH=CH₂ | H | OCH₃ | OCH₂CF₃ | CH | |
| C₂H₅ | OCH₂CH=CH₂ | H | OCH₃ | OCH₂CF₃ | N | |
| C₂H₅ | OCH₂CH=CH₂ | H | OCH₃ | OCH₂CHF₂ | CH | |
| C₂H₅ | OCH₂CH=CH₂ | H | OCH₃ | OCH₂CHF₂ | N | |
| C₂H₅ | OCH₂CH=CH₂ | H | CH₃ | OCH₂CHF₂ | N | |
| C₂H₅ | OCH₂CH=CH₂ | H | OCH₃ | OCH₂CH₂F | CH | |
| C₂H₅ | OCH₂CH=CH₂ | H | OCH₃ | OCH₂CH₂F | N | |
| C₂H₅ | OCH₂CH=CH₂ | CH₃ | OCH₃ | OCH₃ | CH | |
| C₂H₅ | OCH₂CH=CH₂ | CH₃ | CH₃ | OCH₃ | N | |
| C₂H₅ | OCH₂CH=CH₂ | CH₃ | OCH₃ | OCH₃ | N | |
| n-C₃H₇ | OCH₂CH=CH₂ | H | OCH₃ | OCH₃ | CH | |
| n-C₃H₇ | OCH₂CH=CH₂ | H | CH₃ | OCH₃ | N | |
| CH(CH₃)₂ | OCH₂CH=CH₂ | H | OCH₃ | CH₃ | CH | |
| CH(CH₃)₂ | OCH₂CH=CH₂ | H | OCH₃ | OCH₃ | CH | |
| CH(CH₃)₂ | OCH₂CH=CH₂ | H | Cl | OCH₃ | CH | |
| CH(CH₃)₂ | OCH₂CH=CH₂ | H | OCH₃ | CH₃ | N | |
| CH(CH₃)₂ | OCH₂CH=CH₂ | H | OCH₃ | OCH₃ | N | |
| CH(CH₃)₂ | OCH₂CH=CH₂ | H | OCH₃ | N(CH₃)₂ | N | |
| CH₃ | OCH₂CH=CHCH₃ | H | CH₃ | CH₃ | CH | |
| CH₃ | OCH₂CH=CHCH₃ | H | OCH₃ | CH₃ | CH | |
| CH₃ | OCH₂CH=CHCH₃ | H | OCH₃ | OCH₃ | CH | |
| CH₃ | OCH₂CH=CHCH₃ | H | Cl | OCH₃ | CH | |
| CH₃ | OCH₂CH=CHCH₃ | H | CH₃ | CH₃ | N | |
| CH₃ | OCH₂CH=CHCH₃ | H | OCH₃ | CH₃ | N | |
| CH₃ | OCH₂CH=CHCH₃ | H | OCH₃ | OCH₃ | N | |
| CH₃ | OCH₂CH=CHCH₃ | H | OCH₃ | N(CH₃)₂ | CH | |
| CH₃ | OCH₂CH=CHCH₃ | H | OCH₃ | N(CH₃)₂ | N | |

TABLE I-continued

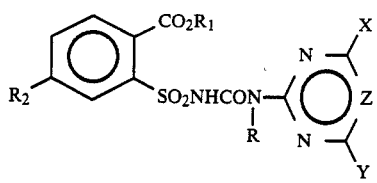

| R₁ | R₂ | R | X | Y | Z | m.p. (°C.) |
|---|---|---|---|---|---|---|
| CH₃ | OCH₂CH=CHCH₃ | H | OCH₃ | OCH₂CF₃ | N | |
| CH₃ | OCH₂CH=CHCH₃ | CH₃ | OCH₃ | CH₃ | N | |
| CH₃ | OCH₂CH=CHCH₃ | CH₃ | OCH₃ | OCH₃ | N | |
| CH₃ | OCH₂CH=CHCH₃ | CH₃ | CH₃ | OCH₃ | CH | |
| CH₃ | OCH₂CH=CHCH₃ | CH₃ | OCH₃ | OCH₃ | CH | |
| CH₃ | OCH₂CH=CHCH₃ | H | Br | OCH₃ | CH | |
| CH₃ | OCH₂CH=CHCH₃ | H | CH₃ | OCH₂CF₃ | N | |
| CH₃ | OCH₂CH=CHCH₃ | H | CH₃ | OCH₂CF₃ | CH | |
| CH₃ | OCH₂CH=CHCH₃ | H | OCH₃ | OCH₂CF₃ | CH | |
| CH₃ | OCH₂CH=CHCH₃ | H | OCH₃ | NHCH₃ | N | |
| C₂H₅ | OCH₂CH=CHCH₃ | H | CH₃ | CH₃ | CH | |
| C₂H₅ | OCH₂CH=CHCH₃ | H | OCH₃ | CH₃ | CH | |
| C₂H₅ | OCH₂CH=CHCH₃ | H | OCH₃ | OCH₃ | CH | |
| C₂H₅ | OCH₂CH=CHCH₃ | H | Cl | OCH₃ | CH | |
| C₂H₅ | OCH₂CH=CHCH₃ | H | OCH₃ | CH₃ | N | |
| C₂H₅ | OCH₂CH=CHCH₃ | H | OCH₃ | N(CH₃)₂ | CH | |
| CH(CH₃)₂ | OCH₂CH=CHCH₃ | H | OCH₃ | CH₃ | CH | |
| CH(CH₃)₂ | OCH₂CH=CHCH₃ | H | OCH₃ | OCH₃ | CH | |
| CH(CH₃)₂ | OCH₂CH=CHCH₃ | H | Cl | OCH₃ | CH | |
| CH(CH₃)₂ | OCH₂CH=CHCH₃ | H | OCH₃ | CH₃ | N | |
| CH(CH₃)₂ | OCH₂CH=CHCH₃ | H | OCH₃ | OCH₃ | N | |
| CH₃ | OCH₂CH=CHC₂H₅ | H | CH₃ | CH₃ | CH | |
| CH₃ | OCH₂CH=CHC₂H₅ | H | OCH₃ | CH₃ | CH | |
| CH₃ | OCH₂CH=CHC₂H₅ | H | OCH₃ | OCH₃ | CH | |
| CH₃ | OCH₂CH=CHC₂H₅ | H | Cl | OCH₃ | CH | |
| CH₃ | OCH₂CH=CHC₂H₅ | H | CH₃ | CH₃ | N | |
| CH₃ | OCH₂CH=CHC₂H₅ | H | OCH₃ | CH₃ | N | |
| CH₃ | OCH₂CH=CHC₂H₅ | H | OCH₃ | OCH₃ | N | |
| CH₃ | OCH₂CH=CHC₂H₅ | H | OCH₃ | N(CH₃)₂ | CH | |
| CH₃ | OCH₂CH=CHC₂H₅ | H | OCH₃ | N(CH₃)₂ | N | |
| CH₃ | OCH₂CH=CHC₂H₅ | H | OCH₃ | OCH₂CF₃ | N | |
| CH₃ | OCH₂CH=CHC₂H₅ | CH₃ | OCH₃ | CH₃ | N | |
| CH₃ | OCH₂CH=CHC₂H₅ | CH₃ | OCH₃ | OCH₃ | N | |
| CH₃ | OCH₂CH=CHC₂H₅ | CH₃ | CH₃ | OCH₃ | CH | |
| CH₃ | OCH₂CH=CHC₂H₅ | CH₃ | OCH₃ | OCH₃ | CH | |
| CH₃ | OCH₂CH=CHC₂H₅ | H | Br | OCH₃ | CH | |
| CH₃ | OCH₂CH=CHC₂H₅ | H | CH₃ | OCH₂CF₃ | N | |
| CH₃ | OCH₂CH=CHC₂H₅ | H | CH₃ | OCH₂CF₃ | CH | |
| CH₃ | OCH₂CH=CHC₂H₅ | H | OCH₃ | OCH₂CF₃ | CH | |
| CH₃ | OCH₂CH=CHC₂H₅ | H | OCH₃ | NHCH₃ | N | |
| C₂H₅ | OCH₂CH=CHC₂H₅ | H | CH₃ | CH₃ | CH | |
| C₂H₅ | OCH₂CH=CHC₂H₅ | H | OCH₃ | CH₃ | CH | |
| C₂H₅ | OCH₂CH=CHC₂H₅ | H | OCH₃ | OCH₃ | CH | |
| C₂H₅ | OCH₂CH=CHC₂H₅ | H | Cl | OCH₃ | CH | |
| C₂H₅ | OCH₂CH=CHC₂H₅ | H | OCH₃ | CH₃ | N | |
| C₂H₅ | OCH₂CH=CHC₂H₅ | H | OCH₃ | N(CH₃)₂ | CH | |
| CH(CH₃)₂ | OCH₂CH=CHC₂H₅ | H | OCH₃ | CH₃ | CH | |
| CH(CH₃)₂ | OCH₂CH=CHC₂H₅ | H | OCH₃ | OCH₃ | CH | |
| CH(CH₃)₂ | OCH₂CH=CHC₂H₅ | H | Cl | OCH₃ | CH | |
| CH(CH₃)₂ | OCH₂CH=CHC₂H₅ | H | OCH₃ | CH₃ | N | |
| CH(CH₃)₂ | OCH₂CH=CHC₂H₅ | H | OCH₃ | OCH₃ | N | |
| CH₃ | O(CH₂)₂CH=CH₂ | H | CH₃ | OCH₃ | CH | |
| CH₃ | O(CH₂)₃CH=CH₂ | H | OCH₃ | OCH₃ | CH | |
| CH₃ | O(CH₂)₂C(CH₃)=CH₂ | H | CH₃ | OCH₃ | N | |
| CH₃ | O(CH₂)₂CH=CHCH₃ | H | OCH₃ | OCH₃ | N | |
| CH₃ | OCH₂C≡CH | H | CH₃ | CH₃ | CH | |
| CH₃ | OCH₂C≡CH | H | OCH₃ | CH₃ | CH | |
| CH₃ | OCH₂C≡CH | H | OCH₃ | OCH₃ | CH | |
| CH₃ | OCH₂C≡CH | H | Cl | OCH₃ | CH | |
| CH₃ | OCH₂C≡CH | H | OCH₃ | N(CH₃)₂ | CH | |
| CH₃ | OCH₂C≡CH | H | CH₃ | CH₃ | N | |
| CH₃ | OCH₂C≡CH | H | OCH₃ | CH₃ | N | |
| CH₃ | OCH₂C≡CH | H | OCH₃ | OCH₃ | N | |
| CH₃ | OCH₂C≡CH | H | OCH₃ | N(CH₃)₂ | N | |
| CH₃ | OCH₂C≡CH | H | OCH₃ | OCH₂CF₃ | N | |
| CH₃ | OCH₂C≡CH | CH₃ | OCH₃ | CH₃ | N | |
| CH₃ | OCH₂C≡CH | CH₃ | OCH₃ | OCH₃ | N | |
| CH₃ | OCH₂C≡CH | CH₃ | CH₃ | OCH₃ | CH | |
| CH₃ | OCH₂C≡CH | CH₃ | OCH₃ | OCH₃ | CH | |
| CH₃ | OCH₂C≡CH | H | Br | OCH₃ | CH | |
| CH₃ | OCH₂C≡CH | CH₃ | OCH₃ | N(CH₃)₂ | N | |

TABLE I-continued

| $R_1$ | $R_2$ | R | X | Y | Z | m.p. (°C.) |
|---|---|---|---|---|---|---|
| $CH_3$ | $OCH_2C\equiv CH$ | H | $CH_3$ | $OCH_2CF_3$ | N | |
| $CH_3$ | $OCH_2C\equiv CH$ | H | $CH_3$ | $OCH_2CF_3$ | CH | |
| $CH_3$ | $OCH_2C\equiv CH$ | H | $OCH_3$ | $OCH_2CF_3$ | CH | |
| $CH_3$ | $OCH_2C\equiv CH$ | H | $OCH_3$ | $C_2H_5$ | CH | |
| $CH_3$ | $OCH_2C\equiv CH$ | H | $OCH_3$ | $C_2H_5$ | N | |
| $CH_3$ | $OCH_2C\equiv CH$ | H | $OCH_3$ | $NHCH_3$ | CH | |
| $CH_3$ | $OCH_2C\equiv CH$ | H | $OCH_3$ | $NHCH_3$ | N | |
| $CH_3$ | $OCH_2C\equiv CH$ | H | $CH_3$ | $OC_2H_5$ | CH | |
| $CH_3$ | $OCH_2C\equiv CH$ | H | $OCH_3$ | $OC_2H_5$ | CH | |
| $CH_3$ | $OCH_2C\equiv CH$ | H | $CH_3$ | $OC_2H_5$ | N | |
| $CH_3$ | $OCH_2C\equiv CH$ | H | $OCH_3$ | $OC_2H_5$ | N | |
| $CH_3$ | $OCH_2C\equiv CH$ | H | $CH_3$ | $OCH_2CHF_2$ | CH | |
| $CH_3$ | $OCH_2C\equiv CH$ | H | $OCH_3$ | $OCH_2CHF_2$ | CH | |
| $CH_3$ | $OCH_2C\equiv CH$ | H | $CH_3$ | $OCH_2CHF_2$ | N | |
| $CH_3$ | $OCH_2C\equiv CH$ | H | $OCH_3$ | $OCH_2CHF_2$ | N | |
| $CH_3$ | $OCH_2C\equiv CH$ | H | $CH_3$ | $OCH_2CH_2F$ | CH | |
| $CH_3$ | $OCH_2C\equiv CH$ | H | $OCH_3$ | $OCH_2CH_2F$ | CH | |
| $CH_3$ | $OCH_2C\equiv CH$ | H | $CH_3$ | $OCH_2CF_3$ | N | |
| $CH_3$ | $OCH_2C\equiv CH$ | $CH_3$ | $OCH_3$ | $OCH_2CF_3$ | N | |
| $CH_3$ | $OCH_2C\equiv CH$ | $CH_3$ | Cl | $OCH_3$ | CH | |
| $CH_3$ | $OCH_2C\equiv CH$ | H | Cl | $N(CH_3)_2$ | CH | |
| $CH_3$ | $OCH_2C\equiv CH$ | H | Cl | $OC_2H_5$ | CH | |
| $C_2H_5$ | $OCH_2C\equiv CH$ | H | $CH_3$ | $CH_3$ | CH | |
| $C_2H_5$ | $OCH_2C\equiv CH$ | H | $OCH_3$ | $CH_3$ | CH | |
| $C_2H_5$ | $OCH_2C\equiv CH$ | H | $OCH_3$ | $OCH_3$ | CH | 171–176 |
| $C_2H_5$ | $OCH_2C\equiv CH$ | H | Cl | $OCH_3$ | CH | 171–181 (d) |
| $C_2H_5$ | $OCH_2C\equiv CH$ | H | $CH_3$ | $CH_3$ | N | |
| $C_2H_5$ | $OCH_2C\equiv CH$ | H | $OCH_3$ | $CH_3$ | N | |
| $C_2H_5$ | $OCH_2C\equiv CH$ | H | $OCH_3$ | $OCH_3$ | N | |
| $C_2H_5$ | $OCH_2C\equiv CH$ | H | Br | $OCH_3$ | CH | |
| $C_2H_5$ | $OCH_2C\equiv CH$ | H | $OCH_3$ | $N(CH_3)_2$ | CH | |
| $C_2H_5$ | $OCH_2C\equiv CH$ | H | $OCH_3$ | $N(CH_3)_2$ | N | |
| $C_2H_5$ | $OCH_2C\equiv CH$ | H | $OCH_3$ | $NHCH_3$ | N | |
| $C_2H_5$ | $OCH_2C\equiv CH$ | H | $OCH_3$ | $C_2H_5$ | CH | |
| $C_2H_5$ | $OCH_2C\equiv CH$ | H | $OCH_3$ | $C_2H_5$ | N | |
| $C_2H_5$ | $OCH_2C\equiv CH$ | H | $CH_3$ | $OC_2H_5$ | CH | |
| $C_2H_5$ | $OCH_2C\equiv CH$ | H | $CH_3$ | $OC_2H_5$ | N | |
| $C_2H_5$ | $OCH_2C\equiv CH$ | H | $OCH_3$ | $OC_2H_5$ | CH | |
| $C_2H_5$ | $OCH_2C\equiv CH$ | H | $OCH_3$ | $OC_2H_5$ | N | |
| $C_2H_5$ | $OCH_2C\equiv CH$ | H | $CH_3$ | $OCH_2CF_3$ | CH | |
| $C_2H_5$ | $OCH_2C\equiv CH$ | H | $CH_3$ | $OCH_2CF_3$ | N | |
| $C_2H_5$ | $OCH_2C\equiv CH$ | H | $OCH_3$ | $OCH_2CF_3$ | CH | |
| $C_2H_5$ | $OCH_2C\equiv CH$ | H | $OCH_3$ | $OCH_2CF_3$ | N | |
| $C_2H_5$ | $OCH_2C\equiv CH$ | H | $OCH_3$ | $OCH_2CHF_2$ | CH | |
| $C_2H_5$ | $OCH_2C\equiv CH$ | H | $OCH_3$ | $OCH_2CHF_2$ | N | |
| $C_2H_5$ | $OCH_2C\equiv CH$ | H | $CH_3$ | $OCH_2CHF_2$ | N | |
| $C_2H_5$ | $OCH_2C\equiv CH$ | H | $OCH_3$ | $OCH_2CH_2F$ | CH | |
| $C_2H_5$ | $OCH_2C\equiv CH$ | H | $OCH_3$ | $OCH_2CH_2F$ | N | |
| $C_2H_5$ | $OCH_2C\equiv CH$ | $CH_3$ | $OCH_3$ | $OCH_3$ | CH | |
| $C_2H_5$ | $OCH_2C\equiv CH$ | $CH_3$ | $CH_3$ | $OCH_3$ | N | |
| $C_2H_5$ | $OCH_2C\equiv CH$ | $CH_3$ | $OCH_3$ | $OCH_3$ | N | |
| $n$-$C_3H_7$ | $OCH_2C\equiv CH$ | H | $OCH_3$ | $OCH_3$ | CH | |
| $n$-$C_3H_7$ | $OCH_2C\equiv CH$ | H | $CH_3$ | $OCH_3$ | N | |
| $CH(CH_3)_2$ | $OCH_2C\equiv CH$ | H | $OCH_3$ | $CH_3$ | CH | |
| $CH(CH_3)_2$ | $OCH_2C\equiv CH$ | H | $OCH_3$ | $OCH_3$ | CH | |
| $CH(CH_3)_2$ | $OCH_2C\equiv CH$ | H | Cl | $OCH_3$ | CH | |
| $CH(CH_3)_2$ | $OCH_2C\equiv CH$ | H | $OCH_3$ | $CH_3$ | N | |
| $CH(CH_3)_2$ | $OCH_2C\equiv CH$ | H | $OCH_3$ | $OCH_3$ | N | |
| $CH(CH_3)_2$ | $OCH_2C\equiv CH$ | H | $OCH_3$ | $N(CH_3)_2$ | N | |
| $CH_3$ | $OCH_2C\equiv CCH_3$ | H | $CH_3$ | $CH_3$ | CH | |
| $CH_3$ | $OCH_2C\equiv CCH_3$ | H | $OCH_3$ | $CH_3$ | CH | |
| $CH_3$ | $OCH_2C\equiv CCH_3$ | H | $OCH_3$ | $OCH_3$ | CH | |
| $CH_3$ | $OCH_2C\equiv CCH_3$ | H | Cl | $OCH_3$ | CH | |
| $CH_3$ | $OCH_2C\equiv CCH_3$ | H | $CH_3$ | $CH_3$ | N | |
| $CH_3$ | $OCH_2C\equiv CCH_3$ | H | $OCH_3$ | $CH_3$ | N | |
| $CH_3$ | $OCH_2C\equiv CCH_3$ | H | $OCH_3$ | $OCH_3$ | N | |
| $CH_3$ | $OCH_2C\equiv CCH_3$ | H | $OCH_3$ | $N(CH_3)_2$ | CH | |
| $CH_3$ | $OCH_2C\equiv CCH_3$ | H | $OCH_3$ | $N(CH_3)_2$ | N | |
| $CH_3$ | $OCH_2C\equiv CCH_3$ | H | $OCH_3$ | $OCH_2CF_3$ | N | |
| $CH_3$ | $OCH_2C\equiv CCH_3$ | $CH_3$ | $OCH_3$ | $CH_3$ | N | |
| $CH_3$ | $OCH_2C\equiv CCH_3$ | $CH_3$ | $OCH_3$ | $OCH_3$ | N | |

TABLE I-continued

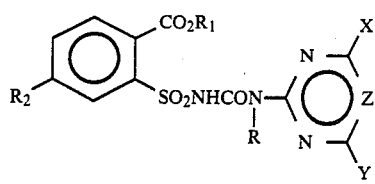

| R₁ | R₂ | R | X | Y | Z | m.p. (°C.) |
|---|---|---|---|---|---|---|
| CH₃ | OCH₂C≡CCH₃ | CH₃ | CH₃ | OCH₃ | CH | |
| CH₃ | OCH₂C≡CCH₃ | CH₃ | OCH₃ | OCH₃ | CH | |
| CH₃ | OCH₂C≡CCH₃ | H | Br | OCH₃ | CH | |
| CH₃ | OCH₂C≡CCH₃ | H | CH₃ | OCH₂CF₃ | N | |
| CH₃ | OCH₂C≡CCH₃ | H | CH₃ | OCH₂CF₃ | CH | |
| CH₃ | OCH₂C≡CCH₃ | H | OCH₃ | OCH₂CF₃ | CH | |
| CH₃ | OCH₂C≡CCH₃ | H | OCH₃ | NHCH₃ | N | |
| C₂H₅ | OCH₂C≡CCH₃ | H | CH₃ | CH₃ | CH | |
| C₂H₅ | OCH₂C≡CCH₃ | H | OCH₃ | CH₃ | CH | |
| C₂H₅ | OCH₂C≡CCH₃ | H | OCH₃ | OCH₃ | CH | |
| C₂H₅ | OCH₂C≡CCH₃ | H | Cl | OCH₃ | CH | |
| C₂H₅ | OCH₂C≡CCH₃ | H | OCH₃ | CH₃ | N | |
| C₂H₅ | OCH₂C≡CCH₃ | H | OCH₃ | N(CH₃)₂ | CH | |
| CH(CH₃)₂ | OCH₂C≡CCH₃ | H | OCH₃ | CH₃ | CH | |
| CH(CH₃)₂ | OCH₂C≡CCH₃ | H | OCH₃ | OCH₃ | CH | |
| CH(CH₃)₂ | OCH₂C≡CCH₃ | H | Cl | OCH₃ | CH | |
| CH(CH₃)₂ | OCH₂C≡CCH₃ | H | OCH₃ | CH₃ | N | |
| CH(CH₃)₂ | OCH₂C≡CCH₃ | H | OCH₃ | OCH₃ | N | |
| CH₃ | OCH₂C≡CC₂H₅ | H | CH₃ | CH₃ | CH | |
| CH₃ | OCH₂C≡CC₂H₅ | H | OCH₃ | CH₃ | CH | |
| CH₃ | OCH₂C≡CC₂H₅ | H | OCH₃ | OCH₃ | CH | |
| CH₃ | OCH₂C≡CC₂H₅ | H | Cl | OCH₃ | CH | |
| CH₃ | OCH₂C≡CC₂H₅ | H | CH₃ | CH₃ | N | |
| CH₃ | OCH₂C≡CC₂H₅ | H | OCH₃ | CH₃ | N | |
| CH₃ | OCH₂C≡CC₂H₅ | H | OCH₃ | OCH₃ | N | |
| CH₃ | OCH₂C≡CC₂H₅ | H | OCH₃ | N(CH₃)₂ | CH | |
| CH₃ | OCH₂C≡CC₂H₅ | H | OCH₃ | N(CH₃)₂ | N | |
| CH₃ | OCH₂C≡CC₂H₅ | H | OCH₃ | OCH₂CF₃ | N | |
| CH₃ | OCH₂C≡CC₂H₅ | CH₃ | OCH₃ | CH₃ | N | |
| CH₃ | OCH₂C≡CC₂H₅ | CH₃ | OCH₃ | OCH₃ | N | |
| CH₃ | OCH₂C≡CC₂H₅ | CH₃ | CH₃ | OCH₃ | CH | |
| CH₃ | OCH₂C≡CC₂H₅ | CH₃ | OCH₃ | OCH₃ | CH | |
| CH₃ | OCH₂C≡CC₂H₅ | H | Br | OCH₃ | CH | |
| CH₃ | OCH₂C≡CC₂H₅ | H | CH₃ | OCH₂CF₃ | N | |
| CH₃ | OCH₂C≡CC₂H₅ | H | CH₃ | OCH₂CF₃ | CH | |
| CH₃ | OCH₂C≡CC₂H₅ | H | OCH₃ | OCH₂CF₃ | CH | |
| CH₃ | OCH₂C≡CC₂H₅ | H | OCH₃ | NHCH₃ | N | |
| C₂H₅ | OCH₂C≡CC₂H₅ | H | CH₃ | CH₃ | CH | |
| C₂H₅ | OCH₂C≡CC₂H₅ | H | OCH₃ | CH₃ | CH | |
| C₂H₅ | OCH₂C≡CC₂H₅ | H | OCH₃ | OCH₃ | CH | |
| C₂H₅ | OCH₂C≡CC₂H₅ | H | Cl | OCH₃ | CH | |
| C₂H₅ | OCH₂C≡CC₂H₅ | H | OCH₃ | CH₃ | N | |
| C₂H₅ | OCH₂C≡CC₂H₅ | H | OCH₃ | N(CH₃)₂ | CH | |
| CH(CH₃)₂ | OCH₂C≡CC₂H₅ | H | OCH₃ | CH₃ | CH | |
| CH(CH₃)₂ | OCH₂C≡CC₂H₅ | H | OCH₃ | OCH₃ | CH | |
| CH(CH₃)₂ | OCH₂C≡CC₂H₅ | H | Cl | OCH₃ | CH | |
| CH(CH₃)₂ | OCH₂C≡CC₂H₅ | H | OCH₃ | CH₃ | N | |
| CH(CH₃)₂ | OCH₂C≡CC₂H₅ | H | OCH₃ | OCH₃ | N | |
| CH₃ | O(CH₂)₂C≡CH | H | CH₃ | OCH₃ | CH | |
| CH₃ | O(CH₂)₃C≡CH | H | OCH₃ | OCH₃ | CH | |
| CH₃ | O(CH₂)₂C≡CCH₃ | H | CH₃ | OCH₃ | N | |
| CH₃ | SCH₂CH=CH₂ | H | CH₃ | CH₃ | CH | |
| CH₃ | SCH₂CH=CH₂ | H | OCH₃ | CH₃ | CH | |
| CH₃ | SCH₂CH=CH₂ | H | OCH₃ | OCH₃ | CH | |
| CH₃ | SCH₂CH=CH₂ | H | Cl | OCH₃ | CH | |
| CH₃ | SCH₂CH=CH₂ | H | OCH₃ | N(CH₃)₂ | N | |
| CH₃ | SCH₂CH=CH₂ | H | CH₃ | CH₃ | N | |
| CH₃ | SCH₂CH=CH₂ | H | OCH₃ | CH₃ | N | |
| CH₃ | SCH₂CH=CH₂ | H | OCH₃ | OCH₃ | N | |
| CH₃ | SCH₂CH=CH₂ | H | OCH₃ | N(CH₃)₂ | N | |
| CH₃ | SCH₂CH=CH₂ | H | OCH₃ | OCH₂CF₃ | N | |
| CH₃ | SCH₂CH=CH₂ | CH₃ | OCH₃ | CH₃ | N | |
| CH₃ | SCH₂CH=CH₂ | CH₃ | OCH₃ | OCH₃ | N | |
| CH₃ | SCH₂CH=CH₂ | CH₃ | CH₃ | OCH₃ | CH | |
| CH₃ | SCH₂CH=CH₂ | CH₃ | OCH₃ | OCH₃ | CH | |
| CH₃ | SCH₂CH=CH₂ | H | Br | OCH₃ | CH | |
| CH₃ | SCH₂CH=CH₂ | CH₃ | OCH₃ | N(CH₃)₂ | N | |
| CH₃ | SCH₂CH=CH₂ | H | CH₃ | OCH₂CF₃ | N | |
| CH₃ | SCH₂CH=CH₂ | H | CH₃ | OCH₂CF₃ | CH | |
| CH₃ | SCH₂CH=CH₂ | H | OCH₃ | OCH₂CF₃ | CH | |
| CH₃ | SCH₂CH=CH₂ | H | OCH₃ | C₂H₅ | CH | |

TABLE I-continued

| R₁ | R₂ | R | X | Y | Z | m.p. (°C.) |
|---|---|---|---|---|---|---|
| CH₃ | SCH₂CH=CH₂ | H | OCH₃ | C₂H₅ | CH | |
| CH₃ | SCH₂CH=CH₂ | H | OCH₃ | NHCH₃ | CH | |
| CH₃ | SCH₂CH=CH₂ | H | OCH₃ | NHCH₃ | N | |
| CH₃ | SCH₂CH=CH₂ | H | CH₃ | OC₂H₅ | CH | |
| CH₃ | SCH₂CH=CH₂ | H | OCH₃ | OC₂H₅ | CH | |
| CH₃ | SCH₂CH=CH₂ | H | CH₃ | OC₂H₅ | N | |
| CH₃ | SCH₂CH=CH₂ | H | OCH₃ | OC₂H₅ | N | |
| CH₃ | SCH₂CH=CH₂ | H | CH₃ | OCH₂CHF₂ | CH | |
| CH₃ | SCH₂CH=CH₂ | H | OCH₃ | OCH₂CHF₂ | CH | |
| CH₃ | SCH₂CH=CH₂ | H | CH₃ | OCH₂CHF₂ | N | |
| CH₃ | SCH₂CH=CH₂ | H | OCH₃ | OCH₂CHF₂ | N | |
| CH₃ | SCH₂CH=CH₂ | H | CH₃ | OCH₂CH₂F | CH | |
| CH₃ | SCH₂CH=CH₂ | H | OCH₃ | OCH₂CH₂F | CH | |
| CH₃ | SCH₂CH=CH₂ | H | CH₃ | OCH₂CH₂F | N | |
| CH₃ | SCH₂CH=CH₂ | H | OCH₃ | OCH₂CH₂F | N | |
| CH₃ | SCH₂CH=CH₂ | CH₃ | Cl | OCH₃ | CH | |
| CH₃ | SCH₂CH=CH₂ | H | Cl | N(CH₃)₂ | CH | |
| CH₃ | SCH₂CH=CH₂ | H | Cl | OC₂H₅ | CH | |
| C₂H₅ | SCH₂CH=CH₂ | H | CH₃ | CH₃ | CH | |
| C₂H₅ | SCH₂CH=CH₂ | H | OCH₃ | CH₃ | CH | |
| C₂H₅ | SCH₂CH=CH₂ | H | OCH₃ | OCH₃ | CH | |
| C₂H₅ | SCH₂CH=CH₂ | H | Cl | OCH₃ | CH | |
| C₂H₅ | SCH₂CH=CH₂ | H | CH₃ | CH₃ | N | |
| C₂H₅ | SCH₂CH=CH₂ | H | OCH₃ | CH₃ | N | |
| C₂H₅ | SCH₂CH=CH₂ | H | OCH₃ | OCH₃ | N | |
| C₂H₅ | SCH₂CH=CH₂ | H | Br | OCH₃ | CH | |
| C₂H₅ | SCH₂CH=CH₂ | H | OCH₃ | N(CH₃)₂ | CH | |
| C₂H₅ | SCH₂CH=CH₂ | H | OCH₃ | N(CH₃)₂ | N | |
| C₂H₅ | SCH₂CH=CH₂ | H | OCH₃ | NHCH₃ | N | |
| C₂H₅ | SCH₂CH=CH₂ | H | OCH₃ | C₂H₅ | CH | |
| C₂H₅ | SCH₂CH=CH₂ | H | OCH₃ | C₂H₅ | N | |
| C₂H₅ | SCH₂CH=CH₂ | H | CH₃ | OC₂H₅ | CH | |
| C₂H₅ | SCH₂CH=CH₂ | H | CH₃ | OC₂H₅ | N | |
| C₂H₅ | SCH₂CH=CH₂ | H | OCH₃ | OC₂H₅ | CH | |
| C₂H₅ | SCH₂CH=CH₂ | H | OCH₃ | OC₂H₅ | N | |
| C₂H₅ | SCH₂CH=CH₂ | H | CH₃ | OCH₂CF₃ | CH | |
| C₂H₅ | SCH₂CH=CH₂ | H | CH₃ | OCH₂CF₃ | N | |
| C₂H₅ | SCH₂CH=CH₂ | H | OCH₃ | OCH₂CF₃ | CH | |
| C₂H₅ | SCH₂CH=CH₂ | H | OCH₃ | OCH₂CF₃ | N | |
| C₂H₅ | SCH₂CH=CH₂ | H | OCH₃ | OCH₂CF₂ | CH | |
| C₂H₅ | SCH₂CH=CH₂ | H | OCH₃ | OCH₂CHF₂ | N | |
| C₂H₅ | SCH₂CH=CH₂ | H | CH₃ | OCH₂CHF₂ | N | |
| C₂H₅ | SCH₂CH=CH₂ | H | OCH₃ | OCH₂CH₂F | CH | |
| C₂H₅ | SCH₂CH=CH₂ | H | OCH₃ | OCH₂CH₂F | N | |
| C₂H₅ | SCH₂CH=CH₂ | CH₃ | OCH₃ | OCH₃ | CH | |
| C₂H₅ | SCH₂CH=CH₂ | CH₃ | CH₃ | OCH₃ | N | |
| C₂H₅ | SCH₂CH=CH₂ | CH₃ | OCH₃ | OCH₃ | N | |
| n-C₃H₇ | SCH₂CH=CH₂ | H | OCH₃ | OCH₃ | CH | |
| n-C₃H₇ | SCH₂CH=CH₂ | H | CH | OCH₃ | N | |
| CH(CH₃)₂ | SCH₂CH=CH₂ | H | OCH₃ | CH₃ | CH | |
| CH(CH₃)₂ | SCH₂CH=CH₂ | H | OCH₃ | OCH₃ | CH | |
| CH(CH₃)₂ | SCH₂CH=CH₂ | H | Cl | OCH₃ | CH | |
| CH(CH₃)₂ | SCH₂CH=CH₂ | H | OCH₃ | CH₃ | N | |
| CH(CH₃)₂ | SCH₂CH=CH₂ | H | OCH₃ | OCH₃ | N | |
| CH(CH₃)₂ | SCH₂CH=CH₂ | H | OCH₃ | N(CH₃)₂ | N | |
| CH₃ | SCH₂CH=CHCH₃ | H | CH₃ | CH₃ | CH | |
| CH₃ | SCH₂CH=CHCH₃ | H | OCH₃ | CH₃ | CH | |
| CH₃ | SCH₂CH=CHCH₃ | H | OCH₃ | OCH₃ | CH | |
| CH₃ | SCH₂CH=CHCH₃ | H | Cl | OCH₃ | CH | |
| CH₃ | SCH₂CH=CHCH₃ | H | CH₃ | CH₃ | N | |
| CH₃ | SCH₂CH=CHCH₃ | H | OCH₃ | CH₃ | N | |
| CH₃ | SCH₂CH=CHCH₃ | H | OCH₃ | OCH₃ | N | |
| CH₃ | SCH₂CH=CHCH₃ | H | OCH₃ | N(CH₃)₂ | CH | |
| CH₃ | SCH₂CH=CHCH₃ | H | OCH₃ | N(CH₃)₂ | N | |
| CH₃ | SCH₂CH=CHCH₃ | H | OCH₃ | OCH₂CF₃ | N | |
| CH₃ | SCH₂CH=CHCH₃ | CH₃ | OCH₃ | CH₃ | N | |
| CH₃ | SCH₂CH=CHCH₃ | CH₃ | OCH₃ | OCH₃ | N | |
| CH₃ | SCH₂CH=CHCH₃ | CH₃ | CH₃ | OCH₃ | CH | |
| CH₃ | SCH₂CH=CHCH₃ | CH₃ | OCH₃ | OCH₃ | CH | |
| CH₃ | SCH₂CH=CHCH₃ | H | Br | OCH₃ | CH | |
| CH₃ | SCH₂CH=CHCH₃ | H | CH₃ | OCH₂CF₃ | N | |

TABLE I-continued

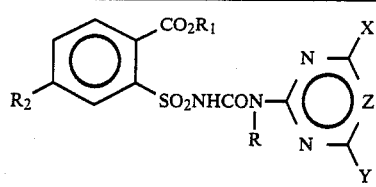

| $R_1$ | $R_2$ | R | X | Y | Z | m.p. (°C.) |
|---|---|---|---|---|---|---|
| $CH_3$ | $SCH_2CH=CHCH_3$ | H | $CH_3$ | $OCH_2CF_3$ | CH | |
| $CH_3$ | $SCH_2CH=CHCH_3$ | H | $OCH_3$ | $OCH_2CF_3$ | CH | |
| $CH_3$ | $SCH_2CH=CHCH_3$ | H | $OCH_3$ | $NHCH_3$ | N | |
| $C_2H_5$ | $SCH_2CH=CHCH_3$ | H | $CH_3$ | $CH_3$ | CH | |
| $C_2H_5$ | $SCH_2CH=CHCH_3$ | H | $OCH_3$ | $CH_3$ | CH | |
| $C_2H_5$ | $SCH_2CH=CHCH_3$ | H | $OCH_3$ | $OCH_3$ | CH | |
| $C_2H_5$ | $SCH_2CH=CHCH_3$ | H | Cl | $OCH_3$ | CH | |
| $C_2H_5$ | $SCH_2CH=CHCH_3$ | H | $OCH_3$ | $CH_3$ | N | |
| $C_2H_5$ | $SCH_2CH=CHCH_3$ | H | $OCH_3$ | $N(CH_3)_2$ | CH | |
| $CH(CH_3)_2$ | $SCH_2CH=CHCH_3$ | H | $OCH_3$ | $CH_3$ | CH | |
| $CH(CH_3)_2$ | $SCH_2CH=CHCH_3$ | H | $OCH_3$ | $OCH_3$ | CH | |
| $CH(CH_3)_2$ | $SCH_2CH=CHCH_3$ | H | Cl | $OCH_3$ | CH | |
| $CH(CH_3)_2$ | $SCH_2CH=CHCH_3$ | H | $OCH_3$ | $CH_3$ | N | |
| $CH(CH_3)_2$ | $SCH_2CH=CHCH_3$ | H | $OCH_3$ | $OCH_3$ | N | |
| $CH_3$ | $SCH_2CH=CHC_2H_5$ | H | $CH_3$ | $CH_3$ | CH | |
| $CH_3$ | $SCH_2CH=CHC_2H_5$ | H | $OCH_3$ | $CH_3$ | CH | |
| $CH_3$ | $SCH_2CH=CHC_2H_5$ | H | $OCH_3$ | $OCH_3$ | CH | |
| $CH_3$ | $SCH_2CH=CHC_2H_5$ | H | Cl | $OCH_3$ | CH | |
| $CH_3$ | $SCH_2CH=CHC_2H_5$ | H | $CH_3$ | $CH_3$ | N | |
| $CH_3$ | $SCH_2CH=CHC_2H_5$ | H | $OCH_3$ | $CH_3$ | N | |
| $CH_3$ | $SCH_2CH=CHC_2H_5$ | H | $OCH_3$ | $OCH_3$ | N | |
| $CH_3$ | $SCH_2CH=CHC_2H_5$ | H | $OCH_3$ | $N(CH_3)_2$ | CH | |
| $CH_3$ | $SCH_2CH=CHC_2H_5$ | H | $OCH_3$ | $N(CH_3)_2$ | N | |
| $CH_3$ | $SCH_2CH=CHC_2H_5$ | H | $OCH_3$ | $OCH_2CF_3$ | N | |
| $CH_3$ | $SCH_2CH=CHC_2H_5$ | $CH_3$ | $OCH_3$ | $CH_3$ | N | |
| $CH_3$ | $SCH_2CH=CHC_2H_5$ | $CH_3$ | $OCH_3$ | $OCH_3$ | N | |
| $CH_3$ | $SCH_2CH=CHC_2H_5$ | $CH_3$ | $CH_3$ | $OCH_3$ | CH | |
| $CH_3$ | $SCH_2CH=CHC_2H_5$ | $CH_3$ | $OCH_3$ | $OCH_3$ | CH | |
| $CH_3$ | $SCH_2CH=CHC_2H_5$ | H | Br | $OCH_3$ | CH | |
| $CH_3$ | $SCH_2CH=CHC_2H_5$ | H | $CH_3$ | $OCH_2CF_3$ | N | |
| $CH_3$ | $SCH_2CH=CHC_2H_5$ | H | $CH_3$ | $OCH_2CF_3$ | CH | |
| $CH_3$ | $SCH_2CH=CHC_2H_5$ | H | $OCH_3$ | $OCH_2CF_3$ | CH | |
| $CH_3$ | $SCH_2CH=CHC_2H_5$ | H | $OCH_3$ | $NHCH_3$ | N | |
| $C_2H_5$ | $SCH_2CH=CHC_2H_5$ | H | $CH_3$ | $CH_3$ | CH | |
| $C_2H_5$ | $SCH_2CH=CHC_2H_5$ | H | $OCH_3$ | $CH_3$ | CH | |
| $C_2H_5$ | $SCH_2CH=CHC_2H_5$ | H | $OCH_3$ | $OCH_3$ | CH | |
| $C_2H_5$ | $SCH_2CH=CHC_2H_5$ | H | Cl | $OCH_3$ | CH | |
| $C_2H_5$ | $SCH_2CH=CHC_2H_5$ | H | $OCH_3$ | $CH_3$ | N | |
| $C_2H_5$ | $SCH_2CH=CHC_2H_5$ | H | $OCH_3$ | $N(CH_3)_2$ | CH | |
| $CH(CH_3)_2$ | $SCH_2CH=CHC_2H_5$ | H | $OCH_3$ | $CH_3$ | CH | |
| $CH(CH_3)_2$ | $SCH_2CH=CHC_2H_5$ | H | $OCH_3$ | $OCH_3$ | CH | |
| $CH(CH_3)_2$ | $SCH_2CH=CHC_2H_5$ | H | Cl | $OCH_3$ | CH | |
| $CH(CH_3)_2$ | $SCH_2CH=CHC_2H_5$ | H | $OCH_3$ | $CH_3$ | N | |
| $CH(CH_3)_2$ | $SCH_2CH=CHC_2H_5$ | H | $OCH_3$ | $OCH_3$ | N | |
| $CH_3$ | $S(CH_2)_2CH=CH_2$ | H | $CH_3$ | $OCH_3$ | CH | |
| $CH_3$ | $S(CH_2)_2CH=CH_2$ | H | $OCH_3$ | $OCH_3$ | CH | |
| $CH_3$ | $S(CH_2)_2CH=CH_2$ | H | $CH_3$ | $OCH_3$ | N | |
| $CH_3$ | $S(CH_2)_2CH=CH_2$ | H | $OCH_3$ | $OCH_3$ | N | |
| $CH_3$ | $S(O)(CH_2CH=CH_2)$ | H | $CH_3$ | $CH_3$ | CH | |
| $CH_3$ | $S(O)(CH_2CH=CH_2)$ | H | $OCH_3$ | $CH_3$ | CH | |
| $CH_3$ | $S(O)(CH_2CH=CH_2)$ | H | $OCH_3$ | $OCH_3$ | CH | |
| $CH_3$ | $S(O)(CH_2CH=CH_2)$ | H | Cl | $OCH_3$ | CH | |
| $CH_3$ | $S(O)(CH_2CH=CH_2)$ | H | $CH_3$ | $CH_3$ | N | |
| $CH_3$ | $S(O)(CH_2CH=CH_2)$ | H | $OCH_3$ | $CH_3$ | N | |
| $CH_3$ | $S(O)(CH_2CH=CH_2)$ | H | $OCH_3$ | $OCH_3$ | N | |
| $CH_3$ | $S(O)(CH_2CH=CH_2)$ | H | $OCH_3$ | $N(CH_3)_2$ | CH | |
| $CH_3$ | $S(O)(CH_2CH=CH_2)$ | H | $OCH_3$ | $N(CH_3)_2$ | N | |
| $CH_3$ | $S(O)(CH_2CH=CH_2)$ | H | $OCH_3$ | $OCH_2CF_3$ | N | |
| $CH_3$ | $S(O)(CH_2CH=CH_2)$ | $CH_3$ | $OCH_3$ | $CH_3$ | N | |
| $CH_3$ | $S(O)(CH_2CH=CH_2)$ | $CH_3$ | $OCH_3$ | $OCH_3$ | N | |
| $CH_3$ | $S(O)(CH_2CH=CH_2)$ | $CH_3$ | $CH_3$ | $OCH_3$ | CH | |
| $CH_3$ | $S(O)(CH_2CH=CH_2)$ | $CH_3$ | $OCH_3$ | $OCH_3$ | CH | |
| $CH_3$ | $S(O)(CH_2CH=CH_2)$ | H | Br | $OCH_3$ | CH | |
| $CH_3$ | $S(O)(CH_2CH=CH_2)$ | H | $CH_3$ | $OCH_2CF_3$ | N | |
| $CH_3$ | $S(O)(CH_2CH=CH_2)$ | H | $CH_3$ | $OCH_2CF_3$ | CH | |
| $CH_3$ | $S(O)(CH_2CH=CH_2)$ | H | $OCH_3$ | $OCH_2CF_3$ | CH | |
| $CH_3$ | $S(O)(CH_2CH=CH_2)$ | H | $OCH_3$ | $NHCH_3$ | N | |
| $C_2H_5$ | $S(O)(CH_2CH=CH_2)$ | H | $CH_3$ | $CH_3$ | CH | |
| $C_2H_5$ | $S(O)(CH_2CH=CH_2)$ | H | $OCH_3$ | $CH_3$ | CH | |
| $C_2H_5$ | $S(O)(CH_2CH=CH_2)$ | H | $OCH_3$ | $OCH_3$ | CH | |
| $C_2H_5$ | $S(O)(CH_2CH=CH_2)$ | H | Cl | $OCH_3$ | CH | |

TABLE I-continued $$\begin{array}{c}\text{structure with } CO_2R_1, R_2, SO_2NHCON(R)\text{-pyrimidine/triazine with X, Y, Z}\end{array}$$

| R₁ | R₂ | R | X | Y | Z | m.p. (°C.) |
|---|---|---|---|---|---|---|
| C₂H₅ | S(O)(CH₂CH=CH₂) | H | OCH₃ | CH₃ | N | |
| C₂H₅ | S(O)(CH₂CH=CH₂) | H | OCH₃ | N(CH₃)₂ | N | |
| CH(CH₃)₂ | S(O)(CH₂CH=CH₂) | H | OCH₃ | CH₃ | CH | |
| CH(CH₃)₂ | S(O)(CH₂CH=CH₂) | H | OCH₃ | OCH₃ | CH | |
| CH(CH₃)₂ | S(O)(CH₂CH=CH₂) | H | Cl | OCH₃ | CH | |
| CH(CH₃)₂ | S(O)(CH₂CH=CH₂) | H | OCH₃ | CH₃ | N | |
| CH(CH₃)₂ | S(O)(CH₂CH=CH₂) | H | OCH₃ | OCH₃ | N | |
| CH₃ | S(O)(CH₂CH=CHCH₃) | H | OCH₃ | CH₃ | CH | |
| CH₃ | S(O)(CH₂CH=CHCH₃) | H | OCH₃ | OCH₃ | CH | |
| CH₃ | S(O)(CH₂CH=CHCH₃) | H | Cl | OCH₃ | CH | |
| CH₃ | S(O)(CH₂CH=CHCH₃) | H | OCH₃ | CH₃ | N | |
| CH₃ | S(O)(CH₂CH=CHCH₃) | H | OCH₃ | OCH₃ | N | |
| CH₃ | S(O)((CH₂)₂CH=CH₂) | H | OCH₃ | CH₃ | CH | |
| CH₃ | S(O)(CH₂CH=CHCH₂CH₃) | H | OCH₃ | OCH₃ | CH | |
| CH₃ | S(O)(CH₂CH=CH(CH₂)₂CH₃) | H | OCH₃ | CH₃ | N | |
| CH₃ | S(O)((CH₂)₂CH=CHCH₂CH₃) | H | OCH₃ | OCH₃ | N | |
| CH₃ | S(O)(CH₂CH=C(CH₃)₂) | H | OCH₃ | CH₃ | CH | |
| CH₃ | SCH₂C≡CH | H | CH₃ | CH₃ | CH | |
| CH₃ | SCH₂C≡CH | H | OCH₃ | CH₃ | CH | |
| CH₃ | SCH₂C≡CH | H | OCH₃ | OCH₃ | CH | |
| CH₃ | SCH₂C≡CH | H | Cl | OCH₃ | CH | |
| CH₃ | SCH₂C≡CH | H | OCH₃ | N(CH₃)₂ | N | |
| CH₃ | SCH₂C≡CH | H | CH₃ | CH₃ | N | |
| CH₃ | SCH₂C≡CH | H | OCH₃ | CH₃ | N | |
| CH₃ | SCH₂C≡CH | H | OCH₃ | OCH₃ | N | |
| CH₃ | SCH₂C≡CH | H | OCH₃ | N(CH₃)₂ | N | |
| CH₃ | SCH₂C≡CH | H | OCH₃ | OCH₂CF₃ | N | |
| CH₃ | SCH₂C≡CH | CH₃ | OCH₃ | CH₃ | N | |
| CH₃ | SCH₂C≡CH | CH₃ | OCH₃ | OCH₃ | N | |
| CH₃ | SCH₂C≡CH | CH₃ | CH₃ | OCH₃ | CH | |
| CH₃ | SCH₂C≡CH | CH₃ | OCH₃ | OCH₃ | CH | |
| CH₃ | SCH₂C≡CH | H | Br | OCH₃ | CH | |
| CH₃ | SCH₂C≡CH | CH₃ | OCH₃ | N(CH₃)₂ | N | |
| CH₃ | SCH₂C≡CH | H | CH₃ | OCH₂CF₃ | N | |
| CH₃ | SCH₂C≡CH | H | CH₃ | OCH₂CF₃ | CH | |
| CH₃ | SCH₂C≡CH | H | OCH₃ | OCH₂CF₃ | CH | |
| CH₃ | SCH₂C≡CH | H | OCH₃ | C₂H₅ | CH | |
| CH₃ | SCH₂C≡CH | H | OCH₃ | C₂H₅ | CH | |
| CH₃ | SCH₂C≡CH | H | OCH₃ | NHCH₃ | CH | |
| CH₃ | SCH₂C≡CH | H | OCH₃ | NHCH₃ | N | |
| CH₃ | SCH₂C≡CH | H | CH₃ | OC₂H₅ | CH | |
| CH₃ | SCH₂C≡CH | H | OCH₃ | OC₂H₅ | CH | |
| CH₃ | SCH₂C≡CH | H | CH₃ | OC₂H₅ | N | |
| CH₃ | SCH₂C≡CH | H | OCH₃ | OC₂H₅ | N | |
| CH₃ | SCH₂C≡CH | H | CH₃ | OCH₂CHF₂ | CH | |
| CH₃ | SCH₂C≡CH | H | OCH₃ | OCH₂CHF₂ | CH | |
| CH₃ | SCH₂C≡CH | H | CH | OCH₂CHF₂ | N | |
| CH₃ | SCH₂C≡CH | H | OCH₃ | OCH₂CHF₂ | N | |
| CH₃ | SCH₂C≡CH | H | CH₃ | OCH₂CH₂F | CH | |
| CH₃ | SCH₂C≡CH | H | OCH₃ | OCH₂CH₂F | CH | |
| CH₃ | SCH₂C≡CH | H | CH₃ | OCH₂CH₂F | N | |
| CH₃ | SCH₂C≡CH | H | OCH₃ | OCH₂CH₂F | N | |
| CH₃ | SCH₂C≡CH | CH₃ | Cl | OCH₃ | CH | |
| CH₃ | SCH₂C≡CH | H | Cl | N(CH₃)₂ | CH | |
| CH₃ | SCH₂C≡CH | H | Cl | OC₂H₅ | CH | |
| C₂H₅ | SCH₂C≡CH | H | CH₃ | CH₃ | CH | |
| C₂H₅ | SCH₂C≡CH | H | OCH₃ | CH₃ | CH | |
| C₂H₅ | SCH₂C≡CH | H | OCH₃ | OCH₃ | CH | |
| C₂H₅ | SCH₂C≡CH | H | Cl | OCH₃ | CH | |
| C₂H₅ | SCH₂C≡CH | H | CH₃ | CH₃ | N | |
| C₂H₅ | SCH₂C≡CH | H | OCH₃ | CH₃ | N | |
| C₂H₅ | SCH₂C≡CH | H | OCH₃ | OCH₃ | N | |
| C₂H₅ | SCH₂C≡CH | H | Br | OCH₃ | CH | |
| C₂H₅ | SCH₂C≡CH | H | OCH₃ | N(CH₃)₂ | CH | |
| C₂H₅ | SCH₂C≡CH | H | OCH₃ | N(CH₃)₂ | N | |
| C₂H₅ | SCH₂C≡CH | H | OCH₃ | NHCH₃ | N | |
| C₂H₅ | SCH₂C≡CH | H | OCH₃ | C₂H₅ | CH | |
| C₂H₅ | SCH₂C≡CH | H | OCH₃ | C₂H₅ | N | |
| C₂H₅ | SCH₂C≡CH | H | CH₃ | OC₂H₅ | CH | |
| C₂H₅ | SCH₂C≡CH | H | CH₃ | OC₂H₅ | N | |
| C₂H₅ | SCH₂C≡CH | H | OCH₃ | OC₂H₅ | CH | |

TABLE I-continued

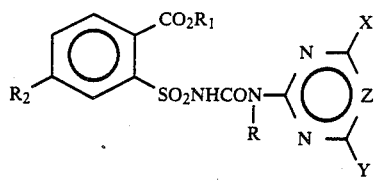

| R₁ | R₂ | R | X | Y | Z | m.p. (°C.) |
|---|---|---|---|---|---|---|
| C₂H₅ | SCH₂C≡CH | H | OCH₃ | OC₂H₅ | N | |
| C₂H₅ | SCH₂C≡CH | H | CH₃ | OCH₂CF₃ | CH | |
| C₂H₅ | SCH₂C≡CH | H | CH₃ | OCH₂CF₃ | N | |
| C₂H₅ | SCH₂C≡CH | H | OCH₃ | OCH₂CF₃ | CH | |
| C₂H₅ | SCH₂C≡CH | H | OCH₃ | OCH₂CF₃ | N | |
| C₂H₅ | SCH₂C≡CH | H | OCH₃ | OCH₂CF₂ | CH | |
| C₂H₅ | SCH₂C≡CH | H | OCH₃ | OCH₂CHF₂ | N | |
| C₂H₅ | SCH₂C≡CH | H | CH₃ | OCH₂CHF₂ | N | |
| C₂H₅ | SCH₂C≡CH | H | OCH₃ | OCH₂CH₂F | CH | |
| C₂H₅ | SCH₂C≡CH | H | OCH₃ | OCH₂CH₂F | N | |
| C₂H₅ | SCH₂C≡CH | CH₃ | OCH₃ | OCH₃ | CH | |
| C₂H₅ | SCH₂C≡CH | CH₃ | CH₃ | OCH₃ | N | |
| C₂H₅ | SCH₂C≡CH | CH₃ | OCH₃ | OCH₃ | N | |
| n-C₃H₇ | SCH₂C≡CH | H | OCH₃ | OCH₃ | CH | |
| n-C₃H₇ | SCH₂C≡CH | H | CH₃ | OCH₃ | N | |
| CH(CH₃)₂ | SCH₂C≡CH | H | OCH₃ | CH₃ | CH | |
| CH(CH₃)₂ | SCH₂C≡CH | H | OCH₃ | OCH₃ | CH | |
| CH(CH₃)₂ | SCH₂C≡CH | H | Cl | OCH₃ | CH | |
| CH(CH₃)₂ | SCH₂C≡CH | H | OCH₃ | CH₃ | N | |
| CH(CH₃)₂ | SCH₂C≡CH | H | OCH₃ | OCH₃ | N | |
| CH(CH₃)₂ | SCH₂C≡CH | H | OCH₃ | N(CH₃)₂ | N | |
| CH₃ | SCH₂C≡CCH₃ | H | CH₃ | CH₃ | CH | |
| CH₃ | SCH₂C≡CCH₃ | H | OCH₃ | CH₃ | CH | |
| CH₃ | SCH₂C≡CCH₃ | H | OCH₃ | OCH₃ | CH | |
| CH₃ | SCH₂C≡CCH₃ | H | Cl | OCH₃ | CH | |
| CH₃ | SCH₂C≡CCH₃ | H | CH₃ | CH₃ | N | |
| CH₃ | SCH₂C≡CCH₃ | H | OCH₃ | CH₃ | N | |
| CH₃ | SCH₂C≡CCH₃ | H | OCH₃ | OCH₃ | N | |
| CH₃ | SCH₂C≡CCH₃ | H | OCH₃ | N(CH₃)₂ | CH | |
| CH₃ | SCH₂C≡CCH₃ | H | OCH₃ | N(CH₃)₂ | N | |
| CH₃ | SCH₂C≡CCH₃ | H | OCH₃ | OCH₂CF₃ | N | |
| CH₃ | SCH₂C≡CCH₃ | CH₃ | OCH₃ | CH₃ | N | |
| CH₃ | SCH₂C≡CCH₃ | CH₃ | OCH₃ | OCH₃ | N | |
| CH₃ | SCH₂C≡CCH₃ | CH₃ | CH₃ | OCH₃ | CH | |
| CH₃ | SCH₂C≡CCH₃ | CH₃ | OCH₃ | OCH₃ | CH | |
| CH₃ | SCH₂C≡CCH₃ | H | Br | OCH₃ | CH | |
| CH₃ | SCH₂C≡CCH₃ | H | CH₃ | OCH₂CF₃ | N | |
| CH₃ | SCH₂C≡CCH₃ | H | CH₃ | OCH₂CF₃ | CH | |
| CH₃ | SCH₂C≡CCH₃ | H | OCH₃ | OCH₂CF₃ | CH | |
| CH₃ | SCH₂C≡CCH₃ | H | OCH₃ | NHCH₃ | N | |
| C₂H₅ | SCH₂C≡CCH₃ | H | CH₃ | CH₃ | CH | |
| C₂H₅ | SCH₂C≡CCH₃ | H | OCH₃ | CH₃ | CH | |
| C₂H₅ | SCH₂C≡CCH₃ | H | OCH₃ | OCH₃ | CH | |
| C₂H₅ | SCH₂C≡CCH₃ | H | Cl | OCH₃ | CH | |
| C₂H₅ | SCH₂C≡CCH₃ | H | OCH₃ | CH₃ | N | |
| C₂H₅ | SCH₂C≡CCH₃ | H | OCH₃ | N(CH₃)₂ | CH | |
| CH(CH₃)₂ | SCH₂C≡CCH₃ | H | OCH₃ | CH₃ | CH | |
| CH(CH₃)₂ | SCH₂C≡CCH₃ | H | OCH₃ | OCH₃ | CH | |
| CH(CH₃)₂ | SCH₂C≡CCH₃ | H | Cl | OCH₃ | CH | |
| CH(CH₃)₂ | SCH₂C≡CCH₃ | H | OCH₃ | CH₃ | N | |
| CH(CH₃)₂ | SCH₂C≡CCH₃ | H | OCH₃ | OCH₃ | N | |
| CH₃ | SCH₂C≡CC₂H₅ | H | CH₃ | CH₃ | CH | |
| CH₃ | SCH₂C≡CC₂H₅ | H | OCH₃ | CH₃ | CH | |
| CH₃ | SCH₂C≡CC₂H₅ | H | OCH₃ | OCH₃ | CH | |
| CH₃ | SCH₂C≡CC₂H₅ | H | Cl | OCH₃ | CH | |
| CH₃ | SCH₂C≡CC₂H₅ | H | CH₃ | CH₃ | N | |
| CH₃ | SCH₂C≡CC₂H₅ | H | OCH₃ | CH₃ | N | |
| CH₃ | SCH₂C≡CC₂H₅ | H | OCH₃ | OCH₃ | N | |
| CH₃ | SCH₂C≡CC₂H₅ | H | OCH₃ | N(CH₃)₂ | CH | |
| CH₃ | SCH₂C≡CC₂H₅ | H | OCH₃ | N(CH₃)₂ | N | |
| CH₃ | SCH₂C≡CC₂H₅ | H | OCH₃ | OCH₂CF₃ | N | |
| CH₃ | SCH₂C≡CC₂H₅ | CH₃ | OCH₃ | CH₃ | N | |
| CH₃ | SCH₂C≡CC₂H₅ | CH₃ | OCH₃ | OCH₃ | N | |
| CH₃ | SCH₂C≡CC₂H₅ | CH₃ | CH₃ | OCH₃ | CH | |
| CH₃ | SCH₂C≡CC₂H₅ | CH₃ | OCH₃ | OCH₃ | CH | |
| CH₃ | SCH₂C≡CC₂H₅ | H | Br | OCH₃ | CH | |
| CH₃ | SCH₂C≡CC₂H₅ | H | CH₃ | OCH₂CF₃ | N | |
| CH₃ | SCH₂C≡CC₂H₅ | H | CH₃ | OCH₂CF₃ | CH | |
| CH₃ | SCH₂C≡CC₂H₅ | H | OCH₃ | OCH₂CF₃ | CH | |
| CH₃ | SCH₂C≡CC₂H₅ | H | OCH₃ | NHCH₃ | N | |
| C₂H₅ | SCH₂C≡CC₂H₅ | H | CH₃ | CH₃ | CH | |

TABLE I-continued

[Structure: benzene ring with CO₂R₁° and SO₂NHCON(R)- linked to a pyrimidine/triazine ring with X, Y, Z substituents; R₂ on benzene]

| R₁ | R₂ | R | X | Y | Z | m.p. (°C.) |
|---|---|---|---|---|---|---|
| C₂H₅ | SCH₂C≡CC₂H₅ | H | OCH₃ | CH₃ | CH | |
| C₂H₅ | SCH₂C≡CC₂H₅ | H | OCH₃ | OCH₃ | CH | |
| C₂H₅ | SCH₂C≡CC₂H₅ | H | Cl | OCH₃ | CH | |
| C₂H₅ | SCH₂C≡CC₂H₅ | H | OCH₃ | CH₃ | N | |
| C₂H₅ | SCH₂C≡CC₂H₅ | H | OCH₃ | N(CH₃)₂ | CH | |
| CH(CH₃)₂ | SCH₂C≡CC₂H₅ | H | OCH₃ | CH₃ | CH | |
| CH(CH₃)₂ | SCH₂C≡CC₂H₅ | H | OCH₃ | OCH₃ | CH | |
| CH(CH₃)₂ | SCH₂C≡CC₂H₅ | H | Cl | OCH₃ | CH | |
| CH(CH₃)₂ | SCH₂C≡CC₂H₅ | H | OCH₃ | CH₃ | N | |
| CH(CH₃)₂ | SCH₂C≡CC₂H₅ | H | OCH₃ | OCH₃ | N | |
| CH₃ | S(CH₂)₂C≡CH | H | CH₃ | OCH₃ | CH | |
| CH₃ | S(CH₂)₂C≡CH | H | OCH₃ | OCH₃ | CH | |
| CH₃ | S(CH₂)₂C≡CH | H | CH₃ | OCH₃ | N | |
| CH₃ | S(O)(CH₂C≡CH) | H | CH₃ | CH₃ | CH | |
| CH₃ | S(O)(CH₂C≡CH) | H | OCH₃ | CH₃ | CH | |
| CH₃ | S(O)(CH₂C≡CH) | H | OCH₃ | OCH₃ | CH | |
| CH₃ | S(O)(CH₂C≡CH) | H | Cl | OCH₃ | CH | |
| CH₃ | S(O)(CH₂C≡CH) | H | CH₃ | CH₃ | N | |
| CH₃ | S(O)(CH₂C≡CH) | H | OCH₃ | CH₃ | N | |
| CH₃ | S(O)(CH₂C≡CH) | H | OCH₃ | OCH₃ | N | |
| CH₃ | S(O)(CH₂C≡CH) | H | OCH₃ | N(CH₃)₂ | CH | |
| CH₃ | S(O)(CH₂C≡CH) | H | OCH₃ | N(CH₃)₂ | N | |
| CH₃ | S(O)(CH₂C≡CH) | H | OCH₃ | OCH₂CF₃ | N | |
| CH₃ | S(O)(CH₂C≡CH) | CH₃ | OCH₃ | CH₃ | N | |
| CH₃ | S(O)(CH₂C≡CH) | CH₃ | OCH₃ | OCH₃ | N | |
| CH₃ | S(O)(CH₂C≡CH) | CH₃ | CH₃ | OCH₃ | CH | |
| CH₃ | S(O)(CH₂C≡CH) | CH₃ | OCH₃ | OCH₃ | CH | |
| CH₃ | S(O)(CH₂C≡CH) | H | Br | OCH₃ | CH | |
| CH₃ | S(O)(CH₂C≡CH) | H | CH₃ | OCH₂CF₃ | N | |
| CH₃ | S(O)(CH₂C≡CH) | H | CH₃ | OCH₂CF₃ | CH | |
| CH₃ | S(O)(CH₂C≡CH) | H | OCH₃ | OCH₂CF₃ | CH | |
| CH₃ | S(O)(CH₂C≡CH) | H | OCH₃ | NHCH₃ | N | |
| C₂H₅ | S(O)(CH₂C≡CH) | H | CH₃ | CH₃ | CH | |
| C₂H₅ | S(O)(CH₂C≡CH) | H | OCH₃ | CH₃ | CH | |
| C₂H₅ | S(O)(CH₂C≡CH) | H | OCH₃ | OCH₃ | CH | |
| C₂H₅ | S(O)(CH₂C≡CH) | H | Cl | OCH₃ | CH | |
| C₂H₅ | S(O)(CH₂C≡CH) | H | OCH₃ | CH₃ | N | |
| C₂H₅ | S(O)(CH₂C≡CH) | H | OCH₃ | N(CH₃)₂ | N | |
| CH(CH₃)₂ | S(O)(CH₂C≡CH) | H | OCH₃ | CH₃ | CH | |
| CH(CH₃)₂ | S(O)(CH₂C≡CH) | H | OCH₃ | OCH₃ | CH | |
| CH(CH₃)₂ | S(O)(CH₂C≡CH) | H | Cl | OCH₃ | CH | |
| CH(CH₃)₂ | S(O)(CH₂C≡CH) | H | OCH₃ | CH₃ | N | |
| CH(CH₃)₂ | S(O)(CH₂C≡CH) | H | OCH₃ | OCH₃ | N | |
| CH₃ | S(O)(CH₂C≡CCH₃) | H | OCH₃ | CH₃ | CH | |
| CH₃ | S(O)(CH₂C≡CCH₃) | H | OCH₃ | OCH₃ | CH | |
| CH₃ | S(O)(CH₂C≡CCH₃) | H | Cl | OCH₃ | CH | |
| CH₃ | S(O)(CH₂C≡CCH₃) | H | OCH₃ | CH₃ | N | |
| CH₃ | S(O)(CH₂C≡CCH₃) | H | OCH₃ | OCH₃ | N | |
| CH₃ | S(O)((CH₂)₂C≡CH) | H | OCH₃ | CH₃ | CH | |
| CH₃ | S(O)(CH₂≡CCH₂CH₃) | H | OCH₃ | OCH₃ | CH | |
| CH₃ | S(O)((CH₂)₂C≡CCH₃) | H | OCH₃ | CH₃ | CH | |
| CH₃ | S(O)((CH₂)₂C≡CCH≡CH₃) | H | OCH₃ | OCH₃ | CH | |
| CH₃ | S(O)((CH₂)₄C≡CH) | H | OCH₃ | CH₃ | N | |
| CH₃ | S(O)₂(CH₂CH=CH₂) | H | CH₃ | CH₃ | CH | |
| CH₃ | S(O)₂(CH₂CH=CH₂) | H | OCH₃ | CH₃ | CH | |
| CH₃ | S(O)₂(CH₂CH=CH₂) | H | OCH₃ | OCH₃ | CH | |
| CH₃ | S(O)₂(CH₂CH=CH₂) | H | Cl | OCH₃ | CH | |
| CH₃ | S(O)₂(CH₂CH=CH₂) | H | CH₃ | CH₃ | N | |
| CH₃ | S(O)₂(CH₂CH=CH₂) | H | OCH₃ | CH₃ | N | |
| CH₃ | S(O)₂(CH₂CH=CH₂) | H | OCH₃ | OCH₃ | N | |
| CH₃ | S(O)₂(CH₂CH=CHCH₃) | H | OCH₃ | CH₃ | CH | |
| CH₃ | S(O)₂(CH₂CH=CHCH₃) | H | OCH₃ | OCH₃ | CH | |
| CH₃ | S(O)₂(CH₂CH=CHCH₃) | H | Cl | OCH₃ | CH | |
| CH₃ | S(O)₂(CH₂CH=CHCH₃) | H | OCH₃ | CH₃ | N | |
| CH₃ | S(O)₂(CH₂CH=CHCH₃) | H | OCH₃ | OCH₃ | N | |
| CH₃ | S(O)₂((CH₂)₂CH=CH₂) | H | OCH₃ | CH₃ | CH | |
| CH₃ | S(O)₂(CH₂CH=CHCH₂CH₃) | H | OCH₃ | OCH₃ | N | |
| CH₃ | S(O)₂(CH₂CH=CH(CH₂)₂CH₃) | H | OCH₃ | CH₃ | N | |
| CH₃ | S(O)₂((CH₂)₂CH=CH(CH₂)₂CH₃) | H | OCH₃ | OCH₃ | CH | |
| CH₃ | S(O)₂(CH₂CH=C(CH₃)₂) | H | OCH₃ | CH₃ | CH | |
| CH₃ | S(O)₂(CH₂C≡CH) | H | CH₃ | CH₃ | CH | |

TABLE I-continued

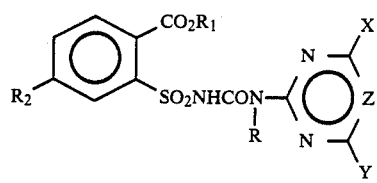

| R₁ | R₂ | R | X | Y | Z | m.p. (°C.) |
|---|---|---|---|---|---|---|
| CH₃ | S(O)₂(CH₂C≡CH) | H | OCH₃ | CH₃ | CH | |
| CH₃ | S(O)₂(CH₂C≡CH) | H | OCH₃ | OCH₃ | CH | |
| CH₃ | S(O)₂(CH₂C≡CH) | H | Cl | OCH₃ | CH | |
| CH₃ | S(O)₂(CH₂C≡CH) | H | CH₃ | CH₃ | N | |
| CH₃ | S(O)₂(CH₂C≡CH) | H | OCH₃ | CH₃ | N | |
| CH₃ | S(O)₂(CH₂C≡CH) | H | OCH₃ | OCH₃ | N | |
| CH₃ | S(O)₂(CH₂C≡CCH₃) | H | OCH₃ | CH₃ | CH | |
| CH₃ | S(O)₂(CH₂C≡CCH₃) | H | OCH₃ | OCH₃ | CH | |
| CH₃ | S(O)₂(CH₂C≡CCH₃) | H | Cl | OCH₃ | CH | |
| CH₃ | S(O)₂(CH₂C≡CCH₃) | H | OCH₃ | CH₃ | N | |
| CH₃ | S(O)₂(CH₂C≡CCH₃) | H | OCH₃ | OCH₃ | N | |
| CH₃ | S(O)₂((CH₂)₂C≡CH) | H | OCH₃ | OCH₃ | N | |
| CH₃ | S(O)₂((CH₂)₂C≡CCH₂CH₃) | H | CH₃ | OCH₃ | CH | |
| CH₃ | S(O)₂((CH₂)₂C≡CCH₃) | H | OCH₃ | OCH₃ | CH | |
| CH₃ | S(O)₂((CH₂)₂C≡CCH₂CH₃) | H | CH₃ | OCH₃ | CH | |
| CH₃ | S(O)₂((CH₂)₄C≡CH) | H | OCH₃ | CH₃ | CH | |
| CH₃ | CH₂CH₂F | H | CH₃ | CH₃ | CH | |
| CH₃ | CH₂CH₂F | H | OCH₃ | CH₃ | CH | |
| CH₃ | CH₂CH₂F | H | OCH₃ | OCH₃ | CH | |
| CH₃ | CH₂CH₂F | H | Cl | OCH₃ | CH | |
| CH₃ | CH₂CH₂F | H | OCH₃ | N(CH₃)₂ | CH | |
| CH₃ | CH₂CH₂F | H | CH₃ | CH₃ | N | |
| CH₃ | CH₂CH₂F | H | OCH₃ | CH₃ | N | |
| CH₃ | CH₂CH₂F | H | OCH₃ | OCH₃ | N | |
| CH₃ | CH₂CH₂F | H | OCH₃ | N(CH₃)₂ | N | |
| CH₃ | CH₂CH₂F | H | OCH₃ | OCH₂CF₃ | N | |
| CH₃ | CH₂CH₂F | CH₃ | OCH₃ | CH₃ | N | |
| CH₃ | CH₂CH₂F | CH₃ | OCH₃ | OCH₃ | N | |
| CH₃ | CH₂CH₂F | CH₃ | CH₃ | OCH₃ | CH | |
| CH₃ | CH₂CH₂F | CH₃ | OCH₃ | OCH₃ | CH | |
| CH₃ | CH₂CH₂F | H | Br | OCH₃ | CH | |
| CH₃ | CH₂CH₂F | CH₃ | OCH₃ | N(CH₃)₂ | N | |
| CH₃ | CH₂CH₂F | H | CH₃ | OCH₂CF₃ | N | |
| CH₃ | CH₂CH₂F | H | CH₃ | OCH₂CF₃ | CH | |
| CH₃ | CH₂CH₂F | H | OCH₃ | OCH₂CF₃ | CH | |
| CH₃ | CH₂CH₂F | H | OCH₃ | C₂H₅ | CH | |
| CH₃ | CH₂CH₂F | H | OCH₃ | C₂H₅ | N | |
| CH₃ | CH₂CH₂F | H | OCH₃ | NHCH₃ | CH | |
| CH₃ | CH₂CH₂F | H | OCH₃ | NHCH₃ | N | |
| CH₃ | CH₂CH₂F | H | CH₃ | OC₂H₅ | CH | |
| CH₃ | CH₂CH₂F | H | OCH₃ | OC₂H₅ | CH | |
| CH₃ | CH₂CH₂F | H | CH₃ | OC₂H₅ | N | |
| CH₃ | CH₂CH₂F | H | OCH₃ | OC₂H₅ | N | |
| CH₃ | CH₂CH₂F | H | CH₃ | OCH₂CHF₂ | CH | |
| CH₃ | CH₂CH₂F | H | OCH₃ | OCH₂CHF₂ | CH | |
| CH₃ | CH₂CH₂F | H | CH₃ | OCH₂CHF₂ | N | |
| CH₃ | CH₂CH₂F | H | OCH₃ | OCH₂CHF₂ | N | |
| CH₃ | CH₂CH₂F | H | CH₃ | OCH₂CH₂F | CH | |
| CH₃ | CH₂CH₂F | H | OCH₃ | OCH₂CH₂F | CH | |
| CH₃ | CH₂CH₂F | H | CH₃ | OCH₂CF₃ | N | |
| CH₃ | CH₂CH₂F | CH₃ | OCH₃ | OCH₂CF₃ | N | |
| CH₃ | CH₂CH₂F | CH₃ | Cl | OCH₃ | CH | |
| CH₃ | CH₂CH₂F | H | Cl | N(CH₃)₂ | CH | |
| CH₃ | CH₂CH₂F | H | Cl | OC₂H₅ | CH | |
| C₂H₅ | CH₂CH₂F | H | CH₃ | CH₃ | CH | |
| C₂H₅ | CH₂CH₂F | H | OCH₃ | CH₃ | CH | |
| C₂H₅ | CH₂CH₂F | H | OCH₃ | OCH₃ | CH | |
| C₂H₅ | CH₂CH₂F | H | Cl | OCH₃ | CH | |
| C₂H₅ | CH₂CH₂F | H | CH₃ | CH₃ | N | |
| C₂H₅ | CH₂CH₂F | H | OCH₃ | CH₃ | N | |
| C₂H₅ | CH₂CH₂F | H | OCH₃ | OCH₃ | N | |
| C₂H₅ | CH₂CH₂F | H | Br | OCH₃ | CH | |
| C₂H₅ | CH₂CH₂F | H | OCH₃ | N(CH₃)₂ | CH | |
| C₂H₅ | CH₂CH₂F | H | OCH₃ | N(CH₃)₂ | N | |
| C₂H₅ | CH₂CH₂F | H | OCH₃ | NHCH₃ | N | |
| C₂H₅ | CH₂CH₂F | H | OCH₃ | C₂H₅ | CH | |
| C₂H₅ | CH₂CH₂F | H | OCH₃ | C₂H₅ | N | |
| C₂H₅ | CH₂CH₂F | H | CH₃ | OC₂H₅ | CH | |
| C₂H₅ | CH₂CH₂F | H | CH₃ | OC₂H₅ | N | |
| C₂H₅ | CH₂CH₂F | H | OCH₃ | OC₂H₅ | CH | |
| C₂H₅ | CH₂CH₂F | H | OCH₃ | OC₂H₅ | N | |

TABLE I-continued

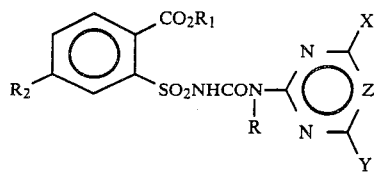

| R₁ | R₂ | R | X | Y | Z | m.p. (°C.) |
|---|---|---|---|---|---|---|
| C₂H₅ | CH₂CH₂F | H | CH₃ | OCH₂CF₃ | CH | |
| C₂H₅ | CH₂CH₂F | H | CH₃ | OCH₂CF₃ | N | |
| C₂H₅ | CH₂CH₂F | H | OCH₃ | OCH₂CF₃ | CH | |
| C₂H₅ | CH₂CH₂F | H | OCH₃ | OCH₂CF₃ | N | |
| C₂H₅ | CH₂CH₂F | H | OCH₃ | OCH₂CHF₂ | CH | |
| C₂H₅ | CH₂CH₂F | H | OCH₃ | OCH₂CHF₂ | N | |
| C₂H₅ | CH₂CH₂F | H | CH₃ | OCH₂CHF₂ | N | |
| C₂H₅ | CH₂CH₂F | H | OCH₃ | OCH₂CH₂F | CH | |
| C₂H₅ | CH₂CH₂F | H | OCH₃ | OCH₂CH₂F | N | |
| C₂H₅ | CH₂CH₂F | CH₃ | OCH₃ | OCH₃ | CH | |
| C₂H₅ | CH₂CH₂F | CH₃ | CH₃ | OCH₃ | N | |
| C₂H₅ | CH₂CH₂F | CH₃ | OCH₃ | OCH₃ | N | |
| n-C₃H₇ | CH₂CH₂F | H | OCH₃ | OCH₃ | CH | |
| n-C₃H₇ | CH₂CH₂F | H | CH₃ | OCH₃ | N | |
| CH(CH₃)₂ | CH₂CH₂F | H | OCH₃ | CH₃ | CH | |
| CH(CH₃)₂ | CH₂CH₂F | H | OCH₃ | OCH₃ | CH | |
| CH(CH₃)₂ | CH₂CH₂F | H | Cl | OCH₃ | CH | |
| CH(CH₃)₂ | CH₂CH₂F | H | OCH₃ | CH₃ | N | |
| CH(CH₃)₂ | CH₂CH₂F | H | OCH₃ | OCH₃ | N | |
| CH(CH₃)₂ | CH₂CH₂F | H | OCH₃ | N(CH₃)₂ | N | |
| CH₃ | CH₂CHF₂ | H | CH₃ | CH₃ | CH | |
| CH₃ | CH₂CHF₂ | H | OCH₃ | CH₃ | CH | |
| CH₃ | CH₂CHF₂ | H | OCH₃ | OCH₃ | CH | |
| CH₃ | CH₂CHF₂ | H | Cl | OCH₃ | CH | |
| CH₃ | CH₂CHF₂ | H | OCH₃ | N(CH₃)₂ | CH | |
| CH₃ | CH₂CHF₂ | H | CH₃ | CH₃ | N | |
| CH₃ | CH₂CHF₂ | H | OCH₃ | CH₃ | N | |
| CH₃ | CH₂CHF₂ | H | OCH₃ | OCH₃ | N | |
| CH₃ | CH₂CHF₂ | H | OCH₃ | N(CH₃)₂ | N | |
| CH₃ | CH₂CHF₂ | H | OCH₃ | OCH₂CF₃ | N | |
| CH₃ | CH₂CHF₂ | CH₃ | OCH₃ | CH₃ | N | |
| CH₃ | CH₂CHF₂ | CH₃ | OCH₃ | OCH₃ | N | |
| CH₃ | CH₂CHF₂ | CH₃ | CH₃ | OCH₃ | CH | |
| CH₃ | CH₂CHF₂ | CH₃ | OCH₃ | OCH₃ | CH | |
| CH₃ | CH₂CHF₂ | H | Br | OCH₃ | CH | |
| CH₃ | CH₂CHF₂ | CH₃ | OCH₃ | N(CH₃)₂ | N | |
| CH₃ | CH₂CHF₂ | H | CH₃ | OCH₂CF₃ | N | |
| CH₃ | CH₂CHF₂ | H | CH₃ | OCH₂CF₃ | CH | |
| CH₃ | CH₂CHF₂ | H | OCH₃ | OCH₂CF₃ | CH | |
| CH₃ | CH₂CHF₂ | H | OCH₃ | C₂H₅ | CH | |
| CH₃ | CH₂CHF₂ | H | OCH₃ | C₂H₅ | N | |
| CH₃ | CH₂CHF₂ | H | OCH₃ | NHCH₃ | CH | |
| CH₃ | CH₂CHF₂ | H | OCH₃ | NHCH₃ | N | |
| CH₃ | CH₂CHF₂ | H | CH₃ | OC₂H₅ | CH | |
| CH₃ | CH₂CHF₂ | H | OCH₃ | OC₂H₅ | CH | |
| CH₃ | CH₂CHF₂ | H | CH₃ | OC₂H₅ | N | |
| CH₃ | CH₂CHF₂ | H | OCH₃ | OC₂H₅ | N | |
| CH₃ | CH₂CHF₂ | H | CH₃ | OCH₂CHF₂ | CH | |
| CH₃ | CH₂CHF₂ | H | OCH₃ | OCH₂CHF₂ | CH | |
| CH₃ | CH₂CHF₂ | H | CH₃ | OCH₂CHF₂ | N | |
| CH₃ | CH₂CHF₂ | H | OCH₃ | OCH₂CHF₂ | N | |
| CH₃ | CH₂CHF₂ | H | CH₃ | OCH₂CH₂F | CH | |
| CH₃ | CH₂CHF₂ | H | OCH₃ | OCH₂CH₂F | CH | |
| CH₃ | CH₂CHF₂ | H | CH₃ | OCH₂CF₃ | N | |
| CH₃ | CH₂CHF₂ | CH₃ | OCH₃ | OCH₂CF₃ | N | |
| CH₃ | CH₂CHF₂ | CH₃ | Cl | OCH₃ | CH | |
| CH₃ | CH₂CHF₂ | H | Cl | N(CH₃)₂ | CH | |
| C₂H₅ | CH₂CHF₂ | H | CH₃ | CH₃ | CH | |
| C₂H₅ | CH₂CHF₂ | H | OCH₃ | CH₃ | CH | |
| C₂H₅ | CH₂CHF₂ | H | OCH₃ | OCH₃ | CH | |
| C₂H₅ | CH₂CHF₂ | H | Cl | OCH₃ | CH | |
| C₂H₅ | CH₂CHF₂ | H | CH₃ | CH₃ | N | |
| C₂H₅ | CH₂CHF₂ | H | OCH₃ | CH₃ | N | |
| C₂H₅ | CH₂CHF₂ | H | OCH₃ | OCH₃ | N | |
| C₂H₅ | CH₂CHF₂ | H | Br | OCH₃ | CH | |
| C₂H₅ | CH₂CHF₂ | H | OCH₃ | N(CH₃)₂ | CH | |
| C₂H₅ | CH₂CHF₂ | H | OCH₃ | N(CH₃)₂ | N | |
| C₂H₅ | CH₂CHF₂ | H | OCH₃ | NHCH₃ | N | |
| C₂H₅ | CH₂CHF₂ | H | OCH₃ | C₂H₅ | CH | |
| C₂H₅ | CH₂CHF₂ | H | OCH₃ | C₂H₅ | N | |
| C₂H₅ | CH₂CHF₂ | H | CH₃ | OC₂H₅ | CH | |

TABLE I-continued

[Structure: benzene ring with $CO_2R_1$ and $SO_2NHCON(R)$- substituents, $R_2$ on ring; connected to a heterocycle with N, X, Y, Z positions]

| $R_1$ | $R_2$ | R | X | Y | Z | m.p. (°C.) |
|---|---|---|---|---|---|---|
| $C_2H_5$ | $CH_2CHF_2$ | H | $CH_3$ | $OC_2H_5$ | N | |
| $C_2H_5$ | $CH_2CHF_2$ | H | $OCH_3$ | $OC_2H_5$ | CH | |
| $C_2H_5$ | $CH_2CHF_2$ | H | $OCH_3$ | $OC_2H_5$ | N | |
| $C_2H_5$ | $CH_2CHF_2$ | H | $CH_3$ | $OCH_2CF_3$ | CH | |
| $C_2H_5$ | $CH_2CHF_2$ | H | $CH_3$ | $OCH_2CF_3$ | N | |
| $C_2H_5$ | $CH_2CHF_2$ | H | $OCH_3$ | $OCH_2CF_3$ | CH | |
| $C_2H_5$ | $CH_2CHF_2$ | H | $OCH_3$ | $OCH_2CF_3$ | N | |
| $C_2H_5$ | $CH_2CHF_2$ | H | $OCH_3$ | $OCH_2CHF_2$ | CH | |
| $C_2H_5$ | $CH_2CHF_2$ | H | $OCH_3$ | $OCH_2CHF_2$ | N | |
| $C_2H_5$ | $CH_2CHF_2$ | H | $CH_3$ | $OCH_2CHF_2$ | N | |
| $C_2H_5$ | $CH_2CHF_2$ | H | $OCH_3$ | $OCH_2CH_2F$ | CH | |
| $C_2H_5$ | $CH_2CHF_2$ | H | $OCH_3$ | $OCH_2CH_2F$ | N | |
| $C_2H_5$ | $CH_2CHF_2$ | $CH_3$ | $OCH_3$ | $OCH_3$ | CH | |
| $C_2H_5$ | $CH_2CHF_2$ | $CH_3$ | $CH_3$ | $OCH_3$ | N | |
| $C_2H_5$ | $CH_2CHF_2$ | $CH_3$ | $OCH_3$ | $OCH_3$ | N | |
| n-$C_3H_7$ | $CH_2CHF_2$ | H | $OCH_3$ | $OCH_3$ | CH | |
| n-$C_3H_7$ | $CH_2CHF_2$ | H | $CH_3$ | $OCH_3$ | N | |
| $CH(CH_3)_2$ | $CH_2CHF_2$ | H | $OCH_3$ | $CH_3$ | CH | |
| $CH(CH_3)_2$ | $CH_2CHF_2$ | H | $OCH_3$ | $OCH_3$ | CH | |
| $CH(CH_3)_2$ | $CH_2CHF_2$ | H | Cl | $OCH_3$ | CH | |
| $CH(CH_3)_2$ | $CH_2CHF_2$ | H | $OCH_3$ | $CH_3$ | N | |
| $CH(CH_3)_2$ | $CH_2CHF_2$ | H | $OCH_3$ | $OCH_3$ | N | |
| $CH(CH_3)_2$ | $CH_2CHF_2$ | H | $OCH_3$ | $N(CH_3)_2$ | N | |
| $CH_3$ | $CH_2CF_3$ | H | $CH_3$ | $CH_3$ | CH | |
| $CH_3$ | $CH_2CF_3$ | H | $OCH_3$ | $CH_3$ | CH | |
| $CH_3$ | $CH_2CF_3$ | H | $OCH_3$ | $OCH_3$ | CH | |
| $CH_3$ | $CH_2CF_3$ | H | Cl | $OCH_3$ | CH | |
| $CH_3$ | $CH_2CF_3$ | H | $OCH_3$ | $N(CH_3)_2$ | CH | |
| $CH_3$ | $CH_2CF_3$ | H | $CH_3$ | $CH_3$ | N | |
| $CH_3$ | $CH_2CF_3$ | H | $OCH_3$ | $CH_3$ | N | |
| $CH_3$ | $CH_2CF_3$ | H | $OCH_3$ | $OCH_3$ | N | |
| $CH_3$ | $CH_2CF_3$ | H | $OCH_3$ | $N(CH_3)_2$ | N | |
| $CH_3$ | $CH_2CF_3$ | H | $OCH_3$ | $OCH_2CF_3$ | N | |
| $CH_3$ | $CH_2CF_3$ | $CH_3$ | $OCH_3$ | $CH_3$ | N | |
| $CH_3$ | $CH_2CF_3$ | $CH_3$ | $OCH_3$ | $OCH_3$ | N | |
| $CH_3$ | $CH_2CF_3$ | $CH_3$ | $CH_3$ | $OCH_3$ | CH | |
| $CH_3$ | $CH_2CF_3$ | $CH_3$ | $OCH_3$ | $OCH_3$ | CH | |
| $CH_3$ | $CH_2CF_3$ | H | Br | $OCH_3$ | CH | |
| $CH_3$ | $CH_2CF_3$ | $CH_3$ | $OCH_3$ | $N(CH_3)_2$ | N | |
| $CH_3$ | $CH_2CF_3$ | H | $CH_3$ | $OCH_2CF_3$ | N | |
| $CH_3$ | $CH_2CF_3$ | H | $CH_3$ | $OCH_2CF_3$ | CH | |
| $CH_3$ | $CH_2CF_3$ | H | $OCH_3$ | $OCH_2CF_3$ | CH | |
| $CH_3$ | $CH_2CF_3$ | H | $OCH_3$ | $C_2H_5$ | CH | |
| $CH_3$ | $CH_2CF_3$ | H | $OCH_3$ | $C_2H_5$ | N | |
| $CH_3$ | $CH_2CF_3$ | H | $OCH_3$ | $NHCH_3$ | CH | |
| $CH_3$ | $CH_2CF_3$ | H | $OCH_3$ | $NHCH_3$ | N | |
| $CH_3$ | $CH_2CF_3$ | H | $CH_3$ | $OC_2H_5$ | CH | |
| $CH_3$ | $CH_2CF_3$ | H | $OCH_3$ | $OC_2H_5$ | CH | |
| $CH_3$ | $CH_2CF_3$ | H | $CH_3$ | $OC_2H_5$ | N | |
| $CH_3$ | $CH_2CF_3$ | H | $OCH_3$ | $OC_2H_5$ | N | |
| $CH_3$ | $CH_2CF_3$ | H | $CH_3$ | $OCH_2CHF_2$ | CH | |
| $CH_3$ | $CH_2CF_3$ | H | $OCH_3$ | $OCH_2CHF_2$ | CH | |
| $CH_3$ | $CH_2CF_3$ | H | $CH_3$ | $OCH_2CHF_2$ | N | |
| $CH_3$ | $CH_2CF_3$ | H | $OCH_3$ | $OCH_2CHF_2$ | N | |
| $CH_3$ | $CH_2CF_3$ | H | $CH_3$ | $OCH_2CH_2F$ | CH | |
| $CH_3$ | $CH_2CF_3$ | H | $OCH_3$ | $OCH_2CH_2F$ | CH | |
| $CH_3$ | $CH_2CF_3$ | H | $CH_3$ | $OCH_2CH_2F$ | N | |
| $CH_3$ | $CH_2CF_3$ | $CH_3$ | $OCH_3$ | $OCH_2CH_2F$ | N | |
| $CH_3$ | $CH_2CF_3$ | $CH_3$ | Cl | $OCH_3$ | CH | |
| $CH_3$ | $CH_2CF_3$ | H | Cl | $N(CH_3)_2$ | CH | |
| $CH_3$ | $CH_2CF_3$ | H | Cl | $OC_2H_5$ | CH | |
| $C_2H_5$ | $CH_2CF_3$ | H | $CH_3$ | $CH_3$ | CH | |
| $C_2H_5$ | $CH_2CF_3$ | H | $OCH_3$ | $CH_3$ | CH | |
| $C_2H_5$ | $CH_2CF_3$ | H | $OCH_3$ | $OCH_3$ | CH | |
| $C_2H_5$ | $CH_2CF_3$ | H | Cl | $OCH_3$ | CH | |
| $C_2H_5$ | $CH_2CF_3$ | H | $CH_3$ | $CH_3$ | N | |
| $C_2H_5$ | $CH_2CF_3$ | H | $OCH_3$ | $CH_3$ | N | |
| $C_2H_5$ | $CH_2CF_3$ | H | $OCH_3$ | $OCH_3$ | N | |
| $C_2H_5$ | $CH_2CF_3$ | H | Br | $OCH_3$ | CH | |
| $C_2H_5$ | $CH_2CF_3$ | H | $OCH_3$ | $N(CH_3)_2$ | CH | |
| $C_2H_5$ | $CH_2CF_3$ | H | $OCH_3$ | $N(CH_3)_2$ | N | |

TABLE I-continued $$\underset{R_2}{\text{}} \text{-C}_6\text{H}_3(\text{CO}_2\text{R}_1)(\text{SO}_2\text{NHCON}(\text{R})\text{-pyrimidine/triazine}(X,Y,Z))$$

| R₁ | R₂ | R | X | Y | Z | m.p. (°C) |
|---|---|---|---|---|---|---|
| C₂H₅ | CH₂CF₃ | H | OCH₃ | NHCH₃ | N | |
| C₂H₅ | CH₂CF₃ | H | OCH₃ | C₂H₅ | CH | |
| C₂H₅ | CH₂CF₃ | H | OCH₃ | C₂H₅ | N | |
| C₂H₅ | CH₂CF₃ | H | CH₃ | OC₂H₅ | CH | |
| C₂H₅ | CH₂CF₃ | H | CH₃ | OC₂H₅ | N | |
| C₂H₅ | CH₂CF₃ | H | OCH₃ | OC₂H₅ | CH | |
| C₂H₅ | CH₂CF₃ | H | OCH₃ | OC₂H₅ | N | |
| C₂H₅ | CH₂CF₃ | H | CH₃ | OCH₂CF₃ | CH | |
| C₂H₅ | CH₂CF₃ | H | CH₃ | OCH₂CF₃ | N | |
| C₂H₅ | CH₂CF₃ | H | OCH₃ | OCH₂CF₃ | CH | |
| C₂H₅ | CH₂CF₃ | H | OCH₃ | OCH₂CF₃ | N | |
| C₂H₅ | CH₂CF₃ | H | OCH₃ | OCH₂CHF₂ | CH | |
| C₂H₅ | CH₂CF₃ | H | OCH₃ | OCH₂CHF₂ | N | |
| C₂H₅ | CH₂CF₃ | H | CH₃ | OCH₂CHF₂ | N | |
| C₂H₅ | CH₂CF₃ | H | OCH₃ | OCH₂CH₂F | CH | |
| C₂H₅ | CH₂CF₃ | H | OCH₃ | OCH₂CH₂F | N | |
| C₂H₅ | CH₂CF₃ | CH₃ | OCH₃ | OCH₃ | CH | |
| C₂H₅ | CH₂CF₃ | CH₃ | CH₃ | OCH₃ | N | |
| C₂H₅ | CH₂CF₃ | CH₃ | OCH₃ | OCH₃ | N | |
| n-C₃H₇ | CH₂CF₃ | H | OCH₃ | OCH₃ | CH | |
| n-C₃H₇ | CH₂CF₃ | H | CH₃ | OCH₃ | N | |
| CH(CH₃)₂ | CH₂CF₃ | H | OCH₃ | CH₃ | CH | |
| CH(CH₃)₂ | CH₂CF₃ | H | OCH₃ | OCH₃ | CH | |
| CH(CH₃)₂ | CH₂CF₃ | H | Cl | OCH₃ | CH | |
| CH(CH₃)₂ | CH₂CF₃ | H | OCH₃ | CH₃ | N | |
| CH(CH₃)₂ | CH₂CF₃ | H | OCH₃ | OCH₃ | N | |
| CH(CH₃)₂ | CH₂CF₃ | H | OCH₃ | N(CH₃)₂ | N | |
| CH₃ | CHFCH₃ | H | CH₃ | CH₃ | CH | |
| CH₃ | CHFCH₃ | H | OCH₃ | CH₃ | CH | |
| CH₃ | CHFCH₃ | H | OCH₃ | OCH₃ | CH | |
| CH₃ | CHFCH₃ | H | Cl | OCH₃ | CH | |
| CH₃ | CHFCH₃ | H | OCH₃ | N(CH₃)₂ | CH | |
| CH₃ | CHFCH₃ | H | CH₃ | CH₃ | N | |
| CH₃ | CHFCH₃ | H | OCH₃ | CH₃ | N | |
| CH₃ | CHFCH₃ | H | OCH₃ | OCH₃ | N | |
| CH₃ | CHFCH₃ | H | OCH₃ | N(CH₃)₂ | N | |
| CH₃ | CHFCH₃ | H | OCH₃ | OCH₂CF₃ | N | |
| CH₃ | CHFCH₃ | CH₃ | OCH₃ | CH₃ | N | |
| CH₃ | CHFCH₃ | CH₃ | OCH₃ | OCH₃ | N | |
| CH₃ | CHFCH₃ | CH₃ | CH₃ | OCH₃ | CH | |
| CH₃ | CHFCH₃ | CH₃ | OCH₃ | OCH₃ | CH | |
| CH₃ | CHFCH₃ | H | Br | OCH₃ | CH | |
| CH₃ | CHFCH₃ | CH₃ | OCH₃ | N(CH₃)₂ | N | |
| CH₃ | CHFCH₃ | H | CH₃ | OCH₂CF₃ | N | |
| CH₃ | CHFCH₃ | H | CH₃ | OCH₂CF₃ | CH | |
| CH₃ | CHFCH₃ | H | OCH₃ | OCH₂CF₃ | CH | |
| CH₃ | CHFCH₃ | H | OCH₃ | C₂H₅ | CH | |
| CH₃ | CHFCH₃ | H | OCH₃ | NHCH₃ | CH | |
| CH₃ | CHFCH₃ | H | OCH₃ | NHCH₃ | N | |
| CH₃ | CHFCH₃ | H | CH₃ | OC₂H₅ | CH | |
| CH₃ | CHFCH₃ | H | OCH₃ | OC₂H₅ | CH | |
| CH₃ | CHFCH₃ | H | CH₃ | OC₂H₅ | N | |
| CH₃ | CHFCH₃ | H | OCH₃ | OC₂H₅ | N | |
| CH₃ | CHFCH₃ | H | CH₃ | OCH₂CHF₂ | CH | |
| CH₃ | CHFCH₃ | H | OCH₃ | OCH₂CHF₂ | CH | |
| CH₃ | CHFCH₃ | H | CH₃ | OCH₂CHF₂ | N | |
| CH₃ | CHFCH₃ | H | OCH₃ | OCH₂CHF₂ | N | |
| CH₃ | CHFCH₃ | H | CH₃ | OCH₂CH₂F | CH | |
| CH₃ | CHFCH₃ | H | OCH₃ | OCH₂CH₂F | CH | |
| CH₃ | CHFCH₃ | H | CH₃ | OCH₂CF₃ | N | |
| CH₃ | CHFCH₃ | CH₃ | OCH₃ | OCH₂CF₃ | N | |
| CH₃ | CHFCH₃ | CH₃ | Cl | OCH₃ | CH | |
| CH₃ | CHFCH₃ | H | Cl | N(CH₃)₂ | CH | |
| CH₃ | CHFCH₃ | H | Cl | OC₂H₅ | CH | |
| C₂H₅ | CHFCH₃ | H | CH₃ | CH₃ | CH | |
| C₂H₅ | CHFCH₃ | H | OCH₃ | CH₃ | CH | |
| C₂H₅ | CHFCH₃ | H | OCH₃ | OCH₃ | CH | |
| C₂H₅ | CHFCH₃ | H | Cl | OCH₃ | CH | |
| C₂H₅ | CHFCH₃ | H | CH₃ | CH₃ | N | |
| C₂H₅ | CHFCH₃ | H | OCH₃ | CH₃ | N | |
| C₂H₅ | CHFCH₃ | H | OCH₃ | OCH₃ | N | |

TABLE I-continued

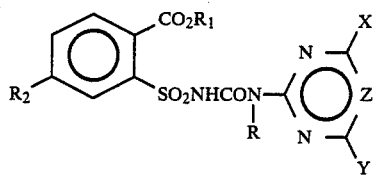

| $R_1$ | $R_2$ | R | X | Y | Z | m.p. (°C.) |
|---|---|---|---|---|---|---|
| $C_2H_5$ | $CHFCH_3$ | H | Br | $OCH_3$ | CH | |
| $C_2H_5$ | $CHFCH_3$ | H | $OCH_3$ | $N(CH_3)_2$ | CH | |
| $C_2H_5$ | $CHFCH_3$ | H | $OCH_3$ | $N(CH_3)_2$ | N | |
| $C_2H_5$ | $CHFCH_3$ | H | $OCH_3$ | $NHCH_3$ | N | |
| $C_2H_5$ | $CHFCH_3$ | H | $OCH_3$ | $C_2H_5$ | CH | |
| $C_2H_5$ | $CHFCH_3$ | H | $OCH_3$ | $C_2H_5$ | N | |
| $C_2H_5$ | $CHFCH_3$ | H | $CH_3$ | $OC_2H_5$ | CH | |
| $C_2H_5$ | $CHFCH_3$ | H | $CH_3$ | $OC_2H_5$ | N | |
| $C_2H_5$ | $CHFCH_3$ | H | $OCH_3$ | $OC_2H_5$ | CH | |
| $C_2H_5$ | $CHFCH_3$ | H | $OCH_3$ | $OC_2H_5$ | N | |
| $C_2H_5$ | $CHFCH_3$ | H | $CH_3$ | $OCH_2CF_3$ | CH | |
| $C_2H_5$ | $CHFCH_3$ | H | $CH_3$ | $OCH_2CF_3$ | N | |
| $C_2H_5$ | $CHFCH_3$ | H | $OCH_3$ | $OCH_2CF_3$ | CH | |
| $C_2H_5$ | $CHFCH_3$ | H | $OCH_3$ | $OCH_2CF_3$ | N | |
| $C_2H_5$ | $CHFCH_3$ | H | $OCH_3$ | $OCH_2CHF_2$ | CH | |
| $C_2H_5$ | $CHFCH_3$ | H | $OCH_3$ | $OCH_2CHF_2$ | N | |
| $C_2H_5$ | $CHFCH_3$ | H | $CH_3$ | $OCH_2CHF_2$ | N | |
| $C_2H_5$ | $CHFCH_3$ | H | $OCH_3$ | $OCH_2CH_2F$ | CH | |
| $C_2H_5$ | $CHFCH_3$ | H | $OCH_3$ | $OCH_2CH_2F$ | N | |
| $C_2H_5$ | $CHFCH_3$ | $CH_3$ | $OCH_3$ | $OCH_3$ | CH | |
| $C_2H_5$ | $CHFCH_3$ | $CH_3$ | $CH_3$ | $OCH_3$ | N | |
| $C_2H_5$ | $CHFCH_3$ | $CH_3$ | $OCH_3$ | $OCH_3$ | N | |
| n-$C_3H_7$ | $CHFCH_3$ | H | $OCH_3$ | $OCH_3$ | CH | |
| n-$C_3H_7$ | $CHFCH_3$ | H | $CH_3$ | $OCH_3$ | N | |
| $CH(CH_3)_2$ | $CHFCH_3$ | H | $OCH_3$ | $CH_3$ | CH | |
| $CH(CH_3)_2$ | $CHFCH_3$ | H | $OCH_3$ | $OCH_3$ | CH | |
| $CH(CH_3)_2$ | $CHFCH_3$ | H | Cl | $OCH_3$ | CH | |
| $CH(CH_3)_2$ | $CHFCH_3$ | H | $OCH_3$ | $CH_3$ | N | |
| $CH(CH_3)_2$ | $CHFCH_3$ | H | $OCH_3$ | $OCH_3$ | N | |
| $CH(CH_3)_2$ | $CHFCH_3$ | H | $OCH_3$ | $N(CH_3)_2$ | N | |
| $CH_3$ | $CF_2CH_3$ | H | $CH_3$ | $CH_3$ | CH | |
| $CH_3$ | $CF_2CH_3$ | H | $OCH_3$ | $CH_3$ | CH | |
| $CH_3$ | $CF_2CH_3$ | H | $OCH_3$ | $OCH_3$ | CH | |
| $CH_3$ | $CF_2CH_3$ | H | Cl | $OCH_3$ | CH | |
| $CH_3$ | $CF_2CH_3$ | H | $OCH_3$ | $N(CH_3)_2$ | CH | |
| $CH_3$ | $CF_2CH_3$ | H | $CH_3$ | $CH_3$ | N | |
| $CH_3$ | $CF_2CH_3$ | H | $OCH_3$ | $CH_3$ | N | |
| $CH_3$ | $CF_2CH_3$ | H | $OCH_3$ | $OCH_3$ | N | |
| $CH_3$ | $CF_2CH_3$ | H | $OCH_3$ | $N(CH_3)_2$ | N | |
| $CH_3$ | $CF_2CH_3$ | H | $OCH_3$ | $OCH_2CF_3$ | N | |
| $CH_3$ | $CF_2CH_3$ | $CH_3$ | $OCH_3$ | $CH_3$ | N | |
| $CH_3$ | $CF_2CH_3$ | $CH_3$ | $OCH_3$ | $OCH_3$ | N | |
| $CH_3$ | $CF_2CH_3$ | $CH_3$ | $CH_3$ | $OCH_3$ | CH | |
| $CH_3$ | $CF_2CH_3$ | $CH_3$ | $OCH_3$ | $OCH_3$ | CH | |
| $CH_3$ | $CF_2CH_3$ | H | Br | $OCH_3$ | CH | |
| $CH_3$ | $CF_2CH_3$ | $CH_3$ | $OCH_3$ | $N(CH_3)_2$ | N | |
| $CH_3$ | $CF_2CH_3$ | H | $CH_3$ | $OCH_2CF_3$ | CH | |
| $CH_3$ | $CF_2CH_3$ | H | $OCH_3$ | $OCH_2CF_3$ | CH | |
| $CH_3$ | $CF_2CH_3$ | H | $OCH_3$ | $C_2H_5$ | CH | |
| $CH_3$ | $CF_2CH_3$ | H | $OCH_3$ | $C_2H_5$ | N | |
| $CH_3$ | $CF_2CH_3$ | H | $OCH_3$ | $NHCH_3$ | CH | |
| $CH_3$ | $CF_2CH_3$ | H | $OCH_3$ | $NHCH_3$ | N | |
| $CH_3$ | $CF_2CH_3$ | H | $CH_3$ | $OC_2H_5$ | CH | |
| $CH_3$ | $CF_2CH_3$ | H | $OCH_3$ | $OC_2H_5$ | CH | |
| $CH_3$ | $CF_2CH_3$ | H | $CH_3$ | $OC_2H_5$ | N | |
| $CH_3$ | $CF_2CH_3$ | H | $OCH_3$ | $OC_2H_5$ | N | |
| $CH_3$ | $CF_2CH_3$ | H | $CH_3$ | $OCH_2CHF_2$ | CH | |
| $CH_3$ | $CF_2CH_3$ | H | $OCH_3$ | $OCH_2CHF_2$ | CH | |
| $CH_3$ | $CF_2CH_3$ | H | $CH_3$ | $OCH_2CHF_2$ | N | |
| $CH_3$ | $CF_2CH_3$ | H | $OCH_3$ | $OCH_2CHF_2$ | N | |
| $CH_3$ | $CF_2CH_3$ | H | $CH_3$ | $OCH_2CH_2F$ | CH | |
| $CH_3$ | $CF_2CH_3$ | H | $OCH_3$ | $OCH_2CH_2F$ | CH | |
| $CH_3$ | $CF_2CH_3$ | H | $CH_3$ | $OCH_2CF_3$ | N | |
| $CH_3$ | $CF_2CH_3$ | $CH_3$ | $OCH_3$ | $OCH_2CF_3$ | N | |
| $CH_3$ | $CF_2CH_3$ | $CH_3$ | Cl | $OCH_3$ | CH | |
| $CH_3$ | $CF_2CH_3$ | H | Cl | $N(CH_3)_2$ | CH | |
| $CH_3$ | $CF_2CH_3$ | H | Cl | $OC_2H_5$ | CH | |
| $C_2H_5$ | $CF_2CH_3$ | H | $CH_3$ | $CH_3$ | CH | |
| $C_2H_5$ | $CF_2CH_3$ | H | $OCH_3$ | $CH_3$ | CH | |
| $C_2H_5$ | $CF_2CH_3$ | H | $OCH_3$ | $OCH_3$ | CH | |

TABLE I-continued

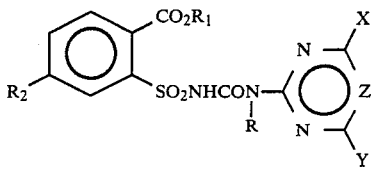

| $R_1$ | $R_2$ | R | X | Y | Z | m.p. (°C.) |
|---|---|---|---|---|---|---|
| $C_2H_5$ | $CF_2CH_3$ | H | Cl | $OCH_3$ | CH | |
| $C_2H_5$ | $CF_2CH_3$ | H | $CH_3$ | $CH_3$ | N | |
| $C_2H_5$ | $CF_2CH_3$ | H | $OCH_3$ | $CH_3$ | N | |
| $C_2H_5$ | $CF_2CH_3$ | H | $OCH_3$ | $OCH_3$ | N | |
| $C_2H_5$ | $CF_2CH_3$ | H | Br | $OCH_3$ | CH | |
| $C_2H_5$ | $CF_2CH_3$ | H | $OCH_3$ | $N(CH_3)_2$ | CH | |
| $C_2H_5$ | $CF_2CH_3$ | H | $OCH_3$ | $N(CH_3)_2$ | N | |
| $C_2H_5$ | $CF_2CH_3$ | H | $OCH_3$ | $NHCH_3$ | N | |
| $C_2H_5$ | $CF_2CH_3$ | H | $OCH_3$ | $C_2H_5$ | CH | |
| $C_2H_5$ | $CF_2CH_3$ | H | $OCH_3$ | $C_2H_5$ | N | |
| $C_2H_5$ | $CF_2CH_3$ | H | $CH_3$ | $OC_2H_5$ | CH | |
| $C_2H_5$ | $CF_2CH_3$ | H | $CH_3$ | $OC_2H_5$ | N | |
| $C_2H_5$ | $CF_2CH_3$ | H | $OCH_3$ | $OC_2H_5$ | CH | |
| $C_2H_5$ | $CF_2CH_3$ | H | $OCH_3$ | $OC_2H_5$ | N | |
| $C_2H_5$ | $CF_2CH_3$ | H | $CH_3$ | $OCH_2CF_3$ | CH | |
| $C_2H_5$ | $CF_2CH_3$ | H | $CH_3$ | $OCH_2CF_3$ | N | |
| $C_2H_5$ | $CF_2CH_3$ | H | $OCH_3$ | $OCH_2CF_3$ | CH | |
| $C_2H_5$ | $CF_2CH_3$ | H | $OCH_3$ | $OCH_2CF_3$ | N | |
| $C_2H_5$ | $CF_2CH_3$ | H | $OCH_3$ | $OCH_2CHF_2$ | CH | |
| $C_2H_5$ | $CF_2CH_3$ | H | $OCH_3$ | $OCH_2CHF_2$ | N | |
| $C_2H_5$ | $CF_2CH_3$ | H | $CH_3$ | $OCH_2CHF_2$ | N | |
| $C_2H_5$ | $CF_2CH_3$ | H | $OCH_3$ | $OCH_2CH_2F$ | CH | |
| $C_2H_5$ | $CF_2CH_3$ | H | $OCH_3$ | $OCH_2CH_2F$ | N | |
| $C_2H_5$ | $CF_2CH_3$ | $CH_3$ | $OCH_3$ | $OCH_3$ | CH | |
| $C_2H_5$ | $CF_2CH_3$ | $CH_3$ | $CH_3$ | $OCH_3$ | N | |
| $C_2H_5$ | $CF_2CH_3$ | $CH_3$ | $OCH_3$ | $OCH_3$ | N | |
| n-$C_3H_7$ | $CF_2CH_3$ | H | $OCH_3$ | $OCH_3$ | CH | |
| n-$C_3H_7$ | $CF_2CH_3$ | H | $CH_3$ | $OCH_3$ | N | |
| $CH(CH_3)_2$ | $CF_2CH_3$ | H | $OCH_3$ | $CH_3$ | CH | |
| $CH(CH_3)_2$ | $CF_2CH_3$ | H | $OCH_3$ | $OCH_3$ | CH | |
| $CH(CH_3)_2$ | $CF_2CH_3$ | H | Cl | $OCH_3$ | CH | |
| $CH(CH_3)_2$ | $CF_2CH_3$ | H | $OCH_3$ | $CH_3$ | N | |
| $CH(CH_3)_2$ | $CF_2CH_3$ | H | $OCH_3$ | $OCH_3$ | N | |
| $CH(CH_3)_2$ | $CF_2CH_3$ | H | $OCH_3$ | $N(CH_3)_2$ | N | |
| $CH_3$ | $CH_2CH_2Cl$ | H | $CH_3$ | $CH_3$ | CH | |
| $CH_3$ | $CH_2CH_2Cl$ | H | $OCH_3$ | $CH_3$ | CH | |
| $CH_3$ | $CH_2CH_2Cl$ | H | $OCH_3$ | $OCH_3$ | CH | |
| $CH_3$ | $CH_2CH_2Cl$ | H | Cl | $OCH_3$ | CH | |
| $CH_3$ | $CH_2CH_2Cl$ | H | $OCH_3$ | $N(CH_3)_2$ | CH | |
| $CH_3$ | $CH_2CH_2Cl$ | H | $CH_3$ | $CH_3$ | N | |
| $CH_3$ | $CH_2CH_2Cl$ | H | $OCH_3$ | $CH_3$ | N | |
| $CH_3$ | $CH_2CH_2Cl$ | H | $OCH_3$ | $OCH_3$ | N | |
| $CH_3$ | $CH_2CH_2Cl$ | H | $OCH_3$ | $N(CH_3)_2$ | N | |
| $CH_3$ | $CH_2CH_2Cl$ | H | $OCH_3$ | $OCH_2CF_3$ | N | |
| $CH_3$ | $CH_2CH_2Cl$ | $CH_3$ | $OCH_3$ | $CH_3$ | N | |
| $CH_3$ | $CH_2CH_2Cl$ | $CH_3$ | $OCH_3$ | $OCH_3$ | N | |
| $CH_3$ | $CH_2CH_2Cl$ | $CH_3$ | $CH_3$ | $OCH_3$ | CH | |
| $CH_3$ | $CH_2CH_2Cl$ | $CH_3$ | $OCH_3$ | $OCH_3$ | CH | |
| $CH_3$ | $CH_2CH_2Cl$ | H | Br | $OCH_3$ | CH | |
| $CH_3$ | $CH_2CH_2Cl$ | $CH_3$ | $OCH_3$ | $N(CH_3)_2$ | N | |
| $CH_3$ | $CH_2CH_2Cl$ | H | $CH_3$ | $OCH_2CF_3$ | N | |
| $CH_3$ | $CH_2CH_2Cl$ | H | $OCH_3$ | $OCH_2CF_3$ | CH | |
| $CH_3$ | $CH_2CH_2Cl$ | H | $OCH_3$ | $C_2H_5$ | CH | |
| $CH_3$ | $CH_2CH_2Cl$ | H | $OCH_3$ | $C_2H_5$ | N | |
| $CH_3$ | $CH_2CH_2Cl$ | H | $OCH_3$ | $NHCH_3$ | CH | |
| $CH_3$ | $CH_2CH_2Cl$ | H | $OCH_3$ | $NHCH_3$ | N | |
| $CH_3$ | $CH_2CH_2Cl$ | H | $CH_3$ | $OC_2H_5$ | CH | |
| $CH_3$ | $CH_2CH_2Cl$ | H | $OCH_3$ | $OC_2H_5$ | CH | |
| $CH_3$ | $CH_2CH_2Cl$ | H | $CH_3$ | $OC_2H_5$ | N | |
| $CH_3$ | $CH_2CH_2Cl$ | H | $OCH_3$ | $OC_2H_5$ | N | |
| $CH_3$ | $CH_2CH_2Cl$ | H | $CH_3$ | $OCH_2CHF_2$ | CH | |
| $CH_3$ | $CH_2CH_2Cl$ | H | $OCH_3$ | $OCH_2CHF_2$ | CH | |
| $CH_3$ | $CH_2CH_2Cl$ | H | $CH_3$ | $OCH_2CHF_2$ | N | |
| $CH_3$ | $CH_2CH_2Cl$ | H | $OCH_3$ | $OCH_2CHF_2$ | N | |
| $CH_3$ | $CH_2CH_2Cl$ | H | $CH_3$ | $OCH_2CH_2F$ | CH | |
| $CH_3$ | $CH_2CH_2Cl$ | H | $OCH_3$ | $OCH_2CH_2F$ | CH | |
| $CH_3$ | $CH_2CH_2Cl$ | H | $CH_3$ | $OCH_2CF_3$ | N | |
| $CH_3$ | $CH_2CH_2Cl$ | $CH_3$ | $OCH_3$ | $OCH_2CF_3$ | N | |
| $CH_3$ | $CH_2CH_2Cl$ | $CH_3$ | Cl | $OCH_3$ | CH | |
| $CH_3$ | $CH_2CH_2Cl$ | H | Cl | $N(CH_3)_2$ | CH | |

TABLE I-continued

| $R_1$ | $R_2$ | R | X | Y | Z | m.p. (°C.) |
|---|---|---|---|---|---|---|
| $CH_3$ | $CH_2CH_2Cl$ | H | Cl | $OC_2H_5$ | CH | |
| $C_2H_5$ | $CH_2CH_2Cl$ | H | $CH_3$ | $CH_3$ | CH | |
| $C_2H_5$ | $CH_2CH_2Cl$ | H | $OCH_3$ | $CH_3$ | CH | |
| $C_2H_5$ | $CH_2CH_2Cl$ | H | $OCH_3$ | $OCH_3$ | CH | |
| $C_2H_5$ | $CH_2CH_2Cl$ | H | Cl | $OCH_3$ | CH | |
| $C_2H_5$ | $CH_2CH_2Cl$ | H | $CH_3$ | $CH_3$ | N | |
| $C_2H_5$ | $CH_2CH_2Cl$ | H | $OCH_3$ | $CH_3$ | N | |
| $C_2H_5$ | $CH_2CH_2Cl$ | H | $OCH_3$ | $OCH_3$ | N | |
| $C_2H_5$ | $CH_2CH_2Cl$ | H | Br | $OCH_3$ | CH | |
| $C_2H_5$ | $CH_2CH_2Cl$ | H | $OCH_3$ | $N(CH_3)_2$ | CH | |
| $C_2H_5$ | $CH_2CH_2Cl$ | H | $OCH_3$ | $N(CH_3)_2$ | N | |
| $C_2H_5$ | $CH_2CH_2Cl$ | H | $OCH_3$ | $NHCH_3$ | N | |
| $C_2H_5$ | $CH_2CH_2Cl$ | H | $OCH_3$ | $C_2H_5$ | CH | |
| $C_2H_5$ | $CH_2CH_2Cl$ | H | $OCH_3$ | $C_2H_5$ | N | |
| $C_2H_5$ | $CH_2CH_2Cl$ | H | $CH_3$ | $OC_2H_5$ | CH | |
| $C_2H_5$ | $CH_2CH_2Cl$ | H | $CH_3$ | $OC_2H_5$ | N | |
| $C_2H_5$ | $CH_2CH_2Cl$ | H | $OCH_3$ | $OC_2H_5$ | CH | |
| $C_2H_5$ | $CH_2CH_2Cl$ | H | $OCH_3$ | $OC_2H_5$ | N | |
| $C_2H_5$ | $CH_2CH_2Cl$ | H | $CH_3$ | $OCH_2CF_3$ | CH | |
| $C_2H_5$ | $CH_2CH_2Cl$ | H | $CH_3$ | $OCH_2CF_3$ | N | |
| $C_2H_5$ | $CH_2CH_2Cl$ | H | $OCH_3$ | $OCH_2CF_3$ | CH | |
| $C_2H_5$ | $CH_2CH_2Cl$ | H | $OCH_3$ | $OCH_2CF_3$ | N | |
| $C_2H_5$ | $CH_2CH_2Cl$ | H | $OCH_3$ | $OCH_2CHF_2$ | CH | |
| $C_2H_5$ | $CH_2CH_2Cl$ | H | $OCH_3$ | $OCH_2CHF_2$ | N | |
| $C_2H_5$ | $CH_2CH_2Cl$ | H | $CH_3$ | $OCH_2CHF_2$ | N | |
| $C_2H_5$ | $CH_2CH_2Cl$ | H | $OCH_3$ | $OCH_2CH_2F$ | CH | |
| $C_2H_5$ | $CH_2CH_2Cl$ | H | $OCH_3$ | $OCH_2CH_2F$ | N | |
| $C_2H_5$ | $CH_2CH_2Cl$ | $CH_3$ | $OCH_3$ | $OCH_3$ | CH | |
| $C_2H_5$ | $CH_2CH_2Cl$ | $CH_3$ | $CH_3$ | $OCH_3$ | N | |
| $C_2H_5$ | $CH_2CH_2Cl$ | $CH_3$ | $OCH_3$ | $OCH_3$ | N | |
| n-$C_3H_7$ | $CH_2CH_2Cl$ | H | $OCH_3$ | $OCH_3$ | CH | |
| n-$C_3H_7$ | $CH_2CH_2Cl$ | H | $CH_3$ | $OCH_3$ | N | |
| $CH(CH_3)_2$ | $CH_2CH_2Cl$ | H | $OCH_3$ | $CH_3$ | CH | |
| $CH(CH_3)_2$ | $CH_2CH_2Cl$ | H | $OCH_3$ | $OCH_3$ | CH | |
| $CH(CH_3)_2$ | $CH_2CH_2Cl$ | H | Cl | $OCH_3$ | CH | |
| $CH(CH_3)_2$ | $CH_2CH_2Cl$ | H | $OCH_3$ | $CH_3$ | N | |
| $CH(CH_3)_2$ | $CH_2CH_2Cl$ | H | $OCH_3$ | $OCH_3$ | N | |
| $CH(CH_3)_2$ | $CH_2CH_2Cl$ | H | $OCH_3$ | $N(CH_3)_2$ | N | |
| $CH_3$ | $CH_2CHCl_2$ | H | $CH_3$ | $CH_3$ | CH | |
| $CH_3$ | $CH_2CHCl_2$ | H | $OCH_3$ | $CH_3$ | CH | |
| $CH_3$ | $CH_2CHCl_2$ | H | $OCH_3$ | $OCH_3$ | CH | |
| $CH_3$ | $CH_2CHCl_2$ | H | Cl | $OCH_3$ | CH | |
| $CH_3$ | $CH_2CHCl_2$ | H | $OCH_3$ | $N(CH_3)_2$ | CH | |
| $CH_3$ | $CH_2CHCl_2$ | H | $CH_3$ | $CH_3$ | N | |
| $CH_3$ | $CH_2CHCl_2$ | H | $OCH_3$ | $CH_3$ | N | |
| $CH_3$ | $CH_2CHCl_2$ | H | $OCH_3$ | $OCH_3$ | N | |
| $CH_3$ | $CH_2CHCl_2$ | H | $OCH_3$ | $N(CH_3)_2$ | N | |
| $CH_3$ | $CH_2CHCl_2$ | H | $OCH_3$ | $OCH_2CF_3$ | N | |
| $CH_3$ | $CH_2CHCl_2$ | $CH_3$ | $OCH_3$ | $CH_3$ | N | |
| $CH_3$ | $CH_2CHCl_2$ | $CH_3$ | $OCH_3$ | $OCH_3$ | N | |
| $CH_3$ | $CH_2CHCl_2$ | $CH_3$ | $CH_3$ | $OCH_3$ | CH | |
| $CH_3$ | $CH_2CHCl_2$ | $CH_3$ | $OCH_3$ | $OCH_3$ | CH | |
| $CH_3$ | $CH_2CHCl_2$ | H | Br | $OCH_3$ | CH | |
| $CH_3$ | $CH_2CHCl_2$ | $CH_3$ | $OCH_3$ | $N(CH_3)_2$ | N | |
| $CH_3$ | $CH_2CHCl_2$ | H | $CH_3$ | $OCH_2CF_3$ | N | |
| $CH_3$ | $CH_2CHCl_2$ | H | $CH_3$ | $OCH_2CF_3$ | CH | |
| $CH_3$ | $CH_2CHCl_2$ | H | $OCH_3$ | $OCH_2CF_3$ | CH | |
| $CH_3$ | $CH_2CHCl_2$ | H | $OCH_3$ | $C_2H_5$ | CH | |
| $CH_3$ | $CH_2CHCl_2$ | H | $OCH_3$ | $C_2H_5$ | N | |
| $CH_3$ | $CH_2CHCl_2$ | H | $OCH_3$ | $NHCH_3$ | CH | |
| $CH_3$ | $CH_2CHCl_2$ | H | $OCH_3$ | $NHCH_3$ | N | |
| $CH_3$ | $CH_2CHCl_2$ | H | $CH_3$ | $OC_2H_5$ | CH | |
| $CH_3$ | $CH_2CHCl_2$ | H | $OCH_3$ | $OC_2H_5$ | CH | |
| $CH_3$ | $CH_2CHCl_2$ | H | $CH_3$ | $OC_2H_5$ | N | |
| $CH_3$ | $CH_2CHCl_2$ | H | $OCH_3$ | $OC_2H_5$ | N | |
| $CH_3$ | $CH_2CHCl_2$ | H | $CH_3$ | $OCH_2CHF_2$ | CH | |
| $CH_3$ | $CH_2CHCl_2$ | H | $OCH_3$ | $OCH_2CHF_2$ | CH | |
| $CH_3$ | $CH_2CHCl_2$ | H | $CH_3$ | $OCH_2CHF_2$ | N | |
| $CH_3$ | $CH_2CHCl_2$ | H | $OCH_3$ | $OCH_2CHF_2$ | N | |
| $CH_3$ | $CH_2CHCl_2$ | H | $CH_3$ | $OCH_2CH_2F$ | CH | |
| $CH_3$ | $CH_2CHCl_2$ | H | $OCH_3$ | $OCH_2CH_2F$ | CH | |

TABLE I-continued

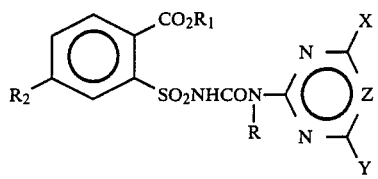

| R₁ | R₂ | R | X | Y | Z | m.p. (°C.) |
|---|---|---|---|---|---|---|
| CH₃ | CH₂CHCl₂ | H | CH₃ | OCH₂CF₃ | N | |
| CH₃ | CH₂CHCl₂ | CH₃ | OCH₃ | OCH₂CF₃ | N | |
| CH₃ | CH₂CHCl₂ | CH₃ | Cl | OCH₃ | CH | |
| CH₃ | CH₂CHCl₂ | H | Cl | N(CH₃)₂ | CH | |
| CH₃ | CH₂CHCl₂ | H | Cl | OC₂H₅ | CH | |
| C₂H₅ | CH₂CHCl₂ | H | CH₃ | CH₃ | CH | |
| C₂H₅ | CH₂CHCl₂ | H | OCH₃ | CH₃ | CH | |
| C₂H₅ | CH₂CHCl₂ | H | OCH₃ | OCH₃ | CH | |
| C₂H₅ | CH₂CHCl₂ | H | Cl | OCH₃ | CH | |
| C₂H₅ | CH₂CHCl₂ | H | CH₃ | CH₃ | N | |
| C₂H₅ | CH₂CHCl₂ | H | OCH₃ | CH₃ | N | |
| C₂H₅ | CH₂CHCl₂ | H | OCH₃ | OCH₃ | N | |
| C₂H₅ | CH₂CHCl₂ | H | Br | OCH₃ | CH | |
| C₂H₅ | CH₂CHCl₂ | H | OCH₃ | N(CH₃)₂ | CH | |
| C₂H₅ | CH₂CHCl₂ | H | OCH₃ | N(CH₃)₂ | N | |
| C₂H₅ | CH₂CHCl₂ | H | OCH₃ | NHCH₃ | N | |
| C₂H₅ | CH₂CHCl₂ | H | OCH₃ | C₂H₅ | CH | |
| C₂H₅ | CH₂CHCl₂ | H | OCH₃ | C₂H₅ | N | |
| C₂H₅ | CH₂CHCl₂ | H | CH₃ | OC₂H₅ | CH | |
| C₂H₅ | CH₂CHCl₂ | H | CH₃ | OC₂H₅ | N | |
| C₂H₅ | CH₂CHCl₂ | H | OCH₃ | OC₂H₅ | CH | |
| C₂H₅ | CH₂CHCl₂ | H | OCH₃ | OC₂H₅ | N | |
| C₂H₅ | CH₂CHCl₂ | H | CH₃ | OCH₂CF₃ | CH | |
| C₂H₅ | CH₂CHCl₂ | H | CH₃ | OCH₂CF₃ | N | |
| C₂H₅ | CH₂CHCl₂ | H | OCH₃ | OCH₂CF₃ | CH | |
| C₂H₅ | CH₂CHCl₂ | H | OCH₃ | OCH₂CF₃ | N | |
| C₂H₅ | CH₂CHCl₂ | H | OCH₃ | OCH₂CHF₂ | CH | |
| C₂H₅ | CH₂CHCl₂ | H | OCH₃ | OCH₂CHF₂ | N | |
| C₂H₅ | CH₂CHCl₂ | H | CH₃ | OCH₂CHF₂ | N | |
| C₂H₅ | CH₂CHCl₂ | H | OCH₃ | OCH₂CH₂F | CH | |
| C₂H₅ | CH₂CHCl₂ | H | OCH₃ | OCH₂CH₂F | N | |
| C₂H₅ | CH₂CHCl₂ | CH₃ | OCH₃ | OCH₃ | CH | |
| C₂H₅ | CH₂CHCl₂ | CH₃ | CH₃ | CH₃ | N | |
| C₂H₅ | CH₂CHCl₂ | CH₃ | OCH₃ | OCH₃ | N | |
| n-C₃H₇ | CH₂CHCl₂ | H | OCH₃ | OCH₃ | CH | |
| n-C₃H₇ | CH₂CHCl₂ | H | CH₃ | OCH₃ | N | |
| CH(CH₃)₂ | CH₂CHCl₂ | H | OCH₃ | CH₃ | CH | |
| CH(CH₃)₂ | CH₂CHCl₂ | H | OCH₃ | OCH₃ | CH | |
| CH(CH₃)₂ | CH₂CHCl₂ | H | Cl | OCH₃ | CH | |
| CH(CH₃)₂ | CH₂CHCl₂ | H | OCH₃ | CH₃ | N | |
| CH(CH₃)₂ | CH₂CHCl₂ | H | OCH₃ | OCH₃ | N | |
| CH(CH₃)₂ | CH₂CHCl₂ | H | OCH₃ | N(CH₃)₂ | N | |
| CH₃ | CH₂CCl₃ | H | CH₃ | CH₃ | CH | |
| CH₃ | CH₂CCl₃ | H | OCH₃ | CH₃ | CH | |
| CH₃ | CH₂CCl₃ | H | OCH₃ | OCH₃ | CH | |
| CH₃ | CH₂CCl₃ | H | Cl | OCH₃ | CH | |
| CH₃ | CH₂CCl₃ | H | OCH₃ | N(CH₃)₂ | CH | |
| CH₃ | CH₂CCl₃ | H | CH₃ | CH₃ | N | |
| CH₃ | CH₂CCl₃ | H | OCH₃ | CH₃ | N | |
| CH₃ | CH₂CCl₃ | H | OCH₃ | OCH₃ | N | |
| CH₃ | CH₂CCl₃ | H | OCH₃ | N(CH₃)₂ | N | |
| CH₃ | CH₂CCl₃ | H | OCH₃ | OCH₂CF₃ | N | |
| CH₃ | CH₂CCl₃ | CH₃ | OCH₃ | CH₃ | N | |
| CH₃ | CH₂CCl₃ | CH₃ | OCH₃ | OCH₃ | N | |
| CH₃ | CH₂CCl₃ | CH₃ | CH₃ | OCH₃ | CH | |
| CH₃ | CH₂CCl₃ | CH₃ | OCH₃ | OCH₃ | CH | |
| CH₃ | CH₂CCl₃ | H | Br | OCH₃ | CH | |
| CH₃ | CH₂CCl₃ | CH₃ | OCH₃ | N(CH₃)₂ | N | |
| CH₃ | CH₂CCl₃ | H | CH₃ | OCH₂CF₃ | N | |
| CH₃ | CH₂CCl₃ | H | CH₃ | OCH₂CF₃ | CH | |
| CH₃ | CH₂CCl₃ | H | OCH₃ | OCH₂CF₃ | CH | |
| CH₃ | CH₂CCl₃ | H | OCH₃ | C₂H₅ | CH | |
| CH₃ | CH₂CCl₃ | H | OCH₃ | C₂H₅ | N | |
| CH₃ | CH₂CCl₃ | H | OCH₃ | NHCH₃ | CH | |
| CH₃ | CH₂CCl₃ | H | OCH₃ | NHCH₃ | N | |
| CH₃ | CH₂CCl₃ | H | CH₃ | OC₂H₅ | CH | |
| CH₃ | CH₂CCl₃ | H | OCH₃ | OC₂H₅ | CH | |
| CH₃ | CH₂CCl₃ | H | CH₃ | OC₂H₅ | N | |
| CH₃ | CH₂CCl₃ | H | OCH₃ | OC₂H₅ | N | |
| CH₃ | CH₂CCl₃ | H | CH₃ | OCH₂CHF₂ | CH | |
| CH₃ | CH₂CCl₃ | H | OCH₃ | OCH₂CHF₂ | CH | |

TABLE I-continued

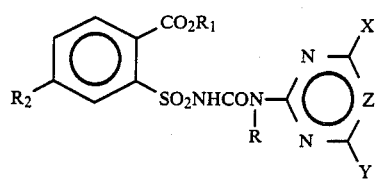

| R₁ | R₂ | R | X | Y | Z | m.p. (°C.) |
|---|---|---|---|---|---|---|
| CH₃ | CH₂CCl₃ | H | CH₃ | OCH₂CHF₂ | N | |
| CH₃ | CH₂CCl₃ | H | OCH₃ | OCH₂CHF₂ | N | |
| CH₃ | CH₂CCl₃ | H | CH₃ | OCH₂CH₂F | CH | |
| CH₃ | CH₂CCl₃ | H | OCH₃ | OCH₂CH₂F | CH | |
| CH₃ | CH₂CCl₃ | H | CH₃ | OCH₂CH₂F | N | |
| CH₃ | CH₂CCl₃ | CH₃ | OCH₃ | OCH₂CH₂F | N | |
| CH₃ | CH₂CCl₃ | CH₃ | Cl | OCH₃ | CH | |
| CH₃ | CH₂CCl₃ | H | Cl | N(CH₃)₂ | CH | |
| CH₃ | CH₂CCl₃ | H | Cl | OC₂H₅ | CH | |
| C₂H₅ | CH₂CCl₃ | H | CH₃ | CH₃ | CH | |
| C₂H₅ | CH₂CCl₃ | H | OCH₃ | CH₃ | CH | |
| C₂H₅ | CH₂CCl₃ | H | OCH₃ | OCH₃ | CH | |
| C₂H₅ | CH₂CCl₃ | H | Cl | OCH₃ | CH | |
| C₂H₅ | CH₂CCl₃ | H | CH₃ | CH₃ | N | |
| C₂H₅ | CH₂CCl₃ | H | OCH₃ | CH₃ | N | |
| C₂H₅ | CH₂CCl₃ | H | OCH₃ | OCH₃ | N | |
| C₂H₅ | CH₂CCl₃ | H | Br | OCH₃ | CH | |
| C₂H₅ | CH₂CCl₃ | H | OCH₃ | N(CH₃)₂ | CH | |
| C₂H₅ | CH₂CCl₃ | H | OCH₃ | N(CH₃)₂ | N | |
| C₂H₅ | CH₂CCl₃ | H | OCH₃ | NHCH₃ | N | |
| C₂H₅ | CH₂CCl₃ | H | OCH₃ | C₂H₅ | CH | |
| C₂H₅ | CH₂CCl₃ | H | OCH₃ | C₂H₅ | N | |
| C₂H₅ | CH₂CCl₃ | H | CH₃ | OC₂H₅ | CH | |
| C₂H₅ | CH₂CCl₃ | H | CH₃ | OC₂H₅ | N | |
| C₂H₅ | CH₂CCl₃ | H | OCH₃ | OC₂H₅ | CH | |
| C₂H₅ | CH₂CCl₃ | H | OCH₃ | OC₂H₅ | N | |
| C₂H₅ | CH₂CCl₃ | H | CH₃ | OCH₂CF₃ | CH | |
| C₂H₅ | CH₂CCl₃ | H | CH₃ | OCH₂CF₃ | N | |
| C₂H₅ | CH₂CCl₃ | H | OCH₃ | OCH₂CF₃ | CH | |
| C₂H₅ | CH₂CCl₃ | H | OCH₃ | OCH₂CF₃ | N | |
| C₂H₅ | CH₂CCl₃ | H | OCH₃ | OCH₂CHF₂ | CH | |
| C₂H₅ | CH₂CCl₃ | H | OCH₃ | OCH₂CHF₂ | N | |
| C₂H₅ | CH₂CCl₃ | H | CH₃ | OCH₂CHF₂ | N | |
| C₂H₅ | CH₂CCl₃ | H | OCH₃ | OCH₂CH₂F | CH | |
| C₂H₅ | CH₂CCl₃ | H | OCH₃ | OCH₂CH₂F | N | |
| C₂H₅ | CH₂CCl₃ | CH₃ | OCH₃ | OCH₃ | CH | |
| C₂H₅ | CH₂CCl₃ | CH₃ | CH₃ | OCH₃ | N | |
| C₂H₅ | CH₂CCl₃ | CH₃ | OCH₃ | OCH₃ | N | |
| n-C₃H₇ | CH₂CCl₃ | H | OCH₃ | OCH₃ | CH | |
| n-C₃H₇ | CH₂CCl₃ | H | CH₃ | OCH₃ | N | |
| CH(CH₃)₂ | CH₂CCl₃ | H | OCH₃ | CH₃ | CH | |
| CH(CH₃)₂ | CH₂CCl₃ | H | OCH₃ | OCH₃ | CH | |
| CH(CH₃)₂ | CH₂CCl₃ | H | Cl | OCH₃ | CH | |
| CH(CH₃)₂ | CH₂CCl₃ | H | OCH₃ | CH₃ | N | |
| CH(CH₃)₂ | CH₂CCl₃ | H | OCH₃ | OCH₃ | N | |
| CH(CH₃)₂ | CH₂CCl₃ | H | OCH₃ | N(CH₃)₂ | N | |
| CH₃ | CF₂CH₂F | H | CH₃ | OCH₃ | CH | |
| CH₃ | CHFCH₂F | H | OCH₃ | OCH₃ | N | |
| CH₃ | CHFCHF₂ | H | OCH₃ | CH₃ | N | |
| CH₃ | CH₂CH₂CH₂F | H | OCH₃ | OCH₃ | CH | |
| CH₃ | CH₂CH₂CHF₂ | H | CH₃ | OCH₃ | CH | |
| CH₃ | CH₂CH₂CF₃ | H | OCH₃ | OCH₃ | N | |
| CH₃ | CHFCH₂CH₃ | H | OCH₃ | CH₃ | N | |
| CH₃ | CF₂CH₂CH₃ | H | OCH₃ | OCH₃ | CH | |
| CH₃ | CF₂CH₂CH₂F | H | CH₃ | OCH₃ | CH | |
| CH₃ | CF₂CHFCH₃ | H | OCH₃ | OCH₃ | N | |
| CH₃ | CHFCHFCH₂F | H | OCH₃ | CH₃ | N | |
| CH₃ | CF(CH₃)₂ | H | OCH₃ | OCH₃ | CH | |
| CH₃ | CH(CH₃)CF₃ | H | CH₃ | OCH₃ | CH | |
| CH₃ | CHClCH₃ | H | OCH₃ | OCH₃ | N | |
| CH₃ | CCl₂CH₃ | H | OCH₃ | CH₃ | N | |
| CH₃ | CCl₂CH₂Cl | H | OCH₃ | OCH₃ | CH | |
| CH₃ | CHClCH₂Cl | H | CH₃ | OCH₃ | CH | |
| CH₃ | CHClCHCl₂ | H | OCH₃ | OCH₃ | N | |
| CH₃ | CH₂CH₂CH₂Cl | H | OCH₃ | CH₃ | N | |
| CH₃ | CH₂CH₂CHCl₂ | H | OCH₃ | OCH₃ | CH | |
| CH₃ | CH₂CH₂CCl₃ | H | CH₃ | OCH₃ | CH | |
| CH₃ | CHClCH₂CH₃ | H | OCH₃ | OCH₃ | N | |
| CH₃ | CCl₂CH₂CH₃ | H | OCH₃ | CH₃ | N | |
| CH₃ | CCl₂CH₂CH₂Cl | H | OCH₃ | OCH₃ | CH | |
| CH₃ | CCl₂CHClCH₃ | H | CH₃ | OCH₃ | CH | |

TABLE I-continued

| $R_1$ | $R_2$ | R | X | Y | Z | m.p. (°C.) |
|---|---|---|---|---|---|---|
| $CH_3$ | $CHClCHClCH_2Cl$ | H | $OCH_3$ | $OCH_3$ | N | |
| $CH_3$ | $CCl(CH_3)_2$ | H | $OCH_3$ | $CH_3$ | N | |
| $CH_3$ | $CH(CH_3)(CCl_3)$ | H | $OCH_3$ | $OCH_3$ | CH | |
| $CH_3$ | $(CH_2)_3CF_3$ | H | $CH_3$ | $OCH_3$ | CH | |
| $CH_3$ | $(CH_2)_4CF_3$ | H | $OCH_3$ | $OCH_3$ | N | |
| $CH_3$ | $(CH_2)_5CF_3$ | H | $CH_3$ | $OCH_3$ | N | |
| $CH_3$ | $CHF(CH_2)_2CH_3$ | H | $OCH_3$ | $OCH_3$ | CH | |
| $CH_3$ | $CHF(CH_2)_3CH_3$ | H | $CH_3$ | $OCH_3$ | CH | |
| $CH_3$ | $CHF(CH_2)_4CH_3$ | H | $OCH_3$ | $OCH_3$ | N | |
| $CH_3$ | $CF_2(CH_2)_2CH_3$ | H | $CH_3$ | $OCH_3$ | N | |
| $CH_3$ | $CF_2(CH_2)_3CH_3$ | H | $OCH_3$ | $OCH_3$ | CH | |
| $CH_3$ | $CF_2(CH_2)_4CH_3$ | H | $CH_3$ | $OCH_3$ | CH | |
| $CH_3$ | $CH_2CHF(CH_2)_3CH_3$ | H | $OCH_3$ | $OCH_3$ | N | |
| $CH_3$ | $(CH_2)_2CHF(CH_2)_2CH_3$ | H | $CH_3$ | $OCH_3$ | N | |
| $CH_3$ | $(CH_2)_3CHFCH_2CH_3$ | H | $OCH_3$ | $OCH_3$ | CH | |
| $CH_3$ | $(CH_2)_4CHFCH_3$ | H | $CH_3$ | $OCH_3$ | CH | |
| $CH_3$ | $(CH_2)_3CH(CH_3)(CF_3)$ | H | $OCH_3$ | $OCH_3$ | N | |
| $CH_3$ | $(CH_2)_3CH_2Cl$ | H | $CH_3$ | $OCH_3$ | N | |
| $CH_3$ | $(CH_2)_4CH_2Cl$ | H | $OCH_3$ | $OCH_3$ | CH | |
| $CH_3$ | $(CH_2)_5CH_2Cl$ | H | $CH_3$ | $OCH_3$ | CH | |
| $CH_3$ | $(CH_2)_3CHCl_2$ | H | $OCH_3$ | $OCH_3$ | N | |
| $CH_3$ | $(CH_2)_4CHCl_2$ | H | $CH_3$ | $OCH_3$ | N | |
| $CH_3$ | $(CH_2)_5CHCl_2$ | H | $OCH_3$ | $OCH_3$ | CH | |
| $CH_3$ | $(CH_2)_3CCl_3$ | H | $CH_3$ | $OCH_3$ | CH | |
| $CH_3$ | $(CH_2)_4CCl_3$ | H | $OCH_3$ | $OCH_3$ | N | |
| $CH_3$ | $(CH_2)_5CCl_3$ | H | $CH_3$ | $OCH_3$ | N | |
| $CH_3$ | $CH_2(CHCl)_2CH_3$ | H | $OCH_3$ | $OCH_3$ | CH | |
| $CH_3$ | $CH_2CHClCH_2CHClCH_3$ | H | $CH_3$ | $OCH_3$ | CH | |
| $CH_3$ | $CH_2F$ | H | $CH_3$ | $CH_3$ | CH | |
| $CH_3$ | $CH_2F$ | H | $OCH_3$ | $CH_3$ | CH | |
| $CH_3$ | $CH_2F$ | H | $OCH_3$ | $OCH_3$ | CH | |
| $CH_3$ | $CH_2F$ | H | Cl | $OCH_3$ | CH | |
| $CH_3$ | $CH_2F$ | H | $OCH_3$ | $N(CH_3)_2$ | CH | |
| $CH_3$ | $CH_2F$ | H | $CH_3$ | $CH_3$ | N | |
| $CH_3$ | $CH_2F$ | H | $OCH_3$ | $CH_3$ | N | |
| $CH_3$ | $CH_2F$ | H | $OCH_3$ | $OCH_3$ | N | |
| $CH_3$ | $CH_2F$ | H | $OCH_3$ | $N(CH_3)_2$ | N | |
| $CH_3$ | $CH_2F$ | H | $OCH_3$ | $OCH_2CF_3$ | N | |
| $CH_3$ | $CH_2F$ | $CH_3$ | $OCH_3$ | $CH_3$ | N | |
| $CH_3$ | $CH_2F$ | $CH_3$ | $OCH_3$ | $OCH_3$ | N | |
| $CH_3$ | $CH_2F$ | $CH_3$ | $CH_3$ | $OCH_3$ | CH | |
| $CH_3$ | $CH_2F$ | $CH_3$ | $OCH_3$ | $OCH_3$ | CH | |
| $CH_3$ | $CH_2F$ | H | Br | $OCH_3$ | CH | |
| $CH_3$ | $CH_2F$ | $CH_3$ | $OCH_3$ | $N(CH_3)_2$ | N | |
| $CH_3$ | $CH_2F$ | H | $CH_3$ | $OCH_2CF_3$ | N | |
| $CH_3$ | $CH_2F$ | H | $CH_3$ | $OCH_2CF_3$ | CH | |
| $CH_3$ | $CH_2F$ | H | $OCH_3$ | $OCH_2CF_3$ | CH | |
| $CH_3$ | $CH_2F$ | H | $OCH_3$ | $C_2H_5$ | CH | |
| $CH_3$ | $CH_2F$ | H | $OCH_3$ | $C_2H_5$ | N | |
| $CH_3$ | $CH_2F$ | H | $OCH_3$ | $NHCH_3$ | CH | |
| $CH_3$ | $CH_2F$ | H | $OCH_3$ | $NHCH_3$ | N | |
| $CH_3$ | $CH_2F$ | H | $CH_3$ | $OC_2H_5$ | CH | |
| $CH_3$ | $CH_2F$ | H | $OCH_3$ | $OC_2H_5$ | CH | |
| $CH_3$ | $CH_2F$ | H | $CH_3$ | $OC_2H_5$ | N | |
| $CH_3$ | $CH_2F$ | H | $OCH_3$ | $OC_2H_5$ | N | |
| $CH_3$ | $CH_2F$ | H | $CH_3$ | $OCH_2CHF_2$ | CH | |
| $CH_3$ | $CH_2F$ | H | $OCH_3$ | $OCH_2CHF_2$ | CH | |
| $CH_3$ | $CH_2F$ | H | $CH_3$ | $OCH_2CHF_2$ | N | |
| $CH_3$ | $CH_2F$ | H | $OCH_3$ | $OCH_2CHF_2$ | N | |
| $CH_3$ | $CH_2F$ | H | $CH_3$ | $OCH_2CH_2F$ | CH | |
| $CH_3$ | $CH_2F$ | H | $OCH_3$ | $OCH_2CH_2F$ | CH | |
| $CH_3$ | $CH_2F$ | H | $CH_3$ | $OCH_2CH_2F$ | N | |
| $CH_3$ | $CH_2F$ | $CH_3$ | $OCH_3$ | $OCH_2CH_2F$ | N | |
| $CH_3$ | $CH_2F$ | $CH_3$ | Cl | $OCH_3$ | CH | |
| $CH_3$ | $CH_2F$ | H | Cl | $N(CH_3)_2$ | CH | |
| $CH_3$ | $CH_2F$ | H | Cl | $OC_2H_5$ | CH | |
| $C_2H_5$ | $CH_2F$ | H | $CH_3$ | $CH_3$ | CH | |
| $C_2H_5$ | $CH_2F$ | H | $OCH_3$ | $CH_3$ | CH | |
| $C_2H_5$ | $CH_2F$ | H | $OCH_3$ | $OCH_3$ | CH | |
| $C_2H_5$ | $CH_2F$ | H | Cl | $OCH_3$ | CH | |
| $C_2H_5$ | $CH_2F$ | H | $CH_3$ | $CH_3$ | N | |

TABLE I-continued

| R₁ | R₂ | R | X | Y | Z | m.p. (°C.) |
|---|---|---|---|---|---|---|
| $C_2H_5$ | $CH_2F$ | H | $OCH_3$ | $CH_3$ | N | |
| $C_2H_5$ | $CH_2F$ | H | $OCH_3$ | $OCH_3$ | N | |
| $C_2H_5$ | $CH_2F$ | H | Br | $OCH_3$ | CH | |
| $C_2H_5$ | $CH_2F$ | H | $OCH_3$ | $N(CH_3)_2$ | CH | |
| $C_2H_5$ | $CH_2F$ | H | $OCH_3$ | $N(CH_3)_2$ | N | |
| $C_2H_5$ | $CH_2F$ | H | $OCH_3$ | $NHCH_3$ | N | |
| $C_2H_5$ | $CH_2F$ | H | $OCH_3$ | $C_2H_5$ | CH | |
| $C_2H_5$ | $CH_2F$ | H | $OCH_3$ | $C_2H_5$ | N | |
| $C_2H_5$ | $CH_2F$ | H | $CH_3$ | $OC_2H_5$ | CH | |
| $C_2H_5$ | $CH_2F$ | H | $CH_3$ | $OC_2H_5$ | N | |
| $C_2H_5$ | $CH_2F$ | H | $OCH_3$ | $OC_2H_5$ | CH | |
| $C_2H_5$ | $CH_2F$ | H | $OCH_3$ | $OC_2H_5$ | N | |
| $C_2H_5$ | $CH_2F$ | H | $CH_3$ | $OCH_2CF_3$ | CH | |
| $C_2H_5$ | $CH_2F$ | H | $CH_3$ | $OCH_2CF_3$ | N | |
| $C_2H_5$ | $CH_2F$ | H | $OCH_3$ | $OCH_2CF_3$ | CH | |
| $C_2H_5$ | $CH_2F$ | H | $OCH_3$ | $OCH_2CF_3$ | N | |
| $C_2H_5$ | $CH_2F$ | H | $OCH_3$ | $OCH_2CHF_2$ | CH | |
| $C_2H_5$ | $CH_2F$ | H | $OCH_3$ | $OCH_2CHF_2$ | N | |
| $C_2H_5$ | $CH_2F$ | H | $CH_3$ | $OCH_2CHF_2$ | N | |
| $C_2H_5$ | $CH_2F$ | H | $OCH_3$ | $OCH_2CH_2F$ | CH | |
| $C_2H_5$ | $CH_2F$ | H | $OCH_3$ | $OCH_2CH_2F$ | N | |
| $C_2H_5$ | $CH_2F$ | $CH_3$ | $OCH_3$ | $OCH_3$ | CH | |
| $C_2H_5$ | $CH_2F$ | $CH_3$ | $CH_3$ | $OCH_3$ | N | |
| $C_2H_5$ | $CH_2F$ | $CH_3$ | $OCH_3$ | $OCH_3$ | N | |
| n-$C_3H_7$ | $CH_2F$ | H | $OCH_3$ | $OCH_3$ | CH | |
| n-$C_3H_7$ | $CH_2F$ | H | $CH_3$ | $OCH_3$ | N | |
| $CH(CH_3)_2$ | $CH_2F$ | H | $OCH_3$ | $CH_3$ | CH | |
| $CH(CH_3)_2$ | $CH_2F$ | H | $OCH_3$ | $OCH_3$ | CH | |
| $CH(CH_3)_2$ | $CH_2F$ | H | Cl | $OCH_3$ | CH | |
| $CH(CH_3)_2$ | $CH_2F$ | H | $OCH_3$ | $CH_3$ | N | |
| $CH(CH_3)_2$ | $CH_2F$ | H | $OCH_3$ | $OCH_3$ | N | |
| $CH(CH_3)_2$ | $CH_2F$ | H | $OCH_3$ | $N(CH_3)_2$ | N | |
| $CH_3$ | $CHF_2$ | H | $CH_3$ | $CH_3$ | CH | |
| $CH_3$ | $CHF_2$ | H | $OCH_3$ | $CH_3$ | CH | |
| $CH_3$ | $CHF_2$ | H | $OCH_3$ | $OCH_3$ | CH | |
| $CH_3$ | $CHF_2$ | H | Cl | $OCH_3$ | CH | |
| $CH_3$ | $CHF_2$ | H | $OCH_3$ | $N(CH_3)_2$ | CH | |
| $CH_3$ | $CHF_2$ | H | $CH_3$ | $CH_3$ | N | |
| $CH_3$ | $CHF_2$ | H | $OCH_3$ | $CH_3$ | N | |
| $CH_3$ | $CHF_2$ | H | $OCH_3$ | $OCH_3$ | N | |
| $CH_3$ | $CHF_2$ | H | $OCH_3$ | $N(CH_3)_2$ | N | |
| $CH_3$ | $CHF_2$ | H | $OCH_3$ | $OCH_2CF_3$ | N | |
| $CH_3$ | $CHF_2$ | $CH_3$ | $OCH_3$ | $CH_3$ | N | |
| $CH_3$ | $CHF_2$ | $CH_3$ | $OCH_3$ | $OCH_3$ | N | |
| $CH_3$ | $CHF_2$ | $CH_3$ | $CH_3$ | $OCH_3$ | CH | |
| $CH_3$ | $CHF_2$ | $CH_3$ | $OCH_3$ | $OCH_3$ | CH | |
| $CH_3$ | $CHF_2$ | H | Br | $OCH_3$ | CH | |
| $CH_3$ | $CHF_2$ | $CH_3$ | $OCH_3$ | $N(CH_3)_2$ | N | |
| $CH_3$ | $CHF_2$ | H | $CH_3$ | $OCH_2CF_3$ | N | |
| $CH_3$ | $CHF_2$ | H | $CH_3$ | $OCH_2CF_3$ | CH | |
| $CH_3$ | $CHF_2$ | H | $OCH_3$ | $OCH_2CF_3$ | CH | |
| $CH_3$ | $CHF_2$ | H | $OCH_3$ | $C_2H_5$ | CH | |
| $CH_3$ | $CHF_2$ | H | $OCH_3$ | $C_2H_5$ | N | |
| $CH_3$ | $CHF_2$ | H | $OCH_3$ | $NHCH_3$ | CH | |
| $CH_3$ | $CHF_2$ | H | $OCH_3$ | $NHCH_3$ | N | |
| $CH_3$ | $CHF_2$ | H | $CH_3$ | $OC_2H_5$ | CH | |
| $CH_3$ | $CHF_2$ | H | $OCH_3$ | $OC_2H_5$ | CH | |
| $CH_3$ | $CHF_2$ | H | $CH_3$ | $OC_2H_5$ | N | |
| $CH_3$ | $CHF_2$ | H | $OCH_3$ | $OC_2H_5$ | N | |
| $CH_3$ | $CHF_2$ | H | $CH_3$ | $OCH_2CHF_2$ | CH | |
| $CH_3$ | $CHF_2$ | H | $OCH_3$ | $OCH_2CHF_2$ | CH | |
| $CH_3$ | $CHF_2$ | H | $CH_3$ | $OCH_2CHF_2$ | N | |
| $CH_3$ | $CHF_2$ | H | $OCH_3$ | $OCH_2CHF_2$ | N | |
| $CH_3$ | $CHF_2$ | H | $CH_3$ | $OCH_2CH_2F$ | CH | |
| $CH_3$ | $CHF_2$ | H | $OCH_3$ | $OCH_2CH_2F$ | CH | |
| $CH_3$ | $CHF_2$ | H | $CH_3$ | $OCH_2CH_2F$ | N | |
| $CH_3$ | $CHF_2$ | $CH_3$ | $OCH_3$ | $OCH_2CH_2F$ | N | |
| $CH_3$ | $CHF_2$ | $CH_3$ | Cl | $OCH_3$ | CH | |
| $CH_3$ | $CHF_2$ | H | Cl | $N(CH_3)_2$ | CH | |
| $CH_3$ | $CHF_2$ | H | Cl | $OC_2H_5$ | CH | |
| $C_2H_5$ | $CHF_2$ | H | $CH_3$ | $CH_3$ | CH | |

TABLE I-continued

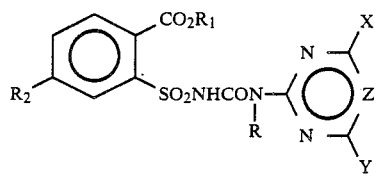

| $R_1$ | $R_2$ | R | X | Y | Z | m.p. (°C.) |
|---|---|---|---|---|---|---|
| $C_2H_5$ | $CHF_2$ | H | $OCH_3$ | $CH_3$ | CH | |
| $C_2H_5$ | $CHF_2$ | H | $OCH_3$ | $OCH_3$ | CH | |
| $C_2H_5$ | $CHF_2$ | H | Cl | $OCH_3$ | CH | |
| $C_2H_5$ | $CHF_2$ | H | $CH_3$ | $CH_3$ | N | |
| $C_2H_5$ | $CHF_2$ | H | $OCH_3$ | $CH_3$ | N | |
| $C_2H_5$ | $CHF_2$ | H | $OCH_3$ | $OCH_3$ | N | |
| $C_2H_5$ | $CHF_2$ | H | Br | $OCH_3$ | CH | |
| $C_2H_5$ | $CHF_2$ | H | $OCH_3$ | $N(CH_3)_2$ | CH | |
| $C_2H_5$ | $CHF_2$ | H | $OCH_3$ | $N(CH_3)_2$ | N | |
| $C_2H_5$ | $CHF_2$ | H | $OCH_3$ | $NHCH_3$ | N | |
| $C_2H_5$ | $CHF_2$ | H | $OCH_3$ | $C_2H_5$ | CH | |
| $C_2H_5$ | $CHF_2$ | H | $OCH_3$ | $C_2H_5$ | N | |
| $C_2H_5$ | $CHF_2$ | H | $CH_3$ | $OC_2H_5$ | CH | |
| $C_2H_5$ | $CHF_2$ | H | $CH_3$ | $OC_2H_5$ | N | |
| $C_2H_5$ | $CHF_2$ | H | $OCH_3$ | $OC_2H_5$ | CH | |
| $C_2H_5$ | $CHF_2$ | H | $OCH_3$ | $OC_2H_5$ | N | |
| $C_2H_5$ | $CHF_2$ | H | $CH_3$ | $OCH_2CF_3$ | CH | |
| $C_2H_5$ | $CHF_2$ | H | $CH_3$ | $OCH_2CF_3$ | N | |
| $C_2H_5$ | $CHF_2$ | H | $OCH_3$ | $OCH_2CF_3$ | CH | |
| $C_2H_5$ | $CHF_2$ | H | $OCH_3$ | $OCH_2CF_3$ | N | |
| $C_2H_5$ | $CHF_2$ | H | $OCH_3$ | $OCH_2CHF_2$ | CH | |
| $C_2H_5$ | $CHF_2$ | H | $OCH_3$ | $OCH_2CHF_2$ | N | |
| $C_2H_5$ | $CHF_2$ | H | $CH_3$ | $OCH_2CHF_2$ | N | |
| $C_2H_5$ | $CHF_2$ | H | $OCH_3$ | $OCH_2CH_2F$ | CH | |
| $C_2H_5$ | $CHF_2$ | H | $OCH_3$ | $OCH_2CH_2F$ | N | |
| $C_2H_5$ | $CHF_2$ | $CH_3$ | $OCH_3$ | $OCH_3$ | CH | |
| $C_2H_5$ | $CHF_2$ | $CH_3$ | $CH_3$ | $OCH_3$ | N | |
| $C_2H_5$ | $CHF_2$ | $CH_3$ | $OCH_3$ | $OCH_3$ | N | |
| $n$-$C_3H_7$ | $CHF_2$ | H | $OCH_3$ | $OCH_3$ | CH | |
| $n$-$C_3H_7$ | $CHF_2$ | H | $CH_3$ | $OCH_3$ | N | |
| $CH(CH_3)_2$ | $CHF_2$ | H | $OCH_3$ | $CH_3$ | CH | |
| $CH(CH_3)_2$ | $CHF_2$ | H | $OCH_3$ | $OCH_3$ | CH | |
| $CH(CH_3)_2$ | $CHF_2$ | H | Cl | $OCH_3$ | CH | |
| $CH(CH_3)_2$ | $CHF_2$ | H | $OCH_3$ | $CH_3$ | N | |
| $CH(CH_3)_2$ | $CHF_2$ | H | $OCH_3$ | $OCH_3$ | N | |
| $CH(CH_3)_2$ | $CHF_2$ | H | $OCH_3$ | $N(CH_3)_2$ | N | |
| $CH_3$ | $CH_2OCH_3$ | H | $CH_3$ | $CH_3$ | CH | |
| $CH_3$ | $CH_2OCH_3$ | H | $OCH_3$ | $CH_3$ | CH | 147–148 (d) |
| $CH_3$ | $CH_2OCH_3$ | H | $OCH_3$ | $OCH_3$ | CH | 151–153 (d) |
| $CH_3$ | $CH_2OCH_3$ | H | Cl | $OCH_3$ | CH | |
| $CH_3$ | $CH_2OCH_3$ | H | $OCH_3$ | $N(CH_3)_2$ | CH | |
| $CH_3$ | $CH_2OCH_3$ | H | $CH_3$ | $CH_3$ | N | |
| $CH_3$ | $CH_2OCH_3$ | H | $OCH_3$ | $CH_3$ | N | 110–112 (d) |
| $CH_3$ | $CH_2OCH_3$ | H | $OCH_3$ | $OCH_3$ | N | 105–106 (d) |
| $CH_3$ | $CH_2OCH_3$ | H | $OCH_3$ | $N(CH_3)_2$ | N | |
| $CH_3$ | $CH_2OCH_3$ | H | $OCH_3$ | $OCH_2CF_3$ | N | |
| $CH_3$ | $CH_2OCH_3$ | $CH_3$ | $OCH_3$ | $CH_3$ | N | |
| $CH_3$ | $CH_2OCH_3$ | $CH_3$ | $OCH_3$ | $OCH_3$ | N | |
| $CH_3$ | $CH_2OCH_3$ | $CH_3$ | $CH_3$ | $OCH_3$ | CH | |
| $CH_3$ | $CH_2OCH_3$ | $CH_3$ | $OCH_3$ | $OCH_3$ | CH | |
| $CH_3$ | $CH_2OCH_3$ | H | Br | $OCH_3$ | CH | |
| $CH_3$ | $CH_2OCH_3$ | H | $OCH_3$ | $N(CH_3)_2$ | CH | |
| $CH_3$ | $CH_2OCH_3$ | $CH_3$ | $OCH_3$ | $N(CH_3)_2$ | N | |
| $CH_3$ | $CH_2OCH_3$ | H | $CH_3$ | $OCH_2CF_3$ | N | |
| $CH_3$ | $CH_2OCH_3$ | H | $CH_3$ | $OCH_2CF_3$ | CH | |
| $CH_3$ | $CH_2OCH_3$ | H | $OCH_3$ | $OCH_2CF_3$ | CH | |
| $CH_3$ | $CH_2OCH_3$ | H | $OCH_3$ | $C_2H_5$ | CH | |
| $CH_3$ | $CH_2OCH_3$ | H | $OCH_3$ | $C_2H_5$ | N | |
| $CH_3$ | $CH_2OCH_3$ | H | $OCH_3$ | $NHCH_3$ | CH | |
| $CH_3$ | $CH_2OCH_3$ | H | $OCH_3$ | $NHCH_3$ | N | |
| $CH_3$ | $CH_2OCH_3$ | H | $CH_3$ | $OC_2H_5$ | CH | |
| $CH_3$ | $CH_2OCH_3$ | H | $OCH_3$ | $OC_2H_5$ | CH | |
| $CH_3$ | $CH_2OCH_3$ | H | $CH_3$ | $OC_2H_5$ | N | |
| $CH_3$ | $CH_2OCH_3$ | H | $OCH_3$ | $OC_2H_5$ | N | |
| $CH_3$ | $CH_2OCH_3$ | H | $CH_3$ | $OCH_2CHF_2$ | CH | |
| $CH_3$ | $CH_2OCH_3$ | H | $OCH_3$ | $OCH_2CHF_2$ | CH | |
| $CH_3$ | $CH_2OCH_3$ | H | $CH_3$ | $OCH_2CHF_2$ | N | |
| $CH_3$ | $CH_2OCH_3$ | H | $OCH_3$ | $OCH_2CHF_2$ | N | |
| $CH_3$ | $CH_2OCH_3$ | H | $CH_3$ | $OCH_2CH_2F$ | CH | |
| $CH_3$ | $CH_2OCH_3$ | H | $OCH_3$ | $OCH_2CH_2F$ | CH | |
| $CH_3$ | $CH_2OCH_3$ | H | $CH_3$ | $OCH_2CF_3$ | N | |

TABLE I-continued

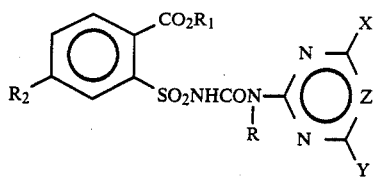

| R₁ | R₂ | R | X | Y | Z | m.p. (°C.) |
|---|---|---|---|---|---|---|
| CH₃ | CH₂OCH₃ | CH₃ | OCH₃ | OCH₂CF₃ | N | |
| CH₃ | CH₂OCH₃ | CH₃ | Cl | OCH₃ | CH | |
| CH₃ | CH₂OCH₃ | H | Cl | N(CH₃)₂ | CH | |
| CH₃ | CH₂OCH₃ | H | Cl | OC₂H₅ | CH | |
| C₂H₅ | CH₂OCH₃ | H | CH₃ | CH₃ | CH | |
| C₂H₅ | CH₂OCH₃ | H | OCH₃ | CH₃ | CH | |
| C₂H₅ | CH₂OCH₃ | H | OCH₃ | OCH₃ | CH | |
| C₂H₅ | CH₂OCH₃ | H | Cl | OCH₃ | CH | |
| C₂H₅ | CH₂OCH₃ | H | CH₃ | CH₃ | N | |
| C₂H₅ | CH₂OCH₃ | H | OCH₃ | CH₃ | N | |
| C₂H₅ | CH₂OCH₃ | H | OCH₃ | OCH₃ | N | |
| C₂H₅ | CH₂OCH₃ | H | Br | OCH₃ | CH | |
| C₂H₅ | CH₂OCH₃ | H | OCH₃ | N(CH₃)₂ | CH | |
| C₂H₅ | CH₂OCH₃ | H | OCH₃ | N(CH₃)₂ | N | |
| C₂H₅ | CH₂OCH₃ | H | OCH₃ | NHCH₃ | N | |
| C₂H₅ | CH₂OCH₃ | H | OCH₃ | C₂H₅ | CH | |
| C₂H₅ | CH₂OCH₃ | H | OCH₃ | C₂H₅ | N | |
| C₂H₅ | CH₂OCH₃ | H | CH₃ | OC₂H₅ | CH | |
| C₂H₅ | CH₂OCH₃ | H | CH₃ | OC₂H₅ | N | |
| C₂H₅ | CH₂OCH₃ | H | OCH₃ | OC₂H₅ | CH | |
| C₂H₅ | CH₂OCH₃ | H | OCH₃ | OC₂H₅ | N | |
| C₂H₅ | CH₂OCH₃ | H | CH₃ | OCH₂CF₃ | CH | |
| C₂H₅ | CH₂OCH₃ | H | CH₃ | OCH₂CF₃ | N | |
| C₂H₅ | CH₂OCH₃ | H | OCH₃ | OCH₂CF₃ | CH | |
| C₂H₅ | CH₂OCH₃ | H | OCH₃ | OCH₂CF₃ | N | |
| C₂H₅ | CH₂OCH₃ | H | OCH₃ | OCH₂CHF₂ | CH | |
| C₂H₅ | CH₂OCH₃ | H | OCH₃ | OCH₂CHF₂ | N | |
| C₂H₅ | CH₂OCH₃ | H | CH₃ | OCH₂CHF₂ | N | |
| C₂H₅ | CH₂OCH₃ | H | OCH₃ | OCH₂CH₂F | CH | |
| C₂H₅ | CH₂OCH₃ | H | OCH₃ | OCH₂CH₂F | N | |
| C₂H₅ | CH₂OCH₃ | CH₃ | OCH₃ | OCH₃ | CH | |
| C₂H₅ | CH₂OCH₃ | CH₃ | CH₃ | OCH₃ | N | |
| C₂H₅ | CH₂OCH₃ | CH₃ | OCH₃ | OCH₃ | N | |
| n-C₃H₇ | CH₂OCH₃ | H | OCH₃ | OCH₃ | CH | |
| n-C₃H₇ | CH₂OCH₃ | H | CH₃ | OCH₃ | N | |
| CH(CH₃)₂ | CH₂OCH₃ | H | OCH₃ | CH₃ | CH | |
| CH(CH₃)₂ | CH₂OCH₃ | H | OCH₃ | OCH₃ | CH | |
| CH(CH₃)₂ | CH₂OCH₃ | H | Cl | OCH₃ | CH | |
| CH(CH₃)₂ | CH₂OCH₃ | H | OCH₃ | CH₃ | N | |
| CH(CH₃)₂ | CH₂OCH₃ | H | OCH₃ | OCH₃ | N | |
| CH(CH₃)₂ | CH₂OCH₃ | H | OCH₃ | N(CH₃)₂ | N | |
| CH₃ | CH₂CH₂OCH₃ | H | CH₃ | CH₃ | CH | |
| CH₃ | CH₂CH₂OCH₃ | H | OCH₃ | CH₃ | CH | |
| CH₃ | CH₂CH₂OCH₃ | H | OCH₃ | OCH₃ | CH | |
| CH₃ | CH₂CH₂OCH₃ | H | Cl | OCH₃ | CH | |
| CH₃ | CH₂CH₂OCH₃ | H | OCH₃ | N(CH₃)₂ | CH | |
| CH₃ | CH₂CH₂OCH₃ | H | CH₃ | CH₃ | N | |
| CH₃ | CH₂CH₂OCH₃ | H | OCH₃ | CH₃ | N | |
| CH₃ | CH₂CH₂OCH₃ | H | OCH₃ | OCH₃ | N | |
| CH₃ | CH₂CH₂OCH₃ | H | OCH₃ | N(CH₃)₂ | N | |
| CH₃ | CH₂CH₂OCH₃ | H | OCH₃ | OCH₂CF₃ | N | |
| CH₃ | CH₂CH₂OCH₃ | CH₃ | OCH₃ | CH₃ | N | |
| CH₃ | CH₂CH₂OCH₃ | CH₃ | OCH₃ | OCH₃ | N | |
| CH₃ | CH₂CH₂OCH₃ | CH₃ | CH₃ | OCH₃ | CH | |
| CH₃ | CH₂CH₂OCH₃ | CH₃ | OCH₃ | OCH₃ | CH | |
| CH₃ | CH₂CH₂OCH₃ | H | Br | OCH₃ | CH | |
| CH₃ | CH₂CH₂OCH₃ | CH₃ | OCH₃ | N(CH₃)₂ | N | |
| CH₃ | CH₂CH₂OCH₃ | H | CH₃ | OCH₂CF₃ | N | |
| CH₃ | CH₂CH₂OCH₃ | H | CH₃ | OCH₂CF₃ | CH | |
| CH₃ | CH₂CH₂OCH₃ | H | OCH₃ | OCH₂CF₃ | CH | |
| CH₃ | CH₂CH₂OCH₃ | H | OCH₃ | C₂H₅ | CH | |
| CH₃ | CH₂CH₂OCH₃ | H | OCH₃ | C₂H₅ | N | |
| CH₃ | CH₂CH₂OCH₃ | H | OCH₃ | NHCH₃ | CH | |
| CH₃ | CH₂CH₂OCH₃ | H | OCH₃ | NHCH₃ | N | |
| CH₃ | CH₂CH₂OCH₃ | H | CH₃ | OC₂H₅ | CH | |
| CH₃ | CH₂CH₂OCH₃ | H | OCH₃ | OC₂H₅ | CH | |
| CH₃ | CH₂CH₂OCH₃ | H | CH₃ | OC₂H₅ | N | |
| CH₃ | CH₂CH₂OCH₃ | H | OCH₃ | OC₂H₅ | N | |
| CH₃ | CH₂CH₂OCH₃ | H | CH₃ | OCH₂CHF₂ | CH | |
| CH₃ | CH₂CH₂OCH₃ | H | OCH₃ | OCH₂CHF₂ | CH | |
| CH₃ | CH₂CH₂OCH₃ | H | CH₃ | OCH₂CHF₂ | N | |

TABLE I-continued

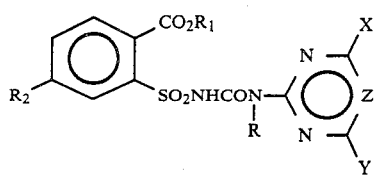

| R₁ | R₂ | R | X | Y | Z | m.p. (°C.) |
|---|---|---|---|---|---|---|
| CH₃ | CH₂CH₂OCH₃ | H | OCH₃ | OCH₂CHF₂ | N | |
| CH₃ | CH₂CH₂OCH₃ | H | CH₃ | OCH₂CH₂F | CH | |
| CH₃ | CH₂CH₂OCH₃ | H | OCH₃ | OCH₂CH₂F | CH | |
| CH₃ | CH₂CH₂OCH₃ | H | CH₃ | OCH₂CF₃ | N | |
| CH₃ | CH₂CH₂OCH₃ | CH₃ | OCH₃ | OCH₂CF₃ | N | |
| CH₃ | CH₂CH₂OCH₃ | CH₃ | Cl | OCH₃ | CH | |
| CH₃ | CH₂CH₂OCH₃ | H | Cl | N(CH₃)₂ | CH | |
| C₂H₅ | CH₂CH₂OCH₃ | H | Cl | OC₂H₅ | CH | |
| C₂H₅ | CH₂CH₂OCH₃ | H | CH₃ | CH₃ | CH | |
| C₂H₅ | CH₂CH₂OCH₃ | H | OCH₃ | CH₃ | CH | |
| C₂H₅ | CH₂CH₂OCH₃ | H | OCH₃ | OCH₃ | CH | |
| C₂H₅ | CH₂CH₂OCH₃ | H | Cl | OCH₃ | CH | |
| C₂H₅ | CH₂CH₂OCH₃ | H | CH₃ | CH₃ | N | |
| C₂H₅ | CH₂CH₂OCH₃ | H | OCH₃ | CH₃ | N | |
| C₂H₅ | CH₂CH₂OCH₃ | H | OCH₃ | OCH₃ | N | |
| C₂H₅ | CH₂CH₂OCH₃ | H | Br | OCH₃ | CH | |
| C₂H₅ | CH₂CH₂OCH₃ | H | OCH₃ | N(CH₃)₂ | CH | |
| C₂H₅ | CH₂CH₂OCH₃ | H | OCH₃ | N(CH₃)₂ | N | |
| C₂H₅ | CH₂CH₂OCH₃ | H | OCH₃ | NHCH₃ | N | |
| C₂H₅ | CH₂CH₂OCH₃ | H | OCH₃ | C₂H₅ | CH | |
| C₂H₅ | CH₂CH₂OCH₃ | H | OCH₃ | C₂H₅ | N | |
| C₂H₅ | CH₂CH₂OCH₃ | H | CH₃ | OC₂H₅ | CH | |
| C₂H₅ | CH₂CH₂OCH₃ | H | CH₃ | OC₂H₅ | N | |
| C₂H₅ | CH₂CH₂OCH₃ | H | OCH₃ | OC₂H₅ | CH | |
| C₂H₅ | CH₂CH₂OCH₃ | H | OCH₃ | OC₂H₅ | N | |
| C₂H₅ | CH₂CH₂OCH₃ | H | CH₃ | OCH₂CF₃ | CH | |
| C₂H₅ | CH₂CH₂OCH₃ | H | CH₃ | OCH₂CF₃ | N | |
| C₂H₅ | CH₂CH₂OCH₃ | H | OCH₃ | OCH₂CF₃ | CH | |
| C₂H₅ | CH₂CH₂OCH₃ | H | OCH₃ | OCH₂CF₃ | N | |
| C₂H₅ | CH₂CH₂OCH₃ | H | OCH₃ | OCH₂CHF₂ | CH | |
| C₂H₅ | CH₂CH₂OCH₃ | H | OCH₃ | OCH₂CHF₂ | N | |
| C₂H₅ | CH₂CH₂OCH₃ | H | CH₃ | OCH₂CHF₂ | N | |
| C₂H₅ | CH₂CH₂OCH₃ | H | OCH₃ | OCH₂CH₂F | CH | |
| C₂H₅ | CH₂CH₂OCH₃ | H | OCH₃ | OCH₂CH₂F | N | |
| C₂H₅ | CH₂CH₂OCH₃ | CH₃ | OCH₃ | OCH₃ | CH | |
| C₂H₅ | CH₂CH₂OCH₃ | CH₃ | CH₃ | OCH₃ | N | |
| C₂H₅ | CH₂CH₂OCH₃ | CH₃ | OCH₃ | OCH₃ | N | |
| n-C₃H₇ | CH₂CH₂OCH₃ | H | OCH₃ | OCH₃ | CH | |
| n-C₃H₇ | CH₂CH₂OCH₃ | H | CH₃ | OCH₃ | N | |
| CH(CH₃)₂ | CH₂CH₂OCH₃ | H | OCH₃ | CH₃ | CH | |
| CH(CH₃)₂ | CH₂CH₂OCH₃ | H | OCH₃ | OCH₃ | CH | |
| CH(CH₃)₂ | CH₂CH₂OCH₃ | H | Cl | OCH₃ | CH | |
| CH(CH₃)₂ | CH₂CH₂OCH₃ | H | OCH₃ | CH₃ | N | |
| CH(CH₃)₂ | CH₂CH₂OCH₃ | H | OCH₃ | OCH₃ | N | |
| CH(CH₃)₂ | CH₂CH₂OCH₃ | H | OCH₃ | N(CH₃)₂ | N | |
| CH₃ | CH(CH₃)(OCH₃) | H | OCH₃ | CH₃ | CH | |
| CH₃ | CH(CH₃)(OCH₃) | H | OCH₃ | OCH₃ | CH | |
| CH₃ | CH(CH₃)(OCH₃) | H | OCH₃ | Cl | CH | |
| CH₃ | CH(CH₃)(OCH₃) | H | OCH₃ | CH₃ | N | |
| CH₃ | CH(CH₃)(OCH₃) | H | OCH₃ | OCH₃ | N | |
| C₂H₅ | CH(CH₃)(OCH₃) | H | OCH₃ | CH₃ | CH | |
| C₂H₅ | CH(CH₃)(OCH₃) | H | OCH₃ | OCH₃ | CH | |
| C₂H₅ | CH(CH₃)(OCH₃) | H | OCH₃ | Cl | CH | |
| C₂H₅ | CH(CH₃)(OCH₃) | H | OCH₃ | CH₃ | N | |
| C₂H₅ | CH(CH₃)(OCH₃) | H | OCH₃ | OCH₃ | N | |
| CH₃ | (CH₂)₃OCH₃ | H | CH₃ | CH₃ | CH | |
| CH₃ | (CH₂)₃OCH₃ | H | OCH₃ | CH₃ | CH | |
| CH₃ | (CH₂)₃OCH₃ | H | OCH₃ | OCH₃ | CH | |
| CH₃ | (CH₂)₃OCH₃ | H | Cl | OCH₃ | CH | |
| CH₃ | (CH₂)₃OCH₃ | H | CH₃ | CH₃ | N | |
| CH₃ | (CH₂)₃OCH₃ | H | OCH₃ | CH₃ | N | |
| CH₃ | (CH₂)₃OCH₃ | H | OCH₃ | OCH₃ | N | |
| CH₃ | (CH₂)₃OCH₃ | H | OCH₃ | N(CH₃)₂ | CH | |
| CH₃ | (CH₂)₃OCH₃ | H | OCH₃ | N(CH₃)₂ | N | |
| CH₃ | (CH₂)₃OCH₃ | H | OCH₃ | OCH₂CF₃ | N | |
| CH₃ | (CH₂)₃OCH₃ | CH₃ | OCH₃ | CH₃ | N | |
| CH₃ | (CH₂)₃OCH₃ | CH₃ | OCH₃ | OCH₃ | N | |
| CH₃ | (CH₂)₃OCH₃ | CH₃ | CH₃ | OCH₃ | CH | |
| CH₃ | (CH₂)₃OCH₃ | CH₃ | OCH₃ | OCH₃ | CH | |
| CH₃ | (CH₂)₃OCH₃ | H | Br | OCH₃ | CH | |
| CH₃ | (CH₂)₃OCH₃ | H | CH₃ | OCH₂CF₃ | N | |

TABLE I-continued

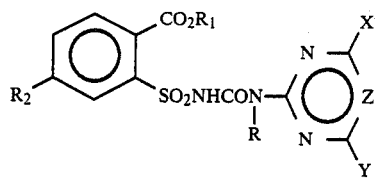

| R₁ | R₂ | R | X | Y | Z | m.p. (°C.) |
|---|---|---|---|---|---|---|
| CH₃ | (CH₂)₃OCH₃ | H | CH₃ | OCH₂CF₃ | CH | |
| CH₃ | (CH₂)₃OCH₃ | H | OCH₃ | OCH₂CF₃ | CH | |
| CH₃ | (CH₂)₃OCH₃ | H | OCH₃ | NHCH₃ | N | |
| C₂H₅ | (CH₂)₃OCH₃ | H | CH₃ | CH₃ | CH | |
| C₂H₅ | (CH₂)₃OCH₃ | H | OCH₃ | CH₃ | CH | |
| C₂H₅ | (CH₂)₃OCH₃ | H | OCH₃ | OCH₃ | CH | |
| C₂H₅ | (CH₂)₃OCH₃ | H | Cl | OCH₃ | CH | |
| C₂H₅ | (CH₂)₃OCH₃ | H | OCH₃ | CH₃ | N | |
| C₂H₅ | (CH₂)₃OCH₃ | H | OCH₃ | N(CH₃)₂ | CH | |
| CH(CH₃)₂ | (CH₂)₃OCH₃ | H | OCH₃ | CH₃ | CH | |
| CH(CH₃)₂ | (CH₂)₃OCH₃ | H | OCH₃ | OCH₃ | CH | |
| CH(CH₃)₂ | (CH₂)₃OCH₃ | H | Cl | OCH₃ | CH | |
| CH(CH₃)₂ | (CH₂)₃OCH₃ | H | OCH₃ | CH₃ | N | |
| CH(CH₃)₂ | (CH₂)₃OCH₃ | H | OCH₃ | OCH₃ | N | |
| CH₃ | (CH₂)₄OCH₃ | H | CH₃ | CH₃ | CH | |
| CH₃ | (CH₂)₄OCH₃ | H | OCH₃ | CH₃ | CH | |
| CH₃ | (CH₂)₄OCH₃ | H | OCH₃ | OCH₃ | CH | |
| CH₃ | (CH₂)₄OCH₃ | H | Cl | OCH₃ | CH | |
| CH₃ | (CH₂)₄OCH₃ | H | CH₃ | CH₃ | N | |
| CH₃ | (CH₂)₄OCH₃ | H | OCH₃ | CH₃ | N | |
| CH₃ | (CH₂)₄OCH₃ | H | OCH₃ | OCH₃ | N | |
| CH₃ | (CH₂)₄OCH₃ | H | OCH₃ | N(CH₃)₂ | CH | |
| CH₃ | (CH₂)₄OCH₃ | H | OCH₃ | N(CH₃)₂ | N | |
| CH₃ | (CH₂)₄OCH₃ | H | OCH₃ | OCH₂CF₃ | N | |
| CH₃ | (CH₂)₄OCH₃ | CH₃ | OCH₃ | CH₃ | N | |
| CH₃ | (CH₂)₄OCH₃ | CH₃ | OCH₃ | OCH₃ | N | |
| CH₃ | (CH₂)₄OCH₃ | CH₃ | CH₃ | OCH₃ | CH | |
| CH₃ | (CH₂)₄OCH₃ | CH₃ | OCH₃ | OCH₃ | CH | |
| CH₃ | (CH₂)₄OCH₃ | H | Br | OCH₃ | CH | |
| CH₃ | (CH₂)₄OCH₃ | H | CH₃ | OCH₂CF₃ | N | |
| CH₃ | (CH₂)₄OCH₃ | H | CH₃ | OCH₂CF₃ | CH | |
| CH₃ | (CH₂)₄OCH₃ | H | OCH₃ | OCH₂CF₃ | CH | |
| CH₃ | (CH₂)₄OCH₃ | H | OCH₃ | NHCH₃ | N | |
| C₂H₅ | (CH₂)₄OCH₃ | H | CH₃ | CH₃ | CH | |
| C₂H₅ | (CH₂)₄OCH₃ | H | OCH₃ | CH₃ | CH | |
| C₂H₅ | (CH₂)₄OCH₃ | H | OCH₃ | OCH₃ | CH | |
| C₂H₅ | (CH₂)₄OCH₃ | H | Cl | OCH₃ | CH | |
| C₂H₅ | (CH₂)₄OCH₃ | H | OCH₃ | CH₃ | N | |
| C₂H₅ | (CH₂)₄OCH₃ | H | OCH₃ | N(CH₃)₂ | CH | |
| CH(CH₃)₂ | (CH₂)₄OCH₃ | H | OCH₃ | CH₃ | CH | |
| CH(CH₃)₂ | (CH₂)₄OCH₃ | H | OCH₃ | OCH₃ | CH | |
| CH(CH₃)₂ | (CH₂)₄OCH₃ | H | Cl | OCH₃ | CH | |
| CH(CH₃)₂ | (CH₂)₄OCH₃ | H | OCH₃ | CH₃ | N | |
| CH(CH₃)₂ | (CH₂)₄OCH₃ | H | OCH₃ | OCH₃ | N | |
| CH₃ | CH₂OC₂H₅ | H | CH₃ | CH₃ | CH | |
| CH₃ | CH₂OC₂H₅ | H | OCH₃ | CH₃ | CH | |
| CH₃ | CH₂OC₂H₅ | H | OCH₃ | OCH₃ | CH | |
| CH₃ | CH₂OC₂H₅ | H | Cl | OCH₃ | CH | |
| CH₃ | CH₂OC₂H₅ | H | CH₃ | CH₃ | N | |
| CH₃ | CH₂OC₂H₅ | H | OCH₃ | CH₃ | N | |
| CH₃ | CH₂OC₂H₅ | H | OCH₃ | OCH₃ | N | |
| CH₃ | CH₂OC₂H₅ | H | OCH₃ | N(CH₃)₂ | CH | |
| CH₃ | CH₂OC₂H₅ | H | OCH₃ | N(CH₃)₂ | N | |
| CH₃ | CH₂OC₂H₅ | H | OCH₃ | OCH₂CF₃ | N | |
| CH₃ | CH₂OC₂H₅ | CH₃ | OCH₃ | CH₃ | N | |
| CH₃ | CH₂OC₂H₅ | CH₃ | OCH₃ | OCH₃ | N | |
| CH₃ | CH₂OC₂H₅ | CH₃ | CH₃ | OCH₃ | CH | |
| CH₃ | CH₂OC₂H₅ | CH₃ | OCH₃ | OCH₃ | CH | |
| CH₃ | CH₂OC₂H₅ | H | Br | OCH₃ | CH | |
| CH₃ | CH₂OC₂H₅ | H | CH₃ | OCH₂CF₃ | N | |
| CH₃ | CH₂OC₂H₅ | H | CH₃ | OCH₂CF₃ | CH | |
| CH₃ | CH₂OC₂H₅ | H | OCH₃ | OCH₂CF₃ | CH | |
| CH₃ | CH₂OC₂H₅ | H | OCH₃ | NHCH₃ | N | |
| C₂H₅ | CH₂OC₂H₅ | H | CH₃ | CH₃ | CH | |
| C₂H₅ | CH₂OC₂H₅ | H | OCH₃ | CH₃ | CH | |
| C₂H₅ | CH₂OC₂H₅ | H | OCH₃ | OCH₃ | CH | |
| C₂H₅ | CH₂OC₂H₅ | H | Cl | OCH₃ | CH | |
| C₂H₅ | CH₂OC₂H₅ | H | OCH₃ | CH₃ | N | |
| C₂H₅ | CH₂OC₂H₅ | H | OCH₃ | N(CH₃)₂ | CH | |
| CH(CH₃)₂ | CH₂OC₂H₅ | H | OCH₃ | CH₃ | CH | |
| CH(CH₃)₂ | CH₂OC₂H₅ | H | OCH₃ | OCH₃ | CH | |

TABLE I-continued

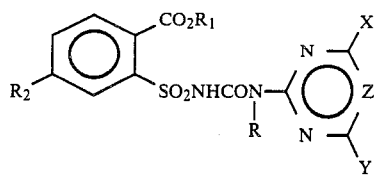

| R₁ | R₂ | R | X | Y | Z | m.p. (°C.) |
|---|---|---|---|---|---|---|
| CH(CH₃)₂ | CH₂OC₂H₅ | H | Cl | OCH₃ | CH | |
| CH(CH₃)₂ | CH₂OC₂H₅ | H | OCH₃ | CH₃ | N | |
| CH(CH₃)₂ | CH₂OC₂H₅ | H | OCH₃ | OCH₃ | N | |
| CH₃ | (CH₂)₂OC₂H₅ | H | CH₃ | CH₃ | CH | |
| CH₃ | (CH₂)₂OC₂H₅ | H | OCH₃ | CH₃ | CH | |
| CH₃ | (CH₂)₂OC₂H₅ | H | OCH₃ | OCH₃ | CH | |
| CH₃ | (CH₂)₂OC₂H₅ | H | Cl | OCH₃ | CH | |
| CH₃ | (CH₂)₂OC₂H₅ | H | CH₃ | CH₃ | N | |
| CH₃ | (CH₂)₂OC₂H₅ | H | OCH₃ | CH₃ | N | |
| CH₃ | (CH₂)₂OC₂H₅ | H | OCH₃ | OCH₃ | N | |
| CH₃ | (CH₂)₂OC₂H₅ | H | OCH₃ | N(CH₃)₂ | CH | |
| CH₃ | (CH₂)₂OC₂H₅ | H | OCH₃ | N(CH₃)₂ | N | |
| CH₃ | (CH₂)₂OC₂H₅ | H | OCH₃ | OCH₂CF₃ | N | |
| CH₃ | (CH₂)₂OC₂H₅ | CH₃ | OCH₃ | CH₃ | N | |
| CH₃ | (CH₂)₂OC₂H₅ | CH₃ | OCH₃ | OCH₃ | N | |
| CH₃ | (CH₂)₂OC₂H₅ | CH₃ | CH₃ | OCH₃ | CH | |
| CH₃ | (CH₂)₂OC₂H₅ | CH₃ | OCH₃ | OCH₃ | CH | |
| CH₃ | (CH₂)₂OC₂H₅ | H | Br | OCH₃ | CH | |
| CH₃ | (CH₂)₂OC₂H₅ | H | CH₃ | OCH₂CF₃ | N | |
| CH₃ | (CH₂)₂OC₂H₅ | H | CH₃ | OCH₂CF₃ | CH | |
| CH₃ | (CH₂)₂OC₂H₅ | H | OCH₃ | OCH₂CF₃ | CH | |
| CH₃ | (CH₂)₂OC₂H₅ | H | OCH₃ | NHCH₃ | N | |
| C₂H₅ | (CH₂)₂OC₂H₅ | H | CH₃ | CH₃ | CH | |
| C₂H₅ | (CH₂)₂OC₂H₅ | H | OCH₃ | CH₃ | CH | |
| C₂H₅ | (CH₂)₂OC₂H₅ | H | OCH₃ | OCH₃ | CH | |
| C₂H₅ | (CH₂)₂OC₂H₅ | H | Cl | OCH₃ | CH | |
| C₂H₅ | (CH₂)₂OC₂H₅ | H | OCH₃ | CH₃ | N | |
| C₂H₅ | (CH₂)₂OC₂H₅ | H | OCH₃ | N(CH₃)₂ | CH | |
| CH(CH₃)₂ | (CH₂)₂OC₂H₅ | H | OCH₃ | CH₃ | CH | |
| CH(CH₃)₂ | (CH₂)₂OC₂H₅ | H | OCH₃ | OCH₃ | CH | |
| CH(CH₃)₂ | (CH₂)₂OC₂H₅ | H | Cl | OCH₃ | CH | |
| CH(CH₃)₂ | (CH₂)₂OC₂H₅ | H | OCH₃ | CH₃ | N | |
| CH(CH₃)₂ | (CH₂)₂OC₂H₅ | H | OCH₃ | OCH₃ | N | |
| CH₃ | (CH₂)₃OC₂H₅ | H | CH₃ | CH₃ | CH | |
| CH₃ | (CH₂)₃OC₂H₅ | H | OCH₃ | CH₃ | CH | |
| CH₃ | (CH₂)₃OC₂H₅ | H | OCH₃ | OCH₃ | CH | |
| CH₃ | (CH₂)₃OC₂H₅ | H | Cl | OCH₃ | CH | |
| CH₃ | (CH₂)₃OC₂H₅ | H | CH₃ | CH₃ | N | |
| CH₃ | (CH₂)₃OC₂H₅ | H | OCH₃ | CH₃ | N | |
| CH₃ | (CH₂)₃OC₂H₅ | H | OCH₃ | OCH₃ | N | |
| CH₃ | (CH₂)₃OC₂H₅ | H | OCH₃ | N(CH₃)₂ | CH | |
| CH₃ | (CH₂)₃OC₂H₅ | H | OCH₃ | N(CH₃)₂ | N | |
| CH₃ | (CH₂)₃OC₂H₅ | H | OCH₃ | OCH₂CF₃ | N | |
| CH₃ | (CH₂)₃OC₂H₅ | CH₃ | OCH₃ | CH₃ | N | |
| CH₃ | (CH₂)₃OC₂H₅ | CH₃ | OCH₃ | OCH₃ | N | |
| CH₃ | (CH₂)₃OC₂H₅ | CH₃ | CH₃ | OCH₃ | CH | |
| CH₃ | (CH₂)₃OC₂H₅ | CH₃ | OCH₃ | OCH₃ | CH | |
| CH₃ | (CH₂)₃OC₂H₅ | H | Br | OCH₃ | CH | |
| CH₃ | (CH₂)₃OC₂H₅ | H | CH₃ | OCH₂CF₃ | N | |
| CH₃ | (CH₂)₃OC₂H₅ | H | CH₃ | OCH₂CF₃ | CH | |
| CH₃ | (CH₂)₃OC₂H₅ | H | OCH₃ | OCH₂CF₃ | CH | |
| CH₃ | (CH₂)₃OC₂H₅ | H | OCH₃ | NHCH₃ | N | |
| C₂H₅ | (CH₂)₃OC₂H₅ | H | CH₃ | CH₃ | CH | |
| C₂H₅ | (CH₂)₃OC₂H₅ | H | OCH₃ | CH₃ | CH | |
| C₂H₅ | (CH₂)₃OC₂H₅ | H | OCH₃ | OCH₃ | CH | |
| C₂H₅ | (CH₂)₃OC₂H₅ | H | Cl | OCH₃ | CH | |
| C₂H₅ | (CH₂)₃OC₂H₅ | H | OCH₃ | CH₃ | N | |
| C₂H₅ | (CH₂)₃OC₂H₅ | H | OCH₃ | N(CH₃)₂ | CH | |
| CH(CH₃)₂ | (CH₂)₃OC₂H₅ | H | OCH₃ | CH₃ | CH | |
| CH(CH₃)₂ | (CH₂)₃OC₂H₅ | H | OCH₃ | OCH₃ | CH | |
| CH(CH₃)₂ | (CH₂)₃OC₂H₅ | H | Cl | OCH₃ | CH | |
| CH(CH₃)₂ | (CH₂)₃OC₂H₅ | H | OCH₃ | CH₃ | N | |
| CH(CH₃)₂ | (CH₂)₃OC₂H₅ | H | OCH₃ | OCH₃ | N | |
| CH₃ | (CH₂)₄OC₂H₅ | H | OCH₃ | CH₃ | CH | |
| CH₃ | (CH₂)₄OC₂H₅ | H | OCH₃ | OCH₃ | CH | |
| CH₃ | (CH₂)₄OC₂H₅ | H | Cl | OCH₃ | CH | |
| CH₃ | (CH₂)₄OC₂H₅ | H | OCH₃ | CH₃ | N | |
| CH₃ | (CH₂)₄OC₂H₅ | H | OCH₃ | OCH₃ | N | |
| CH₃ | CH₂CH(CH₃)(OCH₃) | H | CH₃ | OCH₃ | CH | |
| CH₃ | (CH₂)₂CH(CH₃)(OCH₃) | H | OCH₃ | OCH₃ | N | |
| CH₃ | CH₂CH(CH₃)(OC₂H₅) | H | CH₃ | OCH₃ | N | |

TABLE I-continued

| R₁ | R₂ | R | X | Y | Z | m.p. (°C.) |
|---|---|---|---|---|---|---|
| CH₃ | (CH₂)₂CH(CH₃)(OC₂H₅) | H | OCH₃ | OCH₃ | CH | |
| CH₃ | CH(C₂H₅)(OCH₃) | H | CH₃ | OCH₃ | CH | |
| CH₃ | CH(C₂H₅)(OC₂H₅) | H | OCH₃ | OCH₃ | N | |
| CH₃ | CH₂CH(C₂H₅)(OCH₃) | H | CH₃ | OCH₃ | N | |
| CH₃ | CH₂CH(C₂H₅)(OC₂H₅) | H | OCH₃ | OCH₃ | CH | |
| CH₃ | CH(CH₃)(CH₂OCH₃) | H | CH₃ | OCH₃ | CH | |
| CH₃ | CH₂CH(CH₃)(CH₂OCH₃) | H | OCH₃ | OCH₃ | N | |
| CH₃ | CH₂SCH₃ | H | CH₃ | CH₃ | CH | 163–165 |
| CH₃ | CH₂SCH₃ | H | OCH₃ | CH₃ | CH | 152–154 |
| CH₃ | CH₂SCH₃ | H | OCH₃ | OCH₃ | CH | 146–148 |
| CH₃ | CH₂SCH₃ | H | Cl | OCH₃ | CH | 140–142 |
| CH₃ | CH₂SCH₃ | H | OCH₃ | N(CH₃)₂ | CH | |
| CH₃ | CH₂SCH₃ | H | CH₃ | CH₃ | N | |
| CH₃ | CH₂SCH₃ | H | OCH₃ | CH₃ | N | 131–135 |
| CH₃ | CH₂SCH₃ | H | OCH₃ | OCH₃ | N | 123–125 |
| CH₃ | CH₂SCH₃ | H | OCH₃ | N(CH₃)₂ | N | |
| CH₃ | CH₂SCH₃ | H | OCH₃ | OCH₂CF₃ | N | |
| CH₃ | CH₂SCH₃ | CH₃ | OCH₃ | CH₃ | N | |
| CH₃ | CH₂SCH₃ | CH₃ | OCH₃ | OCH₃ | N | |
| CH₃ | CH₂SCH₃ | CH₃ | CH₃ | OCH₃ | CH | |
| CH₃ | CH₂SCH₃ | CH₃ | OCH₃ | OCH₃ | CH | |
| CH₃ | CH₂SCH₃ | H | Br | OCH₃ | CH | |
| CH₃ | CH₂SCH₃ | CH₃ | OCH₃ | N(CH₃)₂ | N | |
| CH₃ | CH₂SCH₃ | H | CH₃ | OCH₂CF₃ | N | |
| CH₃ | CH₂SCH₃ | H | CH₃ | OCH₂CF₃ | CH | |
| CH₃ | CH₂SCH₃ | H | OCH₃ | OCH₂CF₃ | CH | |
| CH₃ | CH₂SCH₃ | H | OCH₃ | C₂H₅ | CH | |
| CH₃ | CH₂SCH₃ | H | OCH₃ | C₂H₅ | N | |
| CH₃ | CH₂SCH₃ | H | OCH₃ | NHCH₃ | CH | |
| CH₃ | CH₂SCH₃ | H | OCH₃ | NHCH₃ | N | |
| CH₃ | CH₂SCH₃ | H | CH₃ | OC₂H₅ | CH | |
| CH₃ | CH₂SCH₃ | H | OCH₃ | OC₂H₅ | CH | |
| CH₃ | CH₂SCH₃ | H | CH₃ | OC₂H₅ | N | |
| CH₃ | CH₂SCH₃ | H | OCH₃ | OC₂H₅ | N | |
| CH₃ | CH₂SCH₃ | H | CH₃ | OCH₂CHF₂ | CH | |
| CH₃ | CH₂SCH₃ | H | OCH₃ | OCH₂CHF₂ | CH | |
| CH₃ | CH₂SCH₃ | H | CH₃ | OCH₂CHF₂ | N | |
| CH₃ | CH₂SCH₃ | H | OCH₃ | OCH₂CHF₂ | N | |
| CH₃ | CH₂SCH₃ | H | CH₃ | OCH₂CH₂F | CH | |
| CH₃ | CH₂SCH₃ | H | OCH₃ | OCH₂CH₂F | CH | |
| CH₃ | CH₂SCH₃ | H | CH₃ | OCH₂CH₂F | N | |
| CH₃ | CH₂SCH₃ | H | OCH₃ | OCH₂CH₂F | N | |
| CH₃ | CH₂SCH₃ | CH₃ | OCH₃ | OCH₂CH₂F | N | |
| CH₃ | CH₂SCH₃ | CH₃ | Cl | OCH₃ | CH | |
| CH₃ | CH₂SCH₃ | H | Cl | N(CH₃)₂ | CH | |
| CH₃ | CH₂SCH₃ | H | Cl | OC₂H₅ | CH | |
| C₂H₅ | CH₂SCH₃ | H | CH₃ | CH₃ | CH | |
| C₂H₅ | CH₂SCH₃ | H | OCH₃ | CH₃ | CH | |
| C₂H₅ | CH₂SCH₃ | H | OCH₃ | OCH₃ | CH | |
| C₂H₅ | CH₂SCH₃ | H | Cl | OCH₃ | CH | |
| C₂H₅ | CH₂SCH₃ | H | CH₃ | CH₃ | N | |
| C₂H₅ | CH₂SCH₃ | H | OCH₃ | CH₃ | N | |
| C₂H₅ | CH₂SCH₃ | H | OCH₃ | OCH₃ | N | |
| C₂H₅ | CH₂SCH₃ | H | Br | OCH₃ | CH | |
| C₂H₅ | CH₂SCH₃ | H | OCH₃ | N(CH₃)₂ | CH | |
| C₂H₅ | CH₂SCH₃ | H | OCH₃ | N(CH₃)₂ | N | |
| C₂H₅ | CH₂SCH₃ | H | OCH₃ | NHCH₃ | N | |
| C₂H₅ | CH₂SCH₃ | H | OCH₃ | C₂H₅ | CH | |
| C₂H₅ | CH₂SCH₃ | H | OCH₃ | C₂H₅ | N | |
| C₂H₅ | CH₂SCH₃ | H | CH₃ | OC₂H₅ | CH | |
| C₂H₅ | CH₂SCH₃ | H | CH₃ | OC₂H₅ | N | |
| C₂H₅ | CH₂SCH₃ | H | OCH₃ | OC₂H₅ | CH | |
| C₂H₅ | CH₂SCH₃ | H | OCH₃ | OC₂H₅ | N | |
| C₂H₅ | CH₂SCH₃ | H | CH₃ | OCH₂CF₃ | CH | |
| C₂H₅ | CH₂SCH₃ | H | CH₃ | OCH₂CF₃ | N | |
| C₂H₅ | CH₂SCH₃ | H | OCH₃ | OCH₂CF₃ | CH | |
| C₂H₅ | CH₂SCH₃ | H | OCH₃ | OCH₂CF₃ | N | |
| C₂H₅ | CH₂SCH₃ | H | OCH₃ | OCH₂CHF₂ | CH | |
| C₂H₅ | CH₂SCH₃ | H | OCH₃ | OCH₂CHF₂ | N | |
| C₂H₅ | CH₂SCH₃ | H | CH₃ | OCH₂CHF₂ | N | |
| C₂H₅ | CH₂SCH₃ | H | OCH₃ | OCH₂CH₂F | CH | |
| C₂H₅ | CH₂SCH₃ | H | OCH₃ | OCH CH₂F | N | |

TABLE I-continued

| R₁ | R₂ | R | X | Y | Z | m.p. (°C.) |
|---|---|---|---|---|---|---|
| C₂H₅ | CH₂SCH₃ | CH₃ | OCH₃ | OCH₃ | CH | |
| C₂H₅ | CH₂SCH₃ | CH₃ | CH₃ | OCH₃ | N | |
| C₂H₅ | CH₂SCH₃ | CH₃ | OCH₃ | OCH₃ | N | |
| n-C₃H₇ | CH₂SCH₃ | H | OCH₃ | OCH₃ | CH | |
| n-C₃H₇ | CH₂SCH₃ | H | CH₃ | OCH₃ | N | |
| CH(CH₃)₂ | CH₂SCH₃ | H | OCH₃ | CH₃ | CH | |
| CH(CH₃)₂ | CH₂SCH₃ | H | OCH₃ | OCH₃ | CH | |
| CH(CH₃)₂ | CH₂SCH₃ | H | Cl | OCH₃ | CH | |
| CH(CH₃)₂ | CH₂SCH₃ | H | OCH₃ | CH₃ | N | |
| CH(CH₃)₂ | CH₂SCH₃ | H | OCH₃ | OCH₃ | N | |
| CH(CH₃)₂ | CH₂SCH₃ | H | OCH₃ | N(CH₃)₂ | N | |
| CH₃ | CH₂CH₂SCH₃ | H | CH₃ | CH₃ | CH | |
| CH₃ | CH₂CH₂SCH₃ | H | OCH₃ | CH₃ | CH | |
| CH₃ | CH₂CH₂SCH₃ | H | OCH₃ | OCH₃ | CH | |
| CH₃ | CH₂CH₂SCH₃ | H | Cl | OCH₃ | CH | |
| CH₃ | CH₂CH₂SCH₃ | H | OCH₃ | N(CH₃)₂ | CH | |
| CH₃ | CH₂CH₂SCH₃ | H | CH₃ | CH₃ | N | |
| CH₃ | CH₂CH₂SCH₃ | H | OCH₃ | CH₃ | N | |
| CH₃ | CH₂CH₂SCH₃ | H | OCH₃ | OCH₃ | N | |
| CH₃ | CH₂CH₂SCH₃ | H | OCH₃ | N(CH₃)₂ | N | |
| CH₃ | CH₂CH₂SCH₃ | H | OCH₃ | OCH₂CF₃ | N | |
| CH₃ | CH₂CH₂SCH₃ | CH₃ | OCH₃ | CH₃ | N | |
| CH₃ | CH₂CH₂SCH₃ | CH₃ | OCH₃ | OCH₃ | N | |
| CH₃ | CH₂CH₂SCH₃ | CH₃ | CH₃ | OCH₃ | CH | |
| CH₃ | CH₂CH₂SCH₃ | CH₃ | OCH₃ | OCH₃ | CH | |
| CH₃ | CH₂CH₂SCH₃ | H | Br | OCH₃ | CH | |
| CH₃ | CH₂CH₂SCH₃ | CH₃ | OCH₃ | N(CH₃)₂ | N | |
| CH₃ | CH₂CH₂SCH₃ | H | CH₃ | OCH₂CF₃ | N | |
| CH₃ | CH₂CH₂SCH₃ | H | CH₃ | OCH₂CF₃ | CH | |
| CH₃ | CH₂CH₂SCH₃ | H | OCH₃ | OCH₂CF₃ | CH | |
| CH₃ | CH₂CH₂SCH₃ | H | OCH₃ | C₂H₅ | CH | |
| CH₃ | CH₂CH₂SCH₃ | H | OCH₃ | C₂H₅ | N | |
| CH₃ | CH₂CH₂SCH₃ | H | OCH₃ | NHCH₃ | CH | |
| CH₃ | CH₂CH₂SCH₃ | H | OCH₃ | NHCH₃ | N | |
| CH₃ | CH₂CH₂SCH₃ | H | CH₃ | OC₂H₅ | CH | |
| CH₃ | CH₂CH₂SCH₃ | H | OCH₃ | OC₂H₅ | CH | |
| CH₃ | CH₂CH₂SCH₃ | H | CH₃ | OC₂H₅ | N | |
| CH₃ | CH₂CH₂SCH₃ | H | OCH₃ | OC₂H₅ | N | |
| CH₃ | CH₂CH₂SCH₃ | H | CH₃ | OCH₂CHF₂ | CH | |
| CH₃ | CH₂CH₂SCH₃ | H | OCH₃ | OCH₂CHF₂ | CH | |
| CH₃ | CH₂CH₂SCH₃ | H | CH₃ | OCH₂CHF₂ | N | |
| CH₃ | CH₂CH₂SCH₃ | H | OCH₃ | OCH₂CHF₂ | N | |
| CH₃ | CH₂CH₂SCH₃ | H | CH₃ | OCH₂CH₂F | CH | |
| CH₃ | CH₂CH₂SCH₃ | H | OCH₃ | OCH₂CH₂F | CH | |
| CH₃ | CH₂CH₂SCH₃ | H | CH₃ | OCH₂CH₂F | N | |
| CH₃ | CH₂CH₂SCH₃ | CH₃ | OCH₃ | OCH₂CH₂F | N | |
| CH₃ | CH₂CH₂SCH₃ | CH₃ | Cl | OCH₃ | CH | |
| CH₃ | CH₂CH₂SCH₃ | H | Cl | N(CH₃)₂ | CH | |
| CH₃ | CH₂CH₂SCH₃ | H | Cl | OC₂H₅ | CH | |
| C₂H₅ | CH₂CH₂SCH₃ | H | CH₃ | CH₃ | CH | |
| C₂H₅ | CH₂CH₂SCH₃ | H | OCH₃ | CH₃ | CH | |
| C₂H₅ | CH₂CH₂SCH₃ | H | OCH₃ | OCH₃ | CH | |
| C₂H₅ | CH₂CH₂SCH₃ | H | Cl | OCH₃ | CH | |
| C₂H₅ | CH₂CH₂SCH₃ | H | CH₃ | CH₃ | N | |
| C₂H₅ | CH₂CH₂SCH₃ | H | OCH₃ | CH₃ | N | |
| C₂H₅ | CH₂CH₂SCH₃ | H | OCH₃ | OCH₃ | N | |
| C₂H₅ | CH₂CH₂SCH₃ | H | Br | OCH₃ | CH | |
| C₂H₅ | CH₂CH₂SCH₃ | H | OCH₃ | N(CH₃)₂ | CH | |
| C₂H₅ | CH₂CH₂SCH₃ | H | OCH₃ | N(CH₃)₂ | N | |
| C₂H₅ | CH₂CH₂SCH₃ | H | OCH₃ | NHCH₃ | N | |
| C₂H₅ | CH₂CH₂SCH₃ | H | OCH₃ | C₂H₅ | CH | |
| C₂H₅ | CH₂CH₂SCH₃ | H | OCH₃ | C₂H₅ | N | |
| C₂H₅ | CH₂CH₂SCH₃ | H | CH₃ | OC₂H₅ | CH | |
| C₂H₅ | CH₂CH₂SCH₃ | H | CH₃ | OC₂H₅ | N | |
| C₂H₅ | CH₂CH₂SCH₃ | H | OCH₃ | OC₂H₅ | CH | |
| C₂H₅ | CH₂CH₂SCH₃ | H | CH₃ | OC₂H₅ | N | |
| C₂H₅ | CH₂CH₂SCH₃ | H | CH₃ | OCH₂CF₃ | CH | |
| C₂H₅ | CH₂CH₂SCH₃ | H | CH₃ | OCH₂CF₃ | N | |
| C₂H₅ | CH₂CH₂SCH₃ | H | OCH₃ | OCH₂CF₃ | CH | |
| C₂H₅ | CH₂CH₂SCH₃ | H | OCH₃ | OCH₂CF₃ | N | |
| C₂H₅ | CH₂CH₂SCH₃ | H | OCH₃ | OCH₂CHF₂ | CH | |

TABLE I-continued

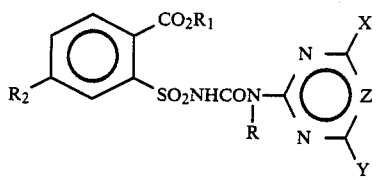

| R₁ | R₂ | R | X | Y | Z | m.p. (°C.) |
|---|---|---|---|---|---|---|
| C₂H₅ | CH₂CH₂SCH₃ | H | OCH₃ | OCH₂CHF₂ | N | |
| C₂H₅ | CH₂CH₂SCH₃ | H | CH₃ | OCH₂CHF₂ | N | |
| C₂H₅ | CH₂CH₂SCH₃ | H | OCH₃ | OCH₂CH₂F | CH | |
| C₂H₅ | CH₂CH₂SCH₃ | H | OCH₃ | OCH₂CH₂F | N | |
| C₂H₅ | CH₂CH₂SCH₃ | CH₃ | OCH₃ | OCH₃ | CH | |
| C₂H₅ | CH₂CH₂SCH₃ | CH₃ | CH₃ | OCH₃ | N | |
| C₂H₅ | CH₂CH₂SCH₃ | CH₃ | OCH₃ | OCH₃ | N | |
| n-C₃H₇ | CH₂CH₂SCH₃ | H | OCH₃ | OCH₃ | CH | |
| n-C₃H₇ | CH₂CH₂SCH₃ | H | CH₃ | OCH₃ | N | |
| CH(CH₃)₂ | CH₂CH₂SCH₃ | H | OCH₃ | CH₃ | CH | |
| CH(CH₃)₂ | CH₂CH₂SCH₃ | H | OCH₃ | OCH₃ | CH | |
| CH(CH₃)₂ | CH₂CH₂SCH₃ | H | Cl | OCH₃ | CH | |
| CH(CH₃)₂ | CH₂CH₂SCH₃ | H | OCH₃ | CH₃ | N | |
| CH(CH₃)₂ | CH₂CH₂SCH₃ | H | OCH₃ | OCH₃ | N | |
| CH(CH₃)₂ | CH₂CH₂SCH₃ | H | OCH₃ | N(CH₃)₂ | N | |
| CH₃ | CH(CH₃)(SCH₃) | H | OCH₃ | CH₃ | CH | |
| CH₃ | CH(CH₃)(SCH₃) | H | OCH₃ | OCH₃ | CH | |
| CH₃ | CH(CH₃)(SCH₃) | H | OCH₃ | CH₃ | N | |
| CH₃ | CH(CH₃)(SCH₃) | H | OCH₃ | OCH₃ | N | |
| CH₃ | CH(CH₃)(SCH₃) | H | OCH₃ | Cl | CH | |
| CH₃ | (CH₂)₃SCH₃ | H | CH₃ | CH₃ | CH | |
| CH₃ | (CH₂)₃SCH₃ | H | OCH₃ | CH₃ | CH | |
| CH₃ | (CH₂)₃SCH₃ | H | OCH₃ | OCH₃ | CH | |
| CH₃ | (CH₂)₃SCH₃ | H | Cl | OCH₃ | CH | |
| CH₃ | (CH₂)₃SCH₃ | H | CH₃ | CH₃ | N | |
| CH₃ | (CH₂)₃SCH₃ | H | OCH₃ | CH₃ | N | |
| CH₃ | (CH₂)₃SCH₃ | H | OCH₃ | OCH₃ | N | |
| CH₃ | (CH₂)₃SCH₃ | H | OCH₃ | N(CH₃)₂ | CH | |
| CH₃ | (CH₂)₃SCH₃ | H | OCH₃ | N(CH₃)₂ | N | |
| CH₃ | (CH₂)₃SCH₃ | H | OCH₃ | OCH₂CF₃ | N | |
| CH₃ | (CH₂)₃SCH₃ | CH₃ | OCH₃ | CH₃ | N | |
| CH₃ | (CH₂)₃SCH₃ | CH₃ | OCH₃ | OCH₃ | N | |
| CH₃ | (CH₂)₃SCH₃ | CH₃ | CH₃ | OCH₃ | CH | |
| CH₃ | (CH₂)₃SCH₃ | CH₃ | OCH₃ | OCH₃ | CH | |
| CH₃ | (CH₂)₃SCH₃ | H | Br | OCH₃ | CH | |
| CH₃ | (CH₂)₃SCH₃ | H | CH₃ | OCH₂CF₃ | N | |
| CH₃ | (CH₂)₃SCH₃ | H | CH₃ | OCH₂CF₃ | CH | |
| CH₃ | (CH₂)₃SCH₃ | H | OCH₃ | OCH₂CF₃ | CH | |
| CH₃ | (CH₂)₃SCH₃ | H | OCH₃ | NHCH₃ | N | |
| C₂H₅ | (CH₂)₃SCH₃ | H | CH₃ | CH₃ | CH | |
| C₂H₅ | (CH₂)₃SCH₃ | H | OCH₃ | CH₃ | CH | |
| C₂H₅ | (CH₂)₃SCH₃ | H | OCH₃ | OCH₃ | CH | |
| C₂H₅ | (CH₂)₃SCH₃ | H | Cl | OCH₃ | CH | |
| C₂H₅ | (CH₂)₃SCH₃ | H | OCH₃ | CH₃ | N | |
| C₂H₅ | (CH₂)₃SCH₃ | H | OCH₃ | N(CH₃)₂ | CH | |
| CH(CH₃)₂ | (CH₂)₃SCH₃ | H | OCH₃ | CH₃ | CH | |
| CH(CH₃)₂ | (CH₂)₃SCH₃ | H | OCH₃ | OCH₃ | CH | |
| CH(CH₃)₂ | (CH₂)₃SCH₃ | H | Cl | OCH₃ | CH | |
| CH(CH₃)₂ | (CH₂)₃SCH₃ | H | OCH₃ | CH₃ | N | |
| CH(CH₃)₂ | (CH₂)₃SCH₃ | H | OCH₃ | OCH₃ | N | |
| CH₃ | (CH₂)₄SCH₃ | H | CH₃ | CH₃ | CH | |
| CH₃ | (CH₂)₄SCH₃ | H | OCH₃ | CH₃ | CH | |
| CH₃ | (CH₂)₄SCH₃ | H | OCH₃ | OCH₃ | CH | |
| CH₃ | (CH₂)₄SCH₃ | H | Cl | OCH₃ | CH | |
| CH₃ | (CH₂)₄SCH₃ | H | CH₃ | CH₃ | N | |
| CH₃ | (CH₂)₄SCH₃ | H | OCH₃ | CH₃ | N | |
| CH₃ | (CH₂)₄SCH₃ | H | OCH₃ | OCH₃ | N | |
| CH₃ | (CH₂)₄SCH₃ | H | OCH₃ | N(CH₃)₂ | CH | |
| CH₃ | (CH₂)₄SCH₃ | H | OCH₃ | N(CH₃)₂ | N | |
| CH₃ | (CH₂)₄SCH₃ | H | OCH₃ | OCH₂CF₃ | N | |
| CH₃ | (CH₂)₄SCH₃ | CH₃ | OCH₃ | CH₃ | N | |
| CH₃ | (CH₂)₄SCH₃ | CH₃ | OCH₃ | OCH₃ | N | |
| CH₃ | (CH₂)₄SCH₃ | CH₃ | CH₃ | OCH₃ | CH | |
| CH₃ | (CH₂)₄SCH₃ | CH₃ | OCH₃ | OCH₃ | CH | |
| CH₃ | (CH₂)₄SCH₃ | H | Br | OCH₃ | CH | |
| CH₃ | (CH₂)₄SCH₃ | H | CH₃ | OCH₂CF₃ | N | |
| CH₃ | (CH₂)₄SCH₃ | H | CH₃ | OCH₂CF₃ | CH | |
| CH₃ | (CH₂)₄SCH₃ | H | OCH₃ | OCH₂CF₃ | CH | |
| CH₃ | (CH₂)₄SCH₃ | H | OCH₃ | NHCH₃ | N | |
| C₂H₅ | (CH₂)₄SCH₃ | H | CH₃ | CH₃ | CH | |
| C₂H₅ | (CH₂)₄SCH₃ | H | OCH₃ | CH₃ | CH | |

TABLE I-continued

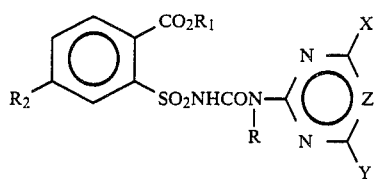

| R₁ | R₂ | R | X | Y | Z | m.p. (°C.) |
|---|---|---|---|---|---|---|
| C₂H₅ | (CH₂)₄SCH₃ | H | OCH₃ | OCH₃ | CH | |
| C₂H₅ | (CH₂)₄SCH₃ | H | Cl | OCH₃ | CH | |
| C₂H₅ | (CH₂)₄SCH₃ | H | OCH₃ | CH₃ | N | |
| C₂H₅ | (CH₂)₄SCH₃ | H | OCH₃ | N(CH₃)₂ | CH | |
| CH(CH₃)₂ | (CH₂)₄SCH₃ | H | OCH₃ | CH₃ | CH | |
| CH(CH₃)₂ | (CH₂)₄SCH₃ | H | OCH₃ | OCH₃ | CH | |
| CH(CH₃)₂ | (CH₂)₄SCH₃ | H | Cl | OCH₃ | CH | |
| CH(CH₃)₂ | (CH₂)₄SCH₃ | H | OCH₃ | CH₃ | N | |
| CH(CH₃)₂ | (CH₂)₄SCH₃ | H | OCH₃ | OCH₃ | N | |
| CH₃ | CH₂SC₂H₅ | H | CH₃ | CH₃ | CH | |
| CH₃ | CH₂SC₂H₅ | H | OCH₃ | CH₃ | CH | |
| CH₃ | CH₂SC₂H₅ | H | OCH₃ | OCH₃ | CH | |
| CH₃ | CH₂SC₂H₅ | H | Cl | OCH₃ | CH | |
| CH₃ | CH₂SC₂H₅ | H | CH₃ | CH₃ | N | |
| CH₃ | CH₂SC₂H₅ | H | OCH₃ | CH₃ | N | |
| CH₃ | CH₂SC₂H₅ | H | OCH₃ | OCH₃ | N | |
| CH₃ | CH₂SC₂H₅ | H | OCH₃ | N(CH₃)₂ | CH | |
| CH₃ | CH₂SC₂H₅ | H | OCH₃ | N(CH₃)₂ | N | |
| CH₃ | CH₂SC₂H₅ | H | OCH₃ | OCH₂CF₃ | N | |
| CH₃ | CH₂SC₂H₅ | CH₃ | OCH₃ | CH₃ | N | |
| CH₃ | CH₂SC₂H₅ | CH₃ | OCH₃ | OCH₃ | N | |
| CH₃ | CH₂SC₂H₅ | CH₃ | CH₃ | OCH₃ | CH | |
| CH₃ | CH₂SC₂H₅ | CH₃ | OCH₃ | OCH₃ | CH | |
| CH₃ | CH₂SC₂H₅ | H | Br | OCH₃ | CH | |
| CH₃ | CH₂SC₂H₅ | H | CH₃ | OCH₂CF₃ | N | |
| CH₃ | CH₂SC₂H₅ | H | CH₃ | OCH₂CF₃ | CH | |
| CH₃ | CH₂SC₂H₅ | H | OCH₃ | OCH₂CF₃ | CH | |
| CH₃ | CH₂SC₂H₅ | H | OCH₃ | NHCH₃ | N | |
| C₂H₅ | CH₂SC₂H₅ | H | CH₃ | CH₃ | CH | |
| C₂H₅ | CH₂SC₂H₅ | H | OCH₃ | CH₃ | CH | |
| C₂H₅ | CH₂SC₂H₅ | H | OCH₃ | OCH₃ | CH | |
| C₂H₅ | CH₂SC₂H₅ | Cl | OCH | CH | | |
| C₂H₅ | CH₂SC₂H₅ | H | OCH₃ | CH₃ | N | |
| C₂H₅ | CH₂SC₂H₅ | H | OCH₃ | N(CH₃)₂ | CH | |
| CH(CH₃)₂ | CH₂SC₂H₅ | H | OCH₃ | CH₃ | CH | |
| CH(CH₃)₂ | CH₂SC₂H₅ | H | OCH₃ | OCH₃ | CH | |
| CH(CH₃)₂ | CH₂SC₂H₅ | H | Cl | OCH₃ | CH | |
| CH(CH₃)₂ | CH₂SC₂H₅ | H | OCH₃ | CH₃ | N | |
| CH(CH₃)₂ | CH₂SC₂H₅ | H | OCH₃ | OCH₃ | N | |
| CH₃ | (CH₂)₂SC₂H₅ | H | CH₃ | CH₃ | CH | |
| CH₃ | (CH₂)₂SC₂H₅ | H | OCH₃ | CH₃ | CH | |
| CH₃ | (CH₂)₂SC₂H₅ | H | OCH₃ | OCH₃ | CH | |
| CH₃ | (CH₂)₂SC₂H₅ | H | Cl | OCH₃ | CH | |
| CH₃ | (CH₂)₂SC₂H₅ | H | CH₃ | CH₃ | N | |
| CH₃ | (CH₂)₂SC₂H₅ | H | OCH₃ | CH₃ | N | |
| CH₃ | (CH₂)₂SC₂H₅ | H | OCH₃ | OCH₃ | N | |
| CH₃ | (CH₂)₂SC₂H₅ | H | OCH₃ | N(CH₃)₂ | CH | |
| CH₃ | (CH₂)₂SC₂H₅ | H | OCH₃ | N(CH₃)₂ | N | |
| CH₃ | (CH₂)₂SC₂H₅ | H | OCH₃ | OCH₂CF₃ | N | |
| CH₃ | (CH₂)₂SC₂H₅ | CH₃ | OCH₃ | CH₃ | N | |
| CH₃ | (CH₂)₂SC₂H₅ | CH₃ | OCH₃ | OCH₃ | N | |
| CH₃ | (CH₂)₂SC₂H₅ | CH₃ | CH₃ | OCH₃ | CH | |
| CH₃ | (CH₂)₂SC₂H₅ | CH₃ | OCH₃ | OCH₃ | CH | |
| CH₃ | (CH₂)₂SC₂H₅ | H | Br | OCH₃ | CH | |
| CH₃ | (CH₂)₂SC₂H₅ | H | CH₃ | OCH₂CF₃ | N | |
| CH₃ | (CH₂)₂SC₂H₅ | H | CH₃ | OCH₂CF₃ | CH | |
| CH₃ | (CH₂)₂SC₂H₅ | H | OCH₃ | OCH₂CF₃ | CH | |
| CH₃ | (CH₂)₂SC₂H₅ | H | OCH₃ | NHCH₃ | N | |
| C₂H₅ | (CH₂)₂SC₂H₅ | H | CH₃ | CH₃ | CH | |
| C₂H₅ | (CH₂)₂SC₂H₅ | H | OCH₃ | CH₃ | CH | |
| C₂H₅ | (CH₂)₂SC₂H₅ | H | OCH₃ | OCH₃ | CH | |
| C₂H₅ | (CH₂)₂SC₂H₅ | H | Cl | OCH₃ | CH | |
| C₂H₅ | (CH₂)₂SC₂H₅ | H | OCH₃ | CH₃ | N | |
| C₂H₅ | (CH₂)₂SC₂H₅ | H | OCH₃ | N(CH₃)₂ | CH | |
| CH(CH₃)₂ | (CH₂)₂SC₂H₅ | H | OCH₃ | CH₃ | CH | |
| CH(CH₃)₂ | (CH₂)₂SC₂H₅ | H | OCH₃ | OCH₃ | CH | |
| CH(CH₃)₂ | (CH₂)₂SC₂H₅ | H | Cl | OCH₃ | CH | |
| CH(CH₃)₂ | (CH₂)₂SC₂H₅ | H | OCH₃ | CH₃ | N | |
| CH(CH₃)₂ | (CH₂)₂SC₂H₅ | H | OCH₃ | OCH₃ | N | |
| CH₃ | (CH₂)₃SC₂H₅ | H | CH₃ | CH₃ | CH | |
| CH₃ | (CH₂)₃SC₂H₅ | H | OCH₃ | CH₃ | CH | |

TABLE I-continued

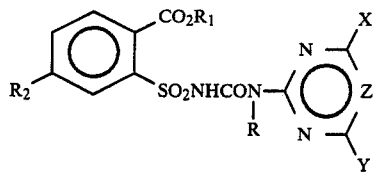

| R₁ | R₂ | R | X | Y | Z | m.p. (°C.) |
|---|---|---|---|---|---|---|
| CH₃ | (CH₂)₃SC₂H₅ | H | OCH₃ | OCH₃ | CH | |
| CH₃ | (CH₂)₃SC₂H₅ | H | Cl | OCH₃ | CH | |
| CH₃ | (CH₂)₃SC₂H₅ | H | CH₃ | CH₃ | N | |
| CH₃ | (CH₂)₃SC₂H₅ | H | OCH₃ | CH₃ | N | |
| CH₃ | (CH₂)₃SC₂H₅ | H | OCH₃ | OCH₃ | N | |
| CH₃ | (CH₂)₃SC₂H₅ | H | OCH₃ | N(CH₃)₂ | CH | |
| CH₃ | (CH₂)₃SC₂H₅ | H | OCH₃ | N(CH₃)₂ | N | |
| CH₃ | (CH₂)₃SC₂H₅ | H | OCH₃ | OCH₂CF₃ | N | |
| CH₃ | (CH₂)₃SC₂H₅ | CH₃ | OCH₃ | CH₃ | N | |
| CH₃ | (CH₂)₃SC₂H₅ | CH₃ | OCH₃ | OCH₃ | N | |
| CH₃ | (CH₂)₃SC₂H₅ | CH₃ | CH₃ | OCH₃ | CH | |
| CH₃ | (CH₂)₃SC₂H₅ | CH₃ | OCH₃ | OCH₃ | CH | |
| CH₃ | (CH₂)₃SC₂H₅ | H | Br | OCH₃ | CH | |
| CH₃ | (CH₂)₃SC₂H₅ | H | CH₃ | OCH₂CF₃ | N | |
| CH₃ | (CH₂)₃SC₂H₅ | H | CH₃ | OCH₂CF₃ | CH | |
| CH₃ | (CH₂)₃SC₂H₅ | H | OCH₃ | OCH₂CF₃ | CH | |
| CH₃ | (CH₂)₃SC₂H₅ | H | OCH₃ | NHCH₃ | N | |
| C₂H₅ | (CH₂)₃SC₂H₅ | H | CH₃ | CH₃ | CH | |
| C₂H₅ | (CH₂)₃SC₂H₅ | H | OCH₃ | CH₃ | CH | |
| C₂H₅ | (CH₂)₃SC₂H₅ | H | OCH₃ | OCH₃ | CH | |
| C₂H₅ | (CH₂)₃SC₂H₅ | H | Cl | OCH₃ | CH | |
| C₂H₅ | (CH₂)₃SC₂H₅ | H | OCH₃ | CH₃ | N | |
| C₂H₅ | (CH₂)₃SC₂H₅ | H | OCH₃ | N(CH₃)₂ | CH | |
| CH(CH₃)₂ | (CH₂)₃SC₂H₅ | H | OCH₃ | CH₃ | | |
| CH(CH₃)₂ | (CH₂)₃SC₂H₅ | H | OCH₃ | OCH₃ | CH | |
| CH(CH₃)₂ | (CH₂)₃SC₂H₅ | H | Cl | OCH₃ | CH | |
| CH(CH₃)₂ | (CH₂)₃SC₂H₅ | H | OCH₃ | CH₃ | N | |
| CH(CH₃)₂ | (CH₂)₃SC₂H₅ | H | OCH₃ | OCH₃ | N | |
| CH₃ | (CH₂)₄SC₂H₅ | H | OCH₃ | CH₃ | CH | |
| CH₃ | (C₂)₄SC₂H₅ | H | OCH₃ | OCH₃ | CH | |
| CH₃ | (CH₂)₄SC₂H₅ | H | Cl | OCH₃ | CH | |
| CH₃ | (CH₂)₄SC₂H₅ | H | OCH₃ | CH₃ | N | |
| CH₃ | (CH₂)₄SC₂H₅ | H | OCH₃ | OCH₃ | N | |
| CH₃ | CH₂CH(CH₃)(SCH₃) | H | CH₃ | OCH₃ | CH | |
| CH₃ | (CH₂)₂CH(CH₃)(SCH₃) | H | OCH₃ | OCH₃ | N | |
| CH₃ | CH₂CH(CH₃)(SC₂H₅) | H | CH₃ | OCH₃ | N | |
| CH₃ | (CH₂)₂CH(CH₃)(SC₂H₅) | H | OCH₃ | OCH₃ | CH | |
| CH₃ | CH(C₂H₅)(SCH₃) | H | CH₃ | OCH₃ | CH | |
| CH₃ | CH(C₂H₅)(SC₂H₅) | H | OCH₃ | OCH₃ | N | |
| CH₃ | CH₂CH(C₂H₅)(SCH₃) | H | CH₃ | OCH₃ | N | |
| CH₃ | CH₂CH(C₂H₅)(SC₂H₅) | H | OCH₃ | OCH₃ | CH | |
| CH₃ | CH(CH₃)(CH₂SCH₃) | H | CH₃ | OCH₃ | CH | |
| CH₃ | CH₂CH(CH₃)(CH₂SCH₃) | H | OCH₃ | OCH₃ | N | |
| CH₃ | CH₂S(O)(CH₃) | H | CH₃ | CH₃ | CH | |
| CH₃ | CH₂S(O)(CH₃) | H | OCH₃ | CH₃ | CH | |
| CH₃ | CH₂S(O)(CH₃) | H | OCH₃ | OCH₃ | CH | |
| CH₃ | CH₂S(O)(CH₃) | H | Cl | OCH₃ | CH | |
| CH₃ | CH₂S(O)(CH₃) | H | OCH₃ | N(CH₃)₂ | CH | |
| CH₃ | CH₂S(O)(CH₃) | H | CH₃ | CH₃ | N | |
| CH₃ | CH₂S(O)(CH₃) | H | OCH₃ | CH₃ | N | |
| CH₃ | CH₂S(O)(CH₃) | H | OCH₃ | OCH₃ | N | |
| CH₃ | CH₂S(O)(CH₃) | H | OCH₃ | N(CH₃)₂ | N | |
| CH₃ | CH₂S(O)(CH₃) | H | OCH₃ | OCH₂CF₃ | N | |
| CH₃ | CH₂S(O)(CH₃) | CH₃ | OCH₃ | CH₃ | N | |
| CH₃ | CH₂S(O)(CH₃) | CH₃ | OCH₃ | OCH₃ | N | |
| CH₃ | CH₂S(O)(CH₃) | CH₃ | CH₃ | OCH₃ | CH | |
| CH₃ | CH₂S(O)(CH₃) | CH₃ | OCH₃ | OCH₃ | CH | |
| CH₃ | CH₂S(O)(CH₃) | H | Br | OCH₃ | CH | |
| CH₃ | CH₂S(O)(CH₃) | H | OCH₃ | N(CH₃)₂ | CH | |
| CH₃ | CH₂S(O)(CH₃) | CH₃ | OCH₃ | N(CH₃)₂ | N | |
| CH₃ | CH₂S(O)(CH₃) | H | CH₃ | OCH₂CF₃ | N | |
| CH₃ | CH₂S(O)(CH₃) | H | CH₃ | OCH₂CF₃ | CH | |
| CH₃ | CH₂S(O)(CH₃) | H | OCH₃ | OCH₂CF₃ | CH | |
| CH₃ | CH₂S(O)(CH₃) | H | OCH₃ | C₂H₅ | CH | |
| CH₃ | CH₂S(O)(CH₃) | H | OCH₃ | C₂H₅ | N | |
| CH₃ | CH₂S(O)(CH₃) | H | OCH₃ | NHCH₃ | CH | |
| CH₃ | CH₂S(O)(CH₃) | H | OCH₃ | NHCH₃ | N | |
| CH₃ | CH₂S(O)(CH₃) | H | CH₃ | OC₂H₅ | CH | |
| CH₃ | CH₂S(O)(CH₃) | H | CH₃ | OC₂H₅ | N | |
| CH₃ | CH₂S(O)(CH₃) | H | OCH₃ | OC₂H₅ | N | |
| CH₃ | CH₂S(O)(CH₃) | H | CH₃ | OCH₂CHF₂ | CH | |

TABLE I-continued

| $R_1$ | $R_2$ | R | X | Y | Z | m.p. (°C.) |
|---|---|---|---|---|---|---|
| $CH_3$ | $CH_2S(O)(CH_3)$ | H | $OCH_3$ | $OCH_2CHF_2$ | CH | |
| $CH_3$ | $CH_2S(O)(CH_3)$ | H | $CH_3$ | $OCH_2CHF_2$ | N | |
| $CH_3$ | $CH_2S(O)(CH_3)$ | H | $OCH_3$ | $OCH_2CHF_2$ | N | |
| $CH_3$ | $CH_2S(O)(CH_3)$ | H | $CH_3$ | $OCH_2CH_2F$ | CH | |
| $CH_3$ | $CH_2S(O)(CH_3)$ | H | $OCH_3$ | $OCH_2CH_2F$ | CH | |
| $CH_3$ | $CH_2S(O)(CH_3)$ | H | $CH_3$ | $OCH_2CH_2F$ | N | |
| $CH_3$ | $CH_2S(O)(CH_3)$ | H | $OCH_3$ | $OCH_2CH_2F$ | N | |
| $CH_3$ | $CH_2S(O)(CH_3)$ | $CH_3$ | Cl | $OCH_3$ | CH | |
| $CH_3$ | $CH_2S(O)(CH_3)$ | H | Cl | $N(CH_3)_2$ | CH | |
| $CH_3$ | $CH_2S(O)(CH_3)$ | H | Cl | $OC_2H_5$ | CH | |
| $C_2H_5$ | $CH_2S(O)(CH_3)$ | H | $CH_3$ | $CH_3$ | CH | |
| $C_2H_5$ | $CH_2S(O)(CH_3)$ | H | $OCH_3$ | $CH_3$ | CH | |
| $C_2H_5$ | $CH_2S(O)(CH_3)$ | H | $OCH_3$ | $OCH_3$ | CH | |
| $C_2H_5$ | $CH_2S(O)(CH_3)$ | H | Cl | $OCH_3$ | CH | |
| $C_2H_5$ | $CH_2S(O)(CH_3)$ | H | $CH_3$ | $CH_3$ | N | |
| $C_2H_5$ | $CH_2S(O)(CH_3)$ | H | $OCH_3$ | $CH_3$ | N | |
| $C_2H_5$ | $CH_2S(O)(CH_3)$ | H | $OCH_3$ | $OCH_3$ | N | |
| $C_2H_5$ | $CH_2S(O)(CH_3)$ | H | Br | $OCH_3$ | CH | |
| $C_2H_5$ | $CH_2S(O)(CH_3)$ | H | $OCH_3$ | $N(CH_3)_2$ | CH | |
| $C_2H_5$ | $CH_2S(O)(CH_3)$ | H | $OCH_3$ | $N(CH_3)_2$ | N | |
| $C_2H_5$ | $CH_2S(O)(CH_3)$ | H | $OCH_3$ | $NHCH_3$ | N | |
| $CH_3$ | $CH_2S(O)(CH_2CH_3)$ | H | $CH_3$ | $CH_3$ | CH | |
| $CH_3$ | $CH_2S(O)(CH_2CH_3)$ | H | $OCH_3$ | $CH_3$ | CH | |
| $CH_3$ | $CH_2S(O)(CH_2CH_3)$ | H | $OCH_3$ | $OCH_3$ | CH | |
| $CH_3$ | $CH_2S(O)(CH_2CH_3)$ | H | Cl | $OCH_3$ | CH | |
| $CH_3$ | $CH_2S(O)(CH_2CH_3)$ | H | $CH_3$ | $CH_3$ | N | |
| $CH_3$ | $CH_2S(O)(CH_2CH_3)$ | H | $OCH_3$ | $CH_3$ | N | |
| $CH_3$ | $CH_2S(O)(CH_2CH_3)$ | H | $OCH_3$ | $OCH_3$ | N | |
| $CH_3$ | $CH_2S(O)(CH_2CH_3)$ | H | $OCH_3$ | $N(CH_3)_2$ | CH | |
| $CH_3$ | $CH_2S(O)(CH_2CH_3)$ | H | $OCH_3$ | $N(CH_3)_2$ | N | |
| $CH_3$ | $CH_2S(O)(CH_2CH_3)$ | H | $OCH_3$ | $OCH_2CF_3$ | N | |
| $CH_3$ | $CH_2S(O)(CH_2CH_3)$ | $CH_3$ | $OCH_3$ | $CH_3$ | N | |
| $CH_3$ | $CH_2S(O)(CH_2CH_3)$ | $CH_3$ | $OCH_3$ | $OCH_3$ | N | |
| $CH_3$ | $CH_2S(O)(CH_2CH_3)$ | $CH_3$ | $CH_3$ | $OCH_3$ | CH | |
| $CH_3$ | $CH_2S(O)(CH_2CH_3)$ | $CH_3$ | OCH | OCH | CH | |
| $CH_3$ | $CH_2S(O)(CH_2CH_3)$ | H | Br | $OCH_3$ | CH | |
| $CH_3$ | $CH_2S(O)(CH_2CH_3)$ | H | $CH_3$ | $OCH_2CF_3$ | N | |
| $CH_3$ | $CH_2S(O)(CH_2CH_3)$ | H | $CH_3$ | $OCH_2CF_3$ | CH | |
| $CH_3$ | $CH_2S(O)(CH_2CH_3)$ | H | $OCH_3$ | $OCH_2CF_3$ | CH | |
| $CH_3$ | $CH_2S(O)(CH_2CH_3)$ | H | $OCH_3$ | $NHCH_3$ | N | |
| $C_2H_5$ | $CH_2S(O)(CH_2CH_3)$ | H | $CH_3$ | $CH_3$ | CH | |
| $C_2H_5$ | $CH_2S(O)(CH_2CH_3)$ | H | $OCH_3$ | $CH_3$ | CH | |
| $C_2H_5$ | $CH_2S(O)(CH_2CH_3)$ | H | $OCH_3$ | $OCH_3$ | CH | |
| $C_2H_5$ | $CH_2S(O)(CH_2CH_3)$ | H | Cl | $OCH_3$ | CH | |
| $C_2H_5$ | $CH_2S(O)(CH_2CH_3)$ | H | $OCH_3$ | $CH_3$ | N | |
| $C_2H_5$ | $CH_2S(O)(CH_2CH_3)$ | H | $OCH_3$ | $N(CH_3)_2$ | N | |
| $CH(CH_3)_2$ | $CH_2S(O)(CH_2CH_3)$ | H | $OCH_3$ | $CH_3$ | CH | |
| $CH(CH_3)_2$ | $CH_2S(O)(CH_2CH_3)$ | H | $OCH_3$ | $OCH_3$ | CH | |
| $CH(CH_3)_2$ | $CH_2S(O)(CH_2CH_3)$ | H | Cl | $OCH_3$ | CH | |
| $CH(CH_3)_2$ | $CH_2S(O)(CH_2CH_3)$ | H | $OCH_3$ | $CH_3$ | N | |
| $CH(CH_3)_2$ | $CH_2S(O)(CH_2CH_3)$ | H | $OCH_3$ | $OCH_3$ | N | |
| $CH_3$ | $(CH_2)_2S(O)(CH_3)$ | H | $OCH_3$ | $CH_3$ | CH | |
| $CH_3$ | $(CH_2)_2S(O)(CH_3)$ | H | $OCH_3$ | $OCH_3$ | CH | |
| $CH_3$ | $(CH_2)_2(CH_2)_2S(O)(CH_3)$ | H | Cl | $OCH_3$ | CH | |
| $CH_3$ | $(CH_2)_2(CH_2)_2S(O)(CH_3)$ | H | $OCH_3$ | $CH_3$ | N | |
| $CH_3$ | $(CH_2)_2(CH_2)_2S(O)(CH_3)$ | H | $OCH_3$ | $OCH_3$ | N | |
| $CH_3$ | $(CH_2)_2S(O)(CH_2CH_3)$ | H | $OCH_3$ | $CH_3$ | CH | |
| $CH_3$ | $(CH_2)_2S(O)(CH_2CH_3)$ | H | $OCH_3$ | $OCH_3$ | CH | |
| $CH_3$ | $(CH_2)_2S(O)(CH_2CH_3)$ | H | Cl | $OCH_3$ | CH | |
| $CH_3$ | $(CH_2)_2S(O)(CH_2CH_3)$ | H | $OCH_3$ | $CH_3$ | N | |
| $CH_3$ | $(CH_2)_2S(O)(CH_2CH_3)$ | H | $OCH_3$ | $OCH_3$ | N | |
| $CH_3$ | $(CH_2)_3S(O)(CH_3)$ | H | $CH_3$ | $OCH_3$ | CH | |
| $CH_3$ | $(CH_2)_3S(O)(CH_3)$ | H | $OCH_3$ | $OCH_3$ | N | |
| $CH_3$ | $(CH_2)_3S(O)(CH_2CH_3)$ | H | $CH_3$ | $OCH_3$ | CH | |
| $CH_3$ | $(CH_2)_4S(O)(CH_2CH_3)$ | H | $OCH_3$ | $OCH_3$ | CH | |
| $CH_3$ | $CH(CH_3)(S(O)(CH_3))$ | H | $CH_3$ | $OCH_3$ | N | |
| $CH_3$ | $CH_2S(O)_2(CH_3)$ | H | $CH_3$ | $CH_3$ | CH | |
| $CH_3$ | $CH_2S(O)_2(CH_3)$ | H | $OCH_3$ | $CH_3$ | CH | |
| $CH_3$ | $CH_2S(O)_2(CH_3)$ | H | $OCH_3$ | $CH_3$ | CH | |
| $CH_3$ | $CH_2S(O)_2(CH_3)$ | H | $OCH_3$ | $OCH_3$ | CH | |
| $CH_3$ | $CH_2S(O)_2(CH_3)$ | H | Cl | $OCH_3$ | CH | |

TABLE I-continued

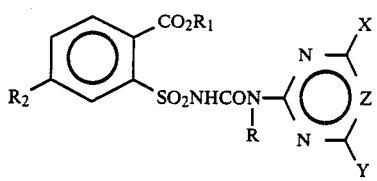

| R₁ | R₂ | R | X | Y | Z | m.p. (°C.) |
|---|---|---|---|---|---|---|
| CH₃ | CH₂S(O)₂(CH₃) | H | OCH₃ | N(CH₃)₂ | CH | |
| CH₃ | CH₂S(O)₂(CH₃) | H | CH₃ | CH₃ | N | |
| CH₃ | CH₂S(O)₂(CH₃) | H | OCH₃ | CH₃ | N | |
| CH₃ | CH₂S(O)₂(CH₃) | H | OCH₃ | OCH₃ | N | |
| CH₃ | CH₂S(O)₂(CH₃) | H | OCH₃ | N(CH₃)₂ | N | |
| CH₃ | CH₂S(O)₂(CH₃) | H | OCH₃ | OCH₂CF₃ | N | |
| CH₃ | CH₂S(O)₂(CH₃) | CH₃ | OCH₃ | CH₃ | N | |
| CH₃ | CH₂S(O)₂(CH₃) | CH₃ | OCH₃ | OCH₃ | N | |
| CH₃ | CH₂S(O)₂(CH₃) | CH₃ | CH₃ | OCH₃ | CH | |
| CH₃ | CH₂S(O)₂(CH₃) | CH₃ | OCH₃ | OCH₃ | CH | |
| CH₃ | CH₂S(O)₂(CH₃) | H | Br | OCH₃ | CH | |
| CH₃ | CH₂S(O)₂(CH₃) | H | OCH₃ | N(CH₃)₂ | CH | |
| CH₃ | CH₂S(O)₂(CH₃) | CH₃ | OCH₃ | N(CH₃)₂ | N | |
| CH₃ | CH₂S(O)₂(CH₃) | H | CH₃ | OCH₂CF₃ | N | |
| CH₃ | CH₂S(O)₂(CH₃) | H | CH₃ | OCH₂CF₃ | CH | |
| CH₃ | CH₂S(O)₂(CH₃) | H | OCH₃ | OCH₂CF₃ | CH | |
| CH₃ | CH₂S(O)₂(CH₃) | H | OCH₃ | C₂H₅ | CH | |
| CH₃ | CH₂S(O)₂(CH₃) | H | OCH₃ | C₂H₅ | N | |
| CH₃ | CH₂S(O)₂(CH₃) | H | OCH₃ | NHCH₃ | CH | |
| CH₃ | CH₂S(O)₂(CH₃) | H | OCH₃ | NHCH₃ | N | |
| CH₃ | CH₂S(O)₂(CH₃) | H | CH₃ | OC₂H₅ | CH | |
| CH₃ | CH₂S(O)₂(CH₃) | H | OCH₃ | OC₂H₅ | CH | |
| CH₃ | CH₂S(O)₂(CH₃) | H | CH₃ | OC₂H₅ | N | |
| CH₃ | CH₂S(O)₂(CH₃) | H | OCH₃ | OC₂H₅ | N | |
| CH₃ | CH₂S(O)₂(CH₃) | H | CH₃ | OCH₂CHF₂ | CH | |
| CH₃ | CH₂S(O)₂(CH₃) | H | OCH₃ | OCH₂CHF₂ | CH | |
| CH₃ | CH₂S(O)₂(CH₃) | H | CH₃ | OCH₂CHF₂ | N | |
| CH₃ | CH₂S(O)₂(CH₃) | H | OCH₃ | OCH₂CHF₂ | N | |
| CH₃ | CH₂S(O)₂(CH₃) | H | CH₃ | OCH₂CH₂F | CH | |
| CH₃ | CH₂S(O)₂(CH₃) | H | OCH₃ | OCH₂CH₂F | CH | |
| CH₃ | CH₂S(O)₂(CH₃) | H | CH₃ | OCH₂CH₂F | N | |
| CH₃ | CH₂S(O)₂(CH₃) | H | OCH₃ | OCH₂CH₂F | N | |
| CH₃ | CH₂S(O)₂(CH₃) | CH₃ | Cl | OCH₃ | CH | |
| CH₃ | CH₂S(O)₂(CH₃) | H | Cl | N(CH₃)₂ | CH | |
| CH₃ | CH₂S(O)₂(CH₃) | H | Cl | OC₂H₅ | CH | |
| C₂H₅ | CH₂S(O)₂(CH₃) | H | CH₃ | CH₃ | CH | |
| C₂H₅ | CH₂S(O)₂(CH₃) | H | OCH₃ | CH₃ | CH | |
| C₂H₅ | CH₂S(O)₂(CH₃) | H | OCH₃ | OCH₃ | CH | |
| C₂H₅ | CH₂S(O)₂(CH₃) | H | Cl | OCH₃ | CH | |
| C₂H₅ | CH₂S(O)₂(CH₃) | H | CH₃ | CH₃ | N | |
| C₂H₅ | CH₂S(O)₂(CH₃) | H | OCH₃ | CH₃ | N | |
| C₂H₅ | CH₂S(O)₂(CH₃) | H | OCH₃ | OCH₃ | N | |
| C₂H₅ | CH₂S(O)₂(CH₃) | H | Br | OCH₃ | CH | |
| C₂H₅ | CH₂S(O)₂(CH₃) | H | OCH₃ | N(CH₃)₂ | CH | |
| C₂H₅ | CH₂S(O)₂(CH₃) | H | OCH₃ | N(CH₃)₂ | N | |
| C₂H₅ | CH₂S(O)₂(CH₃) | H | OCH₃ | NHCH₃ | N | |
| C₂H₅ | CH₂S(O)₂(CH₃) | H | OCH₃ | C₂H₅ | CH | |
| C₂H₅ | CH₂S(O)₂(CH₃) | H | OCH₃ | C₂H₅ | N | |
| C₂H₅ | CH₂S(O)₂(CH₃) | H | CH₃ | OC₂H₅ | CH | |
| C₂H₅ | CH₂S(O)₂(CH₃) | H | CH₃ | OC₂H₅ | CH | |
| C₂H₅ | CH₂S(O)₂(CH₃) | H | CH₃ | OC₂H₅ | N | |
| C₂H₅ | CH₂S(O)₂(CH₃) | H | OCH₃ | OC₂H₅ | CH | |
| C₂H₅ | CH₂S(O)₂(CH₃) | H | OCH₃ | OC₂H₅ | N | |
| C₂H₅ | CH₂S(O)₂(CH₃) | H | CH₃ | OCH₂CF₃ | CH | |
| C₂H₅ | CH₂S(O)₂(CH₃) | H | CH₃ | OCH₂CF₃ | N | |
| C₂H₅ | CH₂S(O)₂(CH₃) | H | OCH₃ | OCH₂CF₃ | CH | |
| C₂H₅ | CH₂S(O)₂(CH₃) | H | OCH₃ | OCH₂CF₃ | N | |
| C₂H₅ | CH₂S(O)₂(CH₃) | H | OCH₃ | OCH₂CHF₂ | CH | |
| C₂H₅ | CH₂S(O)₂(CH₃) | H | OCH₃ | OCH₂CHF₂ | N | |
| C₂H₅ | CH₂S(O)₂(CH₃) | H | CH₃ | OCH₂CHF₂ | N | |
| C₂H₅ | CH₂S(O)₂(CH₃) | H | OCH₃ | OCH₂CH₂F | CH | |
| C₂H₅ | CH₂S(O)₂(CH₃) | H | OCH₃ | OCH₂CH₂F | N | |
| C₂H₅ | CH₂S(O)₂(CH₃) | CH₃ | OCH₃ | OCH₃ | CH | |
| C₂H₅ | CH₂S(O)₂(CH₃) | CH₃ | CH₃ | OCH₃ | N | |
| C₂H₅ | CH₂S(O)₂(CH₃) | CH₃ | OCH₃ | OCH₃ | N | |
| n-C₃H₇ | CH₂S(O)₂(CH₃) | H | OCH₃ | OCH₃ | CH | |
| n-C₃H₇ | CH₂S(O)₂(CH₃) | H | CH₃ | OCH₃ | N | |
| CH(CH₃)₂ | CH₂S(O)₂(CH₃) | H | OCH₃ | CH₃ | CH | |
| CH(CH₃)₂ | CH₂S(O)₂(CH₃) | H | OCH₃ | OCH₃ | CH | |
| CH(CH₃)₂ | CH₂S(O)₂(CH₃) | H | Cl | OCH₃ | CH | |
| CH(CH₃)₂ | CH₂S(O)₂(CH₃) | H | OCH₃ | CH₃ | N | |

TABLE I-continued

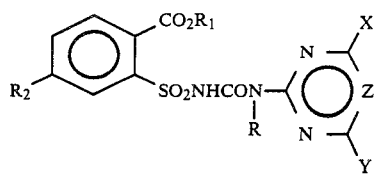

| R₁ | R₂ | R | X | Y | Z | m.p. (°C.) |
|---|---|---|---|---|---|---|
| CH(CH₃)₂ | CH₂S(O)₂(CH₃) | H | OCH₃ | OCH₃ | N | |
| CH(CH₃)₂ | CH₂S(O)₂(CH₃) | H | OCH₃ | N(CH₃)₂ | N | |
| CH₃ | CH₂S(O)₂(CH₂CH₃) | H | CH₃ | CH₃ | CH | |
| CH₃ | CH₂S(O)₂(CH₂CH₃) | H | OCH₃ | CH₃ | CH | |
| CH₃ | CH₂S(O)₂(CH₂CH₃) | H | OCH₃ | OCH₃ | CH | |
| CH₃ | CH₂S(O)₂(CH₂CH₃) | H | Cl | OCH₃ | CH | |
| CH₃ | CH₂S(O)₂(CH₂CH₃) | H | CH₃ | CH₃ | N | |
| CH₃ | CH₂S(O)₂(CH₂CH₃) | H | OCH₃ | CH₃ | N | |
| CH₃ | CH₂S(O)₂(CH₂CH₃) | H | OCH₃ | OCH₃ | N | |
| CH₃ | CH₂S(O)₂(CH₂CH₃) | H | OCH₃ | N(CH₃)₂ | CH | |
| CH₃ | CH₂S(O)₂(CH₂CH₃) | H | OCH₃ | N(CH₃)₂ | N | |
| CH₃ | CH₂S(O)₂(CH₂CH₃) | H | OCH₃ | OCH₂CF₃ | N | |
| CH₃ | CH₂S(O)₂(CH₂CH₃) | CH₃ | OCH₃ | CH₃ | N | |
| CH₃ | CH₂S(O)₂(CH₂CH₃) | CH₃ | OCH₃ | OCH₃ | N | |
| CH₃ | CH₂S(O)₂(CH₂CH₃) | CH₃ | CH₃ | OCH₃ | CH | |
| CH₃ | CH₂S(O)₂(CH₂CH₃) | CH₃ | OCH₃ | OCH₃ | CH | |
| CH₃ | CH₂S(O)₂(CH₂CH₃) | H | Br | OCH₃ | CH | |
| CH₃ | CH₂S(O)₂(CH₂CH₃) | H | CH₃ | OCH₂CF₃ | N | |
| CH₃ | CH₂S(O)₂(CH₂CH₃) | H | CH₃ | OCH₂CF₃ | CH | |
| CH₃ | CH₂S(O)₂(CH₂CH₃) | H | OCH₃ | OCH₂CF₃ | CH | |
| CH₃ | CH₂S(O)₂(CH₂CH₃) | H | OCH₃ | NHCH₃ | N | |
| C₂H₅ | CH₂S(O)₂(CH₂CH₃) | H | CH₃ | CH₃ | CH | |
| C₂H₅ | CH₂S(O)₂(CH₂CH₃) | H | OCH₃ | CH₃ | CH | |
| C₂H₅ | CH₂S(O)₂(CH₂CH₃) | H | OCH₃ | OCH₃ | CH | |
| C₂H₅ | CH₂S(O)₂(CH₂CH₃) | H | Cl | OCH₃ | CH | |
| C₂H₅ | CH₂S(O)₂(CH₂CH₃) | H | OCH₃ | CH₃ | N | |
| C₂H₅ | CH₂S(O)₂(CH₂CH₃) | H | OCH₃ | N(CH₃)₂ | N | |
| CH(CH₃)₂ | CH₂S(O)₂(CH₂CH₃) | H | OCH₃ | CH₃ | CH | |
| CH(CH₃)₂ | CH₂S(O)₂(CH₂CH₃) | H | OCH₃ | OCH₃ | CH | |
| CH(CH₃)₂ | CH₂S(O)₂(CH₂CH₃) | H | Cl | OCH₃ | CH | |
| CH(CH₃)₂ | CH₂S(O)₂(CH₂CH₃) | H | OCH₃ | CH₃ | N | |
| CH(CH₃)₂ | CH₂S(O)₂(CH₂CH₃) | H | OCH₃ | OCH₃ | N | |
| CH₃ | (CH₂)₂S(O)₂(CH₃) | H | OCH₃ | CH₃ | CH | |
| CH₃ | (CH₂)₂S(O)₂(CH₃) | H | OCH₃ | OCH₃ | CH | |
| CH₃ | (CH₂)₂S(O)₂(CH₃) | H | Cl | OCH₃ | CH | |
| CH₃ | (CH₂)₂S(O)₂(CH₃) | H | OCH₃ | CH₃ | N | |
| CH₃ | (CH₂)₂S(O)₂(CH₃) | H | OCH₃ | OCH₃ | N | |
| CH₃ | (CH₂)₂S(O)₂(CH₂CH₃) | H | OCH₃ | CH₃ | CH | |
| CH₃ | (CH₂)₂S(O)₂(CH₂CH₃) | H | OCH₃ | OCH₃ | CH | |
| CH₃ | (CH₂)₂S(O)₂(CH₂CH₃) | H | Cl | OCH₃ | CH | |
| CH₃ | (CH₂)₂S(O)₂(CH₂CH₃) | H | OCH₃ | CH₃ | N | |
| CH₃ | (CH₂)₂S(O)₂(CH₂CH₃) | H | OCH₃ | OCH₃ | N | |
| CH₃ | (CH₂)₃S(O)₂(CH₃) | H | CH₃ | OCH₃ | CH | |
| CH₃ | (CH₂)₄S(O)₂(CH₃) | H | OCH₃ | OCH₃ | N | |
| CH₃ | (CH₂)₃S(O)₂(CH₂CH₃) | H | OCH₃ | OCH₃ | CH | |
| CH₃ | (CH₂)₄S(O)₂(CH₂CH₃) | H | OCH₃ | CH₃ | N | |
| CH₃ | CCF₂H | H | CH₃ | CH₃ | CH | |
| CH₃ | OCF₂H | H | OCH₃ | CH₃ | CH | |
| CH₃ | OCF₂H | H | OCH₃ | OCH₃ | CH | |
| CH₃ | OCF₂H | H | Cl | OCH₃ | CH | |
| CH₃ | OCF₂H | H | OCH₃ | N(CH₃)₂ | CH | |
| CH₃ | OCF₂H | H | CH₃ | CH₃ | N | |
| CH₃ | OCF₂H | H | OCH₃ | CH₃ | N | |
| CH₃ | OCF₂H | H | OCH₃ | OCH₃ | N | |
| CH₃ | OCF₂H | H | OCH₃ | N(CH₃)₂ | N | |
| CH₃ | OCF₂H | H | OCH₃ | OCH₂CF₃ | N | |
| CH₃ | OCF₂H | CH₃ | OCH₃ | CH₃ | N | |
| CH₃ | OCF₂H | CH₃ | OCH₃ | OCH₃ | N | |
| CH₃ | OCF₂H | CH₃ | CH₃ | OCH₃ | CH | |
| CH₃ | OCF₂H | CH₃ | OCH₃ | OCH₃ | CH | |
| CH₃ | OCF₂H | H | Br | OCH₃ | CH | |
| CH₃ | OCF₂H | CH₃ | OCH₃ | N(CH₃)₂ | N | |
| CH₃ | OCF₂H | H | CH₃ | OCH₂CF₃ | N | |
| CH₃ | OCF₂H | H | CH₃ | OCH₂CF₃ | CH | |
| CH₃ | OCF₂H | H | OCH₃ | OCH₂CF₃ | CH | |
| CH₃ | OCF₂H | H | OCH₃ | C₂H₅ | CH | |
| CH₃ | OCF₂H | H | OCH₃ | C₂H₅ | N | |
| CH₃ | OCF₂H | H | OCH₃ | NHCH₃ | CH | |
| CH₃ | OCF₂H | H | OCH₃ | NHCH₃ | N | |
| CH₃ | OCF₂H | H | CH₃ | OC₂H₅ | CH | |
| CH₃ | OCF₂H | H | OCH₃ | OC₂H₅ | CH | |

TABLE I-continued

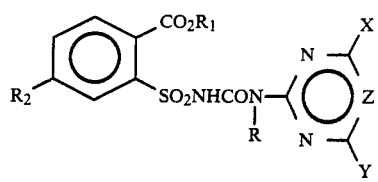

| R₁ | R₂ | R | X | Y | Z | m.p. (°C.) |
|---|---|---|---|---|---|---|
| CH₃ | OCF₂H | H | CH₃ | OC₂H₅ | N | |
| CH₃ | OCF₂H | H | OCH₃ | OC₂H₅ | N | |
| CH₃ | OCF₂H | H | CH₃ | OCH₂CHF₂ | CH | |
| CH₃ | OCF₂H | H | OCH₃ | OCH₂CHF₂ | CH | |
| CH₃ | OCF₂H | H | CH₃ | OCH₂CHF₂ | N | |
| CH₃ | OCF₂H | H | OCH₃ | OCH₂CHF₂ | N | |
| CH₃ | OCF₂H | H | CH₃ | OCH₂CH₂F | CH | |
| CH₃ | OCF₂H | H | OCH₃ | OCH₂CH₂F | CH | |
| CH₃ | OCF₂H | CH₃ | OCH₃ | OCH₂CH₂F | N | |
| CH₃ | OCF₂H | CH₃ | Cl | OCH₃ | CH | |
| CH₃ | OCF₂H | H | Cl | N(CH₃)₂ | CH | |
| CH₃ | OCF₂H | H | Cl | OC₂H₅ | CH | |
| C₂H₅ | OCF₂H | H | CH₃ | CH₃ | CH | |
| C₂H₅ | OCF₂H | H | OCH₃ | CH₃ | CH | |
| C₂H₅ | OCF₂H | H | OCH₃ | OCH₃ | CH | |
| C₂H₅ | OCF₂H | H | Cl | OCH₃ | CH | |
| C₂H₅ | OCF₂H | H | CH₃ | CH₃ | N | |
| C₂H₅ | OCF₂H | H | OCH₃ | CH₃ | N | |
| C₂H₅ | OCF₂H | H | OCH₃ | OCH₃ | N | |
| C₂H₅ | OCF₂H | H | Br | OCH₃ | CH | |
| C₂H₅ | OCF₂H | H | OCH₃ | N(CH₃)₂ | CH | |
| C₂H₅ | OCF₂H | H | OCH₃ | N(CH₃)₂ | N | |
| C₂H₅ | OCF₂H | H | OCH₃ | NHCH₃ | N | |
| C₂H₅ | OCF₂H | H | OCH₃ | C₂H₅ | CH | |
| C₂H₅ | OCF₂H | H | OCH₃ | C₂H₅ | N | |
| C₂H₅ | OCF₂H | H | CH₃ | OC₂H₅ | CH | |
| C₂H₅ | OCF₂H | H | CH₃ | OC₂H₅ | N | |
| C₂H₅ | OCF₂H | H | OCH₃ | OC₂H₅ | CH | |
| C₂H₅ | OCF₂H | H | OCH₃ | OC₂H₅ | N | |
| C₂H₅ | OCF₂H | H | CH₃ | OCH₂CF₃ | CH | |
| C₂H₅ | OCF₂H | H | CH₃ | OCH₂CF₃ | N | |
| C₂H₅ | OCF₂H | H | OCH₃ | OCH₂CF₃ | CH | |
| C₂H₅ | OCF₂H | H | OCH₃ | OCH₂CF₃ | N | |
| C₂H₅ | OCF₂H | H | OCH₃ | OCH₂CHF₂ | CH | |
| C₂H₅ | OCF₂H | H | OCH₃ | OCH₂CHF₂ | N | |
| C₂H₅ | OCF₂H | H | CH₃ | OCH₂CHF₂ | N | |
| C₂H₅ | OCF₂H | H | OCH₃ | OCH₂CH₂F | CH | |
| C₂H₅ | OCF₂H | H | OCH₃ | OCH₂CH₂F | N | |
| C₂H₅ | OCF₂H | CH₃ | OCH₃ | OCH₃ | CH | |
| C₂H₅ | OCF₂H | CH₃ | CH₃ | OCH₃ | N | |
| C₂H₅ | OCF₂H | CH₃ | OCH₃ | OCH₃ | N | |
| n-C₃H₇ | OCF₂H | H | OCH₃ | OCH₃ | CH | |
| n-C₃H₇ | OCF₂H | H | CH₃ | OCH₃ | N | |
| CH(CH₃)₂ | OCF₂H | H | OCH₃ | CH₃ | CH | |
| CH(CH₃)₂ | OCF₂H | H | OCH₃ | OCH₃ | CH | |
| CH(CH₃)₂ | OCF₂H | H | Cl | OCH₃ | CH | |
| CH(CH₃)₂ | OCF₂H | H | OCH₃ | CH₃ | N | |
| CH(CH₃)₂ | OCF₂H | H | OCH₃ | OCH₃ | N | |
| CH(CH₃)₂ | OCF₂H | H | OCH₃ | N(CH₃)₂ | N | |
| CH₃ | OCH₂CH₂F | H | CH₃ | CH₃ | CH | |
| CH₃ | OCH₂CH₂F | H | OCH₃ | CH₃ | CH | 168–170 |
| CH₃ | OCH₂CH₂F | H | OCH₃ | OCH₃ | CH | 205–206 |
| CH₃ | OCH₂CH₂F | H | Cl | OCH₃ | CH | 158–162 (d) |
| CH₃ | OCH₂CH₂F | H | OCH₃ | N(CH₃)₂ | CH | |
| CH₃ | OCH₂CH₂F | H | CH₃ | CH₃ | N | |
| CH₃ | OCH₂CH₂F | H | OCH₃ | CH₃ | N | 138–140 (d) |
| CH₃ | OCH₂CH₂F | H | OCH₃ | OCH₃ | N | |
| CH₃ | OCH₂CH₂F | H | OCH₃ | N(CH₃)₂ | N | |
| CH₃ | OCH₂CH₂F | H | OCH₃ | OCH₂CF₃ | N | |
| CH₃ | OCH₂CH₂F | CH₃ | OCH₃ | CH₃ | N | |
| CH₃ | OCH₂CH₂F | CH₃ | OCH₃ | OCH₃ | N | |
| CH₃ | OCH₂CH₂F | CH₃ | CH₃ | OCH₃ | CH | |
| CH₃ | OCH₂CH₂F | CH₃ | OCH₃ | OCH₃ | CH | |
| CH₃ | OCH₂CH₂F | H | Br | OCH₃ | CH | |
| CH₃ | OCH₂CH₂F | CH₃ | OCH₃ | N(CH₃)₂ | N | |
| CH₃ | OCH₂CH₂F | H | CH₃ | OCH₂CF₃ | N | |
| CH₃ | OCH₂CH₂F | H | CH₃ | OCH₂CF₃ | CH | |
| CH₃ | OCH₂CH₂F | H | OCH₃ | OCH₂CF₃ | CH | |
| CH₃ | OCH₂CH₂F | H | OCH₃ | C₂H₅ | CH | |
| CH₃ | OCH₂CH₂F | H | OCH₃ | C₂H₅ | N | |
| CH₃ | OCH₂CH₂F | H | OCH₃ | NHCH₃ | CH | |

TABLE I-continued

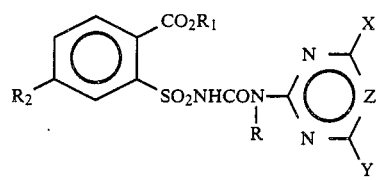

| $R_1$ | $R_2$ | R | X | Y | Z | m.p. (°C.) |
|---|---|---|---|---|---|---|
| $CH_3$ | $OCH_2CH_2F$ | H | $OCH_3$ | $NHCH_3$ | N | |
| $CH_3$ | $OCH_2CH_2F$ | H | $CH_3$ | $OC_2H_5$ | CH | |
| $CH_3$ | $OCH_2CH_2F$ | H | $OCH_3$ | $OC_2H_5$ | CH | |
| $CH_3$ | $OCH_2CH_2F$ | H | $CH_3$ | $OC_2H_5$ | N | |
| $CH_3$ | $OCH_2CH_2F$ | H | $OCH_3$ | $OC_2H_5$ | N | |
| $CH_3$ | $OCH_2CH_2F$ | H | $CH_3$ | $OCH_2CHF_2$ | CH | |
| $CH_3$ | $OCH_2CH_2F$ | H | $OCH_3$ | $OCH_2CHF_2$ | CH | |
| $CH_3$ | $OCH_2CH_2F$ | H | $CH_3$ | $OCH_2CHF_2$ | N | |
| $CH_3$ | $OCH_2CH_2F$ | H | $OCH_3$ | $OCH_2CHF_2$ | N | |
| $CH_3$ | $OCH_2CH_2F$ | H | $CH_3$ | $OCH_2CH_2F$ | CH | |
| $CH_3$ | $OCH_2CH_2F$ | H | $OCH_3$ | $OCH_2CH_2F$ | CH | |
| $CH_3$ | $OCH_2CH_2F$ | H | $CH_3$ | $OCH_2CH_2F$ | N | |
| $CH_3$ | $OCH_2CH_2F$ | $CH_3$ | $OCH_3$ | $OCH_2CH_2F$ | N | |
| $CH_3$ | $OCH_2CH_2F$ | $CH_3$ | Cl | $OCH_3$ | CH | |
| $CH_3$ | $OCH_2CH_2F$ | H | Cl | $N(CH_3)_2$ | CH | |
| $CH_3$ | $OCH_2CH_2F$ | H | Cl | $OC_2H_5$ | CH | |
| $C_2H_5$ | $OCH_2CH_2F$ | H | $CH_3$ | $CH_3$ | CH | |
| $C_2H_5$ | $OCH_2CH_2F$ | H | $OCH_3$ | $CH_3$ | CH | |
| $C_2H_5$ | $OCH_2CH_2F$ | H | $OCH_3$ | $OCH_3$ | CH | |
| $C_2H_5$ | $OCH_2CH_2F$ | H | Cl | $OCH_3$ | CH | |
| $C_2H_5$ | $OCH_2CH_2F$ | H | $CH_3$ | $CH_3$ | N | |
| $C_2H_5$ | $OCH_2CH_2F$ | H | $OCH_3$ | $CH_3$ | N | |
| $C_2H_5$ | $OCH_2CH_2F$ | H | $OCH_3$ | $OCH_3$ | N | |
| $C_2H_5$ | $OCH_2CH_2F$ | H | Br | $OCH_3$ | CH | |
| $C_2H_5$ | $OCH_2CH_2F$ | H | $OCH_3$ | $N(CH_3)_2$ | CH | |
| $C_2H_5$ | $OCH_2CH_2F$ | H | $OCH_3$ | $N(CH_3)_2$ | N | |
| $C_2H_5$ | $OCH_2CH_2F$ | H | $OCH_3$ | $NHCH_3$ | N | |
| $C_2H_5$ | $OCH_2CH_2F$ | H | $OCH_3$ | $C_2H_5$ | CH | |
| $C_2H_5$ | $OCH_2CH_2F$ | H | $OCH_3$ | $C_2H_5$ | N | |
| $C_2H_5$ | $OCH_2CH_2F$ | H | $CH_3$ | $OC_2H_5$ | CH | |
| $C_2H_5$ | $OCH_2CH_2F$ | H | $CH_3$ | $OC_2H_5$ | N | |
| $C_2H_5$ | $OCH_2CH_2F$ | H | $OCH_3$ | $OC_2H_5$ | CH | |
| $C_2H_5$ | $OCH_2CH_2F$ | H | $OCH_3$ | $OC_2H_5$ | N | |
| $C_2H_5$ | $OCH_2CH_2F$ | H | $CH_3$ | $OCH_2CF_3$ | CH | |
| $C_2H_5$ | $OCH_2CH_2F$ | H | $CH_3$ | $OCH_2CF_3$ | N | |
| $C_2H_5$ | $OCH_2CH_2F$ | H | $OCH_3$ | $OCH_2CF_3$ | CH | |
| $C_2H_5$ | $OCH_2CH_2F$ | H | $OCH_3$ | $OCH_2CF_3$ | N | |
| $C_2H_5$ | $OCH_2CH_2F$ | H | $OCH_3$ | $OCH_2CHF_2$ | CH | |
| $C_2H_5$ | $OCH_2CH_2F$ | H | $OCH_3$ | $OCH_2CHF_2$ | N | |
| $C_2H_5$ | $OCH_2CH_2F$ | H | $CH_3$ | $OCH_2CHF_2$ | N | |
| $C_2H_5$ | $OCH_2CH_2F$ | H | $OCH_3$ | $OCH_2CH_2F$ | CH | |
| $C_2H_5$ | $OCH_2CH_2F$ | H | $OCH_3$ | $OCH_2CH_2F$ | N | |
| $C_2H_5$ | $OCH_2CH_2F$ | $CH_3$ | $OCH_3$ | $OCH_3$ | CH | |
| $C_2H_5$ | $OCH_2CH_2F$ | $CH_3$ | $CH_3$ | $OCH_3$ | N | |
| $C_2H_5$ | $OCH_2CH_2F$ | $CH_3$ | $OCH_3$ | $OCH_3$ | N | |
| n-$C_3H_7$ | $OCH_2CH_2F$ | H | $OCH_3$ | $OCH_3$ | CH | |
| n-$C_3H_7$ | $OCH_2CH_2F$ | H | $CH_3$ | $OCH_3$ | N | |
| $CH(CH_3)_2$ | $OCH_2CH_2F$ | H | $OCH_3$ | $CH_3$ | CH | |
| $CH(CH_3)_2$ | $OCH_2CH_2F$ | H | $OCH_3$ | $OCH_3$ | CH | |
| $CH(CH_3)_2$ | $OCH_2CH_2F$ | H | Cl | $OCH_3$ | CH | |
| $CH(CH_3)_2$ | $OCH_2CH_2F$ | H | $OCH_3$ | $CH_3$ | N | |
| $CH(CH_3)_2$ | $OCH_2CH_2F$ | H | $OCH_3$ | $OCH_3$ | N | |
| $CH(CH_3)_2$ | $OCH_2CH_2F$ | H | $OCH_3$ | $N(CH_3)_2$ | N | |
| $CH_3$ | $OCH_2CHF_2$ | H | $CH_3$ | $CH_3$ | CH | |
| $CH_3$ | $OCH_2CHF_2$ | H | $OCH_3$ | $CH_3$ | CH | |
| $CH_3$ | $OCH_2CHF_2$ | H | $OCH_3$ | $OCH_3$ | CH | |
| $CH_3$ | $OCH_2CHF_2$ | H | Cl | $OCH_3$ | CH | |
| $CH_3$ | $OCH_2CHF_2$ | H | $OCH_3$ | $N(CH_3)_2$ | CH | |
| $CH_3$ | $OCH_2CHF_2$ | H | $CH_3$ | $CH_3$ | N | |
| $CH_3$ | $OCH_2CHF_2$ | H | $OCH_3$ | $CH_3$ | N | |
| $CH_3$ | $OCH_2CHF_2$ | H | $OCH_3$ | $OCH_3$ | N | |
| $CH_3$ | $OCH_2CHF_2$ | H | $OCH_3$ | $N(CH_3)_2$ | N | |
| $CH_3$ | $OCH_2CHF_2$ | H | $OCH_3$ | $OCH_2CF_3$ | N | |
| $CH_3$ | $OCH_2CHF_2$ | $CH_3$ | $OCH_3$ | $CH_3$ | N | |
| $CH_3$ | $OCH_2CHF_2$ | $CH_3$ | $OCH_3$ | $OCH_3$ | N | |
| $CH_3$ | $OCH_2CHF_2$ | $CH_3$ | $CH_3$ | $OCH_3$ | CH | |
| $CH_3$ | $OCH_2CHF_2$ | $CH_3$ | $OCH_3$ | $OCH_3$ | CH | |
| $CH_3$ | $OCH_2CHF_2$ | H | Br | $OCH_3$ | CH | |
| $CH_3$ | $OCH_2CHF_2$ | $CH_3$ | $OCH_3$ | $N(CH_3)_2$ | N | |
| $CH_3$ | $OCH_2CHF_2$ | H | $CH_3$ | $OCH_2CF_3$ | N | |
| $CH_3$ | $OCH_2CHF_2$ | H | $CH_3$ | $OCH_2CF_3$ | CH | |

TABLE I-continued

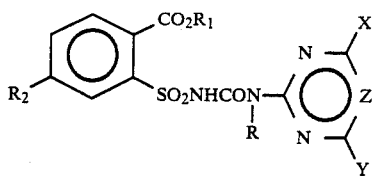

| R₁ | R₂ | R | X | Y | Z | m.p. (°C.) |
|---|---|---|---|---|---|---|
| CH₃ | OCH₂CHF₂ | H | OCH₃ | OCH₂CF₃ | CH | |
| CH₃ | OCH₂CHF₂ | H | OCH₃ | C₂H₅ | CH | |
| CH₃ | OCH₂CHF₂ | H | OCH₃ | C₂H₅ | N | |
| CH₃ | OCH₂CHF₂ | H | OCH₃ | NHCH₃ | CH | |
| CH₃ | OCH₂CHF₂ | H | OCH₃ | NHCH₃ | N | |
| CH₃ | OCH₂CHF₂ | H | CH₃ | OC₂H₅ | CH | |
| CH₃ | OCH₂CHF₂ | H | OCH₃ | OC₂H₅ | CH | |
| CH₃ | OCH₂CHF₂ | H | CH₃ | OC₂H₅ | N | |
| CH₃ | OCH₂CHF₂ | H | OCH₃ | OC₂H₅ | N | |
| CH₃ | OCH₂CHF₂ | H | CH₃ | OCH₂CHF₂ | CH | |
| CH₃ | OCH₂CHF₂ | H | OCH₃ | OCH₂CHF₂ | CH | |
| CH₃ | OCH₂CHF₂ | H | CH₃ | OCH₂CHF₂ | N | |
| CH₃ | OCH₂CHF₂ | H | OCH₃ | OCH₂CHF₂ | N | |
| CH₃ | OCH₂CHF₂ | H | CH₃ | OCH₂CH₂F | CH | |
| CH₃ | OCH₂CHF₂ | H | OCH₃ | OCH₂CH₂F | CH | |
| CH₃ | OCH₂CHF₂ | H | CH₃ | OCH₂CH₂F | N | |
| CH₃ | OCH₂CHF₂ | CH₃ | OCH₃ | OCH₂CH₂F | N | |
| CH₃ | OCH₂CHF₂ | CH₃ | Cl | OCH₃ | CH | |
| CH₃ | OCH₂CHF₂ | H | Cl | N(CH₃)₂ | CH | |
| CH₃ | OCH₂CHF₂ | H | Cl | OC₂H₅ | CH | |
| C₂H₅ | OCH₂CHF₂ | H | CH₃ | CH₃ | CH | |
| C₂H₅ | OCH₂CHF₂ | H | OCH₃ | CH₃ | CH | |
| C₂H₅ | OCH₂CHF₂ | H | OCH₃ | OCH₃ | CH | |
| C₂H₅ | OCH₂CHF₂ | H | Cl | OCH₃ | CH | |
| C₂H₅ | OCH₂CHF₂ | H | CH₃ | CH₃ | N | |
| C₂H₅ | OCH₂CHF₂ | H | OCH₃ | CH₃ | N | |
| C₂H₅ | OCH₂CHF₂ | H | OCH₃ | OCH₃ | N | |
| C₂H₅ | OCH₂CHF₂ | H | Br | OCH₃ | CH | |
| C₂H₅ | OCH₂CHF₂ | H | OCH₃ | N(CH₃)₂ | CH | |
| C₂H₅ | OCH₂CHF₂ | H | OCH₃ | N(CH₃)₂ | N | |
| C₂H₅ | OCH₂CHF₂ | H | OCH₃ | NHCH₃ | N | |
| C₂H₅ | OCH₂CHF₂ | H | OCH₃ | C₂H₅ | CH | |
| C₂H₅ | OCH₂CHF₂ | H | OCH₃ | C₂H₅ | N | |
| C₂H₅ | OCH₂CHF₂ | H | CH₃ | OC₂H₅ | CH | |
| C₂H₅ | OCH₂CHF₂ | H | CH₃ | OC₂H₅ | N | |
| C₂H₅ | OCH₂CHF₂ | H | OCH₃ | OC₂H₅ | CH | |
| C₂H₅ | OCH₂CHF₂ | H | OCH₃ | OC₂H₅ | N | |
| C₂H₅ | OCH₂CHF₂ | H | CH₃ | OCH₂CF₃ | CH | |
| C₂H₅ | OCH₂CHF₂ | H | CH₃ | OCH₂CF₃ | N | |
| C₂H₅ | OCH₂CHF₂ | H | OCH₃ | OCH₂CF₃ | CH | |
| C₂H₅ | OCH₂CHF₂ | H | OCH₃ | OCH₂CF₃ | N | |
| C₂H₅ | OCH₂CHF₂ | H | OCH₃ | OCH₂CHF₂ | CH | |
| C₂H₅ | OCH₂CHF₂ | H | OCH₃ | OCH₂CHF₂ | N | |
| C₂H₅ | OCH₂CHF₂ | H | CH₃ | OCH₂CHF₂ | N | |
| C₂H₅ | OCH₂CHF₂ | H | OCH₃ | OCH₂CH₂F | CH | |
| C₂H₅ | OCH₂CHF₂ | H | OCH₃ | OCH₂CH₂F | N | |
| C₂H₅ | OCH₂CHF₂ | CH₃ | OCH₃ | OCH₃ | CH | |
| C₂H₅ | OCH₂CHF₂ | CH₃ | CH₃ | OCH₃ | N | |
| C₂H₅ | OCH₂CHF₂ | CH₃ | OCH₃ | OCH₃ | N | |
| n-C₃H₇ | OCH₂CHF₂ | H | OCH₃ | OCH₃ | CH | |
| n-C₃H₇ | OCH₂CHF₂ | H | CH₃ | OCH₃ | N | |
| CH(CH₃)₂ | OCH₂CHF₂ | H | OCH₃ | CH₃ | CH | |
| CH(CH₃)₂ | OCH₂CHF₂ | H | OCH₃ | OCH₃ | CH | |
| CH(CH₃)₂ | OCH₂CHF₂ | H | Cl | OCH₃ | CH | |
| CH(CH₃)₂ | OCH₂CHF₂ | H | OCH₃ | CH₃ | N | |
| CH(CH₃)₂ | OCH₂CHF₂ | H | OCH₃ | OCH₃ | N | |
| CH(CH₃)₂ | OCH₂CHF₂ | H | OCH₃ | N(CH₃)₂ | N | |
| CH₃ | OCH₂CF₃ | H | CH₃ | CH₃ | CH | 178–181 (d) |
| CH₃ | OCH₂CF₃ | H | OCH₃ | CH₃ | CH | 177–178 (d) |
| CH₃ | OCH₂CF₃ | H | OCH₃ | OCH₃ | CH | 215–216 (d) |
| CH₃ | OCH₂CF₃ | H | Cl | OCH₃ | CH | 185–187 (d) |
| CH₃ | OCH₂CF₃ | H | OCH₃ | N(CH₃)₂ | CH | |
| CH₃ | OCH₂CF₃ | H | CH₃ | CH₃ | N | |
| CH₃ | OCH₂CF₃ | H | OCH₃ | CH₃ | N | 168–160 (d) |
| CH₃ | OCH₂CF₃ | H | OCH₃ | OCH₃ | N | 178–180 (d) |
| CH₃ | OCH₂CF₃ | H | OCH₃ | N(CH₃)₂ | N | |
| CH₃ | OCH₂CF₃ | H | OCH₃ | OCH₂CF₃ | N | |
| CH₃ | OCH₂CF₃ | H | OC₂H₅ | NHCH₃ | N | |
| CH₃ | OCH₂CF₃ | CH₃ | OCH₃ | CH₃ | N | |
| CH₃ | OCH₂CF₃ | CH₃ | OCH₃ | OCH₃ | N | |
| CH₃ | OCH₂CF₃ | CH₃ | CH₃ | OCH₃ | CH | |

TABLE I-continued

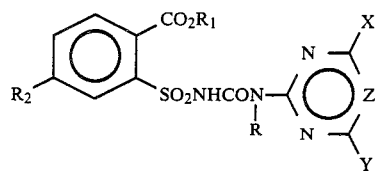

| R₁ | R₂ | R | X | Y | Z | m.p. (°C.) |
|---|---|---|---|---|---|---|
| CH₃ | OCH₂CF₃ | CH₃ | OCH₃ | OCH₃ | CH | |
| CH₃ | OCH₂CF₃ | H | Br | OCH₃ | CH | |
| CH₃ | OCH₂CF₃ | CH₃ | OCH₃ | N(CH₃)₂ | N | |
| CH₃ | OCH₂CF₃ | H | CH₃ | OCH₂CF₃ | N | |
| CH₃ | OCH₂CF₃ | H | CH₃ | OCH₂CF₃ | CH | |
| CH₃ | OCH₂CF₃ | H | OCH₃ | OCH₂CF₃ | CH | |
| CH₃ | OCH₂CF₃ | H | OCH₃ | C₂H₅ | CH | |
| CH₃ | OCH₂CF₃ | H | OCH₃ | C₂H₅ | N | |
| CH₃ | OCH₂CF₃ | H | OCH₃ | NHCH₃ | CH | |
| CH₃ | OCH₂CF₃ | H | OCH₃ | NHCH₃ | N | |
| CH₃ | OCH₂CF₃ | H | CH₃ | OC₂H₅ | CH | |
| CH₃ | OCH₂CF₃ | H | OCH₃ | OC₂H₅ | CH | |
| CH₃ | OCH₂CF₃ | H | CH₃ | OC₂H₅ | N | |
| CH₃ | OCH₂CF₃ | H | OCH₃ | OC₂H₅ | N | |
| CH₃ | OCH₂CF₃ | H | CH₃ | OCH₂CHF₂ | CH | |
| CH₃ | OCH₂CF₃ | H | OCH₃ | OCH₂CHF₂ | CH | |
| CH₃ | OCH₂CF₃ | H | CH₃ | OCH₂CHF₂ | N | |
| CH₃ | OCH₂CF₃ | H | OCH₃ | OCH₂CHF₂ | N | |
| CH₃ | OCH₂CF₃ | H | CH₃ | OCH₂CH₂F | CH | |
| CH₃ | OCH₂CF₃ | H | OCH₃ | OCH₂CH₂F | CH | |
| CH₃ | OCH₂CF₃ | H | CH₃ | OCH₂CH₂F | N | |
| CH₃ | OCH₂CF₃ | CH₃ | OCH₃ | OCH₂CH₂F | N | |
| CH₃ | OCH₂CF₃ | CH₃ | Cl | OCH₃ | CH | |
| CH₃ | OCH₂CF₃ | H | Cl | N(CH₃)₂ | CH | |
| CH₃ | OCH₂CF₃ | H | Cl | OC₂H₅ | CH | |
| C₂H₅ | OCH₂CF₃ | H | CH₃ | CH₃ | CH | |
| C₂H₅ | OCH₂CF₃ | H | OCH₃ | CH₃ | CH | |
| C₂H₅ | OCH₂CF₃ | H | OCH₃ | OCH₃ | CH | |
| C₂H₅ | OCH₂CF₃ | H | Cl | OCH₃ | CH | |
| C₂H₅ | OCH₂CF₃ | H | CH₃ | CH₃ | N | |
| C₂H₅ | OCH₂CF₃ | H | OCH₃ | CH₃ | N | |
| C₂H₅ | OCH₂CF₃ | H | OCH₃ | OCH₃ | N | |
| C₂H₅ | OCH₂CF₃ | H | Br | OCH₃ | CH | |
| C₂H₅ | OCH₂CF₃ | H | OCH₃ | N(CH₃)₂ | CH | |
| C₂H₅ | OCH₂CF₃ | H | OCH₃ | N(CH₃)₂ | N | |
| C₂H₅ | OCH₂CF₃ | H | OCH₃ | NHCH₃ | N | |
| C₂H₅ | OCH₂CF₃ | H | OCH₃ | C₂H₅ | CH | |
| C₂H₅ | OCH₂CF₃ | H | OCH₃ | C₂H₅ | N | |
| C₂H₅ | OCH₂CF₃ | H | CH₃ | OC₂H₅ | CH | |
| C₂H₅ | OCH₂CF₃ | H | CH₃ | OC₂H₅ | N | |
| C₂H₅ | OCH₂CF₃ | H | OCH₃ | OC₂H₅ | CH | |
| C₂H₅ | OCH₂CF₃ | H | OCH₃ | OC₂H₅ | N | |
| C₂H₅ | OCH₂CF₃ | H | CH₃ | OCH₂CF₃ | CH | |
| C₂H₅ | OCH₂CF₃ | H | CH₃ | OCH₂CF₃ | N | |
| C₂H₅ | OCH₂CF₃ | H | OCH₃ | OCH₂CF₃ | CH | |
| C₂H₅ | OCH₂CF₃ | H | OCH₃ | OCH₂CF₃ | N | |
| C₂H₅ | OCH₂CF₃ | H | OCH₃ | OCH₂CHF₂ | CH | |
| C₂H₅ | OCH₂CF₃ | H | OCH₃ | OCH₂CHF₂ | N | |
| C₂H₅ | OCH₂CF₃ | H | CH₃ | OCH₂CHF₂ | N | |
| C₂H₅ | OCH₂CF₃ | H | OCH₃ | OCH₂CH₂F | CH | |
| C₂H₅ | OCH₂CF₃ | H | OCH₃ | OCH₂CH₂F | N | |
| C₂H₅ | OCH₂CF₃ | CH₃ | OCH₃ | OCH₃ | CH | |
| C₂H₅ | OCH₂CF₃ | CH₃ | CH₃ | OCH₃ | N | |
| C₂H₅ | OCH₂CF₃ | CH₃ | OCH₃ | OCH₃ | N | |
| n-C₃H₇ | OCH₂CF₃ | H | OCH₃ | OCH₃ | CH | |
| n-C₃H₇ | OCH₂CF₃ | H | CH₃ | OCH₃ | N | |
| CH(CH₃)₂ | OCH₂CF₃ | H | OCH₃ | CH₃ | CH | |
| CH(CH₃)₂ | OCH₂CF₃ | H | OCH₃ | OCH₃ | CH | |
| CH(CH₃)₂ | OCH₂CF₃ | H | Cl | OCH₃ | CH | |
| CH(CH₃)₂ | OCH₂CF₃ | H | OCH₃ | CH₃ | N | |
| CH(CH₃)₂ | OCH₂CF₃ | H | OCH₃ | OCH₃ | N | |
| CH(CH₃)₂ | OCH₂CF₃ | H | OCH₃ | N(CH₃)₂ | N | |
| CH₃ | OCH₂CH₂Cl | H | CH₃ | CH₃ | CH | |
| CH₃ | OCH₂CH₂Cl | H | OCH₃ | CH₃ | CH | |
| CH₃ | OCH₂CH₂Cl | H | OCH₃ | OCH₃ | CH | |
| CH₃ | OCH₂CH₂Cl | H | Cl | OCH₃ | CH | |
| CH₃ | OCH₂CH₂Cl | H | OCH₃ | N(CH₃)₂ | CH | |
| CH₃ | OCH₂CH₂Cl | H | CH₃ | CH₃ | N | |
| CH₃ | OCH₂CH₂Cl | H | OCH₃ | CH₃ | N | |
| CH₃ | OCH₂CH₂Cl | H | OCH₃ | OCH₃ | N | |
| CH₃ | OCH₂CH₂Cl | H | OCH₃ | N(CH₃)₂ | N | |

TABLE I-continued

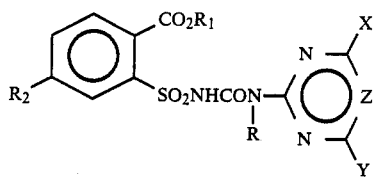

| R₁ | R₂ | R | X | Y | Z | m.p. (°C.) |
|---|---|---|---|---|---|---|
| CH₃ | OCH₂CH₂Cl | H | OCH₃ | OCH₂CF₃ | N | |
| CH₃ | OCH₂CH₂Cl | CH₃ | OCH₃ | CH₃ | N | |
| CH₃ | OCH₂CH₂Cl | CH₃ | OCH₃ | OCH₃ | N | |
| CH₃ | OCH₂CH₂Cl | CH₃ | CH₃ | OCH₃ | CH | |
| CH₃ | OCH₂CH₂Cl | CH₃ | OCH₃ | OCH₃ | CH | |
| CH₃ | OCH₂CH₂Cl | H | Br | OCH₃ | CH | |
| CH₃ | OCH₂CH₂Cl | CH₃ | OCH₃ | N(CH₃)₂ | N | |
| CH₃ | OCH₂CH₂Cl | H | CH₃ | OCH₂CF₃ | N | |
| CH₃ | OCH₂CH₂Cl | H | CH₃ | OCH₂CF₃ | CH | |
| CH₃ | OCH₂CH₂Cl | H | OCH₃ | OCH₂CF₃ | CH | |
| CH₃ | OCH₂CH₂Cl | H | OCH₃ | C₂H₅ | CH | |
| CH₃ | OCH₂CH₂Cl | H | OCH₃ | C₂H₅ | N | |
| CH₃ | OCH₂CH₂Cl | H | OCH₃ | NHCH₃ | CH | |
| CH₃ | OCH₂CH₂Cl | H | OCH₃ | NHCH₃ | N | |
| CH₃ | OCH₂CH₂Cl | H | CH₃ | OC₂H₅ | CH | |
| CH₃ | OCH₂CH₂Cl | H | OCH₃ | OC₂H₅ | CH | |
| CH₃ | OCH₂CH₂Cl | H | CH₃ | OC₂H₅ | N | |
| CH₃ | OCH₂CH₂Cl | H | OCH₃ | OC₂H₅ | N | |
| CH₃ | OCH₂CH₂Cl | H | CH₃ | OCH₂CHF₂ | CH | |
| CH₃ | OCH₂CH₂Cl | H | OCH₃ | OCH₂CHF₂ | CH | |
| CH₃ | OCH₂CH₂Cl | H | CH₃ | OCH₂CHF₂ | N | |
| CH₃ | OCH₂CH₂Cl | H | OCH₃ | OCH₂CHF₂ | N | |
| CH₃ | OCH₂CH₂Cl | H | CH₃ | OCH₂CH₂F | CH | |
| CH₃ | OCH₂CH₂Cl | H | OCH₃ | OCH₂CH₂F | CH | |
| CH₃ | OCH₂CH₂Cl | H | CH₃ | OCH₂CH₂F | N | |
| CH₃ | OCH₂CH₂Cl | CH₃ | OCH₃ | OCH₂CH₂F | N | |
| CH₃ | OCH₂CH₂Cl | CH₃ | Cl | OCH₃ | CH | |
| CH₃ | OCH₂CH₂Cl | H | Cl | N(CH₃)₂ | CH | |
| CH₃ | OCH₂CH₂Cl | H | Cl | OC₂H₅ | CH | |
| C₂H₅ | OCH₂CH₂Cl | H | CH₃ | CH₃ | CH | |
| C₂H₅ | OCH₂CH₂Cl | H | OCH₃ | CH₃ | CH | |
| C₂H₅ | OCH₂CH₂Cl | H | OCH₃ | OCH₃ | CH | |
| C₂H₅ | OCH₂CH₂Cl | H | Cl | OCH₃ | CH | |
| C₂H₅ | OCH₂CH₂Cl | H | CH₃ | CH₃ | N | |
| C₂H₅ | OCH₂CH₂Cl | H | OCH₃ | CH₃ | N | |
| C₂H₅ | OCH₂CH₂Cl | H | OCH₃ | OCH₃ | N | |
| C₂H₅ | OCH₂CH₂Cl | H | Br | OCH₃ | CH | |
| C₂H₅ | OCH₂CH₂Cl | H | OCH₃ | N(CH₃)₂ | CH | |
| C₂H₅ | OCH₂CH₂Cl | H | OCH₃ | N(CH₃)₂ | N | |
| C₂H₅ | OCH₂CH₂Cl | H | OCH₃ | NHCH₃ | N | |
| C₂H₅ | OCH₂CH₂Cl | H | OCH₃ | C₂H₅ | CH | |
| C₂H₅ | OCH₂CH₂Cl | H | OCH₃ | C₂H₅ | N | |
| C₂H₅ | OCH₂CH₂Cl | H | CH₃ | OC₂H | CH | |
| C₂H₅ | OCH₂CH₂Cl | H | CH₃ | OC₂H₅ | N | |
| C₂H₅ | OCH₂CH₂Cl | H | OCH₃ | OC₂H₅ | CH | |
| C₂H₅ | OCH₂CH₂Cl | H | OCH₃ | OC₂H₅ | N | |
| C₂H₅ | OCH₂CH₂Cl | H | CH₃ | OCH₂CF₃ | CH | |
| C₂H₅ | OCH₂CH₂Cl | H | CH₃ | OCH₂CF₃ | N | |
| C₂H₅ | OCH₂CH₂Cl | H | OCH₃ | OCH₂CF₃ | CH | |
| C₂H₅ | OCH₂CH₂Cl | H | OCH₃ | OCH₂CF₃ | N | |
| C₂H₅ | OCH₂CH₂Cl | H | OCH₃ | OCH₂CHF₂ | CH | |
| C₂H₅ | OCH₂CH₂Cl | H | OCH₃ | OCH₂CHF₂ | N | |
| C₂H₅ | OCH₂CH₂Cl | H | CH₃ | OCH₂CHF₂ | CH | |
| C₂H₅ | OCH₂CH₂Cl | H | OCH₃ | OCH₂CH₂F | CH | |
| C₂H₅ | OCH₂CH₂Cl | H | OCH | OCH | N | |
| C₂H₅ | OCH₂CH₂Cl | CH₃ | OCH₃ | OCH₃ | CH | |
| C₂H₅ | OCH₂CH₂Cl | CH₃ | CH₃ | OCH₃ | N | |
| C₂H₅ | OCH₂CH₂Cl | CH₃ | OCH₃ | OCH₃ | N | |
| n-C₃H₇ | OCH₂CH₂Cl | H | OCH₃ | OCH₃ | CH | |
| n-C₃H₇ | OCH₂CH₂Cl | H | CH₃ | OCH₃ | N | |
| CH(CH₃)₂ | OCH₂CH₂Cl | H | OCH₃ | CH₃ | CH | |
| CH(CH₃)₂ | OCH₂CH₂Cl | H | OCH₃ | OCH₃ | CH | |
| CH(CH₃)₂ | OCH₂CH₂Cl | H | Cl | OCH₃ | CH | |
| CH(CH₃)₂ | OCH₂CH₂Cl | H | OCH₃ | CH₃ | N | |
| CH(CH₃)₂ | OCH₂CH₂Cl | H | OCH₃ | OCH₃ | N | |
| CH(CH₃)₂ | OCH₂CH₂Cl | H | OCH₃ | N(CH₃)₂ | N | |
| CH₃ | OCH₂CH₂OCH₃ | H | CH₃ | CH₃ | CH | 167–169 (d) |
| CH₃ | OCH₂CH₂OCH₃ | H | OCH₃ | CH₃ | CH | oil |
| CH₃ | OCH₂CH₂OCH₃ | H | OCH₃ | OCH₃ | CH | 175–177 (d) |
| CH₃ | OCH₂CH₂OCH₃ | H | Cl | OCH₃ | CH | 98–100 (d) |
| CH₃ | OCH₂CH₂OCH₃ | H | OCH₃ | N(CH₃)₂ | CH | |

TABLE I-continued

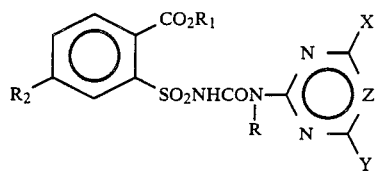

| R₁ | R₂ | R | X | Y | Z | m.p. (°C.) |
|---|---|---|---|---|---|---|
| CH₃ | OCH₂CH₂OCH₃ | H | CH₃ | CH₃ | N | 117–120 (d) |
| CH₃ | OCH₂CH₂OCH₃ | H | OCH₃ | CH₃ | N | 75–80 (d) |
| CH₃ | OCH₂CH₂OCH₃ | H | OCH₃ | OCH₃ | N | 154–156 (d) |
| CH₃ | OCH₂CH₂OCH₃ | H | OCH₃ | N(CH₃)₂ | N | |
| CH₃ | OCH₂CH₂OCH₃ | H | OCH₃ | OCH₂CF₃ | N | |
| CH₃ | OCH₂CH₂OCH₃ | CH₃ | OCH₃ | CH₃ | N | |
| CH₃ | OCH₂CH₂OCH₃ | CH₃ | OCH₃ | OCH₃ | N | |
| CH₃ | OCH₂CH₂OCH₃ | CH₃ | CH₃ | OCH₃ | CH | |
| CH₃ | OCH₂CH₂OCH₃ | CH₃ | OCH₃ | OCH₃ | CH | |
| CH₃ | OCH₂CH₂OCH₃ | H | Br | OCH₃ | CH | |
| CH₃ | OCH₂CH₂OCH₃ | H | CH₃ | OCH₂CF₃ | N | |
| CH₃ | OCH₂CH₂OCH₃ | H | CH₃ | OCH₂CF₃ | CH | |
| CH₃ | OCH₂CH₂OCH₃ | H | OCH₃ | OCH₂CF₃ | CH | |
| CH₃ | OCH₂CH₂OCH₃ | H | OCH₃ | C₂H₅ | CH | |
| CH₃ | OCH₂CH₂OCH₃ | H | OCH₃ | C₂H₅ | N | |
| CH₃ | OCH₂CH₂OCH₃ | H | OCH₃ | NHCH₃ | CH | |
| CH₃ | OCH₂CH₂OCH₃ | H | OCH₃ | NHCH₃ | N | |
| CH₃ | OCH₂CH₂OCH₃ | H | CH₃ | OC₂H₅ | CH | |
| CH₃ | OCH₂CH₂OCH₃ | H | OCH₃ | OC₂H₅ | CH | |
| CH₃ | OCH₂CH₂OCH₃ | H | CH₃ | OC₂H₅ | N | |
| CH₃ | OCH₂CH₂OCH₃ | H | OCH₃ | OC₂H₅ | N | |
| CH₃ | OCH₂CH₂OCH₃ | H | CH₃ | OCH₂CHF₂ | CH | |
| CH₃ | OCH₂CH₂OCH₃ | H | OCH₃ | OCH₂CHF₂ | CH | |
| CH₃ | OCH₂CH₂OCH₃ | H | CH₃ | OCH₂CHF₂ | N | |
| CH₃ | OCH₂CH₂OCH₃ | H | OCH₃ | OCH₂CHF₂ | N | |
| CH₃ | OCH₂CH₂OCH₃ | H | CH₃ | OCH₂CH₂F | CH | |
| CH₃ | OCH₂CH₂OCH₃ | H | OCH₃ | OCH₂CH₂F | CH | |
| CH₃ | OCH₂CH₂OCH₃ | H | CH₃ | OCH₂CF₃ | N | |
| CH₃ | OCH₂CH₂OCH₃ | CH₃ | OCH₃ | OCH₂CF₃ | N | |
| CH₃ | OCH₂CH₂OCH₃ | CH₃ | Cl | OCH₃ | CH | |
| CH₃ | OCH₂CH₂OCH₃ | H | Cl | N(CH₃)₂ | CH | |
| CH₃ | OCH₂CH₂OCH₃ | H | Cl | OC₂H₅ | CH | |
| C₂H₅ | OCH₂CH₂OCH₃ | H | Cl | OC₂H₅ | CH | |
| C₂H₅ | OCH₂CH₂OCH₃ | H | CH₃ | CH₃ | CH | |
| C₂H₅ | OCH₂CH₂OCH₃ | H | OCH₃ | CH₃ | CH | |
| C₂H₅ | OCH₂CH₂OCH₃ | H | OCH₃ | OCH₃ | CH | |
| C₂H₅ | OCH₂CH₂OCH₃ | H | Cl | OCH₃ | CH | |
| C₂H₅ | OCH₂CH₂OCH₃ | H | CH₃ | CH₃ | N | |
| C₂H₅ | OCH₂CH₂OCH₃ | H | OCH₃ | CH₃ | N | |
| C₂H₅ | OCH₂CH₂OCH₃ | H | OCH₃ | OCH₃ | N | |
| C₂H₅ | OCH₂CH₂OCH₃ | H | Br | OCH₃ | CH | |
| C₂H₅ | OCH₂CH₂OCH₃ | H | OCH₃ | N(CH₃)₂ | CH | |
| C₂H₅ | OCH₂CH₂OCH₃ | H | OCH₃ | N(CH₃)₂ | N | |
| C₂H₅ | OCH₂CH₂OCH₃ | H | OCH₃ | NHCH₃ | N | |
| C₂H₅ | OCH₂CH₂OCH₃ | H | OCH₃ | C₂H₅ | CH | |
| C₂H₅ | OCH₂CH₂OCH₃ | H | OCH₃ | C₂H₅ | N | |
| C₂H₅ | OCH₂CH₂OCH₃ | H | CH₃ | OC₂H₅ | CH | |
| C₂H₅ | OCH₂CH₂OCH₃ | H | CH₃ | OC₂H₅ | N | |
| C₂H₅ | OCH₂CH₂OCH₃ | H | OCH₃ | OC₂H₅ | CH | |
| C₂H₅ | OCH₂CH₂OCH₃ | H | OCH₃ | OC₂H₅ | N | |
| C₂H₅ | OCH₂CH₂OCH₃ | H | CH₃ | OCH₂CF₃ | CH | |
| C₂H₅ | OCH₂CH₂OCH₃ | H | CH₃ | OCH₂CF₃ | N | |
| C₂H₅ | OCH₂CH₂OCH₃ | H | OCH₃ | OCH₂CF₃ | CH | |
| C₂H₅ | OCH₂CH₂OCH₃ | H | OCH₃ | OCH₂CF₃ | N | |
| C₂H₅ | OCH₂CH₂OCH₃ | H | OCH₃ | OCH₂CHF₂ | CH | |
| C₂H₅ | OCH₂CH₂OCH₃ | H | OCH₃ | OCH₂CHF₂ | N | |
| C₂H₅ | OCH₂CH₂OCH₃ | H | CH₃ | OCH₂CHF₂ | N | |
| C₂H₅ | OCH₂CH₂OCH₃ | H | OCH₃ | OCH₂CH₂F | CH | |
| C₂H₅ | OCH₂CH₂OCH₃ | H | OCH₃ | OCH₂CH₂F | N | |
| C₂H₅ | OCH₂CH₂OCH₃ | CH₃ | OCH₃ | OCH₃ | CH | |
| C₂H₅ | OCH₂CH₂OCH₃ | CH₃ | CH₃ | OCH₃ | N | |
| C₂H₅ | OCH₂CH₂OCH₃ | CH₃ | OCH₃ | OCH₃ | N | |
| n-C₃H₇ | OCH₂CH₂OCH₃ | H | OCH₃ | OCH₃ | CH | |
| n-C₃H₇ | OCH₂CH₂OCH₃ | H | CH₃ | OCH₃ | N | |
| CH(CH₃)₂ | OCH₂CH₂OCH₃ | H | OCH₃ | CH₃ | CH | |
| CH(CH₃)₂ | OCH₂CH₂OCH₃ | H | OCH₃ | OCH₃ | CH | |
| CH(CH₃)₂ | OCH₂CH₂OCH₃ | H | Cl | OCH₃ | CH | |
| CH(CH₃)₂ | OCH₂CH₂OCH₃ | H | OCH₃ | CH₃ | N | |
| CH(CH₃)₂ | OCH₂CH₂OCH₃ | H | OCH₃ | OCH₃ | N | |
| CH(CH₃)₂ | OCH₂CH₂OCH₃ | H | OCH₃ | N(CH₃)₂ | N | |
| CH₃ | OCH₂CH₂S(O)CH₃ | H | OCH₃ | CH₃ | CH | |

TABLE I-continued

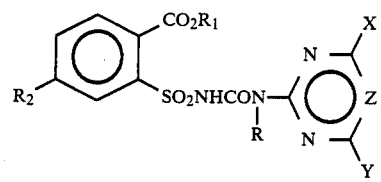

| R₁ | R₂ | R | X | Y | Z | m.p. (°C.) |
|---|---|---|---|---|---|---|
| CH₃ | OCH₂CH₂S(O)CH₃ | H | OCH₃ | OCH₃ | CH | |
| CH₃ | OCH₂CH₂S(O)CH₃ | H | OCH₃ | OCH₃ | N | |
| CH₃ | OCH₂CH₂S(O)CH₃ | H | OCH₃ | CH₃ | N | |
| CH₃ | OCH₂CH₂SO₂CH₃ | H | OCH₃ | OCH₃ | N | |
| CH₃ | OCH₂CH₂SO₂CH₃ | H | OCH₃ | CH₃ | N | |
| CH₃ | OCH₂CH₂SO₂CH₃ | H | OCH₃ | OCH₃ | CH | |
| CH₃ | OCH₂CH₂SO₂CH₃ | H | OCH₃ | CH₃ | CH | |
| CH₃ | OCH₂CH₂SCH₃ | H | CH₃ | CH₃ | CH | |
| CH₃ | OCH₂CH₂SCH₃ | H | OCH₃ | CH₃ | CH | |
| CH₃ | OCH₂CH₂SCH₃ | H | OCH₃ | OCH₃ | CH | |
| CH₃ | OCH₂CH₂SCH₃ | H | Cl | OCH₃ | CH | |
| CH₃ | OCH₂CH₂SCH₃ | H | OCH₃ | N(CH₃)₂ | CH | |
| CH₃ | OCH₂CH₂SCH₃ | H | CH₃ | CH₃ | N | |
| CH₃ | OCH₂CH₂SCH₃ | H | OCH₃ | CH₃ | N | |
| CH₃ | OCH₂CH₂SCH₃ | H | OCH₃ | OCH₃ | N | |
| CH₃ | OCH₂CH₂SCH₃ | H | OCH₃ | N(CH₃)₂ | N | |
| CH₃ | OCH₂CH₂SCH₃ | H | OCH₃ | OCH₂CF₃ | N | |
| CH₃ | OCH₂CH₂SCH₃ | CH₃ | OCH₃ | CH₃ | N | |
| CH₃ | OCH₂CH₂SCH₃ | CH₃ | OCH₃ | OCH₃ | N | |
| CH₃ | OCH₂CH₂SCH₃ | CH₃ | CH₃ | OCH₃ | CH | |
| CH₃ | OCH₂CH₂SCH₃ | CH₃ | OCH₃ | OCH₃ | CH | |
| CH₃ | OCH₂CH₂SCH₃ | H | Br | OCH₃ | CH | |
| CH₃ | OCH₂CH₂SCH₃ | CH₃ | OCH₃ | N(CH₃)₂ | N | |
| CH₃ | OCH₂CH₂SCH₃ | H | CH₃ | OCH₂CF₃ | N | |
| CH₃ | OCH₂CH₂SCH₃ | H | CH₃ | OCH₂CF₃ | CH | |
| CH₃ | OCH₂CH₂SCH₃ | H | OCH₃ | OCH₂CF₃ | CH | |
| CH₃ | OCH₂CH₂SCH₃ | H | OCH₃ | C₂H₅ | CH | |
| CH₃ | OCH₂CH₂SCH₃ | H | OCH₃ | C₂H₅ | N | |
| CH₃ | OCH₂CH₂SCH₃ | H | OCH₃ | NHCH₃ | CH | |
| CH₃ | OCH₂CH₂SCH₃ | H | OCH₃ | NHCH₃ | N | |
| CH₃ | OCH₂CH₂SCH₃ | H | CH₃ | OC₂H₅ | CH | |
| CH₃ | OCH₂CH₂SCH₃ | H | OCH₃ | OC₂H₅ | CH | |
| CH₃ | OCH₂CH₂SCH₃ | H | CH₃ | OC₂H₅ | N | |
| CH₃ | OCH₂CH₂SCH₃ | H | OCH₃ | OC₂H₅ | N | |
| CH₃ | OCH₂CH₂SCH₃ | H | CH₃ | OCH₂CHF₂ | CH | |
| CH₃ | OCH₂CH₂SCH₃ | H | OCH₃ | OCH₂CHF₂ | CH | |
| CH₃ | OCH₂CH₂SCH₃ | H | CH₃ | OCH₂CHF₂ | N | |
| CH₃ | OCH₂CH₂SCH₃ | H | OCH₃ | OCH₂CHF₂ | N | |
| CH₃ | OCH₂CH₂SCH₃ | H | CH₃ | OCH₂CH₂F | CH | |
| CH₃ | OCH₂CH₂SCH₃ | H | OCH₃ | OCH₂CH₂F | CH | |
| CH₃ | OCH₂CH₂SCH₃ | H | CH₃ | OCH₂CH₂F | N | |
| CH₃ | OCH₂CH₂SCH₃ | CH₃ | OCH₃ | OCH₂CH₂F | N | |
| CH₃ | OCH₂CH₂SCH₃ | CH₃ | Cl | OCH₃ | CH | |
| CH₃ | OCH₂CH₂SCH₃ | H | Cl | N(CH₃)₂ | CH | |
| CH₃ | OCH₂CH₂SCH₃ | H | Cl | OC₂H₅ | CH | |
| C₂H₅ | OCH₂CH₂SCH₃ | H | CH₃ | CH₃ | CH | |
| C₂H₅ | OCH₂CH₂SCH₃ | H | OCH₃ | CH₃ | CH | |
| C₂H₅ | OCH₂CH₂SCH₃ | H | OCH₃ | OCH₃ | CH | |
| C₂H₅ | OCH₂CH₂SCH₃ | H | Cl | OCH₃ | CH | |
| C₂H₅ | OCH₂CH₂SCH₃ | H | CH₃ | CH₃ | N | |
| C₂H₅ | OCH₂CH₂SCH₃ | H | OCH₃ | CH₃ | N | |
| C₂H₅ | OCH₂CH₂SCH₃ | H | OCH₃ | OCH₃ | N | |
| C₂H₅ | OCH₂CH₂SCH₃ | H | Br | OCH₃ | CH | |
| C₂H₅ | OCH₂CH₂SCH₃ | H | OCH₃ | N(CH₃)₂ | CH | |
| C₂H₅ | OCH₂CH₂SCH₃ | H | OCH₃ | N(CH₃)₂ | N | |
| C₂H₅ | OCH₂CH₂SCH₃ | H | OCH₃ | NHCH₃ | N | |
| C₂H₅ | OCH₂CH₂SCH₃ | H | OCH₃ | C₂H₅ | CH | |
| C₂H₅ | OCH₂CH₂SCH₃ | H | OCH₃ | C₂H₅ | N | |
| C₂H₅ | OCH₂CH₂SCH₃ | H | CH₃ | OC₂H₅ | CH | |
| C₂H₅ | OCH₂CH₂SCH₃ | H | CH₃ | OC₂H₅ | N | |
| C₂H₅ | OCH₂CH₂SCH₃ | H | OCH₃ | OC₂H₅ | CH | |
| C₂H₅ | OCH₂CH₂SCH₃ | H | OCH₃ | OC₂H₅ | N | |
| C₂H₅ | OCH₂CH₂SCH₃ | H | CH₃ | OCH₂CF₃ | CH | |
| C₂H₅ | OCH₂CH₂SCH₃ | H | CH₃ | OCH₂CF₃ | N | |
| C₂H₅ | OCH₂CH₂SCH₃ | H | OCH₃ | OCH₂CF₃ | CH | |
| C₂H₅ | OCH₂CH₂SCH₃ | H | OCH₃ | OCH₂CF₃ | N | |
| C₂H₅ | OCH₂CH₂SCH₃ | H | OCH₃ | OCH₂CHF₂ | CH | |
| C₂H₅ | OCH₂CH₂SCH₃ | H | OCH₃ | OCH₂CHF₂ | N | |
| C₂H₅ | OCH₂CH₂SCH₃ | H | CH₃ | OCH₂CHF₂ | N | |
| C₂H₅ | OCH₂CH₂SCH₃ | H | OCH₃ | OCH₂CH₂F | CH | |
| C₂H₅ | OCH₂CH₂SCH₃ | H | OCH₃ | OCH₂CH₂F | N | |

TABLE I-continued

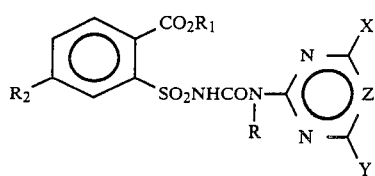

| R₁ | R₂ | R | X | Y | Z | m.p. (°C.) |
|---|---|---|---|---|---|---|
| $C_2H_5$ | $OCH_2CH_2SCH_3$ | $CH_3$ | $OCH_3$ | $OCH_3$ | CH | |
| $C_2H_5$ | $OCH_2CH_2SCH_3$ | $CH_3$ | $CH_3$ | $OCH_3$ | N | |
| $C_2H_5$ | $OCH_2CH_2SCH_3$ | $CH_3$ | $OCH_3$ | $OCH_3$ | N | |
| n-$C_3H_7$ | $OCH_2CH_2SCH_3$ | H | $OCH_3$ | $OCH_3$ | CH | |
| n-$C_3H_7$ | $OCH_2CH_2SCH_3$ | H | $CH_3$ | $OCH_3$ | N | |
| $CH(CH_3)_2$ | $OCH_2CH_2SCH_3$ | H | $OCH_3$ | $CH_3$ | CH | |
| $CH(CH_3)_2$ | $OCH_2CH_2SCH_3$ | H | $OCH_3$ | $OCH_3$ | CH | |
| $CH(CH_3)_2$ | $OCH_2CH_2SCH_3$ | H | Cl | $OCH_3$ | CH | |
| $CH(CH_3)_2$ | $OCH_2CH_2SCH_3$ | H | $OCH_3$ | $CH_3$ | N | |
| $CH(CH_3)_2$ | $OCH_2CH_2SCH_3$ | H | $OCH_3$ | $OCH_3$ | N | |
| $CH(CH_3)_2$ | $OCH_2CH_2SCH_3$ | H | $OCH_3$ | $N(CH_3)_2$ | N | |
| $CH_3$ | $OCH_2CH_3$ | H | $OCH_2CH_3$ | $NHCH_3$ | N | |
| $CH_3$ | $CH_2CH_3$ | H | $OCH_2CH_3$ | $NHCH_3$ | N | |
| $CH_3$ | $SC(CH_3)_3$ | H | $OCH_2CH_3$ | $NHCH_3$ | N | |
| $CH_3$ | $S(O)CH_2CH_3$ | H | $OCH_2CH_3$ | $NHCH_3$ | N | |
| $CH_3$ | $S(O)CH_2CH_2CH_3$ | H | $OCH_2CH_3$ | $NHCH_3$ | N | |

TABLE Ia

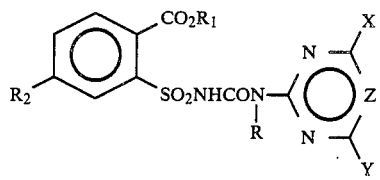

| R₁ | R₂ | R | X | Y | Z | m.p. (°C.) |
|---|---|---|---|---|---|---|
| $CH_3$ | O—cyclopropyl | H | $CH_3$ | $CH_3$ | CH | |
| $CH_3$ | O—cyclopropyl | H | $OCH_3$ | $CH_3$ | CH | |
| $CH_3$ | O—cyclopropyl | H | $OCH_3$ | $OCH_3$ | CH | |
| $CH_3$ | O—cyclopropyl | H | Cl | $OCH_3$ | CH | |
| $CH_3$ | O—cyclopropyl | H | $OCH_3$ | $N(CH_3)_2$ | CH | |
| $CH_3$ | O—cyclopropyl | H | $CH_3$ | $CH_3$ | N | |
| $CH_3$ | O—cyclopropyl | H | $OCH_3$ | $CH_3$ | N | |
| $CH_3$ | O—cyclopropyl | H | $OCH_3$ | $OCH_3$ | N | |
| $CH_3$ | O—cyclopropyl | H | $OCH_3$ | $N(CH_3)_2$ | N | |
| $CH_3$ | O—cyclopropyl | H | $OCH_3$ | $OCH_2CF_3$ | N | |
| $CH_3$ | O—cyclopropyl | $CH_3$ | $OCH_3$ | $CH_3$ | N | |
| $CH_3$ | O—cyclopropyl | $CH_3$ | $OCH_3$ | $OCH_3$ | N | |
| $CH_3$ | O—cyclopropyl | $CH_3$ | $CH_3$ | $OCH_3$ | CH | |
| $CH_3$ | O—cyclopropyl | $CH_3$ | $OCH_3$ | $OCH_3$ | CH | |
| $CH_3$ | O—cyclopropyl | H | Br | $OCH_3$ | CH | |
| $CH_3$ | O—cyclopropyl | $CH_3$ | $OCH_3$ | $N(CH_3)_2$ | N | |
| $CH_3$ | O—cyclopropyl | H | $CH_3$ | $OCH_2CF_3$ | N | |
| $CH_3$ | O—cyclopropyl | H | $CH_3$ | $OCH_2CF_3$ | CH | |
| $CH_3$ | O—cyclopropyl | H | $OCH_3$ | $OCH_2CF_3$ | CH | |
| $CH_3$ | O—cyclopropyl | H | $OCH_3$ | $C_2H_5$ | CH | |
| $CH_3$ | O—cyclopropyl | H | $OCH_3$ | $C_2H_5$ | N | |
| $CH_3$ | O—cyclopropyl | H | $OCH_3$ | $NHCH_3$ | CH | |
| $CH_3$ | O—cyclopropyl | H | $OCH_3$ | $NHCH_3$ | N | |
| $CH_3$ | O—cyclopropyl | H | $CH_3$ | $OC_2H_5$ | CH | |
| $CH_3$ | O—cyclopropyl | H | $OCH_3$ | $OC_2H_5$ | CH | |
| $CH_3$ | O—cyclopropyl | H | $CH_3$ | $OC_2H_5$ | N | |
| $CH_3$ | O—cyclopropyl | H | $OCH_3$ | $OC_2H_5$ | N | |
| $CH_3$ | O—cyclopropyl | H | $CH_3$ | $OCH_2CHF_2$ | CH | |
| $CH_3$ | O—cyclopropyl | H | $OCH_3$ | $OCH_2CHF_2$ | CH | |
| $CH_3$ | O—cyclopropyl | H | $CH_3$ | $OCH_2CHF_2$ | N | |
| $CH_3$ | O—cyclopropyl | H | $OCH_3$ | $OCH_2CHF_2$ | N | |
| $CH_3$ | O—cyclopropyl | H | $CH_3$ | $OCH_2CH_2F$ | CH | |
| $CH_3$ | O—cyclopropyl | H | $OCH_3$ | $OCH_2CH_2F$ | CH | |
| $CH_3$ | O—cyclopropyl | H | $CH_3$ | $OCH_2CH_2F$ | N | |
| $CH_3$ | O—cyclopropyl | $CH_3$ | $OCH_3$ | $OCH_2CH_2F$ | N | |
| $CH_3$ | O—cyclopropyl | $CH_3$ | Cl | $OCH_3$ | CH | |
| $CH_3$ | O—cyclopropyl | H | Cl | $N(CH_3)_2$ | CH | |
| $CH_3$ | O—cyclopropyl | H | Cl | $OC_2H_5$ | CH | |
| $C_2H_5$ | O—cyclopropyl | H | $CH_3$ | $CH_3$ | CH | |
| $C_2H_5$ | O—cyclopropyl | H | $OCH_3$ | $CH_3$ | CH | |

TABLE Ia-continued

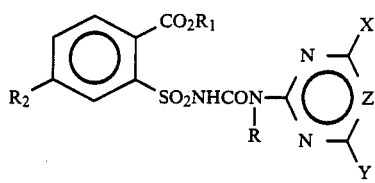

| R₁ | R₂ | R | X | Y | Z | m.p. (°C.) |
|---|---|---|---|---|---|---|
| C₂H₅ | O—cyclopropyl | H | OCH₃ | OCH₃ | CH | |
| C₂H₅ | O—cyclopropyl | H | Cl | OCH₃ | CH | |
| C₂H₅ | O—cyclopropyl | H | CH₃ | CH₃ | N | |
| C₂H₅ | O—cyclopropyl | H | OCH₃ | CH₃ | N | |
| C₂H₅ | O—cyclopropyl | H | OCH₃ | OCH₃ | N | |
| C₂H₅ | O—cyclopropyl | H | Br | OCH₃ | CH | |
| C₂H₅ | O—cyclopropyl | H | OCH₃ | N(CH₃)₂ | CH | |
| C₂H₅ | O—cyclopropyl | H | OCH₃ | N(CH₃)₂ | N | |
| C₂H₅ | O—cyclopropyl | H | OCH₃ | NHCH₃ | N | |
| C₂H₅ | O—cyclopropyl | H | OCH₃ | C₂H₅ | CH | |
| C₂H₅ | O—cyclopropyl | H | OCH₃ | C₂H₅ | N | |
| C₂H₅ | O—cyclopropyl | H | CH₃ | OC₂H₅ | CH | |
| C₂H₅ | O—cyclopropyl | H | CH₃ | OC₂H₅ | N | |
| C₂H₅ | O—cyclopropyl | H | OCH₃ | OC₂H₅ | CH | |
| C₂H₅ | O—cyclopropyl | H | OCH₃ | OC₂H₅ | N | |
| C₂H₅ | O—cyclopropyl | H | CH₃ | OCH₂CF₃ | CH | |
| C₂H₅ | O—cyclopropyl | H | CH₃ | OCH₂CF₃ | N | |
| C₂H₅ | O—cyclopropyl | H | OCH₃ | OCH₂CF₃ | CH | |
| C₂H₅ | O—cyclopropyl | H | OCH₃ | OCH₂CF₃ | N | |
| C₂H₅ | O—cyclopropyl | H | OCH₃ | OCH₂CHF₂ | CH | |
| C₂H₅ | O—cyclopropyl | H | OCH₃ | OCH₂CHF₂ | N | |
| C₂H₅ | O—cyclopropyl | H | CH₃ | OCH₂CHF₂ | N | |
| C₂H₅ | O—cyclopropyl | H | OCH₃ | OCH₂CH₂F | CH | |
| C₂H₅ | O—cyclopropyl | H | OCH₃ | OCH₂CH₂F | N | |
| C₂H₅ | O—cyclopropyl | CH₃ | OCH₃ | OCH₃ | CH | |
| C₂H₅ | O—cyclopropyl | CH₃ | CH₃ | OCH₃ | N | |
| C₂H₅ | O—cyclopropyl | CH₃ | OCH₃ | OCH₃ | N | |
| n-C₃H₇ | O—cyclopropyl | H | OCH₃ | OCH₃ | CH | |
| n-C₃H₇ | O—cyclopropyl | H | CH₃ | OCH₃ | N | |
| CH(CH₃)₂ | O—cyclopropyl | H | OCH₃ | CH₃ | CH | |
| CH(CH₃)₂ | O—cyclopropyl | H | OCH₃ | OCH₃ | CH | |
| CH(CH₃)₂ | O—cyclopropyl | H | Cl | OCH₃ | CH | |
| CH(CH₃)₂ | O—cyclopropyl | H | OCH₃ | CH₃ | N | |
| CH(CH₃)₂ | O—cyclopropyl | H | OCH₃ | OCH₃ | N | |
| CH(CH₃)₂ | O—cyclopropyl | H | OCH₃ | N(CH₃)₂ | N | |
| CH₃ | OCH₂—cyclopropyl | H | OCH₃ | OCH₃ | CH | |
| CH₃ | OCH₂—cyclopropyl | H | OCH₃ | CH₃ | CH | |
| CH₃ | OCH₂—cyclopropyl | H | OCH₃ | Cl | CH | |
| CH₃ | OCH₂—cyclopropyl | H | CH₃ | CH₃ | CH | |
| CH₃ | OCH₂—cyclopropyl | H | OCH₃ | OCH₃ | N | |
| CH₃ | OCH₂—cyclopropyl | H | OCH₃ | CH₃ | N | |
| CH₃ | O—cyclobutyl | H | OCH₃ | OCH₃ | CH | |
| CH₃ | O—cyclobutyl | H | OCH₃ | CH₃ | CH | |
| CH₃ | O—cyclobutyl | H | OCH₃ | Cl | CH | |
| CH₃ | O—cyclobutyl | H | CH₃ | CH₃ | CH | |
| CH₃ | O—cyclobutyl | H | OCH₃ | OCH₃ | N | |
| CH₂CH₃ | O—cyclobutyl | H | OCH₃ | CH₃ | N | |
| CH₃ | OCH₂CF₂CF₃ | H | OCH₃ | OCH₃ | CH | |
| CH₃ | OCH₂CF₂CF₃ | H | OCH₃ | CH₃ | CH | |
| CH₃ | OCH₂CF₂CF₃ | H | OCH₃ | Cl | CH | |
| CH₃ | OCH₂CF₂CF₃ | H | CH₃ | CH₃ | CH | |
| CH₃ | OCH₂CF₂CF₃ | H | OCH₃ | OCH₃ | N | |
| CH₃ | OCH₂CF₂CF₃ | H | OCH₃ | CH₃ | N | |
| CH₃ | OCH(CF₃)CH₃ | H | OCH₃ | OCH₃ | CH | |
| CH₃ | OCH(CF₃)CH₃ | H | OCH₃ | CH₃ | CH | |
| CH₃ | OCH(CF₃)CH₃ | H | OCH₃ | Cl | CH | |
| CH₃ | OCH(CF₃)CH₃ | H | CH₃ | CH₃ | CH | |
| CH₃ | OCH(CF₃)CH₃ | H | OCH₃ | OCH₃ | N | |
| CH₃ | OCH(CF₃)CH₃ | H | OCH₃ | CH₃ | N | |
| CH₃ | OCH₂CF₂CF₂H | H | OCH₃ | OCH₃ | CH | |
| CH₃ | OCH₂CF₂CF₂H | H | OCH₃ | CH₃ | CH | |
| CH₃ | OCH₂CF₂CF₂H | H | OCH₃ | Cl | CH | |
| CH₃ | OCH₂CF₂CF₂H | H | CH₃ | CH₃ | CH | |
| CH₃ | OCH₂CF₂CF₂H | H | OCH₃ | OCH₃ | N | |
| CH₂CH₃ | OCH₂CF₂CF₂H | H | OCH₃ | CH₃ | N | |
| CH₃ | OCH(CH₂F)₂ | H | OCH₃ | OCH₃ | CH | |
| CH₃ | OCH(CH₂F)₂ | H | OCH₃ | CH₃ | CH | |
| CH₃ | OCH(CH₂F)₂ | H | OCH₃ | Cl | CH | |
| CH₃ | OCH(CH₂F)₂ | H | CH₃ | CH₃ | CH | |
| CH₃ | OCH(CH₂F)₂ | H | OCH₃ | OCH₃ | N | |
| CH₃ | OCH(CH₂F)₂ | H | OCH₃ | CH₃ | N | |

TABLE Ia-continued

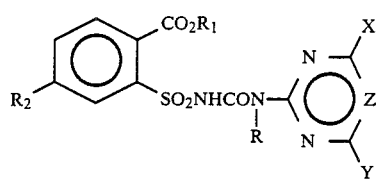

| $R_1$ | $R_2$ | R | X | Y | Z | m.p. (°C.) |
|---|---|---|---|---|---|---|
| $CH_3$ | $OCH(CH_2F)CH_3$ | H | $OCH_3$ | $OCH_3$ | CH | |
| $CH_3$ | $OCH(CH_2F)CH_3$ | H | $OCH_3$ | $CH_3$ | CH | |
| $CH_3$ | $OCH(CH_2F)CH_3$ | H | $OCH_3$ | Cl | CH | |
| $CH_3$ | $OCH(CH_2F)CH_3$ | H | $CH_3$ | $CH_3$ | CH | |
| $CH_3$ | $OCH(CH_2F)CH_3$ | H | $OCH_3$ | $OCH_3$ | N | |
| $CH_3$ | $OCH(CH_2F)CH_3$ | H | $OCH_3$ | $CH_3$ | N | |
| $CH_3$ | $O(CH_2)_5CH_2Cl$ | H | $OCH_3$ | $OCH_3$ | CH | |
| $CH_3$ | $O(CH_2)_5CH_2Cl$ | H | $OCH_3$ | $CH_3$ | CH | |
| $CH_3$ | $O(CH_2)_5CH_2Cl$ | H | $OCH_3$ | Cl | CH | |
| $CH_3$ | $O(CH_2)_5CH_2Cl$ | H | $CH_3$ | $CH_3$ | CH | |
| $CH_3$ | $O(CH_2)_5CH_2Cl$ | H | $OCH_3$ | $OCH_3$ | N | |
| $CH_2CH_3$ | $O(CH_2)_5CH_2Cl$ | H | $OCH_3$ | $CH_3$ | N | |
| $CH_3$ | $OC(Cl)CHCl$ | H | $OCH_3$ | $OCH_3$ | CH | |
| $CH_3$ | $OC(Cl)CHCl$ | H | $OCH_3$ | $CH_3$ | CH | |
| $CH_3$ | $OC(Cl)CHCl$ | H | $OCH_3$ | Cl | CH | |
| $CH_3$ | $OC(Cl)CHCl$ | H | $CH_3$ | $CH_3$ | CH | |
| $CH_3$ | $OC(Cl)CHCl$ | H | $OCH_3$ | $OCH_3$ | N | |
| $CH_3$ | $OC(Cl)CHCl$ | H | $OCH_3$ | $CH_3$ | N | |
| $CH_3$ | $OCH_2C(Cl)CH_2$ | H | $OCH_3$ | $OCH_3$ | CH | |
| $CH_3$ | $OCH_2C(Cl)CH_2$ | H | $OCH_3$ | $CH_3$ | CH | |
| $CH_3$ | $OCH_2C(Cl)CH_2$ | H | $OCH_3$ | Cl | CH | |
| $CH_3$ | $OCH_2C(Cl)CH_2$ | H | $CH_3$ | $CH_3$ | CH | |
| $CH_3$ | $OCH_2C(Cl)CH_2$ | H | $OCH_3$ | $OCH_3$ | N | |
| $CH_3$ | $OCH_2C(Cl)CH_2$ | H | $OCH_3$ | $CH_3$ | N | |
| $CH_3$ | $OCH_2CCCH_2Cl$ | H | $OCH_3$ | $OCH_3$ | CH | |
| $CH_3$ | $OCH_2CCCH_2Cl$ | H | $OCH_3$ | $CH_3$ | CH | |
| $CH_3$ | $OCH_2CCCH_2Cl$ | H | $OCH_3$ | Cl | CH | |
| $CH_3$ | $OCH_2CCCH_2Cl$ | H | $CH_3$ | $CH_3$ | CH | |
| $CH_3$ | $OCH_2CCCH_2Cl$ | H | $OCH_3$ | $OCH_3$ | N | |
| $CH_2CH_3$ | $OCH_2CCCH_2Cl$ | H | $OCH_3$ | $CH_3$ | N | |
| $CH_3$ | $OCH_2OCH_3$ | H | $OCH_3$ | $OCH_3$ | CH | |
| $CH_3$ | $OCH_2OCH_3$ | H | $OCH_3$ | $CH_3$ | CH | |
| $CH_3$ | $OCH_2OCH_3$ | H | $OCH_3$ | Cl | CH | |
| $CH_3$ | $OCH_2OCH_3$ | H | $CH_3$ | $CH_3$ | CH | |
| $CH_3$ | $OCH_2OCH_3$ | H | $OCH_3$ | $OCH_3$ | N | |
| $CH_3$ | $OCH_2OCH_3$ | H | $OCH_3$ | $CH_3$ | N | |
| $CH_3$ | $OCH_2OCH_2CF_3$ | H | $OCH_3$ | $OCH_3$ | CH | |
| $CH_3$ | $OCH_2OCH_2CF_3$ | H | $OCH_3$ | $CH_3$ | CH | |
| $CH_3$ | $OCH_2OCH_2CF_3$ | H | $OCH_3$ | Cl | CH | |
| $CH_3$ | $OCH_2OCH_2CF_3$ | H | $CH_3$ | $CH_3$ | CH | |
| $CH_3$ | $OCH_2OCH_2CF_3$ | H | $OCH_3$ | $OCH_3$ | N | |
| $CH_3$ | $OCH_2OCH_2CF_3$ | H | $OCH_3$ | $CH_3$ | N | |
| $CH_3$ | $OCH_2SCH_3$ | H | $OCH_3$ | $OCH_3$ | CH | |
| $CH_3$ | $OCH_2SCH_3$ | H | $OCH_3$ | $CH_3$ | CH | |
| $CH_3$ | $OCH_2SCH_3$ | H | $OCH_3$ | Cl | CH | |
| $CH_3$ | $OCH_2SCH_3$ | H | $CH_3$ | $CH_3$ | CH | |
| $CH_3$ | $OCH_2SCH_3$ | H | $OCH_3$ | $OCH_3$ | N | |
| $CH_2CH_3$ | $OCH_2SCH_3$ | H | $OCH_3$ | $CH_3$ | N | |
| $CH_3$ | $OCH_2CN$ | H | $OCH_3$ | $OCH_3$ | CH | |
| $CH_3$ | $OCH_2CN$ | H | $OCH_3$ | $CH_3$ | CH | |
| $CH_3$ | $OCH_2CN$ | H | $OCH_3$ | Cl | CH | |
| $CH_3$ | $OCH_2CN$ | H | $CH_3$ | $CH_3$ | CH | |
| $CH_3$ | $OCH_2CN$ | H | $OCH_3$ | $OCH_3$ | N | |
| $CH_3$ | $OCH_2CN$ | H | $OCH_3$ | $CH_3$ | N | |
| $CH_3$ | $OCH_2C(O)CH_3$ | H | $OCH_3$ | $OCH_3$ | CH | |
| $CH_3$ | $OCH_2C(O)CH_3$ | H | $OCH_3$ | $CH_3$ | CH | |
| $CH_3$ | $OCH_2C(O)CH_3$ | H | $OCH_3$ | Cl | CH | |
| $CH_3$ | $OCH_2C(O)CH_3$ | H | $CH_3$ | $CH_3$ | CH | |
| $CH_3$ | $OCH_2C(O)CH_3$ | H | $OCH_3$ | $OCH_3$ | N | |
| $CH_3$ | $OCH_2C(O)CH_3$ | H | $OCH_3$ | $CH_3$ | N | |
| $CH_3$ | $OCH_2CH_2N(CH_3)_2$ | H | $OCH_3$ | $OCH_3$ | CH | |
| $CH_3$ | $OCH_2CH_2N(CH_3)_2$ | H | $OCH_3$ | $CH_3$ | CH | |
| $CH_3$ | $OCH_2CH_2N(CH_3)_2$ | H | $OCH_3$ | Cl | CH | |
| $CH_3$ | $OCH_2CH_2N(CH_3)_2$ | H | $CH_3$ | $CH_3$ | CH | |
| $CH_3$ | $OCH_2CH_2N(CH_3)_2$ | H | $OCH_3$ | $OCH_3$ | N | |
| $CH_2CH_3$ | $OCH_2CH_2N(CH_3)_2$ | H | $OCH_3$ | $CH_3$ | N | |
| $CH_3$ | $OCH_2CH_2OCH_2CF_3$ | H | $OCH_3$ | $OCH_3$ | CH | |
| $CH_3$ | $OCH_2CH_2OCH_2CF_3$ | H | $OCH_3$ | $CH_3$ | CH | |
| $CH_3$ | $OCH_2CH_2OCH_2CF_3$ | H | $OCH_3$ | Cl | CH | |
| $CH_3$ | $OCH_2CH_2OCH_2CF_3$ | H | $CH_3$ | $CH_3$ | CH | |
| $CH_3$ | $OCH_2CH_2OCH_2CF_3$ | H | $OCH_3$ | $OCH_3$ | N | |

TABLE Ia-continued

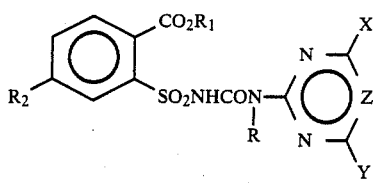

| R₁ | R₂ | R | X | Y | Z | m.p. (°C.) |
|---|---|---|---|---|---|---|
| CH₃ | OCH₂CH₂OCH₂CF₃ | H | OCH₃ | CH₃ | N | |
| CH₃ | OCH₂CH₂SCH₂CF₃ | H | OCH₃ | OCH₃ | CH | |
| CH₃ | OCH₂CH₂SCH₂CF₃ | H | OCH₃ | CH₃ | CH | |
| CH₃ | OCH₂CH₂SCH₂CF₃ | H | OCH₃ | Cl | CH | |
| CH₃ | OCH₂CH₂SCH₂CF₃ | H | CH₃ | CH₃ | CH | |
| CH₃ | OCH₂CH₂SCH₂CF₃ | H | OCH₃ | OCH₃ | N | |
| CH₃ | OCH₂CH₂SCH₂CF₃ | H | OCH₃ | CH₃ | N | |
| CH₃ | OCF₂CF₂H | H | OCH₃ | OCH₃ | CH | |
| CH₃ | OCF₂CF₂H | H | OCH₃ | CH₃ | CH | |
| CH₃ | OCF₂CF₂H | H | OCH₃ | Cl | CH | |
| CH₃ | OCF₂CF₂H | H | CH₃ | CH₃ | CH | |
| CH₃ | OCF₂CF₂H | H | OCH₃ | OCH₃ | N | |
| CH₂CH₃ | OCF₂CF₂H | H | OCH₃ | CH₃ | N | |
| CH₃ | OCH₂CH₂S(O)CH₂CF₃ | H | OCH₃ | OCH₃ | CH | |
| CH₃ | OCH₂CH₂S(O)CH₂CF₃ | H | OCH₃ | CH₃ | CH | |
| CH₃ | OCH₂CH₂S(O)CH₂CF₃ | H | OCH₃ | Cl | CH | |
| CH₃ | OCH₂CH₂S(O)CH₂CF₃ | H | CH₃ | CH₃ | CH | |
| CH₃ | OCH₂CH₂S(O)CH₂CF₃ | H | OCH₃ | OCH₃ | N | |
| CH₃ | OCH₂CH₂S(O)CH₂CF₃ | H | OCH₃ | CH₃ | N | |
| CH₃ | OCH₂CH₂S(O)₂CH₂CF₃ | H | OCH₃ | OCH₃ | CH | |
| CH₃ | OCH₂CH₂S(O)₂CH₂CF₃ | H | OCH₃ | CH₃ | CH | |
| CH₃ | OCH₂CH₂S(O)₂CH₂CF₃ | H | OCH₃ | Cl | CH | |
| CH₃ | OCH₂CH₂S(O)₂CH₂CF₃ | H | CH₃ | CH₃ | CH | |
| CH₃ | OCH₂CH₂S(O)₂CH₂CF₃ | H | OCH₃ | OCH₃ | N | |
| CH₃ | OCH₂CH₂S(O)₂CH₂CF₃ | H | OCH₃ | CH₃ | N | |
| CH₃ | OCH₂CH₂CN | H | OCH₃ | OCH₃ | CH | |
| CH₃ | OCH₂CH₂CN | H | OCH₃ | CH₃ | CH | |
| CH₃ | OCH₂CH₂CN | H | OCH₃ | Cl | CH | |
| CH₃ | OCH₂CH₂CN | H | CH₃ | CH₃ | CH | |
| CH₃ | OCH₂CH₂CN | H | OCH₃ | OCH₃ | N | |
| CH₂CH₃ | OCH₂CH₂CN | H | OCH₃ | CH₃ | N | |
| CH₃ | S—cyclopropyl | H | OCH₃ | OCH₃ | CH | |
| CH₃ | S—cyclopropyl | H | OCH₃ | CH₃ | CH | |
| CH₃ | S—cyclopropyl | H | OCH₃ | Cl | CH | |
| CH₃ | S—cyclopropyl | H | CH₃ | CH₃ | CH | |
| CH₃ | S—cyclopropyl | H | OCH₃ | OCH₃ | N | |
| CH₃ | S—cyclopropyl | H | OCH₃ | CH₃ | N | |
| CH₃ | SCH₂—cyclopropyl | H | OCH₃ | OCH₃ | CH | |
| CH₃ | SCH₂—cyclopropyl | H | OCH₃ | CH₃ | CH | |
| CH₃ | SCH₂—cyclopropyl | H | OCH₃ | Cl | CH | |
| CH₃ | SCH₂—cyclopropyl | H | CH₃ | CH₃ | CH | |
| CH₃ | SCH₂—cyclopropyl | H | OCH₃ | OCH₃ | N | |
| CH₃ | SCH₂—cyclopropyl | H | OCH₃ | CH₃ | N | |
| CH₃ | S—cyclobutyl | H | OCH₃ | OCH₃ | CH | |
| CH₃ | S—cyclobutyl | H | OCH₃ | CH₃ | CH | |
| CH₃ | S—cyclobutyl | H | OCH₃ | Cl | CH | |
| CH₃ | S—cyclobutyl | H | CH₃ | CH₃ | CH | |
| CH₃ | S—cyclobutyl | H | OCH₃ | OCH₃ | N | |
| CH₂CH₃ | S—cyclobutyl | H | OCH₃ | CH₃ | N | |
| CH₃ | SCH₂CF₂CF₃ | H | OCH₃ | OCH₃ | CH | |
| CH₃ | SCH₂CF₂CF₃ | H | OCH₃ | CH₃ | CH | |
| CH₃ | SCH₂CF₂CF₃ | H | OCH₃ | Cl | CH | |
| CH₃ | SCH₂CF₂CF₃ | H | CH₃ | CH₃ | CH | |
| CH₃ | SCH₂CF₂CF₃ | H | OCH₃ | OCH₃ | N | |
| CH₃ | SCH₂CF₂CF₃ | H | OCH₃ | CH₃ | N | |
| CH₃ | SCH(CF₃)CH₃ | H | OCH₃ | OCH₃ | CH | |
| CH₃ | SCH(CF₃)CH₃ | H | OCH₃ | CH₃ | CH | |
| CH₃ | SCH(CF₃)CH₃ | H | OCH₃ | Cl | CH | |
| CH₃ | SCH(CF₃)CH₃ | H | CH₃ | CH₃ | CH | |
| CH₃ | SCH(CF₃)CH₃ | H | OCH₃ | OCH₃ | N | |
| CH₃ | SCH(CF₃)CH₃ | H | OCH₃ | CH₃ | N | |
| CH₃ | SCH₂CF₂CF₂H | H | OCH₃ | OCH₃ | CH | |
| CH₃ | SCH₂CF₂CF₂H | H | OCH₃ | CH₃ | CH | |
| CH₃ | SCH₂CF₂CF₂H | H | OCH₃ | Cl | CH | |
| CH₃ | SCH₂CF₂CF₂H | H | CH₃ | CH₃ | CH | |
| CH₃ | SCH₂CF₂CF₂H | H | OCH₃ | OCH₃ | N | |
| CH₂CH₃ | SCH₂CF₂CF₂H | H | OCH₃ | CH₃ | N | |
| CH₃ | SCH(CH₂F)₂ | H | OCH₃ | OCH₃ | CH | |
| CH₃ | SCH(CH₂F)₂ | H | OCH₃ | CH₃ | CH | |
| CH₃ | SCH(CH₂F)₂ | H | OCH₃ | Cl | CH | |
| CH₃ | SCH(CH₂F)₂ | H | CH₃ | CH₃ | CH | |

TABLE Ia-continued

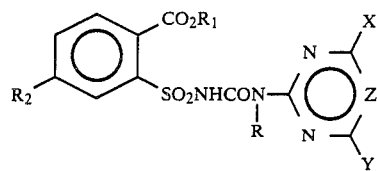

| R₁ | R₂ | R | X | Y | Z | m.p. (°C.) |
|---|---|---|---|---|---|---|
| CH₃ | SCH(CH₂F)₂ | H | OCH₃ | OCH₃ | N | |
| CH₃ | SCH(CH₂F)₂ | H | OCH₃ | CH₃ | N | |
| CH₃ | SCH(CH₂F)CH₃ | H | OCH₃ | OCH₃ | CH | |
| CH₃ | SCH(CH₂F)CH₃ | H | OCH₃ | CH₃ | CH | |
| CH₃ | SCH(CH₂F)CH₃ | H | OCH₃ | Cl | CH | |
| CH₃ | SCH(CH₂F)CH₃ | H | CH₃ | CH₃ | CH | |
| CH₃ | SCH(CH₂F)CH₃ | H | OCH₃ | OCH₃ | N | |
| CH₃ | SCH(CH₂F)CH₃ | H | OCH₃ | CH₃ | N | |
| CH₃ | S(CH₂)₅CH₂Cl | H | OCH₃ | OCH₃ | CH | |
| CH₃ | S(CH₂)₅CH₂Cl | H | OCH₃ | CH₃ | CH | |
| CH₃ | S(CH₂)₅CH₂Cl | H | OCH₃ | Cl | CH | |
| CH₃ | S(CH₂)₅CH₂Cl | H | CH₃ | CH₃ | CH | |
| CH₃ | S(CH₂)₅CH₂Cl | H | OCH₃ | OCH₃ | N | |
| CH₂CH₃ | S(CH₂)₅CH₂Cl | H | OCH₃ | CH₃ | N | |
| CH₃ | SC(Cl)CHCl | H | OCH₃ | OCH₃ | CH | |
| CH₃ | SC(Cl)CHCl | H | OCH₃ | CH₃ | CH | |
| CH₃ | SC(Cl)CHCl | H | OCH₃ | Cl | CH | |
| CH₃ | SC(Cl)CHCl | H | CH₃ | CH₃ | CH | |
| CH₃ | SC(Cl)CHCl | H | OCH₃ | OCH₃ | N | |
| CH₃ | SC(Cl)CHCl | H | OCH₃ | CH₃ | N | |
| CH₃ | SCH₂C(Cl)CH₂ | H | OCH₃ | OCH₃ | CH | |
| CH₃ | SCH₂C(Cl)CH₂ | H | OCH₃ | CH₃ | CH | |
| CH₃ | SCH₂C(Cl)CH₂ | H | OCH₃ | Cl | CH | |
| CH₃ | SCH₂C(Cl)CH₂ | H | CH₃ | CH₃ | CH | |
| CH₃ | SCH₂C(Cl)CH₂ | H | OCH₃ | OCH₃ | N | |
| CH₃ | SCH₂C(Cl)CH₂ | H | OCH₃ | CH₃ | N | |
| CH₃ | SCH₂CCCH₂Cl | H | OCH₃ | OCH₃ | CH | |
| CH₃ | SCH₂CCCH₂Cl | H | OCH₃ | CH₃ | CH | |
| CH₃ | SCH₂CCCH₂Cl | H | OCH₃ | Cl | CH | |
| CH₃ | SCH₂CCCH₂Cl | H | CH₃ | CH₃ | CH | |
| CH₃ | SCH₂CCCH₂Cl | H | OCH₃ | OCH₃ | N | |
| CH₂CH₃ | SCH₂CCCH₂Cl | H | OCH₃ | CH₃ | N | |
| CH₃ | SCH₂OCH₃ | H | OCH₃ | OCH₃ | CH | |
| CH₃ | SCH₂OCH₃ | H | OCH₃ | CH₃ | CH | |
| CH₃ | SCH₂OCH₃ | H | OCH₃ | Cl | CH | |
| CH₃ | SCH₂OCH₃ | H | CH₃ | CH₃ | CH | |
| CH₃ | SCH₂OCH₃ | H | OCH₃ | OCH₃ | N | |
| CH₃ | SCH₂OCH₃ | H | OCH₃ | CH₃ | N | |
| CH₃ | SCH₂OCH₂CF₃ | H | OCH₃ | OCH₃ | CH | |
| CH₃ | SCH₂OCH₂CF₃ | H | OCH₃ | CH₃ | CH | |
| CH₃ | SCH₂OCH₂CF₃ | H | OCH₃ | Cl | CH | |
| CH₃ | SCH₂OCH₂CF₃ | H | CH₃ | CH₃ | CH | |
| CH₃ | SCH₂OCH₂CF₃ | H | OCH₃ | OCH₃ | N | |
| CH₃ | SCH₂OCH₂CF₃ | H | OCH₃ | CH₃ | N | |
| CH₃ | SCH₂SCH₃ | H | OCH₃ | OCH₃ | CH | |
| CH₃ | SCH₂SCH₃ | H | OCH₃ | CH₃ | CH | |
| CH₃ | SCH₂SCH₃ | H | OCH₃ | Cl | CH | |
| CH₃ | SCH₂SCH₃ | H | CH₃ | CH₃ | CH | |
| CH₃ | SCH₂SCH₃ | H | OCH₃ | OCH₃ | N | |
| CH₂CH₃ | SCH₂SCH₃ | H | OCH₃ | CH₃ | N | |
| CH₃ | SCH₂CN | H | OCH₃ | OCH₃ | CH | |
| CH₃ | SCH₂CN | H | OCH₃ | CH₃ | CH | |
| CH₃ | SCH₂CN | H | OCH₃ | Cl | CH | |
| CH₃ | SCH₂CN | H | CH₃ | CH₃ | CH | |
| CH₃ | SCH₂CN | H | OCH₃ | OCH₃ | N | |
| CH₃ | SCH₂CN | H | OCH₃ | CH₃ | N | |
| CH₃ | SCH₂C(O)CH₃ | H | OCH₃ | OCH₃ | CH | |
| CH₃ | SCH₂C(O)CH₃ | H | OCH₃ | CH₃ | CH | |
| CH₃ | SCH₂C(O)CH₃ | H | OCH₃ | Cl | CH | |
| CH₃ | SCH₂C(O)CH₃ | H | CH₃ | CH₃ | CH | |
| CH₃ | SCH₂C(O)CH₃ | H | OCH₃ | OCH₃ | N | |
| CH₃ | SCH₂C(O)CH₃ | H | OCH₃ | CH₃ | N | |
| CH₃ | SCH₂CH₂N(CH₃)₂ | H | OCH₃ | OCH₃ | CH | |
| CH₃ | SCH₂CH₂N(CH₃)₂ | H | OCH₃ | CH₃ | CH | |
| CH₃ | SCH₂CH₂N(CH₃)₂ | H | OCH₃ | Cl | CH | |
| CH₃ | SCH₂CH₂N(CH₃)₂ | H | CH₃ | CH₃ | CH | |
| CH₃ | SCH₂CH₂N(CH₃)₂ | H | OCH₃ | OCH₃ | N | |
| CH₂CH₃ | SCH₂CH₂N(CH₃)₂ | H | OCH₃ | CH₃ | N | |
| CH₃ | SCH₂CH₂OCH₂CF₃ | H | OCH₃ | OCH₃ | CH | |
| CH₃ | SCH₂CH₂OCH₂CF₃ | H | OCH₃ | CH₃ | CH | |
| CH₃ | SCH₂CH₂OCH₂CF₃ | H | OCH₃ | Cl | CH | |

TABLE Ia-continued

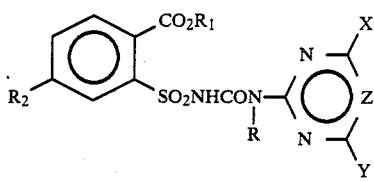

| R₁ | R₂ | R | X | Y | Z | m.p. (°C.) |
|---|---|---|---|---|---|---|
| CH₃ | SCH₂CH₂OCH₂CF₃ | H | CH₃ | CH₃ | CH | |
| CH₃ | SCH₂CH₂OCH₂CF₃ | H | OCH₃ | OCH₃ | N | |
| CH₃ | SCH₂CH₂OCH₂CF₃ | H | OCH₃ | CH₃ | N | |
| CH₃ | SCH₂CH₂SCH₂CF₃ | H | OCH₃ | OCH₃ | CH | |
| CH₃ | SCH₂CH₂SCH₂CF₃ | H | OCH₃ | CH₃ | CH | |
| CH₃ | SCH₂CH₂SCH₂CF₃ | H | OCH₃ | Cl | CH | |
| CH₃ | SCH₂CH₂SCH₂CF₃ | H | CH₃ | CH₃ | CH | |
| CH₃ | SCH₂CH₂SCH₂CF₃ | H | OCH₃ | OCH₃ | N | |
| CH₃ | SCH₂CH₂SCH₂CF₃ | H | OCH₃ | CH₃ | N | |
| CH₃ | SCF₂CF₂H | H | OCH₃ | OCH₃ | CH | |
| CH₃ | SCF₂CF₂H | H | OCH₃ | CH₃ | CH | |
| CH₃ | SCF₂CF₂H | H | OCH₃ | Cl | CH | |
| CH₃ | SCF₂CF₂H | H | CH₃ | CH₃ | CH | |
| CH₃ | SCF₂CF₂H | H | OCH₃ | OCH₃ | N | |
| CH₂CH₃ | SCF₂CF₂H | H | OCH₃ | CH₃ | N | |
| CH₃ | SCH₂CH₂CN | H | OCH₃ | OCH₃ | CH | |
| CH₃ | SCH₂CH₂CN | H | OCH₃ | CH₃ | CH | |
| CH₃ | SCH₂CH₂CN | H | OCH₃ | Cl | CH | |
| CH₃ | SCH₂CH₂CN | H | CH₃ | CH₃ | CH | |
| CH₃ | SCH₂CH₂CN | H | OCH₃ | OCH₃ | N | |
| CH₂CH₃ | SCH₂CH₂CN | H | OCH₃ | CH₃ | N | |
| CH₃ | SCH₂CH₂F | H | OCH₃ | OCH₃ | CH | |
| CH₃ | SCH₂CH₂F | H | OCH₃ | CH₃ | CH | |
| CH₃ | SCH₂CH₂F | H | OCH₃ | Cl | CH | |
| CH₃ | SCH₂CH₂F | H | CH₃ | CH₃ | CH | |
| CH₃ | SCH₂CH₂F | H | OCH₃ | OCH₃ | N | |
| CH₃ | SCH₂CH₂F | H | OCH₃ | CH₃ | N | |
| CH₃ | SCH₂CHF₂ | H | OCH₃ | OCH₃ | CH | |
| CH₃ | SCH₂CHF₂ | H | OCH₃ | CH₃ | CH | |
| CH₃ | SCH₂CHF₂ | H | OCH₃ | Cl | CH | |
| CH₃ | SCH₂CHF₂ | H | CH₃ | CH₃ | CH | |
| CH₃ | SCH₂CHF₂ | H | OCH₃ | OCH₃ | N | |
| CH₃ | SCH₂CHF₂ | H | OCH₃ | CH₃ | N | |
| CH₃ | SCH₂CF₃ | H | OCH₃ | OCH₃ | CH | |
| CH₃ | SCH₂CF₃ | H | OCH₃ | CH₃ | CH | |
| CH₃ | SCH₂CF₃ | H | OCH₃ | Cl | CH | |
| CH₃ | SCH₂CF₃ | H | CH₃ | CH₃ | CH | |
| CH₃ | SCH₂CF₃ | H | OCH₃ | OCH₃ | N | |
| CH₂CH₃ | SCH₂CF₃ | H | OCH₃ | CH₃ | N | |
| CH₃ | S(O)—cyclopropyl | H | OCH₃ | OCH₃ | CH | |
| CH₃ | S(O)—cyclopropyl | H | OCH₃ | CH₃ | CH | |
| CH₃ | S(O)—cyclopropyl | H | OCH₃ | Cl | CH | |
| CH₃ | S(O)—cyclopropyl | H | CH₃ | CH₃ | CH | |
| CH₃ | S(O)—cyclopropyl | H | OCH₃ | OCH₃ | N | |
| CH₃ | S(O)—cyclopropyl | H | OCH₃ | CH₃ | N | |
| CH₃ | S(O)CH₂—cyclopropyl | H | OCH₃ | OCH₃ | CH | |
| CH₃ | S(O)CH₂—cyclopropyl | H | OCH₃ | CH₃ | CH | |
| CH₃ | S(O)CH₂—cyclopropyl | H | OCH₃ | Cl | CH | |
| CH₃ | S(O)CH₂—cyclopropyl | H | CH₃ | CH₃ | CH | |
| CH₃ | S(O)CH₂—cyclopropyl | H | OCH₃ | OCH₃ | N | |
| CH₃ | S(O)CH₂—cyclopropyl | H | OCH₃ | CH₃ | N | |
| CH₃ | S(O)—cyclobutyl | H | OCH₃ | OCH₃ | CH | |
| CH₃ | S(O)—cyclobutyl | H | OCH₃ | CH₃ | CH | |
| CH₃ | S(O)—cyclobutyl | H | OCH₃ | Cl | CH | |
| CH₃ | S(O)—cyclobutyl | H | CH₃ | CH₃ | CH | |
| CH₃ | S(O)—cyclobutyl | H | OCH₃ | OCH₃ | N | |
| CH₂CH₃ | S(O)—cyclobutyl | H | OCH₃ | CH₃ | N | |
| CH₃ | S(O)CH₂CF₂CF₃ | H | OCH₃ | OCH₃ | CH | |
| CH₃ | S(O)CH₂CF₂CF₃ | H | OCH₃ | CH₃ | CH | |
| CH₃ | S(O)CH₂CF₂CF₃ | H | OCH₃ | Cl | CH | |
| CH₃ | S(O)CH₂CF₂CF₃ | H | CH₃ | CH₃ | CH | |
| CH₃ | S(O)CH₂CF₂CF₃ | H | OCH₃ | OCH₃ | N | |
| CH₃ | S(O)CH₂CF₂CF₃ | H | OCH₃ | CH₃ | N | |
| CH₃ | S(O)CH(CF₃)CH₃ | H | OCH₃ | OCH₃ | CH | |
| CH₃ | S(O)CH(CF₃)CH₃ | H | OCH₃ | CH₃ | CH | |
| CH₃ | S(O)CH(CF₃)CH₃ | H | OCH₃ | Cl | CH | |
| CH₃ | S(O)CH(CF₃)CH₃ | H | CH₃ | CH₃ | CH | |
| CH₃ | S(O)CH(CF₃)CH₃ | H | OCH₃ | OCH₃ | N | |
| CH₃ | S(O)CH(CF₃)CH₃ | H | OCH₃ | CH₃ | N | |
| CH₃ | S(O)CH₂CF₂CF₂H | H | OCH₃ | OCH₃ | CH | |
| CH₃ | S(O)CH₂CF₂CF₂H | H | OCH₃ | CH₃ | CH | |

TABLE Ia-continued

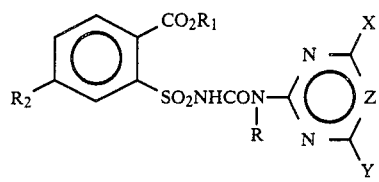

| R₁ | R₂ | R | X | Y | Z | m.p. (°C.) |
|---|---|---|---|---|---|---|
| CH₃ | S(O)CH₂CF₂CF₂H | H | OCH₃ | Cl | CH | |
| CH₃ | S(O)CH₂CF₂CF₂H | H | CH₃ | CH₃ | CH | |
| CH₃ | S(O)CH₂CF₂CF₂H | H | OCH₃ | OCH₃ | N | |
| CH₂CH₃ | S(O)CH₂CF₂CF₂H | H | OCH₃ | CH₃ | N | |
| CH₃ | S(O)CH(CH₂F)₂ | H | OCH₃ | OCH₃ | CH | |
| CH₃ | S(O)CH(CH₂F)₂ | H | OCH₃ | CH₃ | CH | |
| CH₃ | S(O)CH(CH₂F)₂ | H | OCH₃ | Cl | CH | |
| CH₃ | S(O)CH(CH₂F)₂ | H | CH₃ | CH₃ | CH | |
| CH₃ | S(O)CH(CH₂F)₂ | H | OCH₃ | OCH₃ | N | |
| CH₃ | S(O)CH(CH₂F)₂ | H | OCH₃ | CH₃ | N | |
| CH₃ | S(O)CH(CH₂F)CH₃ | H | OCH₃ | OCH₃ | CH | |
| CH₃ | S(O)CH(CH₂F)CH₃ | H | OCH₃ | CH₃ | CH | |
| CH₃ | S(O)CH(CH₂F)CH₃ | H | OCH₃ | Cl | CH | |
| CH₃ | S(O)CH(CH₂F)CH₃ | H | CH₃ | CH₃ | CH | |
| CH₃ | S(O)CH(CH₂F)CH₃ | H | OCH₃ | OCH₃ | N | |
| CH₃ | S(O)CH(CH₂F)CH₃ | H | OCH₃ | CH₃ | N | |
| CH₃ | S(O)(CH₂)₅CH₂Cl | H | OCH₃ | OCH₃ | CH | |
| CH₃ | S(O)(CH₂)₅CH₂Cl | H | OCH₃ | CH₃ | CH | |
| CH₃ | S(O)(CH₂)₅CH₂Cl | H | OCH₃ | Cl | CH | |
| CH₃ | S(O)(CH₂)₅CH₂Cl | H | CH₃ | CH₃ | CH | |
| CH₃ | S(O)(CH₂)₅CH₂Cl | H | OCH₃ | OCH₃ | N | |
| CH₂CH₃ | S(O)(CH₂)₅CH₂Cl | H | OCH₃ | CH₃ | N | |
| CH₃ | S(O)C(Cl)CHCl | H | OCH₃ | OCH₃ | CH | |
| CH₃ | S(O)C(Cl)CHCl | H | OCH₃ | CH₃ | CH | |
| CH₃ | S(O)C(Cl)CHCl | H | OCH₃ | Cl | CH | |
| CH₃ | S(O)C(Cl)CHCl | H | CH₃ | CH₃ | CH | |
| CH₃ | S(O)C(Cl)CHCl | H | OCH₃ | OCH₃ | N | |
| CH₃ | S(O)C(Cl)CHCl | H | OCH₃ | CH₃ | N | |
| CH₃ | S(O)CH₂C(Cl)CH₂ | H | OCH₃ | OCH₃ | CH | |
| CH₃ | S(O)CH₂C(Cl)CH₂ | H | OCH₃ | CH₃ | CH | |
| CH₃ | S(O)CH₂C(Cl)CH₂ | H | OCH₃ | Cl | CH | |
| CH₃ | S(O)CH₂C(Cl)CH₂ | H | CH₃ | CH₃ | CH | |
| CH₃ | S(O)CH₂C(Cl)CH₂ | H | OCH₃ | OCH₃ | N | |
| CH₃ | S(O)CH₂C(Cl)CH₂ | H | OCH₃ | CH₃ | N | |
| CH₃ | S(O)CH₂CCCH₂Cl | H | OCH₃ | OCH₃ | CH | |
| CH₃ | S(O)CH₂CCCH₂Cl | H | OCH₃ | CH₃ | CH | |
| CH₃ | S(O)CH₂CCCH₂Cl | H | OCH₃ | Cl | CH | |
| CH₃ | S(O)CH₂CCCH₂Cl | H | CH₃ | CH₃ | CH | |
| CH₃ | S(O)CH₂CCCH₂Cl | H | OCH₃ | OCH₃ | N | |
| CH₂CH₃ | S(O)CH₂CCCH₂Cl | H | OCH₃ | CH₃ | N | |
| CH₃ | S(O)CH₂OCH₃ | H | OCH₃ | OCH₃ | CH | |
| CH₃ | S(O)CH₂OCH₃ | H | OCH₃ | CH₃ | CH | |
| CH₃ | S(O)CH₂OCH₃ | H | OCH₃ | Cl | CH | |
| CH₃ | S(O)CH₂OCH₃ | H | CH₃ | CH₃ | CH | |
| CH₃ | S(O)CH₂OCH₃ | H | OCH₃ | OCH₃ | N | |
| CH₃ | S(O)CH₂OCH₃ | H | OCH₃ | CH₃ | N | |
| CH₃ | S(O)CH₂OCH₂CF₃ | H | OCH₃ | OCH₃ | CH | |
| CH₃ | S(O)CH₂OCH₂CF₃ | H | OCH₃ | CH₃ | CH | |
| CH₃ | S(O)CH₂OCH₂CF₃ | H | OCH₃ | Cl | CH | |
| CH₃ | S(O)CH₂OCH₂CF₃ | H | CH₃ | CH₃ | CH | |
| CH₃ | S(O)CH₂OCH₂CF₃ | H | OCH₃ | OCH₃ | N | |
| CH₃ | S(O)CH₂OCH₂CF₃ | H | OCH₃ | CH₃ | N | |
| CH₃ | S(O)CH₂CN | H | OCH₃ | OCH₃ | CH | |
| CH₃ | S(O)CH₂CN | H | OCH₃ | CH₃ | CH | |
| CH₃ | S(O)CH₂CN | H | OCH₃ | Cl | CH | |
| CH₃ | S(O)CH₂CN | H | CH₃ | CH₃ | CH | |
| CH₃ | S(O)CH₂CN | H | OCH₃ | OCH₃ | N | |
| CH₃ | S(O)CH₂CN | H | OCH₃ | CH₃ | N | |
| CH₃ | S(O)CH₂C(O)CH₃ | H | OCH₃ | OCH₃ | CH | |
| CH₃ | S(O)CH₂C(O)CH₃ | H | OCH₃ | CH₃ | CH | |
| CH₃ | S(O)CH₂C(O)CH₃ | H | OCH₃ | Cl | CH | |
| CH₃ | S(O)CH₂C(O)CH₃ | H | CH₃ | CH₃ | CH | |
| CH₃ | S(O)CH₂C(O)CH₃ | H | OCH₃ | OCH₃ | N | |
| CH₃ | S(O)CH₂C(O)CH₃ | H | OCH₃ | CH₃ | N | |
| CH₃ | S(O)CH₂CH₂N(CH₃)₂ | H | OCH₃ | OCH₃ | CH | |
| CH₃ | S(O)CH₂CH₂N(CH₃)₂ | H | OCH₃ | CH₃ | CH | |
| CH₃ | S(O)CH₂CH₂N(CH₃)₂ | H | OCH₃ | Cl | CH | |
| CH₃ | S(O)CH₂CH₂N(CH₃)₂ | H | CH₃ | CH₃ | CH | |
| CH₃ | S(O)CH₂CH₂N(CH₃)₂ | H | OCH₃ | OCH₃ | N | |
| CH₂CH₃ | S(O)CH₂CH₂N(CH₃)₂ | H | OCH₃ | CH₃ | N | |
| CH₃ | S(O)CH₂CH₂OCH₂CF₃ | H | OCH₃ | OCH₃ | CH | |

TABLE Ia-continued $$\underset{R_2}{\overset{CO_2R_1}{\underset{SO_2NHCON}{\bigvee}}}\underset{R}{\overset{X}{\underset{N}{\bigvee}}}\underset{Y}{\overset{Z}{\bigvee}}$$

| R₁ | R₂ | R | X | Y | Z | m.p. (°C.) |
|---|---|---|---|---|---|---|
| CH₃ | S(O)CH₂CH₂OCH₂CF₃ | H | OCH₃ | CH₃ | CH | |
| CH₃ | S(O)CH₂CH₂OCH₂CF₃ | H | OCH₃ | Cl | CH | |
| CH₃ | S(O)CH₂CH₂OCH₂CF₃ | H | CH₃ | CH₃ | CH | |
| CH₃ | S(O)CH₂CH₂OCH₂CF₃ | H | OCH₃ | OCH₃ | N | |
| CH₃ | S(O)CH₂CH₂OCH₂CF₃ | H | OCH₃ | CH₃ | N | |
| CH₃ | S(O)CF₂CF₂H | H | OCH₃ | OCH₃ | CH | |
| CH₃ | S(O)CF₂CF₂H | H | OCH₃ | CH₃ | CH | |
| CH₃ | S(O)CF₂CF₂H | H | OCH₃ | Cl | CH | |
| CH₃ | S(O)CF₂CF₂H | H | CH₃ | CH₃ | CH | |
| CH₃ | S(O)CF₂CF₂H | H | OCH₃ | OCH₃ | N | |
| CH₂CH₃ | S(O)CF₂CF₂H | H | OCH₃ | CH₃ | N | |
| CH₃ | S(O)CH₂CH₂CN | H | OCH₃ | OCH₃ | CH | |
| CH₃ | S(O)CH₂CH₂CN | H | OCH₃ | CH₃ | CH | |
| CH₃ | S(O)CH₂CH₂CN | H | OCH₃ | Cl | CH | |
| CH₃ | S(O)CH₂CH₂CN | H | CH₃ | CH₃ | CH | |
| CH₃ | S(O)CH₂CH₂CN | H | OCH₃ | OCH₃ | N | |
| CH₂CH₃ | S(O)CH₂CH₂CN | H | OCH₃ | CH₃ | N | |
| CH₃ | S(O)CH₂CH₂F | H | OCH₃ | OCH₃ | CH | |
| CH₃ | S(O)CH₂CH₂F | H | OCH₃ | CH₃ | CH | |
| CH₃ | S(O)CH₂CH₂F | H | OCH₃ | Cl | CH | |
| CH₃ | S(O)CH₂CH₂F | H | CH₃ | CH₃ | CH | |
| CH₃ | S(O)CH₂CH₂F | H | OCH₃ | OCH₃ | N | |
| CH₃ | S(O)CH₂CH₂F | H | OCH₃ | CH₃ | N | |
| CH₃ | S(O)CH₂CHF₂ | H | OCH₃ | OCH₃ | CH | |
| CH₃ | S(O)CH₂CHF₂ | H | OCH₃ | CH₃ | CH | |
| CH₃ | S(O)CH₂CHF₂ | H | OCH₃ | Cl | CH | |
| CH₃ | S(O)CH₂CHF₂ | H | CH₃ | CH₃ | CH | |
| CH₃ | S(O)CH₂CHF₂ | H | OCH₃ | OCH₃ | N | |
| CH₃ | S(O)CH₂CHF₂ | H | OCH₃ | CH₃ | N | |
| CH₃ | S(O)CH₂CF₃ | H | OCH₃ | OCH₃ | CH | |
| CH₃ | S(O)CH₂CF₃ | H | OCH₃ | CH₃ | CH | |
| CH₃ | S(O)CH₂CF₃ | H | OCH₃ | Cl | CH | |
| CH₃ | S(O)CH₂CF₃ | H | CH₃ | CH₃ | CH | |
| CH₃ | S(O)CH₂CF₃ | H | OCH₃ | OCH₃ | N | |
| CH₂CH₃ | S(O)CH₂CF₃ | H | OCH₃ | CH₃ | N | |
| CH₃ | S(O)₂—cyclopropyl | H | OCH₃ | OCH₃ | CH | |
| CH₃ | S(O)₂—cyclopropyl | H | OCH₃ | CH₃ | CH | |
| CH₃ | S(O)₂—cyclopropyl | H | OCH₃ | Cl | CH | |
| CH₃ | S(O)₂—cyclopropyl | H | CH₃ | CH₃ | CH | |
| CH₃ | S(O)₂—cyclopropyl | H | OCH₃ | OCH₃ | N | |
| CH₃ | S(O)₂—cyclopropyl | H | OCH₃ | CH₃ | N | |
| CH₃ | S(O)₂CH₂—cyclopropyl | H | OCH₃ | OCH₃ | CH | |
| CH₃ | S(O)₂CH₂—cyclopropyl | H | OCH₃ | CH₃ | CH | |
| CH₃ | S(O)₂CH₂—cyclopropyl | H | OCH₃ | Cl | CH | |
| CH₃ | S(O)₂CH₂—cyclopropyl | H | CH₃ | CH₃ | CH | |
| CH₃ | S(O)₂CH₂—cyclopropyl | H | OCH₃ | OCH₃ | N | |
| CH₃ | S(O)₂CH₂—cyclopropyl | H | OCH₃ | CH₃ | N | |
| CH₃ | S(O)₂—cyclobutyl | H | OCH₃ | OCH₃ | CH | |
| CH₃ | S(O)₂—cyclobutyl | H | OCH₃ | CH₃ | CH | |
| CH₃ | S(O)₂—cyclobutyl | H | OCH₃ | Cl | CH | |
| CH₃ | S(O)₂—cyclobutyl | H | CH₃ | CH₃ | CH | |
| CH₃ | S(O)₂—cyclobutyl | H | OCH₃ | OCH₃ | N | |
| CH₂CH₃ | S(O)₂—cyclobutyl | H | OCH₃ | CH₃ | N | |
| CH₃ | S(O)₂CH₂CF₂CF₃ | H | OCH₃ | OCH₃ | CH | |
| CH₃ | S(O)₂CH₂CF₂CF₃ | H | OCH₃ | CH₃ | CH | |
| CH₃ | S(O)₂CH₂CF₂CF₃ | H | OCH₃ | Cl | CH | |
| CH₃ | S(O)₂CH₂Cf₂CF₃ | H | CH₃ | CH₃ | CH | |
| CH₃ | S(O)₂CH₂CF₂CF₃ | H | OCH₃ | OCH₃ | N | |
| CH₃ | S(O)₂CH₂CF₂CF₃ | H | OCH₃ | CH₃ | N | |
| CH₃ | S(O)₂CH(CF₃)CH₃ | H | OCH₃ | OCH₃ | CH | |
| CH₃ | S(O)₂CH(CF₃)CH₃ | H | OCH₃ | CH₃ | CH | |
| CH₃ | S(O)₂CH(CF₃)CH₃ | H | OCH₃ | Cl | CH | |
| CH₃ | S(O)₂CH(CF₃)CH₃ | H | CH₃ | CH₃ | CH | |
| CH₃ | S(O)₂CH(CF₃)CH₃ | H | OCH₃ | OCH₃ | N | |
| CH₃ | S(O)₂CH(CF₃)CH₃ | H | OCH₃ | CH₃ | N | |
| CH₃ | S(O)₂CH₂CF₂CF₂H | H | OCH₃ | OCH₃ | CH | |
| CH₃ | S(O)₂CH₂CF₂CF₂H | H | OCH₃ | CH₃ | CH | |
| CH₃ | S(O)₂CH₂CF₂CF₂H | H | OCH₃ | Cl | CH | |
| CH₃ | S(O)₂CH₂CF₂CF₂H | H | CH₃ | CH₃ | CH | |
| CH₃ | S(O)₂CH₂CF₂CF₂H | H | OCH₃ | OCH₃ | N | |
| CH₂CH₃ | S(O)₂CH₂CF₂CF₂H | H | OCH₃ | CH₃ | N | |

TABLE Ia-continued

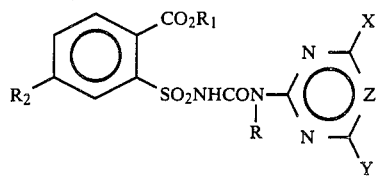

| R₁ | R₂ | R | X | Y | Z | m.p. (°C.) |
|---|---|---|---|---|---|---|
| CH₃ | S(O)₂CH(CH₂F)₂ | H | OCH₃ | OCH₃ | CH | |
| CH₃ | S(O)₂CH(CH₂F)₂ | H | OCH₃ | CH₃ | CH | |
| CH₃ | S(O)₂CH(CH₂F)₂ | H | OCH₃ | Cl | CH | |
| CH₃ | S(O)₂CH(CH₂F)₂ | H | CH₃ | CH₃ | CH | |
| CH₃ | S(O)₂CH(CH₂F)₂ | H | OCH₃ | OCH₃ | N | |
| CH₃ | S(O)₂CH(CH₂F)₂ | H | OCH₃ | CH₃ | N | |
| CH₃ | S(O)₂CH(CH₂F)CH₃ | H | OCH₃ | OCH₃ | CH | |
| CH₃ | S(O)₂CH(CH₂F)CH₃ | H | OCH₃ | CH₃ | CH | |
| CH₃ | S(O)₂CH(CH₂F)CH₃ | H | OCH₃ | Cl | CH | |
| CH₃ | S(O)₂CH(CH₂F)CH₃ | H | CH₃ | CH₃ | CH | |
| CH₃ | S(O)₂CH(CH₂F)CH₃ | H | OCH₃ | OCH₃ | N | |
| CH₃ | S(O)₂CH(CH₂F)CH₃ | H | OCH₃ | CH₃ | N | |
| CH₃ | S(O)₂(CH₂)₅CH₂Cl | H | OCH₃ | OCH₃ | CH | |
| CH₃ | S(O)₂(CH₂)₅CH₂Cl | H | OCH₃ | CH₃ | CH | |
| CH₃ | S(O)₂(CH₂)₅CH₂Cl | H | OCH₃ | Cl | CH | |
| CH₃ | S(O)₂(CH₂)₅CH₂Cl | H | CH₃ | CH₃ | CH | |
| CH₃ | S(O)₂(CH₂)₅CH₂Cl | H | OCH₃ | OCH₃ | N | |
| CH₂CH₃ | S(O)₂(CH₂)₅CH₂Cl | H | OCH₃ | CH₃ | N | |
| CH₃ | S(O)₂C(Cl)CHCl | H | OCH₃ | OCH₃ | CH | |
| CH₃ | S(O)₂C(Cl)CHCl | H | OCH₃ | CH₃ | CH | |
| CH₃ | S(O)₂C(Cl)CHCl | H | OCH₃ | Cl | CH | |
| CH₃ | S(O)₂C(Cl)CHCl | H | CH₃ | CH₃ | CH | |
| CH₃ | S(O)₂C(Cl)CHCl | H | OCH₃ | OCH₃ | N | |
| CH₃ | S(O)₂C(Cl)CHCl | H | OCH₃ | CH₃ | N | |
| CH₃ | S(O)₂CH₂C(Cl)CH₂ | H | OCH₃ | OCH₃ | CH | |
| CH₃ | S(O)₂CH₂C(Cl)CH₂ | H | OCH₃ | CH₃ | CH | |
| CH₃ | S(O)₂CH₂C(Cl)CH₂ | H | OCH₃ | Cl | CH | |
| CH₃ | S(O)₂CH₂C(Cl)CH₂ | H | CH₃ | CH₃ | CH | |
| CH₃ | S(O)₂CH₂C(Cl)CH₂ | H | OCH₃ | OCH₃ | N | |
| CH₃ | S(O)₂CH₂C(Cl)CH₂ | H | OCH₃ | CH₃ | N | |
| CH₃ | S(O)₂CH₂CCCH₂Cl | H | OCH₃ | OCH₃ | CH | |
| CH₃ | S(O)₂CH₂CCCH₂Cl | H | OCH₃ | CH₃ | CH | |
| CH₃ | S(O)₂CH₂CCCH₂Cl | H | OCH₃ | Cl | CH | |
| CH₃ | S(O)₂CH₂CCCH₂Cl | H | CH₃ | CH₃ | CH | |
| CH₃ | S(O)₂CH₂CCCH₂Cl | H | OCH₃ | OCH₃ | N | |
| CH₂CH₃ | S(O)₂CH₂CCCH₂Cl | H | OCH₃ | CH₃ | N | |
| CH₃ | S(O)₂CH₂OCH₃ | H | OCH₃ | OCH₃ | CH | |
| CH₃ | S(O)₂CH₂OCH₃ | H | OCH₃ | CH₃ | CH | |
| CH₃ | S(O)₂CH₂OCH₃ | H | OCH₃ | Cl | CH | |
| CH₃ | S(O)₂CH₂OCH₃ | H | CH₃ | CH₃ | CH | |
| CH₃ | S(O)₂CH₂OCH₃ | H | OCH₃ | OCH₃ | N | |
| CH₃ | S(O)₂CH₂OCH₃ | H | OCH₃ | CH₃ | N | |
| CH₃ | S(O)₂CH₂OCH₂CF₃ | H | OCH₃ | OCH₃ | CH | |
| CH₃ | S(O)₂CH₂OCH₂CF₃ | H | OCH₃ | CH₃ | CH | |
| CH₃ | S(O)₂CH₂OCH₂CF₃ | H | OCH₃ | Cl | CH | |
| CH₃ | S(O)₂CH₂OCH₂CF₃ | H | CH₃ | CH₃ | CH | |
| CH₃ | S(O)₂CH₂OCH₂CF₃ | H | OCH₃ | OCH₃ | N | |
| CH₃ | S(O)₂CH₂OCH₂CF₃ | H | OCH₃ | CH₃ | N | |
| CH₃ | S(O)₂CH₂CN | H | OCH₃ | OCH₃ | CH | |
| CH₃ | S(O)₂CH₂CN | H | OCH₃ | CH₃ | CH | |
| CH₃ | S(O)₂CH₂CN | H | OCH₃ | Cl | CH | |
| CH₃ | S(O)₂CH₂CN | H | CH₃ | CH₃ | CH | |
| CH₃ | S(O)₂CH₂CN | H | OCH₃ | OCH₃ | N | |
| CH₃ | S(O)₂CH₂CN | H | OCH₃ | CH₃ | N | |
| CH₃ | S(O)₂CH₂C(O)CH₃ | H | OCH₃ | OCH₃ | CH | |
| CH₃ | S(O)₂CH₂C(O)CH₃ | H | OCH₃ | CH₃ | CH | |
| CH₃ | S(O)₂CH₂C(O)CH₃ | H | OCH₃ | Cl | CH | |
| CH₃ | S(O)₂CH₂C(O)CH₃ | H | CH₃ | CH₃ | CH | |
| CH₃ | S(O)₂CH₂C(O)CH₃ | H | OCH₃ | OCH₃ | N | |
| CH₃ | S(O)₂CH₂C(O)CH₃ | H | OCH₃ | CH₃ | N | |
| CH₃ | S(O)₂CH₂CH₂N(CH₃)₂ | H | OCH₃ | OCH₃ | CH | |
| CH₃ | S(O)₂CH₂CH₂N(CH₃)₂ | H | OCH₃ | CH₃ | CH | |
| CH₃ | S(O)₂CH₂CH₂N(CH₃)₂ | H | OCH₃ | Cl | CH | |
| CH₃ | S(O)₂CH₂CH₂N(CH₃)₂ | H | CH₃ | CH₃ | CH | |
| CH₃ | S(O)₂CH₂CH₂N(CH₃)₂ | H | OCH₃ | OCH₃ | N | |
| CH₂CH₃ | S(O)₂CH₂CH₂N(CH₃)₂ | H | OCH₃ | CH₃ | N | |
| CH₃ | S(O)₂CH₂CH₂OCH₂CF₃ | H | OCH₃ | OCH₃ | CH | |
| CH₃ | S(O)₂CH₂CH₂OCH₂CF₃ | H | OCH₃ | CH₃ | CH | |
| CH₃ | S(O)₂CH₂CH₂OCH₂CF₃ | H | OCH₃ | Cl | CH | |
| CH₃ | S(O)₂CH₂CH₂OCH₂CF₃ | H | CH₃ | CH₃ | CH | |
| CH₃ | S(O)₂CH₂CH₂OCH₂CF₃ | H | OCH₃ | OCH₃ | N | |

TABLE Ia-continued

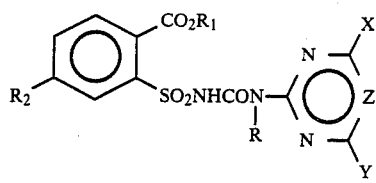

| R₁ | R₂ | R | X | Y | Z | m.p. (°C.) |
|---|---|---|---|---|---|---|
| CH₃ | S(O)₂CH₂CH₂OCH₂CF₃ | H | OCH₃ | CH₃ | N | |
| CH₃ | S(O)₂CF₂CF₂H | H | OCH₃ | OCH₃ | CH | |
| CH₃ | S(O)₂CF₂CF₂H | H | OCH₃ | CH₃ | CH | |
| CH₃ | S(O)₂CF₂CF₂H | H | OCH₃ | Cl | CH | |
| CH₃ | S(O)₂CF₂CF₂H | H | CH₃ | CH₃ | CH | |
| CH₃ | S(O)₂CF₂CF₂H | H | OCH₃ | OCH₃ | N | |
| CH₂CH₃ | S(O)₂CF₂CF₂H | H | OCH₃ | CH₃ | N | |
| CH₃ | S(O)₂CH₂CH₂CN | H | OCH₃ | OCH₃ | CH | |
| CH₃ | S(O)₂CH₂CH₂CN | H | OCH₃ | CH₃ | CH | |
| CH₃ | S(O)₂CH₂CH₂CN | H | OCH₃ | Cl | CH | |
| CH₃ | S(O)₂CH₂CH₂CN | H | CH₃ | CH₃ | CH | |
| CH₃ | S(O)₂CH₂CH₂CN | H | OCH₃ | OCH₃ | N | |
| CH₂CH₃ | S(O)₂CH₂CH₂CN | H | OCH₃ | CH₃ | N | |
| CH₃ | S(O)₂CH₂CH₂F | H | OCH₃ | OCH₃ | CH | |
| CH₃ | S(O)₂CH₂CH₂F | H | OCH₃ | CH₃ | CH | |
| CH₃ | S(O)₂CH₂CH₂F | H | OCH₃ | Cl | CH | |
| CH₃ | S(O)₂CH₂CH₂F | H | CH₃ | CH₃ | CH | |
| CH₃ | S(O)₂CH₂CH₂F | H | OCH₃ | OCH₃ | N | |
| CH₃ | S(O)₂CH₂CH₂F | H | OCH₃ | CH₃ | N | |
| CH₃ | S(O)₂CH₂CHF₂ | H | OCH₃ | OCH₃ | CH | |
| CH₃ | S(O)₂CH₂CHF₂ | H | OCH₃ | CH₃ | CH | |
| CH₃ | S(O)₂CH₂CHF₂ | H | OCH₃ | Cl | CH | |
| CH₃ | S(O)₂CH₂CHF₂ | H | CH₃ | CH₃ | CH | |
| CH₃ | S(O)₂CH₂CHF₂ | H | OCH₃ | OCH₃ | N | |
| CH₃ | S(O)₂CH₂CHF₂ | H | OCH₃ | CH₃ | N | |
| CH₃ | S(O)₂CH₂CF₃ | H | OCH₃ | OCH₃ | CH | |
| CH₃ | S(O)₂CH₂CF₃ | H | OCH₃ | CH₃ | CH | |
| CH₃ | S(O)₂CH₂CF₃ | H | OCH₃ | Cl | CH | |
| CH₃ | S(O)₂CH₂CF₃ | H | CH₃ | CH₃ | CH | |
| CH₃ | S(O)₂CH₂CF₃ | H | OCH₃ | OCH₃ | N | |
| CH₂CH₃ | S(O)₂CH₂CF₃ | H | OCH₃ | CH₃ | N | |
| CH₃ | NHCH₂—cyclopropyl | H | OCH₃ | OCH₃ | CH | |
| CH₃ | NHCH₂—cyclopropyl | H | OCH₃ | CH₃ | CH | |
| CH₃ | NHCH₂—cyclopropyl | H | OCH₃ | Cl | CH | |
| CH₃ | NHCH₂—cyclopropyl | H | CH₃ | CH₃ | CH | |
| CH₃ | NHCH₂—cyclopropyl | H | OCH₃ | OCH₃ | N | |
| CH₃ | NHCH₂—cyclopropyl | H | OCH₃ | CH₃ | N | |
| CH₃ | NHCH₂CF₂CF₃ | H | OCH₃ | OCH₃ | CH | |
| CH₃ | NHCH₂CF₂CF₃ | H | OCH₃ | CH₃ | CH | |
| CH₃ | NHCH₂CF₂CF₃ | H | OCH₃ | Cl | CH | |
| CH₃ | NHCH₂CF₂CF₃ | H | CH₃ | CH₃ | CH | |
| CH₃ | NHCH₂CF₂CF₃ | H | OCH₃ | OCH₃ | N | |
| CH₃ | NHCH₂CF₂CF₃ | H | OCH₃ | CH₃ | N | |
| CH₃ | NHCH(CF₃)CH₃ | H | OCH₃ | OCH₃ | CH | |
| CH₃ | NHCH(CF₃)CH₃ | H | OCH₃ | CH₃ | CH | |
| CH₃ | NHCH(CF₃)CH₃ | H | OCH₃ | Cl | CH | |
| CH₃ | NHCH(CF₃)CH₃ | H | CH₃ | CH₃ | CH | |
| CH₃ | NHCH(CF₃)CH₃ | H | OCH₃ | OCH₃ | N | |
| CH₃ | NHCH(CF₃)CH₃ | H | OCH₃ | CH₃ | N | |
| CH₃ | NHCH₂CF₂CF₂H | H | OCH₃ | OCH₃ | CH | |
| CH₃ | NHCH₂CF₂CF₂H | H | OCH₃ | CH₃ | CH | |
| CH₃ | NHCH₂CF₂CF₂H | H | OCH₃ | Cl | CH | |
| CH₃ | NHCH₂CF₂CF₂H | H | CH₃ | CH₃ | CH | |
| CH₃ | NHCH₂CF₂CF₂H | H | OCH₃ | OCH₃ | N | |
| CH₂CH₃ | NHCH₂CF₂CF₂H | H | OCH₃ | CH₃ | N | |
| CH₃ | NHCH(CH₂F)₂ | H | OCH₃ | OCH₃ | CH | |
| CH₃ | NHCH(CH₂F)₂ | H | OCH₃ | CH₃ | CH | |
| CH₃ | NHCH(CH₂F)₂ | H | OCH₃ | Cl | CH | |
| CH₃ | NHCH(CH₂F)₂ | H | CH₃ | CH₃ | CH | |
| CH₃ | NHCH(CH₂F)₂ | H | OCH₃ | OCH₃ | N | |
| CH₃ | NHCH(CH₂F)₂ | H | OCH₃ | CH₃ | N | |
| CH₃ | NHCH(CH₂F)CH₃ | H | OCH₃ | OCH₃ | CH | |
| CH₃ | NHCH(CH₂F)CH₃ | H | OCH₃ | CH₃ | CH | |
| CH₃ | NHCH(CH₂F)CH₃ | H | OCH₃ | Cl | CH | |
| CH₃ | NHCH(CH₂F)CH₃ | H | CH₃ | CH₃ | CH | |
| CH₃ | NHCH(CH₂F)CH₃ | H | OCH₃ | OCH₃ | N | |
| CH₃ | NHCH(CH₂F)CH₃ | H | OCH₃ | CH₃ | N | |
| CH₃ | NH(CH₂)₃CH₂Cl | H | OCH₃ | OCH₃ | CH | |
| CH₃ | NH(CH₂)₃CH₂Cl | H | OCH₃ | CH₃ | CH | |
| CH₃ | NH(CH₂)₃CH₂Cl | H | OCH₃ | Cl | CH | |
| CH₃ | NH(CH₂)₃CH₂Cl | H | CH₃ | CH₃ | CH | |

TABLE Ia-continued

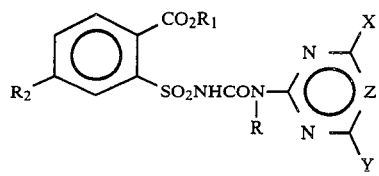

| R₁ | R₂ | R | X | Y | Z | m.p. (°C.) |
|---|---|---|---|---|---|---|
| CH₃ | NH(CH₂)₃CH₂Cl | H | OCH₃ | OCH₃ | N | |
| CH₂CH₃ | NH(CH₂)₃CH₂Cl | H | OCH₃ | CH₃ | N | |
| CH₃ | NHC(Cl)CHCl | H | OCH₃ | OCH₃ | CH | |
| CH₃ | NHC(Cl)CHCl | H | OCH₃ | CH₃ | CH | |
| CH₃ | NHC(Cl)CHCl | H | OCH₃ | Cl | CH | |
| CH₃ | NHC(Cl)CHCl | H | CH₃ | CH₃ | CH | |
| CH₃ | NHC(Cl)CHCl | H | OCH₃ | OCH₃ | N | |
| CH₃ | NHC(Cl)CHCl | H | OCH₃ | CH₃ | N | |
| CH₃ | NHCH₂C(Cl)CH₂ | H | OCH₃ | OCH₃ | CH | |
| CH₃ | NHCH₂C(Cl)CH₂ | H | OCH₃ | CH₃ | CH | |
| CH₃ | NHCH₂C(Cl)CH₂ | H | OCH₃ | Cl | CH | |
| CH₃ | NHCH₂C(Cl)CH₂ | H | CH₃ | CH₃ | CH | |
| CH₃ | NHCH₂C(Cl)CH₂ | H | OCH₃ | OCH₃ | N | |
| CH₃ | NHCH₂C(Cl)CH₂ | H | OCH₃ | CH₃ | N | |
| CH₃ | NHCH₂CCCH₂Cl | H | OCH₃ | OCH₃ | CH | |
| CH₃ | NHCH₂CCCH₂Cl | H | OCH₃ | CH₃ | CH | |
| CH₃ | NHCH₂CCCH₂Cl | H | OCH₃ | Cl | CH | |
| CH₃ | NHCH₂CCCH₂Cl | H | CH₃ | CH₃ | CH | |
| CH₃ | NHCH₂CCCH₂Cl | H | OCH₃ | OCH₃ | N | |
| CH₂CH₃ | NHCH₂CCCH₂Cl | H | OCH₃ | CH₃ | N | |
| CH₃ | NHCH₂OCH₃ | H | OCH₃ | OCH₃ | CH | |
| CH₃ | NHCH₂OCH₃ | H | OCH₃ | CH₃ | CH | |
| CH₃ | NHCH₂OCH₃ | H | OCH₃ | Cl | CH | |
| CH₃ | NHCH₂OCH₃ | H | CH₃ | CH₃ | CH | |
| CH₃ | NHCH₂OCH₃ | H | OCH₃ | OCH₃ | N | |
| CH₃ | NHCH₂OCH₃ | H | OCH₃ | CH₃ | N | |
| CH₃ | NHCH₂SCH₃ | H | OCH₃ | OCH₃ | CH | |
| CH₃ | NHCH₂SCH₃ | H | OCH₃ | CH₃ | CH | |
| CH₃ | NHCH₂SCH₃ | H | OCH₃ | Cl | CH | |
| CH₃ | NHCH₂SCH₃ | H | CH₃ | CH₃ | CH | |
| CH₃ | NHCH₂SCH₃ | H | OCH₃ | OCH₃ | N | |
| CH₂CH₃ | NHCH₂SCH₃ | H | OCH₃ | CH₃ | N | |
| CH₃ | NHCH₂CN | H | OCH₃ | OCH₃ | CH | |
| CH₃ | NHCH₂CN | H | OCH₃ | CH₃ | CH | |
| CH₃ | NHCH₂CN | H | OCH₃ | Cl | CH | |
| CH₃ | NHCH₂CN | H | CH₃ | CH₃ | CH | |
| CH₃ | NHCH₂CN | H | OCH₃ | OCH₃ | N | |
| CH₃ | NHCH₂CN | H | OCH₃ | CH₃ | N | |
| CH₃ | NHCH₂C(O)CH₃ | H | OCH₃ | OCH₃ | CH | |
| CH₃ | NHCH₂C(O)CH₃ | H | OCH₃ | CH₃ | CH | |
| CH₃ | NHCH₂C(O)CH₃ | H | OCH₃ | Cl | CH | |
| CH₃ | NHCH₂C(O)CH₃ | H | CH₃ | CH₃ | CH | |
| CH₃ | NHCH₂C(O)CH₃ | H | OCH₃ | OCH₃ | N | |
| CH₃ | NHCH₂C(O)CH₃ | H | OCH₃ | CH₃ | N | |
| CH₃ | NHCH₂CH₂N(CH₃)₂ | H | OCH₃ | OCH₃ | CH | |
| CH₃ | NHCH₂CH₂N(CH₃)₂ | H | OCH₃ | CH₃ | CH | |
| CH₃ | NHCH₂CH₂N(CH₃)₂ | H | OCH₃ | Cl | CH | |
| CH₃ | NHCH₂CH₂N(CH₃)₂ | H | CH₃ | CH₃ | CH | |
| CH₃ | NHCH₂CH₂N(CH₃)₂ | H | OCH₃ | OCH₃ | N | |
| CH₂CH₃ | NHCH₂CH₂N(CH₃)₂ | H | OCH₃ | CH₃ | N | |
| CH₃ | NHCH₂CH₂OCH₃ | H | OCH₃ | OCH₃ | CH | |
| CH₃ | NHCH₂CH₂OCH₃ | H | OCH₃ | CH₃ | CH | |
| CH₃ | NHCH₂CH₂OCH₃ | H | OCH₃ | Cl | CH | |
| CH₃ | NHCH₂CH₂OCH₃ | H | CH₃ | CH₃ | CH | |
| CH₃ | NHCH₂CH₂OCH₃ | H | OCH₃ | OCH₃ | N | |
| CH₃ | NHCH₂CH₂OCH₃ | H | OCH₃ | CH₃ | N | |
| CH₃ | NHCH₂CH₂CN | H | OCH₃ | OCH₃ | CH | |
| CH₃ | NHCH₂CH₂CN | H | OCH₃ | CH₃ | CH | |
| CH₃ | NHCH₂CH₂CN | H | OCH₃ | Cl | CH | |
| CH₃ | NHCH₂CH₂CN | H | CH₃ | CH₃ | CH | |
| CH₃ | NHCH₂CH₂CN | H | OCH₃ | OCH₃ | N | |
| CH₃ | NHCH₂CH₂CN | H | OCH₃ | CH₃ | N | |
| CH₂CH₃ | NHCH₂CH₂F | H | OCH₃ | OCH₃ | CH | |
| CH₃ | NHCH₂CH₂F | H | OCH₃ | CH₃ | CH | |
| CH₃ | NHCH₂CH₂F | H | OCH₃ | Cl | CH | |
| CH₃ | NHCH₂CH₂F | H | CH₃ | CH₃ | CH | |
| CH₃ | NHCH₂CH₂F | H | OCH₃ | OCH₃ | N | |
| CH₃ | NHCH₂CH₂F | H | OCH₃ | CH₃ | N | |
| CH₃ | NHCH₂CHF₂ | H | OCH₃ | OCH₃ | CH | |
| CH₃ | NHCH₂CHF₂ | H | OCH₃ | CH₃ | CH | |
| CH₃ | NHCH₂CHF₂ | H | OCH₃ | Cl | CH | |

TABLE Ia-continued

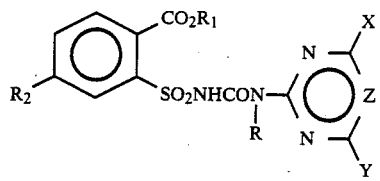

| R₁ | R₂ | R | X | Y | Z | m.p. (°C.) |
|---|---|---|---|---|---|---|
| CH₃ | NHCH₂CHF₂ | H | CH₃ | CH₃ | CH | |
| CH₃ | NHCH₂CHF₂ | H | OCH₃ | OCH₃ | N | |
| CH₃ | NHCH₂CHF₂ | H | OCH₃ | CH₃ | N | |
| CH₃ | NHCH₂CF₃ | H | OCH₃ | OCH₃ | CH | |
| CH₃ | NHCH₂CF₃ | H | OCH₃ | CH₃ | CH | |
| CH₃ | NHCH₂CF₃ | H | OCH₃ | Cl | CH | |
| CH₃ | NHCH₂CF₃ | H | CH₃ | CH₃ | CH | |
| CH₃ | NHCH₂CF₃ | H | OCH₃ | OCH₃ | N | |
| CH₂CH₃ | NHCH₂CF₃ | H | OCH₃ | CH₃ | N | |
| CH₃ | NHCH₂CH₂OH | H | OCH₃ | OCH₃ | CH | |
| CH₃ | NHCH₂CH₂OH | H | OCH₃ | CH₃ | CH | |
| CH₃ | NHCH₂CH₂OH | H | OCH₃ | Cl | CH | |
| CH₃ | NHCH₂CH₂OH | H | CH₃ | CH₃ | CH | |
| CH₃ | NHCH₂CH₂OH | H | OCH₃ | OCH₃ | N | |
| CH₃ | NHCH₂CH₂OH | H | OCH₃ | CH₃ | N | |
| CH₃ | NHCH₂CH₂NH₂ | H | OCH₃ | OCH₃ | CH | |
| CH₃ | NHCH₂CH₂NH₂ | H | OCH₃ | CH₃ | CH | |
| CH₃ | NHCH₂CH₂NH₂ | H | OCH₃ | Cl | CH | |
| CH₃ | NHCH₂CH₂NH₂ | H | CH₃ | CH₃ | CH | |
| CH₃ | NHCH₂CH₂NH₂ | H | OCH₃ | OCH₃ | N | |
| CH₃ | NHCH₂CH₂NH₂ | H | OCH₃ | CH₃ | N | |
| CH₃ | NHCH₃ | H | OCH₃ | OCH₃ | CH | |
| CH₃ | NHCH₃ | H | OCH₃ | CH₃ | CH | |
| CH₃ | NHCH₃ | H | OCH₃ | Cl | CH | |
| CH₃ | NHCH₃ | H | CH₃ | CH₃ | CH | |
| CH₃ | NHCH₃ | H | OCH₃ | OCH₃ | N | |
| CH₂CH₃ | NHCH₃ | H | OCH₃ | CH₃ | N | |
| CH₃ | NHCH₂CH₂SCH₃ | H | OCH₃ | OCH₃ | CH | |
| CH₃ | NHCH₂CH₂SCH₃ | H | OCH₃ | CH₃ | CH | |
| CH₃ | NHCH₂CH₂SCH₃ | H | OCH₃ | Cl | CH | |
| CH₃ | NHCH₂CH₂SCH₃ | H | CH₃ | CH₃ | CH | |
| CH₃ | NHCH₂CH₂SCH₃ | H | OCH₃ | OCH₃ | N | |
| CH₃ | NHCH₂CH₂SCH₃ | H | OCH₃ | CH₃ | N | |
| CH₃ | NHCH₂CH₂S(O)CH₃ | H | OCH₃ | OCH₃ | CH | |
| CH₃ | NHCH₂CH₂S(O)CH₃ | H | OCH₃ | CH₃ | CH | |
| CH₃ | NHCH₂CH₂S(O)CH₃ | H | OCH₃ | Cl | CH | |
| CH₃ | NHCH₂CH₂S(O)CH₃ | H | CH₃ | CH₃ | CH | |
| CH₃ | NHCH₂CH₂S(O)CH₃ | H | OCH₃ | OCH₃ | N | |
| CH₃ | NHCH₂CH₂S(O)CH₃ | H | OCH₃ | CH₃ | N | |
| CH₃ | NHCH₂CH₂S(O)₂CH₃ | H | OCH₃ | OCH₃ | CH | |
| CH₃ | NHCH₂CH₂S(O)₂CH₃ | H | OCH₃ | CH₃ | CH | |
| CH₃ | NHCH₂CH₂S(O)₂CH₃ | H | OCH₃ | Cl | CH | |
| CH₃ | NHCH₂CH₂S(O)₂CH₃ | H | CH₃ | CH₃ | CH | |
| CH₃ | NHCH₂CH₂S(O)₂CH₃ | H | OCH₃ | OCH₃ | N | |
| CH₃ | NHCH₂CH₂S(O)₂CH₃ | H | OCH₃ | CH₃ | N | |
| CH₂CH₃ | CH₂O—cyclopropyl | H | OCH₃ | OCH₃ | CH | |
| CH₃ | CH₂O—cyclopropyl | H | OCH₃ | CH₃ | CH | |
| CH₃ | CH₂O—cyclopropyl | H | OCH₃ | Cl | CH | |
| CH₃ | CH₂O—cyclopropyl | H | CH₃ | CH₃ | CH | |
| CH₃ | CH₂O—cyclopropyl | H | OCH₃ | OCH₃ | N | |
| CH₃ | CH₂O—cyclopropyl | H | OCH₃ | CH₃ | N | |
| CH₃ | CH₂OCH₂—cyclopropyl | H | OCH₃ | OCH₃ | CH | |
| CH₃ | CH₂OCH₂—cyclopropyl | H | OCH₃ | CH₃ | CH | |
| CH₃ | CH₂OCH₂—cyclopropyl | H | OCH₃ | Cl | CH | |
| CH₃ | CH₂OCH₂—cyclopropyl | H | CH₃ | CH₃ | CH | |
| CH₃ | CH₂OCH₂—cyclopropyl | H | OCH₃ | OCH₃ | N | |
| CH₃ | CH₂OCH₂—cyclopropyl | H | OCH₃ | CH₃ | N | |
| CH₃ | CH₂O—cyclobutyl | H | OCH₃ | OCH₃ | CH | |
| CH₃ | CH₂O—cyclobutyl | H | OCH₃ | CH₃ | CH | |
| CH₃ | CH₂O—cyclobutyl | H | OCH₃ | Cl | CH | |
| CH₃ | CH₂O—cyclobutyl | H | CH₃ | CH₃ | CH | |
| CH₃ | CH₂O—cyclobutyl | H | OCH₃ | OCH₃ | N | |
| CH₂CH₃ | CH₂O—cyclobutyl | H | OCH₃ | CH₃ | N | |
| CH₃ | CH₂OCH₂CF₂CF₃ | H | OCH₃ | OCH₃ | CH | |
| CH₃ | CH₂OCH₂CF₂CF₃ | H | OCH₃ | CH₃ | CH | |
| CH₃ | CH₂OCH₂CF₂CF₃ | H | OCH₃ | Cl | CH | |
| CH₃ | CH₂OCH₂CF₂CF₃ | H | CH₃ | CH₃ | CH | |
| CH₃ | CH₂OCH₂CF₂CF₃ | H | OCH₃ | OCH₃ | N | |
| CH₃ | CH₂OCH₂CF₂CF₃ | H | OCH₃ | CH₃ | N | |
| CH₃ | CH₂OCH(CF₃)CH₃ | H | OCH₃ | OCH₃ | CH | |
| CH₃ | CH₂OCH(CF₃)CH₃ | H | OCH₃ | CH₃ | CH | |

TABLE Ia-continued

| R₁ | R₂ | R | X | Y | Z | m.p. (°C.) |
|---|---|---|---|---|---|---|
| CH₃ | CH₂OCH(CF₃)CH₃ | H | OCH₃ | Cl | CH | |
| CH₃ | CH₂OCH(CF₃)CH₃ | H | CH₃ | CH₃ | CH | |
| CH₃ | CH₂OCH(CF₃)CH₃ | H | OCH₃ | OCH₃ | N | |
| CH₃ | CH₂OCH(CF₃)CH₃ | H | OCH₃ | CH₃ | N | |
| CH₃ | CH₂OCH₂CF₂CF₂H | H | OCH₃ | OCH₃ | CH | |
| CH₃ | CH₂OCH₂CF₂CF₂H | H | OCH₃ | CH₃ | CH | |
| CH₃ | CH₂OCH₂CF₂CF₂H | H | OCH₃ | Cl | CH | |
| CH₃ | CH₂OCH₂CF₂CF₂H | H | CH₃ | CH₃ | CH | |
| CH₃ | CH₂OCH₂CF₂CF₂H | H | OCH₃ | OCH₃ | N | |
| CH₂CH₃ | CH₂OCH₂CF₂CF₂H | H | OCH₃ | CH₃ | N | |
| CH₃ | CH₂OCH(CH₂F)₂ | H | OCH₃ | OCH₃ | CH | |
| CH₃ | CH₂OCH(CH₂F)₂ | H | OCH₃ | CH₃ | CH | |
| CH₃ | CH₂OCH(CH₂F)₂ | H | OCH₃ | Cl | CH | |
| CH₃ | CH₂OCH(CH₂F)₂ | H | CH₃ | CH₃ | CH | |
| CH₃ | CH₂OCH(CH₂F)₂ | H | OCH₃ | OCH₃ | N | |
| CH₃ | CH₂OCH(CH₂F)₂ | H | OCH₃ | CH₃ | N | |
| CH₃ | CH₂OCH(CH₂F)CH₃ | H | OCH₃ | OCH₃ | CH | |
| CH₃ | CH₂OCH(CH₂F)CH₃ | H | OCH₃ | CH₃ | CH | |
| CH₃ | CH₂OCH(CH₂F)CH₃ | H | OCH₃ | Cl | CH | |
| CH₃ | CH₂OCH(CH₂F)CH₃ | H | CH₃ | CH₃ | CH | |
| CH₃ | CH₂OCH(CH₂F)CH₃ | H | OCH₃ | OCH₃ | N | |
| CH₃ | CH₂OCH(CH₂F)CH₃ | H | OCH₃ | CH₃ | N | |
| CH₃ | CH₂O(CH₂)₃CH₂Cl | H | OCH₃ | OCH₃ | CH | |
| CH₃ | CH₂O(CH₂)₃CH₂Cl | H | OCH₃ | CH₃ | CH | |
| CH₃ | CH₂O(CH₂)₃CH₂Cl | H | OCH₃ | Cl | CH | |
| CH₃ | CH₂O(CH₂)₃CH₂Cl | H | CH₃ | CH₃ | CH | |
| CH₃ | CH₂O(CH₂)₃CH₂Cl | H | OCH₃ | OCH₃ | N | |
| CH₂CH₃ | CH₂O(CH₂)₃CH₂Cl | H | OCH₃ | CH₃ | N | |
| CH₃ | CH₂OCH₂C(Cl)CH₂ | H | OCH₃ | OCH₃ | CH | |
| CH₃ | CH₂OCH₂C(Cl)CH₂ | H | OCH₃ | CH₃ | CH | |
| CH₃ | CH₂OCH₂C(Cl)CH₂ | H | OCH₃ | Cl | CH | |
| CH₃ | CH₂OCH₂C(Cl)CH₂ | H | CH₃ | CH₃ | CH | |
| CH₃ | CH₂OCH₂C(Cl)CH₂ | H | OCH₃ | OCH₃ | N | |
| CH₃ | CH₂OCH₂C(Cl)CH₂ | H | OCH₃ | CH₃ | N | |
| CH₃ | CH₂OCH₂CCCH₂Cl | H | OCH₃ | OCH₃ | CH | |
| CH₃ | CH₂OCH₂CCCH₂Cl | H | OCH₃ | CH₃ | CH | |
| CH₃ | CH₂OCH₂CCCH₂Cl | H | OCH₃ | Cl | CH | |
| CH₃ | CH₂OCH₂CCCH₂Cl | H | CH₃ | CH₃ | CH | |
| CH₃ | CH₂OCH₂CCCH₂Cl | H | OCH₃ | OCH₃ | N | |
| CH₂CH₃ | CH₂OCH₂CCCH₂Cl | H | OCH₃ | CH₃ | N | |
| CH₃ | CH₂OCH₂OCH₃ | H | OCH₃ | OCH₃ | CH | |
| CH₃ | CH₂OCH₂OCH₃ | H | OCH₃ | CH₃ | CH | |
| CH₃ | CH₂OCH₂OCH₃ | H | OCH₃ | Cl | CH | |
| CH₃ | CH₂OCH₂OCH₃ | H | CH₃ | CH₃ | CH | |
| CH₃ | CH₂OCH₂OCH₃ | H | OCH₃ | OCH₃ | N | |
| CH₃ | CH₂OCH₂OCH₃ | H | OCH₃ | CH₃ | N | |
| CH₃ | CH₂OCH₂OCH₂CF₃ | H | OCH₃ | OCH₃ | CH | |
| CH₃ | CH₂OCH₂OCH₂CF₃ | H | OCH₃ | CH₃ | CH | |
| CH₃ | CH₂OCH₂OCH₂CF₃ | H | OCH₃ | Cl | CH | |
| CH₃ | CH₂OCH₂OCH₂CF₃ | H | CH₃ | CH₃ | CH | |
| CH₃ | CH₂OCH₂OCH₂CF₃ | H | OCH₃ | OCH₃ | N | |
| CH₃ | CH₂OCH₂OCH₂CF₃ | H | OCH₃ | CH₃ | N | |
| CH₃ | CH₂OCH₂SCH₃ | H | OCH₃ | OCH₃ | CH | |
| CH₃ | CH₂OCH₂SCH₃ | H | OCH₃ | CH₃ | CH | |
| CH₃ | CH₂OCH₂SCH₃ | H | OCH₃ | Cl | CH | |
| CH₃ | CH₂OCH₂SCH₃ | H | CH₃ | CH₃ | CH | |
| CH₃ | CH₂OCH₂SCH₃ | H | OCH₃ | OCH₃ | N | |
| CH₂CH₃ | CH₂OCH₂SCH₃ | H | OCH₃ | CH₃ | N | |
| CH₃ | CH₂OCH₂CN | H | OCH₃ | OCH₃ | CH | |
| CH₃ | CH₂OCH₂CN | H | OCH₃ | CH₃ | CH | |
| CH₃ | CH₂OCH₂CN | H | OCH₃ | Cl | CH | |
| CH₃ | CH₂OCH₂CN | H | CH₃ | CH₃ | CH | |
| CH₃ | CH₂OCH₂CN | H | OCH₃ | OCH₃ | N | |
| CH₃ | CH₂OCH₂CN | H | OCH₃ | CH₃ | N | |
| CH₃ | CH₂OCH₂CH₂N(CH₃)₂ | H | OCH₃ | OCH₃ | CH | |
| CH₃ | CH₂OCH₂CH₂N(CH₃)₂ | H | OCH₃ | CH₃ | CH | |
| CH₃ | CH₂OCH₂CH₂N(CH₃)₂ | H | OCH₃ | Cl | CH | |
| CH₃ | CH₂OCH₂CH₂N(CH₃)₂ | H | CH₃ | CH₃ | CH | |
| CH₃ | CH₂OCH₂CH₂N(CH₃)₂ | H | OCH₃ | OCH₃ | N | |
| CH₂CH₃ | CH₂OCH₂CH₂N(CH₃)₂ | H | OCH₃ | CH₃ | N | |
| CH₃ | CH₂OCH₂CH₂F | H | OCH₃ | OCH₃ | CH | 92–95 |

TABLE Ia-continued

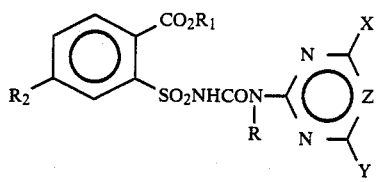

| R₁ | R₂ | R | X | Y | Z | m.p. (°C.) |
|---|---|---|---|---|---|---|
| CH₃ | CH₂OCH₂CH₂F | H | OCH₃ | CH₃ | CH | 115–117 |
| CH₃ | CH₂OCH₂CH₂F | H | OCH₃ | Cl | CH | |
| CH₃ | CH₂OCH₂CH₂F | H | CH₃ | CH₃ | CH | |
| CH₃ | CH₂OCH₂CH₂F | H | OCH₃ | OCH₃ | N | 150–152 |
| CH₃ | CH₂OCH₂CH₂F | H | OCH₃ | CH₃ | N | 100–103 |
| CH₂CH₃ | CH₂OCH₂CH₂F | H | OCH₃ | OCH₃ | CH | 81–83 |
| CH₂CH₃ | CH₂OCH₂CH₂F | H | OCH₃ | CH₃ | CH | 100–101 |
| CH₂CH₃ | CH₂OCH₂CH₂F | H | OCH₃ | Cl | CH | |
| CH₂CH₃ | CH₂OCH₂CH₂F | H | CH₃ | CH₃ | CH | |
| CH₂CH₃ | CH₂OCH₂CH₂F | H | OCH₃ | OCH₃ | N | 125–127 |
| CH₂CH₃ | CH₂OCH₂CH₂F | H | OCH₃ | CH₃ | N | 142–144 |
| CH₃ | CH₂OCH₂CHF₂ | H | OCH₃ | OCH₃ | CH | |
| CH₃ | CH₂OCH₂CHF₂ | H | OCH₃ | CH₃ | CH | |
| CH₃ | CH₂OCH₂CHF₂ | H | OCH₃ | Cl | CH | |
| CH₃ | CH₂OCH₂CHF₂ | H | CH₃ | CH₃ | CH | |
| CH₃ | CH₂OCH₂CHF₂ | H | OCH₃ | OCH₃ | N | |
| CH₃ | CH₂OCH₂CHF₂ | H | OCH₃ | CH₃ | N | |
| CH₃ | CH₂OCH₂CF₃ | H | OCH₃ | OCH₃ | CH | 118–120 |
| CH₃ | CH₂OCH₂CF₃ | H | OCH₃ | CH₃ | CH | 139–141 |
| CH₃ | CH₂OCH₂CF₃ | H | OCH₃ | Cl | CH | 124–125 |
| CH₃ | CH₂OCH₂CF₃ | H | CH₃ | CH₃ | CH | 159–161 |
| CH₃ | CH₂OCH₂CF₃ | H | OCH₃ | OCH₃ | N | 128–130 |
| CH₃ | CH₂OCH₂CF₃ | H | OCH₃ | CH₃ | N | 106–109 |
| CH₂CH₃ | CH₂OCH₂CF₃ | H | OCH₃ | OCH₃ | CH | 85–89 |
| CH₂CH₃ | CH₂OCH₂CF₃ | H | OCH₃ | CH₃ | CH | 110–113 |
| CH₂CH₃ | CH₂OCH₂CF₃ | H | OCH₃ | Cl | CH | 106–110 |
| CH₂CH₃ | CH₂OCH₂CF₃ | H | CH₃ | CH₃ | CH | 134–136 |
| CH₂CH₃ | CH₂OCH₂CF₃ | H | OCH₃ | OCH₃ | N | >250 |
| CH₂CH₃ | CH₂OCH₂CF₃ | H | OCH₃ | CH₃ | N | 126–128 |
| CH₃ | CH₂OCH₂CCH | H | OCH₃ | OCH₃ | CH | |
| CH₃ | CH₂OCH₂CCH | H | OCH₃ | CH₃ | CH | |
| CH₃ | CH₂OCH₂CCH | H | OCH₃ | Cl | CH | |
| CH₃ | CH₂OCH₂CCH | H | CH₃ | CH₃ | CH | |
| CH₃ | CH₂OCH₂CCH | H | OCH₃ | OCH₃ | N | |
| CH₃ | CH₂OCH₂CCH | H | OCH₃ | CH₃ | N | |
| CH₃ | CH₂OC(O)CH₃ | H | OCH₃ | OCH₃ | CH | 100–103 |
| CH₃ | CH₂OC(O)CH₃ | H | OCH₃ | CH₃ | CH | 165–167 |
| CH₃ | CH₂OC(O)CH₃ | H | OCH₃ | Cl | CH | |
| CH₃ | CH₂OC(O)CH₃ | H | CH₃ | CH₃ | CH | |
| CH₃ | CH₂OC(O)CH₃ | H | OCH₃ | OCH₃ | N | |
| CH₃ | CH₂OC(O)CH₃ | H | OCH₃ | CH₃ | N | 127–130 |
| CH₃ | CH₂OC(O)CH₂Cl | H | OCH₃ | OCH₃ | CH | |
| CH₃ | CH₂OC(O)CH₂Cl | H | OCH₃ | CH₃ | CH | |
| CH₃ | CH₂OC(O)CH₂Cl | H | OCH₃ | Cl | CH | |
| CH₃ | CH₂OC(O)CH₂Cl | H | CH₃ | CH₃ | CH | |
| CH₃ | CH₂OC(O)CH₂Cl | H | OCH₃ | OCH₃ | N | |
| CH₂CH₃ | CH₂OC(O)CH₂Cl | H | OCH₃ | CH₃ | N | |
| CH₃ | CH₂OC(O)OCH₃ | H | OCH₃ | OCH₃ | CH | |
| CH₃ | CH₂OC(O)OCH₃ | H | OCH₃ | CH₃ | CH | |
| CH₃ | CH₂OC(O)OCH₃ | H | OCH₃ | Cl | CH | |
| CH₃ | CH₂OC(O)OCH₃ | H | CH₃ | CH₃ | CH | |
| CH₃ | CH₂OC(O)OCH₃ | H | OCH₃ | OCH₃ | N | |
| CH₃ | CH₂OC(O)OCH₃ | H | OCH₃ | CH₃ | N | |
| CH₃ | CH₂OH | H | OCH₃ | OCH₃ | CH | |
| CH₃ | CH₂OH | H | OCH₃ | CH₃ | CH | |
| CH₃ | CH₂OH | H | OCH₃ | Cl | CH | |
| CH₃ | CH₂OH | H | CH₃ | CH₃ | CH | |
| CH₃ | CH₂OH | H | OCH₃ | OCH₃ | N | |
| CH₃ | CH₂OH | H | OCH₃ | CH₃ | N | |
| CH₃ | CH₂OP(O)(OCH₃)₂ | H | OCH₃ | OCH₃ | CH | |
| CH₃ | CH₂OP(O)(OCH₃)₂ | H | OCH₃ | CH₃ | CH | |
| CH₃ | CH₂OP(O)(OCH₃)₂ | H | OCH₃ | Cl | CH | |
| CH₃ | CH₂OP(O)(OCH₃)₂ | H | CH₃ | CH₃ | CH | |
| CH₃ | CH₂OP(O)(OCH₃)₂ | H | OCH₃ | OCH₃ | N | |
| CH₂CH₃ | CH₂OP(O)(OCH₃)₂ | H | OCH₃ | CH₃ | N | |
| CH₃ | CH₂OSO₂CH₃ | H | OCH₃ | OCH₃ | CH | |
| CH₃ | CH₂OSO₂CH₃ | H | OCH₃ | CH₃ | CH | |
| CH₃ | CH₂OSO₂CH₃ | H | OCH₃ | Cl | CH | |
| CH₃ | CH₂OSO₂CH₃ | H | CH₃ | CH₃ | CH | |
| CH₃ | CH₂OSO₂CH₃ | H | OCH₃ | OCH₃ | N | |
| CH₃ | CH₂OSO₂CH₃ | H | OCH₃ | CH₃ | N | |

TABLE Ia-continued

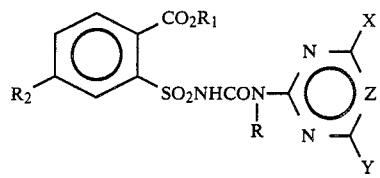

| R₁ | R₂ | R | X | Y | Z | m.p. (°C.) |
|---|---|---|---|---|---|---|
| CH₃ | CH₂OC(O)NHCH₃ | H | OCH₃ | OCH₃ | CH | |
| CH₃ | CH₂OC(O)NHCH₃ | H | OCH₃ | CH₃ | CH | |
| CH₃ | CH₂OC(O)NHCH₃ | H | OCH₃ | Cl | CH | |
| CH₃ | CH₂OC(O)NHCH₃ | H | CH₃ | CH₃ | CH | |
| CH₃ | CH₂OC(O)NHCH₃ | H | OCH₃ | OCH₃ | N | |
| CH₃ | CH₂OC(O)NHCH₃ | H | OCH₃ | CH₃ | N | |
| CH₃ | CH₂OC(O)N(CH₃)₂ | H | OCH₃ | OCH₃ | CH | |
| CH₃ | CH₂OC(O)N(CH₃)₂ | H | OCH₃ | CH₃ | CH | |
| CH₃ | CH₂OC(O)N(CH₃)₂ | H | OCH₃ | Cl | CH | |
| CH₃ | CH₂OC(O)N(CH₃)₂ | H | CH₃ | CH₃ | CH | |
| CH₃ | CH₂OC(O)N(CH₃)₂ | H | OCH₃ | OCH₃ | N | |
| CH₂CH₃ | CH₂OC(O)N(CH₃)₂ | H | OCH₃ | CH₃ | N | |
| CH₃ | CH₂OSi(CH₃)₃ | H | OCH₃ | OCH₃ | CH | |
| CH₃ | CH₂OSi(CH₃)₃ | H | OCH₃ | CH₃ | CH | |
| CH₃ | CH₂OSi(CH₃)₃ | H | OCH₃ | Cl | CH | |
| CH₃ | CH₂OSi(CH₃)₃ | H | CH₃ | CH₃ | CH | |
| CH₃ | CH₂OSi(CH₃)₃ | H | OCH₃ | OCH₃ | N | |
| CH₃ | CH₂OSi(CH₃)₃ | H | OCH₃ | CH₃ | N | |
| CH₃ | CH₂OCH₂CH₂OCH₃ | H | OCH₃ | OCH₃ | CH | 168–170 |
| CH₃ | CH₂OCH₂CH₂OCH₃ | H | OCH₃ | CH₃ | CH | 90–91 |
| CH₃ | CH₂OCH₂CH₂OCH₃ | H | OCH₃ | Cl | CH | 109–111 |
| CH₃ | CH₂OCH₂CH₂OCH₃ | H | CH₃ | CH₃ | CH | 120–122 |
| CH₃ | CH₂OCH₂CH₂OCH₃ | H | OCH₃ | OCH₃ | N | 135–137 |
| CH₃ | CH₂OCH₂CH₂OCH₃ | H | OCH₃ | CH₃ | N | 139–141 |
| CH₃ | CH₂OCH₂CH₂OCH₃ | H | OCH₃ | OCH₃ | CH | 168–170 |
| CH₃ | CH₂OCH₂CH₂OCH₃ | H | OCH₃ | CH₃ | CH | 91–92 |
| CH₃ | CH₂OCH₂CH₂OCH₃ | H | OCH₃ | Cl | CH | 109–111 |
| CH₃ | CH₂OCH₂CH₂OCH₃ | H | CH₃ | CH₃ | CH | 120–122 |
| CH₃ | CH₂OCH₂CH₂OCH₃ | H | OCH₃ | OCH₃ | N | 135–137 |
| CH₃ | CH₂OCH₂CH₂OCH₃ | H | OCH₃ | CH₃ | N | 139–141 |
| CH₃ | CH₂OCH₂C(H)CH₂ | H | OCH₃ | OCH₃ | CH | |
| CH₃ | CH₂OCH₂C(H)CH₂ | H | OCH₃ | CH₃ | CH | |
| CH₃ | CH₂OCH₂C(H)CH₂ | H | OCH₃ | Cl | CH | |
| CH₃ | CH₂OCH₂C(H)CH₂ | H | CH₃ | CH₃ | CH | |
| CH₃ | CH₂OCH₂C(H)CH₂ | H | OCH₃ | OCH₃ | N | |
| CH₃ | CH₂OCH₂C(H)CH₂ | H | OCH₃ | CH₃ | N | |
| CH₃ | CH₂OCH₂C(Cl)CH₂ | H | OCH₃ | OCH₃ | CH | |
| CH₃ | CH₂OCH₂C(Cl)CH₂ | H | OCH₃ | CH₃ | CH | |
| CH₃ | CH₂OCH₂C(Cl)CH₂ | H | OCH₃ | Cl | CH | |
| CH₃ | CH₂OCH₂C(Cl)CH₂ | H | CH₃ | CH₃ | CH | |
| CH₃ | CH₂OCH₂C(Cl)CH₂ | H | OCH₃ | OCH₃ | N | |
| CH₂CH₃ | CH₂OCH₂C(Cl)CH₂ | H | OCH₃ | CH₃ | N | |
| CH₃ | CH₂S—cyclopropyl | H | OCH₃ | OCH₃ | CH | |
| CH₃ | CH₂S—cyclopropyl | H | OCH₃ | CH₃ | CH | |
| CH₃ | CH₂S—cyclopropyl | H | OCH₃ | Cl | CH | |
| CH₃ | CH₂S—cyclopropyl | H | CH₃ | CH₃ | CH | |
| CH₃ | CH₂S—cyclopropyl | H | OCH₃ | OCH₃ | N | |
| CH₃ | CH₂S—cyclopropyl | H | OCH₃ | CH₃ | N | |
| CH₃ | CH₂SCH₂—cyclopropyl | H | OCH₃ | OCH₃ | CH | |
| CH₃ | CH₂SCH₂—cyclopropyl | H | OCH₃ | CH₃ | CH | |
| CH₃ | CH₂SCH₂—cyclopropyl | H | OCH₃ | Cl | CH | |
| CH₃ | CH₂SCH₂—cyclopropyl | H | CH₃ | CH₃ | CH | |
| CH₃ | CH₂SCH₂—cyclopropyl | H | OCH₃ | OCH₃ | N | |
| CH₃ | CH₂SCH₂—cyclopropyl | H | OCH₃ | CH₃ | N | |
| CH₃ | CH₂S—cyclobutyl | H | OCH₃ | OCH₃ | CH | |
| CH₃ | CH₂S—cyclobutyl | H | OCH₃ | CH₃ | CH | |
| CH₃ | CH₂S—cyclobutyl | H | OCH₃ | Cl | CH | |
| CH₃ | CH₂S—cyclobutyl | H | CH₃ | CH₃ | CH | |
| CH₃ | CH₂S—cyclobutyl | H | OCH₃ | OCH₃ | N | |
| CH₂CH₃ | CH₂S—cyclobutyl | H | OCH₃ | CH₃ | N | |
| CH₃ | CH₂SCH₂CF₂CF₃ | H | OCH₃ | OCH₃ | CH | |
| CH₃ | CH₂SCH₂CF₂CF₃ | H | OCH₃ | CH₃ | CH | |
| CH₃ | CH₂SCH₂CF₂CF₃ | H | OCH₃ | Cl | CH | |
| CH₃ | CH₂SCH₂CF₂CF₃ | H | CH₃ | CH₃ | CH | |
| CH₃ | CH₂SCH₂CF₂CF₃ | H | OCH₃ | OCH₃ | N | |
| CH₃ | CH₂SCH₂CF₂CF₃ | H | OCH₃ | CH₃ | N | |
| CH₃ | CH₂SCH(CF₃)CH₃ | H | OCH₃ | OCH₃ | CH | |
| CH₃ | CH₂SCH(CF₃)CH₃ | H | OCH₃ | CH₃ | CH | |
| CH₃ | CH₂SCH(CF₃)CH₃ | H | OCH₃ | Cl | CH | |
| CH₃ | CH₂SCH(CF₃)CH₃ | H | CH₃ | CH₃ | CH | |
| CH₃ | CH₂SCH(CF₃)CH₃ | H | OCH₃ | OCH₃ | N | |

TABLE Ia-continued

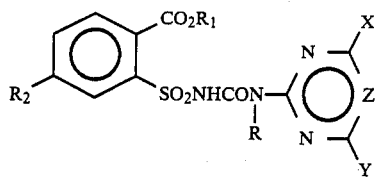

| R₁ | R₂ | R | X | Y | Z | m.p. (°C.) |
|---|---|---|---|---|---|---|
| CH₃ | CH₂SCH(CF₃)CH₃ | H | OCH₃ | CH₃ | N | |
| CH₃ | CH₂SCH₂CF₂CF₂H | H | OCH₃ | OCH₃ | CH | |
| CH₃ | CH₂SCH₂CF₂CF₂H | H | OCH₃ | CH₃ | CH | |
| CH₃ | CH₂SCH₂CF₂CF₂H | H | OCH₃ | Cl | CH | |
| CH₃ | CH₂SCH₂CF₂CF₂H | H | CH₃ | CH₃ | CH | |
| CH₃ | CH₂SCH₂CF₂CF₂H | H | OCH₃ | OCH₃ | N | |
| CH₂CH₃ | CH₂SCH₂CF₂CF₂H | H | OCH₃ | CH₃ | N | |
| CH₃ | CH₂SCH(CH₂F)₂ | H | OCH₃ | OCH₃ | CH | |
| CH₃ | CH₂SCH(CH₂F)₂ | H | OCH₃ | CH₃ | CH | |
| CH₃ | CH₂SCH(CH₂F)₂ | H | OCH₃ | Cl | CH | |
| CH₃ | CH₂SCH(CH₂F)₂ | H | CH₃ | CH₃ | CH | |
| CH₃ | CH₂SCH(CH₂F)₂ | H | OCH₃ | OCH₃ | N | |
| CH₃ | CH₂SCH(CH₂F)₂ | H | OCH₃ | CH₃ | N | |
| CH₃ | CH₂SCH(CH₂F)CH₃ | H | OCH₃ | OCH₃ | CH | |
| CH₃ | CH₂SCH(CH₂F)CH₃ | H | OCH₃ | CH₃ | CH | |
| CH₃ | CH₂SCH(CH₂F)CH₃ | H | OCH₃ | Cl | CH | |
| CH₃ | CH₂SCH(CH₂F)CH₃ | H | CH₃ | CH₃ | CH | |
| CH₃ | CH₂SCH(CH₂F)CH₃ | H | OCH₃ | OCH₃ | N | |
| CH₃ | CH₂SCH(CH₂F)CH₃ | H | OCH₃ | CH₃ | N | |
| CH₃ | CH₂S(CH₂)₃CH₂Cl | H | OCH₃ | OCH₃ | CH | |
| CH₃ | CH₂S(CH₂)₃CH₂Cl | H | OCH₃ | CH₃ | CH | |
| CH₃ | CH₂S(CH₂)₃CH₂Cl | H | OCH₃ | Cl | CH | |
| CH₃ | CH₂S(CH₂)₃CH₂Cl | H | CH₃ | CH₃ | CH | |
| CH₃ | CH₂S(CH₂)₃CH₂Cl | H | OCH₃ | OCH₃ | N | |
| CH₂CH₃ | CH₂S(CH₂)₃CH₂Cl | H | OCH₃ | CH₃ | N | |
| CH₃ | CH₂SCH₂CH₂OCH₃ | H | OCH₃ | OCH₃ | CH | |
| CH₃ | CH₂SCH₂CH₂OCH₃ | H | OCH₃ | CH₃ | CH | |
| CH₃ | CH₂SCH₂CH₂OCH₃ | H | OCH₃ | Cl | CH | |
| CH₃ | CH₂SCH₂CH₂OCH₃ | H | CH₃ | CH₃ | CH | |
| CH₃ | CH₂SCH₂CH₂OCH₃ | H | OCH₃ | OCH₃ | N | |
| CH₃ | CH₂SCH₂CH₂OCH₃ | H | OCH₃ | CH₃ | N | |
| CH₃ | CH₂SCH₂C(Cl)CH₂ | H | OCH₃ | OCH₃ | CH | |
| CH₃ | CH₂SCH₂C(Cl)CH₂ | H | OCH₃ | CH₃ | CH | |
| CH₃ | CH₂SCH₂C(Cl)CH₂ | H | OCH₃ | Cl | CH | |
| CH₃ | CH₂SCH₂C(Cl)CH₂ | H | CH₃ | CH₃ | CH | |
| CH₃ | CH₂SCH₂C(Cl)CH₂ | H | OCH₃ | OCH₃ | N | |
| CH₃ | CH₂SCH₂C(Cl)CH₂ | H | OCH₃ | CH₃ | N | |
| CH₃ | CH₂SCH₂CCCH₂Cl | H | OCH₃ | OCH₃ | CH | |
| CH₃ | CH₂SCH₂CCCH₂Cl | H | OCH₃ | CH₃ | CH | |
| CH₃ | CH₂SCH₂CCCH₂Cl | H | OCH₃ | Cl | CH | |
| CH₃ | CH₂SCH₂CCCH₂Cl | H | CH₃ | CH₃ | CH | |
| CH₃ | CH₂SCH₂CCCH₂Cl | H | OCH₃ | OCH₃ | N | |
| CH₂CH₃ | CH₂SCH₂CCCH₂Cl | H | OCH₃ | CH₃ | N | |
| CH₃ | CH₂SCH₂OCH₃ | H | OCH₃ | OCH₃ | CH | |
| CH₃ | CH₂SCH₂OCH₃ | H | OCH₃ | CH₃ | CH | |
| CH₃ | CH₂SCH₂OCH₃ | H | OCH₃ | Cl | CH | |
| CH₃ | CH₂SCH₂OCH₃ | H | CH₃ | CH₃ | CH | |
| CH₃ | CH₂SCH₂OCH₃ | H | OCH₃ | OCH₃ | N | |
| CH₃ | CH₂SCH₂OCH₃ | H | OCH₃ | CH₃ | N | |
| CH₃ | CH₂SCH₂OCH₂CF₃ | H | OCH₃ | OCH₃ | CH | |
| CH₃ | CH₂SCH₂OCH₂CF₃ | H | OCH₃ | CH₃ | CH | |
| CH₃ | CH₂SCH₂OCH₂CF₃ | H | OCH₃ | Cl | CH | |
| CH₃ | CH₂SCH₂OCH₂CF₃ | H | CH₃ | CH₃ | CH | |
| CH₃ | CH₂SCH₂OCH₂CF₃ | H | OCH₃ | OCH₃ | N | |
| CH₃ | CH₂SCH₂OCH₂CF₃ | H | OCH₃ | CH₃ | N | |
| CH₃ | CH₂SCH₂SCH₃ | H | OCH₃ | OCH₃ | CH | |
| CH₃ | CH₂SCH₂SCH₃ | H | OCH₃ | CH₃ | CH | |
| CH₃ | CH₂SCH₂SCH₃ | H | OCH₃ | Cl | CH | |
| CH₃ | CH₂SCH₂SCH₃ | H | CH₃ | CH₃ | CH | |
| CH₃ | CH₂SCH₂SCH₃ | H | OCH₃ | OCH₃ | N | |
| CH₂CH₃ | CH₂SCH₂SCH₃ | H | OCH₃ | CH₃ | N | |
| CH₃ | CH₂SCH₂CN | H | OCH₃ | OCH₃ | CH | |
| CH₃ | CH₂SCH₂CN | H | OCH₃ | CH₃ | CH | |
| CH₃ | CH₂SCH₂CN | H | OCH₃ | Cl | CH | |
| CH₃ | CH₂SCH₂CN | H | CH₃ | CH₃ | CH | |
| CH₃ | CH₂SCH₂CN | H | OCH₃ | OCH₃ | N | |
| CH₃ | CH₂SCH₂CN | H | OCH₃ | CH₃ | N | |
| CH₃ | CH₂SCH₂CH₂N(CH₃)₂ | H | OCH₃ | OCH₃ | CH | |
| CH₃ | CH₂SCH₂CH₂N(CH₃)₂ | H | OCH₃ | CH₃ | CH | |
| CH₃ | CH₂SCH₂CH₂N(CH₃)₂ | H | OCH₃ | Cl | CH | |
| CH₃ | CH₂SCH₂CH₂N(CH₃)₂ | H | CH₃ | CH₃ | CH | |

TABLE Ia-continued

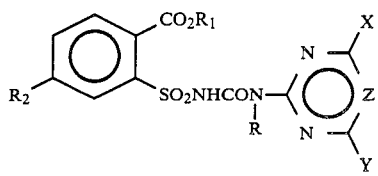

| R₁ | R₂ | R | X | Y | Z | m.p. (°C.) |
|---|---|---|---|---|---|---|
| CH₃ | CH₂SCH₂CH₂N(CH₃)₂ | H | OCH₃ | OCH₃ | N | |
| CH₂CH₃ | CH₂SCH₂CH₂N(CH₃)₂ | H | OCH₃ | CH₃ | N | |
| CH₃ | CH₂SCH₂CH₂F | H | OCH₃ | OCH₃ | CH | |
| CH₃ | CH₂SCH₂CH₂F | H | OCH₃ | CH₃ | CH | |
| CH₃ | CH₂SCH₂CH₂F | H | OCH₃ | Cl | CH | |
| CH₃ | CH₂SCH₂CH₂F | H | CH₃ | CH₃ | CH | |
| CH₃ | CH₂SCH₂CH₂F | H | OCH₃ | OCH₃ | N | |
| CH₃ | CH₂SCH₂CH₂F | H | OCH₃ | CH₃ | N | |
| CH₃ | CH₂SCH₂CHF₂ | H | OCH₃ | OCH₃ | CH | |
| CH₃ | CH₂SCH₂CHF₂ | H | OCH₃ | CH₃ | CH | |
| CH₃ | CH₂SCH₂CHF₂ | H | OCH₃ | Cl | CH | |
| CH₃ | CH₂SCH₂CHF₂ | H | CH₃ | CH₃ | CH | |
| CH₃ | CH₂SCH₂CHF₂ | H | OCH₃ | OCH₃ | N | |
| CH₃ | CH₂SCH₂CHF₂ | H | OCH₃ | CH₃ | N | |
| CH₃ | CH₂SCH₂CF₃ | H | OCH₃ | OCH₃ | CH | |
| CH₃ | CH₂SCH₂CF₃ | H | OCH₃ | CH₃ | CH | |
| CH₃ | CH₂SCH₂CF₃ | H | OCH₃ | Cl | CH | |
| CH₃ | CH₂SCH₂CF₃ | H | CH₃ | CH₃ | CH | |
| CH₃ | CH₂SCH₂CF₃ | H | OCH₃ | OCH₃ | N | |
| CH₂CH₃ | CH₂SCH₂CF₃ | H | OCH₃ | CH₃ | N | |
| CH₃ | CH₂SCH₂CCH | H | OCH₃ | OCH₃ | CH | |
| CH₃ | CH₂SCH₂CCH | H | OCH₃ | CH₃ | CH | |
| CH₃ | CH₂SCH₂CCH | H | OCH₃ | Cl | CH | |
| CH₃ | CH₂SCH₂CCH | H | CH₃ | CH₃ | CH | |
| CH₃ | CH₂SCH₂CCH | H | OCH₃ | OCH₃ | N | |
| CH₃ | CH₂SCH₂CCH | H | OCH₃ | CH₃ | N | |
| CH₃ | CH₂SH | H | OCH₃ | OCH₃ | CH | |
| CH₃ | CH₂SH | H | OCH₃ | CH₃ | CH | |
| CH₃ | CH₂SH | H | OCH₃ | Cl | CH | |
| CH₃ | CH₂SH | H | CH₃ | CH₃ | CH | |
| CH₃ | CH₂SH | H | OCH₃ | OCH₃ | N | |
| CH₃ | CH₂SH | H | OCH₃ | CH₃ | N | |
| CH₃ | CH₂SP(O)(OCH₃)₂ | H | OCH₃ | OCH₃ | CH | |
| CH₃ | CH₂SP(O)(OCH₃)₂ | H | OCH₃ | CH₃ | CH | |
| CH₃ | CH₂SP(O)(OCH₃)₂ | H | OCH₃ | Cl | CH | |
| CH₃ | CH₂SP(O)(OCH₃)₂ | H | CH₃ | CH₃ | CH | |
| CH₃ | CH₂SP(O)(OCH₃)₂ | H | OCH₃ | OCH₃ | N | |
| CH₂CH₃ | CH₂SP(O)(OCH₃)₂ | H | OCH₃ | CH₃ | N | |
| CH₃ | CH₂SCH₂CH₂OCH₃ | H | OCH₃ | OCH₃ | CH | |
| CH₃ | CH₂SCH₂CH₂OCH₃ | H | OCH₃ | CH₃ | CH | |
| CH₃ | CH₂SCH₂CH₂OCH₃ | H | OCH₃ | Cl | CH | |
| CH₃ | CH₂SCH₂CH₂OCH₃ | H | CH₃ | CH₃ | CH | |
| CH₃ | CH₂SCH₂CH₂OCH₃ | H | OCH₃ | OCH₃ | N | |
| CH₃ | CH₂SCH₂CH₂OCH₃ | H | OCH₃ | CH₃ | N | |
| CH₃ | CH₂SCH₂C(H)CH₂ | H | OCH₃ | OCH₃ | CH | |
| CH₃ | CH₂SCH₂C(H)CH₂ | H | OCH₃ | CH₃ | CH | |
| CH₃ | CH₂SCH₂C(H)CH₂ | H | OCH₃ | Cl | CH | |
| CH₃ | CH₂SCH₂C(H)CH₂ | H | CH₃ | CH₃ | CH | |
| CH₃ | CH₂SCH₂C(H)CH₂ | H | OCH₃ | OCH₃ | N | |
| CH₃ | CH₂SCH₂C(H)CH₂ | H | OCH₃ | CH₃ | N | |
| CH₃ | CH₂SCH₂C(Cl)CH₂ | H | OCH₃ | OCH₃ | CH | |
| CH₃ | CH₂SCH₂C(Cl)CH₂ | H | OCH₃ | CH₃ | CH | |
| CH₃ | CH₂SCH₂C(Cl)CH₂ | H | OCH₃ | Cl | CH | |
| CH₃ | CH₂SCH₂C(Cl)CH₂ | H | CH₃ | CH₃ | CH | |
| CH₃ | CH₂SCH₂C(Cl)CH₂ | H | OCH₃ | OCH₃ | N | |
| CH₂CH₃ | CH₂SCH₂C(Cl)CH₂ | H | OCH₂ | CH₃ | N | |
| CH₃ | CH₂S(O)—cyclopropyl | H | OCH₃ | OCH₃ | CH | |
| CH₃ | CH₂S(O)—cyclopropyl | H | OCH₃ | CH₃ | CH | |
| CH₃ | CH₂S(O)—cyclopropyl | H | OCH₃ | Cl | CH | |
| CH₃ | CH₂S(O)—cyclopropyl | H | CH₃ | CH₃ | CH | |
| CH₃ | CH₂S(O)—cyclopropyl | H | OCH₃ | OCH₃ | N | |
| CH₃ | CH₂S(O)—cyclopropyl | H | OCH₃ | CH₃ | N | |
| CH₃ | CH₂S(O)CH₂—cyclopropyl | H | OCH₃ | OCH₃ | CH | |
| CH₃ | CH₂S(O)CH₂—cyclopropyl | H | OCH₃ | CH₃ | CH | |
| CH₃ | CH₂S(O)CH₂—cyclopropyl | H | OCH₃ | Cl | CH | |
| CH₃ | CH₂S(O)CH₂—cyclopropyl | H | CH₃ | CH₃ | CH | |
| CH₃ | CH₂S(O)CH₂—cyclopropyl | H | OCH₃ | OCH₃ | N | |
| CH₃ | CH₂S(O)CH₂—cyclopropyl | H | OCH₃ | CH₃ | N | |
| CH₃ | CH₂S(O)—cyclobutyl | H | OCH₃ | OCH₃ | CH | |
| CH₃ | CH₂S(O)—cyclobutyl | H | OCH₃ | CH₃ | CH | |
| CH₃ | CH₂S(O)—cyclobutyl | H | OCH₃ | Cl | CH | |

TABLE Ia-continued

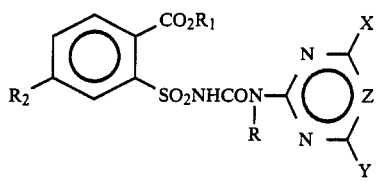

| R₁ | R₂ | R | X | Y | Z | m.p. (°C.) |
|---|---|---|---|---|---|---|
| CH₃ | CH₂S(O)—cyclobutyl | H | CH₃ | CH₃ | CH | |
| CH₃ | CH₂S(O)—cyclobutyl | H | OCH₃ | OCH₃ | N | |
| CH₂CH₃ | CH₂S(O)—cyclobutyl | H | OCH₃ | CH₃ | N | |
| CH₃ | CH₂S(O)CH₂CF₂CF₃ | H | OCH₃ | OCH₃ | CH | |
| CH₃ | CH₂S(O)CH₂CF₂CF₃ | H | OCH₃ | CH₃ | CH | |
| CH₃ | CH₂S(O)CH₂CF₂CF₃ | H | OCH₃ | Cl | CH | |
| CH₃ | CH₂S(O)CH₂CF₂CF₃ | H | CH₃ | CH₃ | CH | |
| CH₃ | CH₂S(O)CH₂CF₂CF₃ | H | OCH₃ | OCH₃ | N | |
| CH₃ | CH₂S(O)CH₂CF₂CF₃ | H | OCH₃ | CH₃ | N | |
| CH₃ | CH₂S(O)CH(CF₃)CH₃ | H | OCH₃ | OCH₃ | CH | |
| CH₃ | CH₂S(O)CH(CF₃)CH₃ | H | OCH₃ | CH₃ | CH | |
| CH₃ | CH₂S(O)CH(CF₃)CH₃ | H | OCH₃ | Cl | CH | |
| CH₃ | CH₂S(O)CH(CF₃)CH₃ | H | CH₃ | CH₃ | CH | |
| CH₃ | CH₂S(O)CH(CF₃)CH₃ | H | OCH₃ | OCH₃ | N | |
| CH₃ | CH₂S(O)CH(CF₃)CH₃ | H | OCH₃ | CH₃ | N | |
| CH₃ | CH₂S(O)CH₂CF₂CF₂H | H | OCH₃ | OCH₃ | CH | |
| CH₃ | CH₂S(O)CH₂CF₂CF₂H | H | OCH₃ | CH₃ | CH | |
| CH₃ | CH₂S(O)CH₂CF₂CF₂H | H | OCH₃ | Cl | CH | |
| CH₃ | CH₂S(O)CH₂CF₂CF₂H | H | CH₃ | CH₃ | CH | |
| CH₃ | CH₂S(O)CH₂CF₂CF₂H | H | OCH₃ | OCH₃ | N | |
| CH₂CH₃ | CH₂S(O)CH₂CF₂CF₂H | H | OCH₃ | CH₃ | N | |
| CH₃ | CH₂S(O)CH(CH₂F)₂ | H | OCH₃ | OCH₃ | CH | |
| CH₃ | CH₂S(O)CH(CH₂F)₂ | H | OCH₃ | CH₃ | CH | |
| CH₃ | CH₂S(O)CH(CH₂F)₂ | H | OCH₃ | Cl | CH | |
| CH₃ | CH₂S(O)CH(CH₂F)₂ | H | CH₃ | CH₃ | CH | |
| CH₃ | CH₂S(O)CH(CH₂F)₂ | H | OCH₃ | OCH₃ | N | |
| CH₃ | CH₂S(O)CH(CH₂F)₂ | H | OCH₃ | CH₃ | N | |
| CH₃ | CH₂S(O)CH(CH₂F)CH₃ | H | OCH₃ | OCH₃ | CH | |
| CH₃ | CH₂S(O)CH(CH₂F)CH₃ | H | OCH₃ | CH₃ | CH | |
| CH₃ | CH₂S(O)CH(CH₂F)CH₃ | H | OCH₃ | Cl | CH | |
| CH₃ | CH₂S(O)CH(CH₂F)CH₃ | H | CH₃ | CH₃ | CH | |
| CH₃ | CH₂S(O)CH(CH₂F)CH₃ | H | OCH₃ | OCH₃ | N | |
| CH₃ | CH₂S(O)CH(CH₂F)CH₃ | H | OCH₃ | CH₃ | N | |
| CH₃ | CH₂S(O)(CH₂)₃CH₂Cl | H | OCH₃ | OCH₃ | CH | |
| CH₃ | CH₂S(O)(CH₂)₃CH₂Cl | H | OCH₃ | CH₃ | CH | |
| CH₃ | CH₂S(O)(CH₂)₃CH₂Cl | H | OCH₃ | Cl | CH | |
| CH₃ | CH₂S(O)(CH₂)₃CH₂Cl | H | CH₃ | CH₃ | CH | |
| CH₃ | CH₂S(O)(CH₂)₃CH₂Cl | H | OCH₃ | OCH₃ | N | |
| CH₂CH₃ | CH₂S(O)(CH₂)₃CH₂Cl | H | OCH₃ | CH₃ | N | |
| CH₃ | CH₂S(O)CH₂CH₂OCH₃ | H | OCH₃ | OCH₃ | CH | |
| CH₃ | CH₂S(O)CH₂CH₂OCH₃ | H | OCH₃ | CH₃ | CH | |
| CH₃ | CH₂S(O)CH₂CH₂OCH₃ | H | OCH₃ | Cl | CH | |
| CH₃ | CH₂S(O)CH₂CH₂OCH₃ | H | CH₃ | CH₃ | CH | |
| CH₃ | CH₂S(O)CH₂CH₂OCH₃ | H | OCH₃ | OCH₃ | N | |
| CH₃ | CH₂S(O)CH₂CH₂OCH₃ | H | OCH₃ | CH₃ | N | |
| CH₃ | CH₂S(O)CH₂C(Cl)CH₂ | H | OCH₃ | OCH₃ | CH | |
| CH₃ | CH₂S(O)CH₂C(Cl)CH₂ | H | OCH₃ | CH₃ | CH | |
| CH₃ | CH₂S(O)CH₂C(Cl)CH₂ | H | OCH₃ | Cl | CH | |
| CH₃ | CH₂S(O)CH₂C(Cl)CH₂ | H | CH₃ | CH₃ | CH | |
| CH₃ | CH₂S(O)CH₂C(Cl)CH₂ | H | OCH₃ | OCH₃ | N | |
| CH₃ | CH₂S(O)CH₂C(Cl)CH₂ | H | OCH₃ | CH₃ | N | |
| CH₃ | CH₂S(O)CH₂CCCH₂Cl | H | OCH₃ | OCH₃ | CH | |
| CH₃ | CH₂S(O)CH₂CCCH₂Cl | H | OCH₃ | CH₃ | CH | |
| CH₃ | CH₂S(O)CH₂CCCH₂Cl | H | OCH₃ | Cl | CH | |
| CH₃ | CH₂S(O)CH₂CCCH₂Cl | H | CH₃ | CH₃ | CH | |
| CH₃ | CH₂S(O)CH₂CCCH₂Cl | H | OCH₃ | OCH₃ | N | |
| CH₂CH₃ | CH₂S(O)CH₂CCCH₂Cl | H | OCH₃ | CH₃ | N | |
| CH₃ | CH₂S(O)CH₂CN | H | OCH₃ | OCH₃ | CH | |
| CH₃ | CH₂S(O)CH₂CN | H | OCH₃ | CH₃ | CH | |
| CH₃ | CH₂S(O)CH₂CN | H | OCH₃ | Cl | CH | |
| CH₃ | CH₂S(O)CH₂CN | H | CH₃ | CH₃ | CH | |
| CH₃ | CH₂S(O)CH₂CN | H | OCH₃ | OCH₃ | N | |
| CH₃ | CH₂S(O)CH₂CN | H | OCH₃ | CH₃ | N | |
| CH₃ | CH₂S(O)CH₂CH₂N(CH₃)₂ | H | OCH₃ | OCH₃ | CH | |
| CH₃ | CH₂S(O)CH₂CH₂N(CH₃)₂ | H | OCH₃ | CH₃ | CH | |
| CH₃ | CH₂S(O)CH₂CH₂N(CH₃)₂ | H | OCH₃ | Cl | CH | |
| CH₃ | CH₂S(O)CH₂CH₂N(CH₃)₂ | H | CH₃ | CH₃ | CH | |
| CH₃ | CH₂S(O)CH₂CH₂N(CH₃)₂ | H | OCH₃ | OCH₃ | N | |
| CH₂CH₃ | CH₂S(O)CH₂CH₂N(CH₃)₂ | H | OCH₃ | CH₃ | N | |
| CH₃ | CH₂S(O)CH₂CH₂F | H | OCH₃ | OCH₃ | CH | |
| CH₃ | CH₂S(O)CH₂CH₂F | H | OCH₃ | CH₃ | CH | |

TABLE Ia-continued

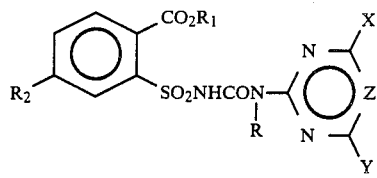

| R₁ | R₂ | R | X | Y | Z | m.p. (°C.) |
|---|---|---|---|---|---|---|
| CH₃ | CH₂S(O)CH₂CH₂F | H | OCH₃ | Cl | CH | |
| CH₃ | CH₂S(O)CH₂CH₂F | H | CH₃ | CH₃ | CH | |
| CH₃ | CH₂S(O)CH₂CH₂F | H | OCH₃ | OCH₃ | N | |
| CH₃ | CH₂S(O)CH₂CH₂F | H | OCH₃ | CH₃ | N | |
| CH₃ | CH₂S(O)CH₂CHF₂ | H | OCH₃ | OCH₃ | CH | |
| CH₃ | CH₂S(O)CH₂CHF₂ | H | OCH₃ | CH₃ | CH | |
| CH₃ | CH₂S(O)CH₂CHF₂ | H | OCH₃ | Cl | CH | |
| CH₃ | CH₂S(O)CH₂CHF₂ | H | CH₃ | CH₃ | CH | |
| CH₃ | CH₂S(O)CH₂CHF₂ | H | OCH₃ | OCH₃ | N | |
| CH₃ | CH₂S(O)CH₂CHF₂ | H | OCH₃ | CH₃ | N | |
| CH₃ | CH₂S(O)CH₂CF₃ | H | OCH₃ | OCH₃ | CH | |
| CH₃ | CH₂S(O)CH₂CF₃ | H | OCH₃ | CH₃ | CH | |
| CH₃ | CH₂S(O)CH₂CF₃ | H | OCH₃ | Cl | CH | |
| CH₃ | CH₂S(O)CH₂CF₃ | H | CH₃ | CH₃ | CH | |
| CH₃ | CH₂S(O)CH₂CF₃ | H | OCH₃ | OCH₃ | N | |
| CH₂CH₃ | CH₂S(O)CH₂CF₃ | H | OCH₃ | CH₃ | N | |
| CH₃ | CH₂S(O)CH₂CCH | H | OCH₃ | OCH₃ | CH | |
| CH₃ | CH₂S(O)CH₂CCH | H | OCH₃ | CH₃ | CH | |
| CH₃ | CH₂S(O)CH₂CCH | H | OCH₃ | Cl | CH | |
| CH₃ | CH₂S(O)CH₂CCH | H | CH₃ | CH₃ | CH | |
| CH₃ | CH₂S(O)CH₂CCH | H | OCH₃ | OCH₃ | N | |
| CH₃ | CH₂S(O)CH₂CCH | H | OCH₃ | CH₃ | N | |
| CH₃ | CH₂S(O)CH₂CH₂OCH₃ | H | OCH₃ | OCH₃ | CH | |
| CH₃ | CH₂S(O)CH₂CH₂OCH₃ | H | OCH₃ | CH₃ | CH | |
| CH₃ | CH₂S(O)CH₂CH₂OCH₃ | H | OCH₃ | Cl | CH | |
| CH₃ | CH₂S(O)CH₂CH₂OCH₃ | H | CH₃ | CH₃ | CH | |
| CH₃ | CH₂S(O)CH₂CH₂OCH₃ | H | OCH₃ | OCH₃ | N | |
| CH₃ | CH₂S(O)CH₂CH₂OCH₃ | H | OCH₃ | CH₃ | N | |
| CH₃ | CH₂S(O)CH₂C(H)CH₂ | H | OCH₃ | OCH₃ | CH | |
| CH₃ | CH₂S(O)CH₂C(H)CH₂ | H | OCH₃ | CH₃ | CH | |
| CH₃ | CH₂S(O)CH₂C(H)CH₂ | H | OCH₃ | Cl | CH | |
| CH₃ | CH₂S(O)CH₂C(H)CH₂ | H | CH₃ | CH₃ | CH | |
| CH₃ | CH₂S(O)CH₂C(H)CH₂ | H | OCH₃ | OCH₃ | N | |
| CH₃ | CH₂S(O)CH₂C(H)CH₂ | H | OCH₃ | CH₃ | N | |
| CH₃ | CH₂S(O)CH₂C(Cl)CH₂ | H | OCH₃ | OCH₃ | CH | |
| CH₃ | CH₂S(O)CH₂C(Cl)CH₂ | H | OCH₃ | CH₃ | CH | |
| CH₃ | CH₂S(O)CH₂C(Cl)CH₂ | H | OCH₃ | Cl | CH | |
| CH₃ | CH₂S(O)CH₂C(Cl)CH₂ | H | CH₃ | CH₃ | CH | |
| CH₃ | CH₂S(O)CH₂C(Cl)CH₂ | H | OCH₃ | OCH₃ | N | |
| CH₂CH₃ | CH₂S(O)CH₂C(Cl)CH₂ | H | OCH₃ | CH₃ | N | |
| CH₃ | CH₂S(O)₂—cyclopropyl | H | OCH₃ | OCH₃ | CH | |
| CH₃ | CH₂S(O)₂—cyclopropyl | H | OCH₃ | CH₃ | CH | |
| CH₃ | CH₂S(O)₂—cyclopropyl | H | OCH₃ | Cl | CH | |
| CH₃ | CH₂S(O)₂—cyclopropyl | H | CH₃ | CH₃ | CH | |
| CH₃ | CH₂S(O)₂—cyclopropyl | H | OCH₃ | OCH₃ | N | |
| CH₃ | CH₂S(O)₂—cyclopropyl | H | OCH₃ | CH₃ | N | |
| CH₃ | CH₂S(O)₂CH₂—cyclopropyl | H | OCH₃ | OCH₃ | CH | |
| CH₃ | CH₂S(O)₂CH₂—cyclopropyl | H | OCH₃ | CH₃ | CH | |
| CH₃ | CH₂S(O)₂CH₂—cyclopropyl | H | OCH₃ | Cl | CH | |
| CH₃ | CH₂S(O)₂CH₂—cyclopropyl | H | CH₃ | CH₃ | CH | |
| CH₃ | CH₂S(O)₂CH₂—cyclopropyl | H | OCH₃ | OCH₃ | N | |
| CH₃ | CH₂S(O)₂CH₂—cyclopropyl | H | OCH₃ | CH₃ | N | |
| CH₃ | CH₂S(O)₂—cyclobutyl | H | OCH₃ | OCH₃ | CH | |
| CH₃ | CH₂S(O)₂—cyclobutyl | H | OCH₃ | CH₃ | CH | |
| CH₃ | CH₂S(O)₂—cyclobutyl | H | OCH₃ | Cl | CH | |
| CH₃ | CH₂S(O)₂—cyclobutyl | H | CH₃ | CH₃ | CH | |
| CH₃ | CH₂S(O)₂—cyclobutyl | H | OCH₃ | OCH₃ | N | |
| CH₂CH₃ | CH₂S(O)₂—cyclobutyl | H | OCH₃ | CH₃ | N | |
| CH₃ | CH₂S(O)₂CH₂CF₂CF₃ | H | OCH₃ | OCH₃ | CH | |
| CH₃ | CH₂S(O)₂CH₂CF₂CF₃ | H | OCH₃ | CH₃ | CH | |
| CH₃ | CH₂S(O)₂CH₂CF₂CF₃ | H | OCH₃ | Cl | CH | |
| CH₃ | CH₂S(O)₂CH₂CF₂CF₃ | H | CH₃ | CH₃ | CH | |
| CH₃ | CH₂S(O)₂CH₂CF₂CF₃ | H | OCH₃ | OCH₃ | N | |
| CH₃ | CH₂S(O)₂CH₂CF₂CF₃ | H | OCH₃ | CH₃ | N | |
| CH₃ | CH₂S(O)₂CH(CF₃)CH₃ | H | OCH₃ | OCH₃ | CH | |
| CH₃ | CH₂S(O)₂CH(CF₃)CH₃ | H | OCH₃ | CH₃ | CH | |
| CH₃ | CH₂S(O)₂CH(CF₃)CH₃ | H | OCH₃ | Cl | CH | |
| CH₃ | CH₂S(O)₂CH(CF₃)CH₃ | H | CH₃ | CH₃ | CH | |
| CH₃ | CH₂S(O)₂CH(CF₃)CH₃ | H | OCH₃ | OCH₃ | N | |
| CH₃ | CH₂S(O)₂CH(CF₃)CH₃ | H | OCH₃ | CH₃ | N | |
| CH₃ | CH₂S(O)₂CH₂CF₂CF₂H | H | OCH₃ | OCH₃ | CH | |

TABLE Ia-continued

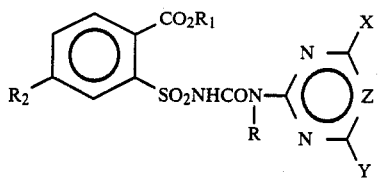

| R₁ | R₂ | R | X | Y | Z | m.p. (°C.) |
|---|---|---|---|---|---|---|
| CH₃ | CH₂S(O)₂CH₂CF₂CF₂H | H | OCH₃ | CH₃ | CH | |
| CH₃ | CH₂S(O)₂CH₂CF₂CF₂H | H | OCH₃ | Cl | CH | |
| CH₃ | CH₂S(O)₂CH₂CF₂CF₂H | H | CH₃ | CH₃ | CH | |
| CH₃ | CH₂S(O)₂CH₂CF₂CF₂H | H | OCH₃ | OCH₃ | N | |
| CH₂CH₃ | CH₂S(O)₂CH₂CF₂CF₂H | H | OCH₃ | CH₃ | N | |
| CH₃ | CH₂S(O)₂CH(CH₂F)₂ | H | OCH₃ | OCH₃ | CH | |
| CH₃ | CH₂S(O)₂CH(CH₂F)₂ | H | OCH₃ | CH₃ | CH | |
| CH₃ | CH₂S(O)₂CH(CH₂F)₂ | H | OCH₃ | Cl | CH | |
| CH₃ | CH₂S(O)₂CH(CH₂F)₂ | H | CH₃ | CH₃ | CH | |
| CH₃ | CH₂S(O)₂CH(CH₂F)₂ | H | OCH₃ | OCH₃ | N | |
| CH₃ | CH₂S(O)₂CH(CH₂F)₂ | H | OCH₃ | CH₃ | N | |
| CH₃ | CH₂S(O)₂CH(CH₂F)CH₃ | H | OCH₃ | OCH₃ | CH | |
| CH₃ | CH₂S(O)₂CH(CH₂F)CH₃ | H | OCH₃ | CH₃ | CH | |
| CH₃ | CH₂S(O)₂CH(CH₂F)CH₃ | H | OCH₃ | Cl | CH | |
| CH₃ | CH₂S(O)₂CH(CH₂F)CH₃ | H | CH₃ | CH₃ | CH | |
| CH₃ | CH₂S(O)₂CH(CH₂F)CH₃ | H | OCH₃ | OCH₃ | N | |
| CH₃ | CH₂S(O)₂CH(CH₂F)CH₃ | H | OCH₃ | CH₃ | N | |
| CH₃ | CH₂S(O)₂(CH₂)₃CH₂Cl | H | OCH₃ | OCH₃ | CH | |
| CH₃ | CH₂S(O)₂(CH₂)₃CH₂Cl | H | OCH₃ | CH₃ | CH | |
| CH₃ | CH₂S(O)₂(CH₂)₃CH₂Cl | H | OCH₃ | Cl | CH | |
| CH₃ | CH₂S(O)₂(CH₂)₃CH₂Cl | H | CH₃ | CH₃ | CH | |
| CH₃ | CH₂S(O)₂(CH₂)₃CH₂Cl | H | OCH₃ | OCH₃ | N | |
| CH₂CH₃ | CH₂S(O)₂(CH₂)₃CH₂Cl | H | OCH₃ | CH₃ | N | |
| CH₃ | CH₂S(O)CH₂CH₂OCH₃ | H | OCH₃ | OCH₃ | CH | |
| CH₃ | CH₂S(O)CH₂CH₂OCH₃ | H | OCH₃ | CH₃ | CH | |
| CH₃ | CH₂S(O)CH₂CH₂OCH₃ | H | OCH₃ | Cl | CH | |
| CH₃ | CH₂S(O)CH₂CH₂OCH₃ | H | CH₃ | CH₃ | CH | |
| CH₃ | CH₂S(O)CH₂CH₂OCH₃ | H | OCH₃ | OCH₃ | N | |
| CH₃ | CH₂S(O)CH₂CH₂OCH₃ | H | OCH₃ | CH₃ | N | |
| CH₃ | CH₂S(O)₂CH₂C(Cl)CH₂ | H | OCH₃ | OCH₃ | CH | |
| CH₃ | CH₂S(O)₂CH₂C(Cl)CH₂ | H | OCH₃ | CH₃ | CH | |
| CH₃ | CH₂S(O)₂CH₂C(Cl)CH₂ | H | OCH₃ | Cl | CH | |
| CH₃ | CH₂S(O)₂CH₂C(Cl)CH₂ | H | CH₃ | CH₃ | CH | |
| CH₃ | CH₂S(O)₂CH₂C(Cl)CH₂ | H | OCH₃ | OCH₃ | N | |
| CH₃ | CH₂S(O)₂CH₂C(Cl)CH₂ | H | OCH₃ | CH₃ | N | |
| CH₃ | CH₂S(O)₂CH₂CCCH₂Cl | H | OCH₃ | OCH₃ | CH | |
| CH₃ | CH₂S(O)₂CH₂CCCH₂Cl | H | OCH₃ | CH₃ | CH | |
| CH₃ | CH₂S(O)₂CH₂CCCH₂Cl | H | OCH₃ | Cl | CH | |
| CH₃ | CH₂S(O)₂CH₂CCCH₂Cl | H | CH₃ | CH₃ | CH | |
| CH₃ | CH₂S(O)₂CH₂CCCH₂Cl | H | OCH₃ | OCH₃ | N | |
| CH₂CH₃ | CH₂S(O)₂CH₂CCCH₂Cl | H | OCH₃ | CH₃ | N | |
| CH₃ | CH₂S(O)₂CH₂CCH | H | OCH₃ | OCH₃ | CH | |
| CH₃ | CH₂S(O)₂CH₂CCH | H | OCH₃ | CH₃ | CH | |
| CH₃ | CH₂S(O)₂CH₂CCH | H | OCH₃ | Cl | CH | |
| CH₃ | CH₂S(O)₂CH₂CCH | H | CH₃ | CH₃ | CH | |
| CH₃ | CH₂S(O)₂CH₂CCH | H | OCH₃ | OCH₃ | N | |
| CH₃ | CH₂S(O)₂CH₂CCH | H | OCH₃ | CH₃ | N | |
| CH₃ | CH₂S(O)₂CH₂CN | H | OCH₃ | OCH₃ | CH | |
| CH₃ | CH₂S(O)₂CH₂CN | H | OCH₃ | CH₃ | CH | |
| CH₃ | CH₂S(O)₂CH₂CN | H | OCH₃ | Cl | CH | |
| CH₃ | CH₂S(O)₂CH₂CN | H | CH₃ | CH₃ | CH | |
| CH₃ | CH₂S(O)₂CH₂CN | H | OCH₃ | OCH₃ | N | |
| CH₃ | CH₂S(O)₂CH₂CN | H | OCH₃ | CH₃ | N | |
| CH₃ | CH₂S(O)₂CH₂CH₂N(CH₃)₂ | H | OCH₃ | OCH₃ | CH | |
| CH₃ | CH₂S(O)₂CH₂CH₂N(CH₃)₂ | H | OCH₃ | CH₃ | CH | |
| CH₃ | CH₂S(O)₂CH₂CH₂N(CH₃)₂ | H | OCH₃ | Cl | CH | |
| CH₃ | CH₂S(O)₂CH₂CH₂N(CH₃)₂ | H | CH₃ | CH₃ | CH | |
| CH₃ | CH₂S(O)₂CH₂CH₂N(CH₃)₂ | H | OCH₃ | OCH₃ | N | |
| CH₂CH₃ | CH₂S(O)₂CH₂CH₂N(CH₃)₂ | H | OCH₃ | CH₃ | N | |
| CH₃ | CH₂S(O)₂CH₂CH₂F | H | OCH₃ | OCH₃ | CH | |
| CH₃ | CH₂S(O)₂CH₂CH₂F | H | OCH₃ | CH₃ | CH | |
| CH₃ | CH₂S(O)₂CH₂CH₂F | H | OCH₃ | Cl | CH | |
| CH₃ | CH₂S(O)₂CH₂CH₂F | H | CH₃ | CH₃ | CH | |
| CH₃ | CH₂S(O)₂CH₂CH₂F | H | OCH₃ | OCH₃ | N | |
| CH₃ | CH₂S(O)₂CH₂CH₂F | H | OCH₃ | CH₃ | N | |
| CH₃ | CH₂S(O)₂CH₂CHF₂ | H | OCH₃ | OCH₃ | CH | |
| CH₃ | CH₂S(O)₂CH₂CHF₂ | H | OCH₃ | CH₃ | CH | |
| CH₃ | CH₂S(O)₂CH₂CHF₂ | H | OCH₃ | Cl | CH | |
| CH₃ | CH₂S(O)₂CH₂CHF₂ | H | CH₃ | CH₃ | CH | |
| CH₃ | CH₂S(O)₂CH₂CHF₂ | H | OCH₃ | OCH₃ | N | |
| CH₃ | CH₂S(O)₂CH₂CHF₂ | H | OCH₃ | CH₃ | N | |

TABLE Ia-continued

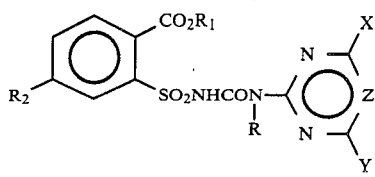

| R₁ | R₂ | R | X | Y | Z | m.p. (°C.) |
|---|---|---|---|---|---|---|
| CH₃ | CH₂S(O)₂CH₂CF₃ | H | OCH₃ | OCH₃ | CH | |
| CH₃ | CH₂S(O)₂CH₂CF₃ | H | OCH₃ | CH₃ | CH | |
| CH₃ | CH₂S(O)₂CH₂CF₃ | H | OCH₃ | Cl | CH | |
| CH₃ | CH₂S(O)₂CH₂CF₃ | H | CH₃ | CH₃ | CH | |
| CH₃ | CH₂S(O)₂CH₂CF₃ | H | OCH₃ | OCH₃ | N | |
| CH₂CH₃ | CH₂S(O)₂CH₂CF₃ | H | OCH₃ | CH₃ | N | |
| CH₃ | CH₂S(O)₂CH₂CH₂OCH₃ | H | OCH₃ | OCH₃ | CH | |
| CH₃ | CH₂S(O)₂CH₂CH₂OCH₃ | H | OCH₃ | CH₃ | CH | |
| CH₃ | CH₂S(O)₂CH₂CH₂OCH₃ | H | OCH₃ | Cl | CH | |
| CH₃ | CH₂S(O)₂CH₂CH₂OCH₃ | H | CH₃ | CH₃ | CH | |
| CH₃ | CH₂S(O)₂CH₂CH₂OCH₃ | H | OCH₃ | OCH₃ | N | |
| CH₃ | CH₂S(O)₂CH₂CH₂OCH₃ | H | OCH₃ | CH₃ | N | |
| CH₃ | CH₂S(O)₂CH₂C(H)CH₂ | H | OCH₃ | OCH₃ | CH | |
| CH₃ | CH₂S(O)₂CH₂C(H)CH₂ | H | OCH₃ | CH₃ | CH | |
| CH₃ | CH₂S(O)₂CH₂C(H)CH₂ | H | OCH₃ | Cl | CH | |
| CH₃ | CH₂S(O)₂CH₂C(H)CH₂ | H | CH₃ | CH₃ | CH | |
| CH₃ | CH₂S(O)₂CH₂C(H)CH₂ | H | OCH₃ | OCH₃ | N | |
| CH₃ | CH₂S(O)₂CH₂C(H)CH₂ | H | OCH₃ | CH₃ | N | |
| CH₃ | CH₂S(O)₂CH₂C(Cl)CH₂ | H | OCH₃ | OCH₃ | CH | |
| CH₃ | CH₂S(O)₂CH₂C(Cl)CH₂ | H | OCH₃ | CH₃ | CH | |
| CH₃ | CH₂S(O)₂CH₂C(Cl)CH₂ | H | OCH₃ | Cl | CH | |
| CH₃ | CH₂S(O)₂CH₂C(Cl)CH₂ | H | CH₃ | CH₃ | CH | |
| CH₃ | CH₂S(O)₂CH₂C(Cl)CH₂ | H | OCH₃ | OCH₃ | N | |
| CH₂CH₃ | CH₂S(O)₂CH₂C(Cl)CH₂ | H | OCH₃ | CH₃ | N | |
| CH₃ | C(H)CH₂ | H | OCH₃ | OCH₃ | CH | |
| CH₃ | C(H)CH₂ | H | OCH₃ | CH₃ | CH | |
| CH₃ | C(H)CH₂ | H | OCH₃ | Cl | CH | |
| CH₃ | C(H)CH₂ | H | CH₃ | CH₃ | CH | |
| CH₃ | C(H)CH₂ | H | OCH₃ | OCH₃ | N | |
| CH₃ | C(H)CH₂ | H | OCH₃ | CH₃ | N | |
| CH₃ | CCH | H | OCH₃ | OCH₃ | CH | |
| CH₃ | CCH | H | OCH₃ | CH₃ | CH | |
| CH₃ | CCH | H | OCH₃ | Cl | CH | |
| CH₃ | CCH | H | CH₃ | CH₃ | CH | |
| CH₃ | CCH | H | OCH₃ | OCH₃ | N | |
| CH₃ | CCH | H | OCH₃ | CH₃ | N | |
| CH₃ | C(Cl)CH₂ | H | OCH₃ | OCH₃ | CH | |
| CH₃ | C(Cl)CH₂ | H | OCH₃ | CH₃ | CH | |
| CH₃ | C(Cl)CH₂ | H | OCH₃ | Cl | CH | |
| CH₃ | C(Cl)CH₂ | H | CH₃ | CH₃ | CH | |
| CH₃ | C(Cl)CH₂ | H | OCH₃ | OCH₃ | N | |
| CH₃ | C(Cl)CH₂ | H | OCH₃ | CH₃ | N | |
| CH₃ | CH₂C(O)NHCH₃ | H | OCH₃ | OCH₃ | CH | |
| CH₃ | CH₂C(O)NHCH₃ | H | OCH₃ | CH₃ | CH | |
| CH₃ | CH₂C(O)NHCH₃ | H | OCH₃ | Cl | CH | |
| CH₃ | CH₂C(O)NHCH₃ | H | CH₃ | CH₃ | CH | |
| CH₃ | CH₂C(O)NHCH₃ | H | OCH₃ | OCH₃ | N | |
| CH₃ | CH₂C(O)NHCH₃ | H | OCH₃ | CH₃ | N | |
| CH₃ | CH₂C(O)N(CH₃)₂ | H | OCH₃ | OCH₃ | CH | |
| CH₃ | CH₂C(O)N(CH₃)₂ | H | OCH₃ | CH₃ | CH | |
| CH₃ | CH₂C(O)N(CH₃)₂ | H | OCH₃ | Cl | CH | |
| CH₃ | CH₂C(O)N(CH₃)₂ | H | CH₃ | CH₃ | CH | |
| CH₃ | CH₂C(O)N(CH₃)₂ | H | OCH₃ | OCH₃ | N | |
| CH₃ | CH₂C(O)N(CH₃)₂ | H | OCH₃ | CH₃ | N | |
| CH₃ | OCF₃ | H | CH₃ | OCH₃ | CH | |
| CH₃ | OCF₃ | H | OCH₃ | OCH₃ | CH | |
| CH₃ | OCF₃ | H | Cl | OCH₃ | CH | |
| CH₃ | OCF₃ | H | CH₃ | OCH₃ | N | |
| CH₃ | OCF₃ | H | OCH₃ | OCH₃ | N | |
| CH₃ | SCF₃ | H | CH₃ | OCH₃ | CH | |
| CH₃ | SCF₃ | H | OCH₃ | OCH₃ | CH | |
| CH₃ | SCF₃ | H | Cl | OCH₃ | CH | |
| CH₃ | SCF₃ | H | CH₃ | OCH₃ | N | |
| CH₃ | SCF₃ | H | OCH₃ | OCH₃ | N | |
| CH₃ | OCH₂CH₂Br | H | CH₃ | OCH₃ | CH | |
| CH₃ | OCH₂CH₂I | H | OCH₃ | OCH₃ | CH | |
| CH₃ | C≡CI | H | CH₃ | OCH₃ | N | |
| CH₃ | CH₂CBr₃ | H | OCH₃ | OCH₃ | CH | |
| CH₃ | N(CH₃)(CH₂CH₃) | H | CH₃ | OCH₃ | CH | |
| CH₃ | CH₂Cl | H | CH₃ | CH₃ | CH | 176–180(d) |
| CH₃ | CH₂Cl | H | CH₃ | OCH₃ | CH | 167–170 |

TABLE Ia-continued

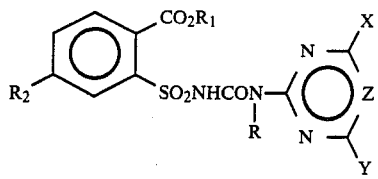

| $R_1$ | $R_2$ | R | X | Y | Z | m.p. (°C.) |
|---|---|---|---|---|---|---|
| $CH_3$ | $CH_2Cl$ | H | $OCH_3$ | $OCH_3$ | CH | 149–153(d) |
| $CH_3$ | $CH_2Cl$ | H | Cl | $OCH_3$ | CH | 164–166 |
| $CH_3$ | $CH_2Cl$ | H | $CH_3$ | $OCH_3$ | N | 148–150 |
| $CH_3$ | $CH_2Cl$ | H | $OCH_3$ | $OCH_3$ | N | 161–162 |
| $CH_2CH_3$ | $CH_2Cl$ | H | $CH_3$ | $CH_3$ | CH | 158–162 |
| $CH_2CH_3$ | $CH_2Cl$ | H | $CH_3$ | $OCH_3$ | CH | |
| $CH_2CH_3$ | $CH_2Cl$ | H | $OCH_3$ | $OCH_3$ | CH | 141–144 |
| $CH_2CH_3$ | $CH_2Cl$ | H | Cl | $OCH_3$ | CH | 158–162 |
| $CH_2CH_3$ | $CH_2Cl$ | H | $CH_3$ | $OCH_3$ | N | 134–142 |
| $CH_2CH_3$ | $CH_2Cl$ | H | $OCH_3$ | $OCH_3$ | N | Gum |
| $CH_2CH_3$ | $CHBr_2$ | H | $OCH_3$ | $OCH_3$ | CH | 181–182 |
| $CH_3$ | $CHBr_2$ | H | $OCH_3$ | $OCH_3$ | CH | |
| $CH_3$ | $CH_2Br$ | H | $OCH_3$ | $OCH_3$ | CH | |
| $CH_3$ | $CHCl_2$ | H | $OCH_3$ | $OCH_3$ | CH | |
| $CH_3$ | $OC(O)CH_3$ | H | $CH_3$ | $CH_3$ | CH | |
| $CH_3$ | $OC(O)CH_3$ | H | $CH_3$ | $OCH_3$ | CH | |
| $CH_3$ | $OC(O)CH_3$ | H | $OCH_3$ | $OCH_3$ | CH | 188–190 |
| $CH_3$ | $OC(O)CH_3$ | H | Cl | $OCH_3$ | CH | |
| $CH_3$ | $OC(O)CH_3$ | H | $CH_3$ | $OCH_3$ | N | |
| $CH_3$ | $OC(O)CH_3$ | H | $OCH_3$ | $OCH_3$ | N | |

Formulations

Useful formulations of the compounds of Formula I can be prepared in conventional ways. They include dusts, granules, pellets, solution, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE II

| | Active Ingredient | Weight Percent* | |
|---|---|---|---|
| | | Diluent(s) | Surfactant(s) |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwall, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science". John Wiley and Sons, Inc., New York, 1961, pp. 81–96; and J. D. Fryer and S. A. Evans, "Control Handbook", 5th Ed., Blackwall Scientific Publications, Oxford, 1968, pp. 101–103.

In the following examples, all parts are by weight unless otherwise indicated.

EXAMPLE 16

| Wettable Powder | |
|---|---|
| 2-[[(4,6-dimethoxypyrimidin-2-yl)aminocarbonyl]-aminosulfonyl]-4-(methylthio)benzoic acid, methyl ester | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 17

| Wettable Powder | |
|---|---|
| 2-[[(4,6-dimethoxypyrimidin-2-yl)aminocarbonyl]-aminosulfonyl]-4-(methylthio)benzoic acid, methyl ester | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 18

| Granule | |
|---|---|
| Wettable Powder of Example 17 | 5% |
| attapulgite granules (U.S.S. 20–40 mesh; 0.84–0.42 mm) | 95% |

A slurry of wettable powder containing 25% solids is sprayed on the surface of attapulgite granules in a double-cone blender. The granules are dried and packaged.

EXAMPLE 19

| Extruded Pellet | |
|---|---|
| 2-[[(4,6-dimethoxypyrimidin-2-yl)aminocarbonyl]-aminosulfonyl]-4-(methylthio)benzoic acid, methyl ester | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 20

| Oil Suspension | |
|---|---|
| 2-[[(4,6-dimethoxypyrimidin-2-yl)aminocarbonyl]-aminosulfonyl]-4-(methylthio)benzoic acid, methyl ester | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 21

| Wettable Powder | |
|---|---|
| 2-[[(4,6-dimethoxypyrimidin-2-yl)aminocarbonyl]-aminosulfonyl]-4-(methylthio)benzoic acid, methyl ester | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 22

| Low Strength Granule | |
|---|---|
| 2-[[(4,6-dimethoxypyrimidin-2-yl)aminocarbonyl]-aminosulfonyl]-4-(methylthio)benzoic acid, methyl ester | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 23

| Aqueous Suspension | |
|---|---|
| 2-[[(4,6-dimethoxypyrimidin-2-yl)aminocarbonyl]-aminosulfonyl]-4-(methylthio)benzoic acid, methyl ester | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 24

| Solution | |
|---|---|
| 2-[[(4,6-dimethoxypyrimidin-2-yl)aminocarbonyl]-aminosulfonyl]-4-(methylthio)benzoic acid, methyl ester | 5% |
| water | 95% |

The salt is added directly to the water with stirring to produce the solution, which may then be packaged for use.

EXAMPLE 25

| Low Strength Granule | |
|---|---|
| 2-[[(4,6-dimethoxypyrimidin-2-yl)aminocarbonyl]-aminosulfonyl]-4-(methylthio)benzoic acid, methyl ester | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 26

| Granule | |
|---|---|
| 2-[[(4,6-dimethoxypyrimidin-2-yl)aminocarbonyl]-aminosulfonyl]-4-(methylthio)benzoic acid, methyl ester | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 27

| High Strength Concentrate | |
|---|---|
| 2-[[(4,6-dimethoxypyrimidin-2-yl)aminocarbonyl]-aminosulfonyl]-4-(methylthio)benzoic acid, methyl ester | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 28

| Wettable Powder | |
|---|---|
| 2-[[(4,6-dimethoxypyrimidin-2-yl)aminocarbonyl]-aminosulfonyl]-4-(methylthio)benzoic acid, methyl ester | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 29

| Wettable Powder | |
|---|---|
| 2-[[(4,6-dimethoxypyrimidin-2-yl)aminocarbonyl]-aminosulfonyl]-4-(methylthio)benzoic acid, methyl ester | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 30

| Oil Suspension | |
|---|---|
| 2-[[(4,6-dimethoxypyrimidin-2-yl)aminocarbonyl]-aminosulfonyl]-4-(methylthio)benzoic acid, methyl ester | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 31

| Dust | |
|---|---|
| 2-[[(4,6-dimethoxypyrimidin-2-yl)aminocarbonyl]-aminosulfonyl]-4-(methylthio)benzoic acid, methyl ester | 10% |
| attapulgite | 10% |
| pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 32

| Emulsifiable Concentrate | |
|---|---|
| 2-[[(4,6-dimethoxypyrimidin-2-yl)aminocarbonyl]-aminosulfonyl]-4-(methylthio)benzoic acid, methyl ester | 20% |
| chlorobenzene | 74% |
| sorbitan monostearate and polyoxyethylene | 6% |

-continued

| Emulsifiable Concentrate |
|---|
| condensates thereof |

The ingredients are combined and stirred to produce a solution which can be emulsified in water for application.

UTILITY

Test results indicate that the compounds of the present invention are highly active preemergent or postemergent herbicides or plant growth regulators. Many of them have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Some of the compounds have utility for selective weed control in crops such as wheat, barley, cotton, soybean, sugar beets and corn. Alternatively, the subject compounds are useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.05 to 10 kg/ha, the lower rates being suggested for use on lighter soils and/or those having a low organic matter content, for plant growth modification or for situations where only short-term persistence is required.

The compounds of this invention may be used in combination with other commercial herbicides. They are particularly useful in combination with the following herbicides.

| Common Name | Chemical Name |
|---|---|
| acifluorfen | 5-[2-chloro-4-(trifluoromethyl)phenoxy]-2-nitrobenzoic acid |
| acrolein | acrolein |
| alachlor | 2-chloro-2',6'-diethyl-N—(methoxymethyl)acetanilide |
| ametryn | 2-(ethylamino)-4-(isopropylamino)-6-methylthio)-s-triazine |
| amitrole | 3-amino-s-triazole |
| AMS | ammonium sulfamate |
| asulam | methyl sulfanilylcarbamate |
| atrazine | 2-chloro-4-(ethylamino)-6-(isopropylamino)-s-triazine |
| barban | 4-chloro-2-butynyl m-chlorocarbanilate |
| benefin | N—butyl-N—ethyl-α,α,α-trifluoro-2,6-dinitro-p-toluidine |
| bensulide | O,O—diisopropyl phosphorodithioate S—ester with N—(2-mercaptoethyl)benzenesulfonamide |
| bentazon | 3-isopropyl-1H—2,1,3-benzothiadiazin-4(3H)—one 2,2-dioxide |
| benzipram | 3,5-dimethyl-N—(1-methylethyl)-N—(phenylmethyl)benzamide |
| benzoylprop | N—benzoyl-N—(3,4-dichlorophenyl)-DL-alaine |
| bifenox | methyl 5-(2,4-dichlorophenoxy)-2-nitrobenzoate |
| bromacil | 5-bromo-3-sec-butyl-6-methyluracil |
| bromoxynil | 3,5-dibromo-4-hydroxybenzonitrile |
| butachlor | N—(butoxymethyl)-2-chloro-2',6'-diethylacetanilide |
| butam | 2,2-dimethyl-N—(1-methylethyl)-N—(phenylmethyl)propanamide |
| buthidazole | 3-[5-(1,1-dimethylethyl)-1,3,4-thiadiazol-2-yl]-4-hydroxy-1-methyl-2-imidazolidinone |
| butralin | 4-(1,1-dimethylethyl)-N—(1-methylpropyl)-2,6-dinitrobenzenamine |
| butylate | S—ethyl-diisobutylthiocarbamate |
| cacodylic acid | hydroxydimethylarsine oxide |
| carbetamide | D-N—ethyllactamide carbanilate (ester) |
| CDAA | N—N—diallyl-2-chloroacetamide |
| CDEC | 2-chloroallyl diethyldithiocarbamate |
| chlorbromuron | 3-(4-bromo-3-chlorophenyl)-1-methoxy-1-methylurea |
| chloroxuron | 3-[p-(p-chlorophenoxy)phenyl]-1,1-dimethylurea |
| chlorpropham | isopropyl m-chlorocarbanilate |
| chlorsulfuron | 2-chloro-N—[(4-methoxy-6-methyl-1,3,5-triazin-2-yl)aminocarbonyl]benzenesulfonamide |
| chlortoluron | N'—(3-chloro-4-methylphenyl-N',N'—dimethylurea |
| cisanilide | cis-2,5-dimethyl-N—phenyl-1-pyrrolidinecarboxamide |
| CMA | calcium methanearsonate |
| cyanazine | 2-[[4-chloro-6-(ethylamino)-s-triazin-2-yl]amino]-2-methylpropionitrile |
| cycloate | S—ethyl N—ethylthiocyclohexanecarbamate |
| cycluron | 3-cyclooctyl-1,1-dimethylurea |
| cyperquat | 1-methyl-4-phenylpyridinium |
| cyprazine | 2-chloro-4-(cyclopropylamino)-6-(isopropylamino)-s-triazine |
| cyprazole | N—[5-(2-chloro-1,1-dimethylethyl)-1,3,4-thiadiazol-2-yl] cyclopropanecarboxamide |
| cypromid | 3',4'-dichlorocyclopropanecarboxanilide |
| dalapon | 2,2-dichloropropionic acid |
| dazomet | tetrahydro-3,5-dimethyl-2H—1,3,5-thiadiazine-2-thione |
| DCPA | dimethyl tetrachloroterephthalate |
| desmetryn | 2-(isopropylamino)-4-(methylamino)-6-methylthio)-s-triazine |
| diallate | S—(2,3-dichloroallyl)diisopropylthiocarbamate |
| dicamba | 3,6-dichloro-o-anisic acid |
| dichlobenil | 2,6-dichlorobenzonitrile |
| dichlorprop | 2-(2,4-dichlorophenoxy)propionic acid |
| diclofop | 2-[4-(2,4-dichlorophenoxy)phenoxy]-propanoic acid |
| diethatyl | N—(chloroacetyl)-N—(2,6-diethylphenyl)-glycine |
| difenzoquat | 1,2-dimethyl-3,5-diphenyl-1H—pyrazolium |
| dinitramine | $N^4,N^4$—diethyl-α,α,α-trifluoro-3,5-dinitrotoluene-2,4-diamine |
| dinoseb | 2-sec-butyl-4,6-dinitrophenol |
| diphenamide | N,N—dimethyl-2,2-diphenylacetamide |
| dipropetryn | 2-(ethylthio)-4,6-bis(isopropylamino)-s-triazine |
| diquat | 6,7-dihydrodipyrido[ 1,2-α:2',1'-c]-pyrazinediium ion |
| diuron | 3-(3,4-dichlorophenyl)-1,1-dimethylurea |
| DSMA | disodium methanearsonate |
| endothall | 7-oxabicyclo[2.2.1]heptane-2,3-dicarboxylic acid |
| erbon | 2-(2,4,5-trichlorophenoxy)ethyl 2,2-dichloropropionate |
| ethafluralin | N—ethyl-N—(2-methyl-2-propenyl)-2,6-dinitro-4-(trifluoromethyl)benzenamine |
| ethofumesate | (±)-2-ethoxy-2,3-dihydro-3,3-dimethyl-5-benzofuranyl methanesulfonate |
| fenac | (2,3,6-trichlorophenyl)acetic acid |
| fenoxaprop ethyl | ethyl 2-(4-(6-chloro-2-benzoxazolyloxy)phenoxy)propanoate |
| fenuron | 1,1-dimethyl-3-phenylurea |
| fenuron TCA | 1,1-dimethyl-3-phenylurea mono(trichloroacetate) |
| flamprop | N—benzoyl-N—(3-chloro-4-fluorophenyl)-DL-alanine |
| fluchloralin | N—(2-chloroethyl)-2,6-dinitro-N—propyl- |

| Chemical Name | |
|---|---|
| | 4-(trifluoromethyl)aniline |
| fluometuron | 1,1-dimethyl-3-(α,α,α-trifluoro-m-tolyl)urea |
| fluorodifen | p-nitrophenyl α,α,α-trifluoro-2-nitro-p-tolyl ether |
| fluridone | 1-methyl-3-phenyl-5-[3-(trifluoromethyl)phenyl]-4(1H)—pyridinone |
| fomesafen | 5-(2-chloro-4-trifluoromethylphenoxy)-N—methylsulfonyl-2-nitrobenzamide |
| fosamine | ethyl hydrogen (aminocarbonyl)phosphonate |
| glyphosate | N—(phosphonomethyl)glycine |
| hexaflurate | potassium hexafluoroarsenate |
| hexazinone | 3-cyclohexyl-6-(dimethylamino)-1-methyl-1,3,5-triazine-2,4(1H,3H)—dione |
| imazaquin | 2-(4,5-dihydro-4-methyl-4-(1-methylethyl)-5-oxo-1H—imidazol-2-yl)-3-quinolinecarboxylic acid |
| ioxynil | 4-hydroxy-3,5-diiodobenzonitrile |
| isopropalin | 2,6-dinitro-N,N—dipropylcumidine |
| karbutilate | tert-butylcarbamic acid ester with 3-(m-hydroxyphenyl)-1,1-dimethylurea |
| lactofen | 1'-(carboethoxy)ethyl-5-(2-chloro-4-(trifluoromethyl)phenoxy)-2-nitrobenzoate |
| lenacil | 3-cyclohexyl-6,7-dihydro-1H— cyclopentapyrimidine-2,4(3H,5H)—dione |
| linuron | 3-(3,4-dichlorophenyl)-1-methoxy-1-methylurea |
| MAA | methanearsonic acid |
| MAMA | monoammonium methanearsonate |
| MCPA | [(4-chloro-o-tolyl)oxy]acetic acid |
| MCPB | 4-[(4-chloro-o-tolyl)oxy]butyric acid |
| mecoprop | 2-[(4-chloro-o-tolyl)oxy]propionic acid |
| mefluidide | N—[(2,4-dimethyl-5-[[(trifluoromethyl)sulfonyl]amino]phenyl]acetamide |
| methalpropalin | N—(2-methyl-2-propenyl)-2,6-dinitro-N—propyl-4-(trifluoromethyl)benzenamide |
| methabenzthiazuron | 1,3-dimethyl-3-(2-benzothiazolyl)urea |
| metham | sodium methyldithiocarbamate |
| methazole | 2-(3,4-dichlorophenyl)-4-methyl-1,2,4-oxadiazolidine-3,5-dione |
| methoxuron | N'—(3-chloro-4-methoxyphenyl)N,N—dimethylurea |
| metolachlor | 2-chloro-N—(2-ethyl-6-methylphenyl)-N—(2-methoxy-1-methylethyl)acetamide |
| metribuzin | 4-amino-6-tert-butyl-3-(methylthio)-as-triazine-5(4H)—one |
| metsulfuron methyl | 2-[[(4-methoxy-6-methyl-1,3,5-triazine-2-yl)aminocarbonyl]aminosulfonyl]benzoic acid, methyl ester |
| molinate | S—ethyl hexahydro-1H—azepine-1-carbothioate |
| monolinuron | 3-(p-chlorophenyl)-1-methoxy-1-methylurea |
| monuron | 3-(p-chlorophenyl)-1,1-dimethylurea |
| monuron TCA | 3-(p-chlorophenyl)-1,1-dimethylurea mono(trichloroacetate) |
| MSMA | monosodium methanearsonate |
| napropamide | 2-(α-naphthoxy)-N,N—diethylpropionamide |
| naptalam | N—1-naphthylphthalamic acid |
| neburon | 1-butyl-3-(3,4-dichlorophenyl)-1-methylurea |
| nitralin | 4-(methylsulfonyl)-2,6-dinitro-N,N—dipropylaniline |
| nitrofen | 2,4-dichlorophenyl p-nitrophenyl ether |
| nitrofluorfen | 2-chloro-1-(4-nitrophenoxy)-4-(trifluoromethyl)benzene |
| norea | 3-(hexahydro-4,7-methanoindan-5-yl)-1,1-dimethylurea |
| norflurazon | 4-chloro-5-(methylamino)-2-(α,α,α-trifluoro-m-tolyl)-3(2H)—pyridazinone |
| oryzalin | 3,4-dinitro-N,N—dipropylsulfanilamide |
| oxadiazon | 2-tert-butyl-4-(2,4-dichloro-5-isopropoxyphenyl)Δ²-1,3,4-oxadiazolin-5-one |
| oxyfluorfen | 2-chloro-1-(3-ethoxy-4-nitrophenoxy)-4-(trifluoromethyl)benzene |
| paraquat | 1,1'-dimethyl-4,4'-bipyridinium ion |
| PBA | chlorinated benzoic acid |

| Chemical Name | |
|---|---|
| pendimethalin | N—(1-ethylpropyl)-3,4-dimethyl-2,6-dinitrobenzenamine |
| perfluidone | 1,1,1-trifluoro-N—[2-methyl-4-(phenylsulfonyl)phenyl]methanesulfonamide |
| picloram | 4-amino-3,5,6-trichloropicolinic acid |
| procyazine | 2-[[4-chloro-6-(cyclopropylamino)-1,3,5-triazine-2-yl]amino]-2-methylpropanenitrile |
| profluralin | N—(cyclopropylmethyl)-α,α,α-trifluoro-2,6-dinitro-N—propyl-p-toluidine |
| prometon | 2,4-bis(isopropylamino)-6-methoxy-s-triazine |
| prometryn | 2,4-bis(isopropylamino)-6-(methylthio)-s-triazine |
| pronamide | 3,5-dichloro N—(1,1-dimethyl-2-propynyl)benzamide |
| propachlor | 2-chloro-N—isopropylacetanilide |
| propanil | 3',4'-dichloropropionalide |
| propazine | 2-chloro-4,6-bis(isopropylamino)-s-triazine |
| propham | isopropyl carbanilate |
| prosulfalin | N—[[4-(dipropylamino)-3,5-dinitrophenyl]sulfonyl]-S,S—dimethylsulfilimine |
| prynachlor | 2-chloro-N—(1-methyl-2-propynyl)acetanilide |
| quinofop ethyl | 2-[4-(6-chloroquinoxalin-2-yloxy)phenoxypropanoic acid, ethyl ester |
| secbumeton | N—ethyl-6-methoxy-N'(1-methylpropyl)-1,3,5-triazine-2,4-diamine |
| sethoxydim | 2-[1-(ethoxyimino)butyl]-5-[2-(ethylthio)propyl]-3-hydroxy-2-cyclohexene-1-one |
| siduron | 1-(2-methylcyclohexyl)-3-phenylurea |
| simazine | 2-chloro-4,6-bis(ethylamino)-s-triazine |
| simetryn | 2,4-bis(ethylamino)-6-(methylthio)-s-triazine |
| supriox | 2-[1-(2,5-dimethylphenyl)ethylsulfonyl]-pyridine-N—oxide |
| TCA | trichloroacetic acid |
| tebuthiuron | N—[5-(1,1-dimethylethyl)-1,3,4-thiadiazol-2-yl]-N,N'—dimethylurea |
| terbacil | 3-tert-butyl-5-chloro-6-methyluracil |
| terbuchlor | N—(butoxymethyl)-2-chloro-N—[2-(1,1-dimethylethyl)-6-methylphenyl]-acetamide |
| terbuthylazine | 2-(tert-butylamino)-4-chloro-6-(ethylamino)-s-triazine |
| terbutol | 2,6-di-tert-butyl-p-tolyl methylcarbamate |
| terbutryn | 2-(tert-butylamino)-4-(ethylamino)-6-(methylthio)-s-triazine |
| tetrafluron | N,N—dimethyl-N'—[3-(1,1,2,2-tetrafluoroethoxy)phenyl]urea |
| thiobencarb | S—[(4-chlorophenyl)methyl]diethylcarbamothioate |
| triallate | S—(2,3,3-trichloroallyl)diisopropylthiocarbamate |
| trifluralin | α,α,α-trifluoro-2,6-dinitro-N,N—propyl-p-toluidine |
| trimeturon | 1-(p-chlorophenyl)-2,3,3-trimethylpseudourea |
| vernolate | S—propyl dipropylthiocarbamate |
| | ethyl 5-[2-chloro-4-(trifluoromethyl)phenoxy]-2-nitrobenzoic acid |
| 2,3,6-TBA[b] | 2,3,6-trichlorobenzoic acid |
| 2,4-D | (2,4-dichlorophenoxy)acetic acid |
| 2,4-DB | 4-(2,4-dichlorophenoxy)butyric acid |
| 2,4-DEP | tris[2-(2,4-dichlorophenoxy)ethyl] phosphite |
| Trade name or Code Number | |
| "Cinch" | exo-1-methyl-4-(1-methylethyl)-2-[(2-methylphenyl)methoxy]-7-oxabicyclo-[2.2.1]heptane |
| AC 263,499 | 2-[4,5-dihydro-4-methyl-4-(1-methylethyl)-5-oxo-1H—imidazol-2-yl]-5-ethyl-3-pyridinecarboxylic acid |
| Harmony ™ | 3-[[(4-methoxy-6-methyl-1,3,5-triazin-2-yl)aminocarbonyl]aminosulfonyl]-2- |

-continued

| | Chemical Name |
|---|---|
| PPG-1013 | thiophenecarboxylic acid, methyl ester 5-(2-chloro-4-(trifluoromethyl)phenoxy)-2-nitroacetophenone oxime-O—acetic acid, methyl ester |
| DOWCO 453 ME | 2-(4-(3-chloro-5-trifluoromethylpyridin-2-yloxy)phenoxy)propanoic acid, methyl ester |
| FMC 57020 | 2-(2'-chlorophenyl)methyl-4,4-dimethyl-3-isoxazolidinone |
| AC 222,293 | 6-(4-isopropyl-4-methyl-5-oxo-2-imidazolin-2-yl)-m-toluic acid, methyl ester and 6-(4-isopropyl-4-methyl-5-oxo-2-imidazolin-2-yl-p-toluic acid, methyl ester |
| AC 252,925 | 2-(4-isopropyl-4-methyl-5-oxo-2-imidazolin-2-yl)nicotinic acid with isopropyl amine (1:1) |
| DPX-L5300 | 2-[[N—(4-methoxy-6-methyl-1,3,5-triazine-2-yl)-N—methylaminocarbonyl]-aminosulfonyl]benzoic acid, methyl ester |

The herbicidal properties of the subject compounds pounds were discovered in a number of greenhouse tests. The test procedures and results follow.

TEST A

Seeds of crabgrass (Digitaria sp.), barnyardgrass (Echinochloa crusgalli), wild oats (Avena fatua), cheatgrass (Bromus secalinus), sicklepod (Cassia obtusifolia), morningglory (Ipomoea sp.), cocklebur (Xanthium sp.), velvetleaf (Abutilon theophrasti), sorghum, corn, soybean, sugar beet, cotton, rice, wheat and purple nutsedge (Cyperus rotundus) tubers were planted and treated preemergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table 1, are based on a numerical scale extending from 0=no injury, to 10=complete kill. The accompanying descriptive symbols have the following meanings:

B=burn;
C=chlorosis/necrosis;
D=defoliation;
E=emergence inhibition;
G=growth retardation;
H=formative effects;
U=unusual pigmentation;
S=albinism; and
6Y=abscised buds or flowers.
-=no test Compounds

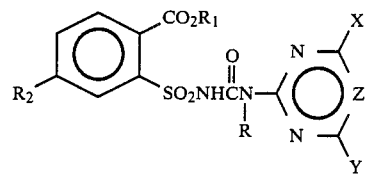

| Cmpd. | R | $R_1$ | $R_2$ | X | Y | Z |
|---|---|---|---|---|---|---|
| 1 | H | $CH_3$ | $OC_2H_5$ | $OCH_3$ | $OCH_3$ | CH |
| 2 | H | $CH_3$ | $OC_2H_5$ | $OCH_3$ | $CH_3$ | N |
| 3 | H | $CH_3$ | $OC_2H_5$ | $CH_3$ | $CH_3$ | N |
| 4 | H | $CH_3$ | $OC_2H_5$ | $CH_3$ | $CH_3$ | CH |
| 5 | H | $CH_3$ | $OC_2H_5$ | $CH_3$ | $OCH_3$ | CH |
| 6 | H | $CH_3$ | $OC_2H_5$ | $OCH_3$ | Cl | CH |
| 7 | H | $CH_3$ | $OC_2H_5$ | $OCH_3$ | $OCH_3$ | N |
| 8 | H | $CH_3$ | $OC_2H_5$ | $OCH_3$ | $OCH_2CF_3$ | N |
| 9 | H | $CH_3$ | $OC_2H_5$ | $OCH_3$ | $N(CH_3)_2$ | N |
| 10 | $CH_3$ | $CH_3$ | $OC_2H_5$ | $OCH_3$ | $CH_3$ | N |
| 11 | H | $CH_3$ | $SCH_3$ | $OCH_3$ | $OCH_3$ | CH |
| 12 | $CH_3$ | $CH_3$ | $OC_2H_5$ | $OCH_3$ | $OCH_3$ | CH |
| 13 | $CH_3$ | $CH_3$ | $OC_2H_5$ | $OCH_3$ | $OCH_3$ | N |
| 14 | H | $CH_3$ | $OC_2H_5$ | $OCH_3$ | $N(CH_3)_2$ | CH |
| 15 | H | $CH_3$ | $OCH_2CH=CH_2$ | $OCH_3$ | $CH_3$ | N |

TABLE 1

| Rate kg/ha | Cmpd. 1 0.05 | Cmpd. 2 0.05 | Cmpd. 3 0.05 | Cmpd. 4 0.05 | Cmpd. 5 0.05 | Cmpd. 6 0.05 | Cmpd. 7 0.05 | Cmpd. 8 0.05 |
|---|---|---|---|---|---|---|---|---|
| POSTEMERGENCE | | | | | | | | |
| Morningglory | 6C,9G | 10C | 9C | 9C | 6C,9G | 9C | 6C,9G | 10C |
| Cocklebur | 9C | 10C | 10C | 10C | 5C,9G | 10C | 10C | 9C |
| Sicklepod | 9C | 9C | 9C | 9C | 6C,9G | 4C,9G | 9C | 9C |
| Nutsedge | 2C,8G | 8G | 2C,8G | 2C,9G | 8G | 9G | 5G | 2C,8G |
| Crabgrass | 4G | 5G | 6G | 8G | 6G | 0 | 3G | 0 |
| Barnyardgrass | 5C,9H | 5C,9H | 5C,9G | 5C,9H | 5C,9H | 3C,5H | 3C,7H | 3H |
| Wild Oats | 3C,5G | 6C,9G | 2C,9G | 2C,9G | 2C,8G | 4G | 5C,9G | 4G |
| Wheat | 3C,6G | 7C,9G | 2C,9G | 3C,9G | 3C,8G | 2G | 5G | 4G |
| Corn | 2C,9G | 9G | 9G | 9G | 9G | 3C,7H | 2C,3H | 7H |
| Soybean | 5C,9G | 9C | 9C | 4C,9G | 6C,9G | 4C,9H | 4C,9G | 5C,9G |
| Rice | 5C,9G | 6C,9G | 5C,9G | 5C,9G | 5C,9G | 3C,9G | 5C,9G | 5C,9G |
| Sorghum | 4C,9H | 3C,9G | 2C,9G | 3C,9H | 3C,9G | 9H | 9G | 3C,8H |
| Sugar beet | 9C | 5C,9G | 5C,9G | 9C | 5C,9G | 5C,9G | 9C | 10C |
| Cotton | 9C | 9C | 9C | 9C | 9C | 9C | 9C | 3C,8G |
| Velvetleaf | — | — | — | — | — | — | — | — |
| Cheatgrass | — | — | — | — | — | — | — | — |
| PREEMERGENCE | | | | | | | | |
| Morningglory | 9G | 9G | 9G | 9G | 9G | 9G | 9G | 9G |
| Cocklebur | 9H | 5C,9H | 9H | 9H | 9H | 3C,8H | 9H | 8H |
| Sicklepod | 8G | 9G | 4C,8G | 8G | 2C,8G | 8G | 8G | 2C |
| Nutsedge | 9G | 8G | 7G | 10E | 8G | 10E | 8G | 0 |
| Crabgrass | 5G | 4G | 3G | 5G | 6G | 2G | 6G | 0 |
| Barnyardgrass | 2C,7G | 5G | 3C,6G | 9H | 5C,9H | 3C,5G | 3C,3G | 0 |
| Wild Oats | 2C,6G | 4C,8H | 3C,7H | 3C,8G | 4C,8G | 2C,4G | 4C,6G | 2C,6G |
| Wheat | 9H | 5C,9H | 3C,9H | 2C,9H | 3C,9H | 5G | 6G | 6G |
| Corn | 2C,8G | 8H | 8G | 9H | 9G | 7G | 1C,7G | 7G |
| Soybean | 2C,3H | 9H | 3C,6H | 8H | 9H | 7H | 8H | 4C,7H |
| Rice | 5C,9G | 10E | 10E | 10E | 10E | 9H | 10E | 4C,8H |

TABLE 1-continued

| | | | | | | | | |
|---|---|---|---|---|---|---|---|---|
| Sorghum | 3C,9G | 7C,9H | 3C,9H | 4C,9H | 5C,9H | 5C,9H | 5C,9H | 3C,7G |
| Sugar beet | 3C,9G | 5C,9G | 5C,9G | 4C,9G | 4C,9G | 4C,8G | 4C,9G | 5C,9G |
| Cotton | 2C,9G | 9G | 9G | 9G | 9G | 9G | 9G | 3G |
| Velvetleaf | — | — | — | — | — | — | — | — |
| Cheatgrass | — | — | — | — | — | — | — | — |

| | Cmpd. 9 | Cmpd. 10 | Cmpd. 11 | Cmpd. 12 | Cmpd. 13 | Cmpd. 14 | Cmpd. 15 |
|---|---|---|---|---|---|---|---|
| Rate kg/ha | 0.05 | 0.05 | 0.05 | 0.05 | 0.05 | 0.05 | 0.05 |
| POSTEMERGENCE | | | | | | | |
| Morningglory | 10C | 5C,9G | 9C | 3C,6G | 9C | 5C,9G | 10C |
| Cocklebur | 10C | 10C | 9C | 4G | 5C,9G | 2C,8H | 9C |
| Sicklepod | 9C | 1C | 9C | 0 | 1C | 3C,3H | — |
| Nutsedge | 7G | 3G | 6C,9G | 0 | 0 | 0 | 4G |
| Crabgrass | 0 | 0 | 4C,9G | 0 | 0 | 2G | 5H |
| Barnyardgrass | 3H | 3H | 9C | 2H | 3C,3H | 2C,8H | 5C,8H |
| Wild Oats | 3C,9G | 2C,8G | 9C | 0 | 2C,6G | 6G | 9C |
| Wheat | 2C,8G | 5G | 9C | 0 | 2G | 0 | 10C |
| Corn | 2C,8H | 1H | 9C | 5G | 0 | 2C,8H | 10C |
| Soybean | 5C,9G | 5C,9G | 5C,9G | 3C,6G | 5C,9G | 3C,8G | 9C |
| Rice | 5C,9G | 6C,9G | 5C,9G | 4C,8G | 5C,9G | 2C,5G | 9C |
| Sorghum | 4C,9G | 2U,9H | 5C,9G | 3C,8G | 5G | 3C,8H | 9C |
| Sugar beet | 10C | 9C | 9C | 3C,8G | 9C | 5C,9G | 9C |
| Cotton | 10C | 5C,9G | 3C,9G | 9C | 9C | 5C,9G | 10C |
| Velvetleaf | — | — | — | — | — | — | 9C |
| Cheatgrass | — | — | — | — | — | — | 6C,9G |
| PREEMERGENCE | | | | | | | |
| Morningglory | 9G | 7G | 9G | 0 | 8G | 2C,6G | 9G |
| Cocklebur | 8H | 8G | 9H | 0 | 8H | 2C,5H | 9H |
| Sicklepod | 3G | 1C | 9G | 0 | 0 | 2C | — |
| Nutsedge | 0 | 0 | 10E | 0 | 0 | 10E | 8G |
| Crabgrass | 0 | 0 | 6C,9G | 0 | 0 | 3G | 2C,5G |
| Barnyardgrass | 3C,3H | 2C | 6C,9H | 0 | 1H | 3C,8H | 4C,5G |
| Wild Oats | 2C,7G | 3G | 6C,9G | 0 | 0 | 2C,7G | 3C,8G |
| Wheat | 6G | 3G | 9C | 0 | 0 | 2C,7G | 8G |
| Corn | 5G | 2G | 2C,9H | 0 | 5G | 2C,8G | 3U,6G |
| Soybean | 3G | 0 | 9H | 0 | 3C,2H | 3C,3H | 2C,6G |
| Rice | 3C,6G | 3C,8H | 10E | 2G | 3C,8H | 5G | 8H |
| Sorghum | 2C,8G | 2G | 4C,9H | 2G | 2C,5G | 3C,8G | 4U,8G |
| Sugar beet | 4C,9G | 3C,9G | 5C,9G | 2G | 8G | 9C | 9C |
| Cotton | 3G | 2G | 9G | 0 | 7G | 0 | 9G |
| Velvetleaf | — | — | — | — | — | — | 9C |
| Cheatgrass | — | — | — | — | — | — | 4C,8G |

TEST B

Postemergence

Two round pans (25 cm diameter by 12.5 cm deep) were filled with Woodstown sandy loam soil. One pan was planted with blackgrass (*Alopecurus myosuroides*), sugar beets, nutsedge (*Cyperus rotundus*) tubers, crabgrass (*Digitaria sanguinalis*), sicklepad (*Cassia obtusifolia*), teaweed (*Sida spinosa*), jimsonweed (*Datura stramonium*), velvetleaf (*Abutilon theophrasti*), and giant foxtail (*Setaria faberii*). The other pan was planted with wheat, cotton, rice, corn, soybean, wild oats (*Avena fatua*), cocklebur (*Xanthium pensylvanicum*), morningglory (*Ipomoea hederacea*), johnsongrass (*Sorghum halepense*) and barnyardgrass (*Echinochloa crusgalli*). The plants were grown for approximately fourteen days, then sprayed postemergence with the chemicals dissolved in a non-phytotoxic solvent.

Preemergence

Two round pans (25 cm diameter by 12.5 cm deep) were filled with Woodstown sandy loam soil. One pan was planted with blackgrass, sugar beets, nutsedge, crabgrass, sicklepod, teaweed, jimsonweed, velvetleaf, and giant foxtail. The other pan was planted with wheat, cotton, rice, corn, soybeans, wild oats, cocklebur, morningglory, johnsongrass, and barnyardgrass. The two pans were sprayed preemergence with the chemicals dissolved in a non-phytotoxic solvent.

Treated plants and controls were maintained in the greenhouse for 28 days, then all treated plants were compared to controls and visually rated for plant response.

Response ratings are based on a scale of 0 to 10: where 0=no effect, and 10=complete control. The type of response is indicated by letters as described for Test 1. A dash (-) response means no test.

Response ratings are contained in Table 2.

TABLE 2

| | POSTEMERGENCE | | | | | | | | | | | | | | | |
|---|---|---|---|---|---|---|---|---|---|---|---|---|---|---|---|---|
| | Compound 1 | | | | Compound 2 | | | | Compound 3 | | | | Compound 4 | | | |
| Rate g/ha | 62 | 16 | 4 | 1 | 62 | 16 | 4 | 1 | 62 | 16 | 4 | 1 | 62 | 16 | 4 | 1 |
| Corn | 8G | 2G | 0 | 0 | 7G | 4G | 2G | 0 | 8G | 2G | 0 | 0 | 8G | 5G | 0 | 0 |
| Wheat | 0 | 0 | 0 | 0 | 9G | 5G | 0 | 0 | 5G | 0 | 0 | 0 | 7G | 3G | 0 | 0 |
| Rice | 8G | 2G | 0 | 0 | 10G | 10G | 5G | 0 | 10G | 9G | 5G | 0 | 10G | 9G | 6G | 0 |
| Soybean | 10G | 9G | 7G | 3G | 10G | 9G | 6G | 3G | 10G | 9G | 7G | 0 | 10G | 10G | 7G | 3G |
| Cotton | 10G | 9G | 9G | 3G | 10G | 10G | 9G | 2G | 10G | 9G | 5G | 0 | 9G | 8G | 3G | 0 |
| Sugar beet | 10G | 10G | 9G | 6G | 10G | 10G | 10G | 9G | 10G | 9G | 8G | 0 | 10G | 10G | 8G | 6G |
| Crabgrass | 7G | 4G | 0 | 0 | 7G | 3G | 0 | 0 | 7G | 6G | 2G | 0 | 9G | 8G | 6G | 0 |

TABLE 2-continued

| | | | | | | | | | | | | | | | |
|---|---|---|---|---|---|---|---|---|---|---|---|---|---|---|---|
| Johnsongrass | 10G | 9G | 8G | 3G | 10G | 9G | 8G | 2G | 10G | 8G | 2G | 10G | 10G | 8G | 3G |
| Blackgrass | 10G | 10G | 8G | 0 | 10G | 10G | 8G | 5G | 10G | 8G | 6G | 10G | 10G | 8G | 7G |
| Barnyardgrass | 2G | 0 | 0 | 0 | 8G | 6G | 4G | 0 | 9G | 7G | 3G | 10G | 9G | 5G | 4G |
| Nutsedge | 7G | 3G | 0 | 0 | 8G | 6G | 3G | 0 | 6G | 0 | 0 | 9G | 7G | 3G | 0 |
| Giant Foxtail | 2G | 0 | 0 | 0 | 6G | 0 | 0 | 0 | 4G | 0 | 0 | 9G | 8G | 2G | 0 |
| Wild Oats | 0 | 0 | 0 | 0 | 10G | 9G | 4G | 0 | 9G | 8G | 0 | 9G | 8G | 0 | 0 |
| Cocklebur | 10G | 9G | 9G | 7G | 10G | 10G | 9G | 7G | 10G | 9G | 8G | 10G | 10G | 9G | 4G |
| Morningglory | 10G | 9G | 8G | 4G | 10G | 10G | 9G | 7G | 10G | 8G | 4G | 9G | 5G | 0 | 0 |
| Teaweed | 9G | 8G | 3G | 0 | 9G | 4G | 0 | 0 | 9G | 8G | 2G | 9G | 9G | 7G | 2G |
| Sicklepod | 10G | 9G | 5G | 0 | 10G | 9G | 8G | 2G | 9G | 8G | 3G | 9G | 9G | 9G | 5G |
| Jimsonweed | 10G | 8G | 6G | 2G | 10G | 10G | 9G | 3G | 9G | 9G | 3G | 10G | 9G | 6G | 3G |
| Velvetleaf | 10G | 10G | 8G | 5G | 10G | 9G | 9G | 5G | 9G | 8G | 7G | 10G | 9G | 9G | 5G |
| Rape | | | | | | | | | | | | | | | |

PREEMERGENCE

| Rate g/ha | 250 | 62 | 16 | 250 | 62 | 16 | 4 | 250 | 62 | 16 | 4 | 250 | 62 | 16 | 4 |
|---|---|---|---|---|---|---|---|---|---|---|---|---|---|---|---|
| Corn | 6G | 3G | 0 | 9G | 7G | 6G | 2G | 9G | 6G | 2G | 0 | 10G | 7G | 2G | 0 |
| Wheat | 5G | 0 | 0 | 10G | 9G | 2G | 0 | 8G | 7G | 2G | 0 | 9G | 7G | 2G | 0 |
| Rice | 9G | 8G | 7G | 10E | 10E | 10G | 9G | 10E | 10E | 9G | 7G | 10E | 9G | 9G | 6G |
| Soybean | 7G | 2G | 0 | 10G | 9G | 8G | 2G | 9G | 7G | 5G | 3G | 10G | 8G | 5G | 2G |
| Cotton | 8G | 3G | 0 | 10G | 8G | 3G | 0 | 10G | 9G | 6G | 3G | 9G | 9G | 8G | 0 |
| Sugar beet | 9G | 8G | 3G | 10G | 10G | 10G | 7G | 10G | 9G | 9G | 7G | 10G | 9G | 7G | 2G |
| Crabgrass | 7G | 3G | 0 | 8G | 3G | 0 | 0 | 6G | 0 | 0 | 0 | 9G | 8G | 5G | 0 |
| Johnsongrass | 9G | 9G | 5G | 10G | 9G | 8G | 4G | 9G | 8G | 6G | 3G | 9G | 9G | 9G | 7G |
| Blackgrass | 9G | 9G | 8G | 10E | 10G | 10G | 9G | 10G | 10G | 9G | 8G | 10G | 9G | 9G | 7G |
| Barnyardgrass | 6G | 2G | 0 | 8G | 7G | 5G | 0 | 10G | 8G | 5G | 3G | 9G | 9G | 8G | 4G |
| Nutsedge | 8G | 2G | 0 | 9G | 8G | 3G | 0 | 10G | 8G | 3G | 0 | 9G | 8G | 6G | 0 |
| Giant Foxtail | 9G | 4G | 0 | 10G | 9G | 7G | 2G | 9G | 7G | 4G | 0 | 10E | 10E | 9G | 3G |
| Wild Oats | 7G | 2G | 0 | 10G | 9G | 9G | 7G | 10G | 9G | 9G | 3G | 9G | 9G | 8G | 6G |
| Cocklebur | 8G | 4G | 2G | 9G | 9G | 7G | 5G | 9G | 8G | 7G | 3G | 9G | 9G | 7G | 0 |
| Morningglory | 9G | 6G | 2G | 10G | 9G | 6G | 3G | 9G | 9G | 5G | 2G | 9G | 8G | 6G | 0 |
| Teaweed | 9G | 8G | 2G | 9G | 9G | 8G | 3G | 9G | 9G | 6G | 2G | 9G | 9G | 6G | 0 |
| Sicklepod | 9G | 7G | 2G | 10G | 9G | 7G | 2G | 10G | 9G | 3G | 0 | 9G | 9G | 6G | 0 |
| Jimsonweed | 9G | 4G | 0 | 10G | 9G | 9G | 5G | 10G | 9G | 8G | 3G | 9G | 8G | 5G | 2G |
| Velvetleaf | 10G | 9G | 7G | 10G | 10G | 9G | 5G | 10G | 10G | 9G | 5G | 10G | 9G | 7G | 5G |
| Rape | | | | | | | | | | | | | | | |

POSTEMERGENCE

| | Compound 6 | | | Compound 7 | | | | Compound 11 | | | | |
|---|---|---|---|---|---|---|---|---|---|---|---|---|
| Rate g/ha | 62 | 16 | 4 | 62 | 16 | 4 | 1 | 250 | 62 | 16 | 4 | 1 |
| Corn | 2G | 0 | 0 | 2G | 0 | 0 | 0 | 100 | 100 | 100 | 90 | 60 |
| Wheat | 0 | 0 | 0 | 2G | 0 | 0 | 0 | 100 | 100 | 90 | 50 | 0 |
| Rice | 8G | 2G | 0 | 9G | 5G | 2G | 0 | 100 | 100 | 100 | 90 | 60 |
| Soybean | 7G | 4G | 2G | 10C | 9G | 8G | 4G | 100 | 100 | 100 | 90 | 80 |
| Cotton | 9G | 5G | 3G | 10C | 8G | 5G | 0 | 100 | 70 | 20 | 0 | 0 |
| Sugar beet | 10G | 10G | 6G | 10C | 10C | 10C | 7C | 100 | 100 | 100 | 100 | 90 |
| Crabgrass | 7G | 3G | 0 | 0 | 0 | 0 | 0 | 100 | 90 | 70 | 20 | 0 |
| Johnsongrass | 9G | 7G | 2G | 8G | 5G | 4G | 0 | 100 | 100 | 100 | 90 | 80 |
| Blackgrass | 10G | 9G | 6G | 10C | 8C | 5G | 0 | 100 | 100 | 100 | 100 | 90 |
| Barnyardgrass | 7G | 3G | 0 | 3G | 0 | 0 | 0 | 100 | 100 | 100 | 80 | 0 |
| Nutsedge | 0 | 0 | 0 | 0 | 0 | 0 | 0 | 100 | 100 | 100 | 90 | 50 |
| Giant Foxtail | 6G | 0 | 0 | 0 | 0 | 0 | 0 | 100 | 100 | 100 | 70 | 0 |
| Wild Oats | 0 | 0 | 0 | 5G | 3G | 0 | 0 | 100 | 100 | 90 | 70 | 20 |
| Cocklebur | 10G | 9G | 6G | 10G | 10G | 9G | 7G | 100 | 100 | 90 | 60 | 20 |
| Morningglory | 10G | 9G | 4G | 10C | 10C | 10G | 7G | 100 | 100 | 100 | 100 | 90 |
| Teaweed | 8G | 6G | 2G | 8G | 8G | 3G | 0 | 100 | 70 | 20 | 0 | 0 |
| Sicklepod | 9G | 9G | 2G | 10C | 10G | 5G | 0 | 100 | 100 | 100 | 70 | 20 |
| Jimsonweed | 10G | 8G | 3G | 10G | 10G | 5G | 0 | 100 | 100 | 100 | 90 | 60 |
| Velvetleaf | 10G | 9G | 6G | 7G | 3G | 0 | 0 | 100 | 100 | 90 | 90 | 30 |
| Rape | | | | | | | | 100 | 100 | 100 | 100 | 80 |

PREEMERGENCE

| Rate g/ha | 62 | 16 | 250 | 62 | 16 | 4 | 62 | 16 | 4 |
|---|---|---|---|---|---|---|---|---|---|
| Corn | 2G | 0 | 2G | 0 | 0 | 0 | 100 | 100 | 30 |
| Wheat | 0 | 0 | 4G | 2G | 0 | 0 | 100 | 90 | 30 |
| Rice | 9G | 7G | 10E | 9G | 9G | 4G | 100 | 100 | 90 |
| Soybean | 0 | 0 | 10G | 6G | 2C | 0 | 95 | 70 | 40 |
| Cotton | 4G | 0 | 10G | 9G | 4G | 0 | 40 | 20 | 0 |
| Sugar beet | 7G | 2G | 10G | 9G | 8G | 4G | 100 | 100 | 80 |
| Crabgrass | 0 | 0 | 0 | 0 | 0 | 0 | 100 | 90 | 50 |
| Johnsongrass | 7G | 3G | 7G | 4G | 0 | 0 | 100 | 100 | 90 |
| Blackgrass | 10G | 9G | 10G | 9G | 7G | 3G | 100 | 100 | 90 |
| Barnyardgrass | 0 | 0 | 2G | 0 | 0 | 0 | 100 | 100 | 70 |
| Nutsedge | 8G | 5G | 3G | 0 | 0 | 0 | 100 | 100 | 70 |
| Giant Foxtail | 0 | 0 | 0 | 0 | 0 | 0 | 100 | 100 | 90 |
| Wild Oats | 4G | 0 | 8G | 7G | 3G | 0 | 100 | 90 | 40 |
| Cocklebur | 5G | 2G | 10G | 9G | 8G | 4G | 95 | 90 | 20 |
| Morningglory | 7G | 2G | 9G | 8G | 4G | 0 | 90 | 80 | 30 |
| Teaweed | 6G | 3G | 10G | 9G | 5G | 0 | 90 | 60 | 30 |
| Sicklepod | 2G | 0 | 10E | 9G | 5G | 0 | 90 | 60 | 30 |
| Jimsonweed | 7G | 3G | 10G | 8G | 4G | 0 | 100 | 100 | 30 |

TABLE 2-continued

| | | | | | | | | | |
|---|---|---|---|---|---|---|---|---|---|
| Velvetleaf | 8G | 6G | 7G | 4G | 0 | 0 | 100 | 60 | 30 |
| Rape | | | | | | | 100 | 100 | 90 |

What is claimed is:

1. An agriculturally suitable composition for controlling the growth of undesired vegetation in a cotton crop comprising an effective amount of a compound of the formula

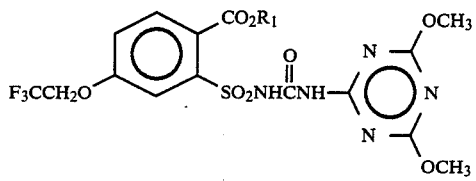

$R_1$ is —CH$_3$ or —CH$_2$CH$_3$ and at least one of the following surfactant, solid or liquid diluent.

2. A method for controlling the growth of undesired vegetation which comprises applying to the locus of a cotton crop an effective amount of the compound of the formula

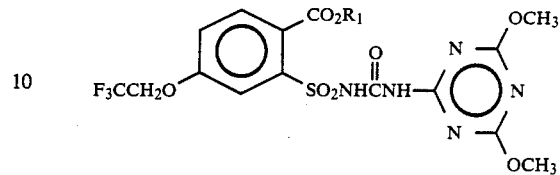

wherein
$R_1$ is —CH$_3$ or —CH$_2$CH$_3$.

3. The composition of claim 1 wherein $R_1$ is —CH$_3$.

4. The composition of claim 1 wherein $R_1$ is —CH$_2$—CH$_3$.

5. The composition of claim 1 which comprises an effective amount of a mixture of the compound with fluometuron.

6. The composition of claim 1 which comprises an effective amount of a mixture of the compound with fluometuron when $R_1$ is —CH$_3$.

7. The composition of claim 1 which comprises an effective amount of a mixture of the compound with fluometuron when $R_1$ is —CH$_2$—CH$_3$.

8. The method of claim 2 wherein $R_1$ is —CH$_3$.

9. The method of claim 2 wherein $R_1$ is —CH$_2$—CH$_3$.

10. The method of claim 2 wherein a mixture of the compound with fluometuron is applied.

11. The method of claim 2 wherein a mixture of the compound with fluometuron is applied and $R_1$ is —CH$_3$.

12. The method of claim 2 wherein a mixture of the compound with fluometuron is applied and $R_1$ is —CH$_2$—CH$_3$.

* * * * *